(12) United States Patent
Shaffrey et al.

(10) Patent No.: US 9,044,272 B2
(45) Date of Patent: Jun. 2, 2015

(54) MULTIPLANAR BONE ANCHOR SYSTEM

(75) Inventors: Christopher Shaffrey, Charlottesville, VA (US); Matthew L. Keiser, Hillsdale, NJ (US); Laurie G. Sanders, Glen Ridge, NJ (US); Gretchen Dougherty Shah, Wayne, NJ (US)

(73) Assignee: EBI, LLC, Parsippany, NJ (US)

( * ) Notice: Subject to any disclaimer, the term of this patent is extended or adjusted under 35 U.S.C. 154(b) by 805 days.

(21) Appl. No.: 13/103,069

(22) Filed: May 8, 2011

(65) Prior Publication Data

US 2012/0016425 A1 Jan. 19, 2012

Related U.S. Application Data

(63) Continuation-in-part of application No. 12/614,734, filed on Nov. 9, 2009, now Pat. No. 8,449,578.

(51) Int. Cl.
*A61B 17/76* (2006.01)
*A61B 17/70* (2006.01)

(52) U.S. Cl.
CPC ......... *A61B 17/7032* (2013.01); *A61B 17/7037* (2013.01); *A61B 17/7038* (2013.01); *A61B 17/7041* (2013.01); *A61B 17/7052* (2013.01); *A61B 17/7055* (2013.01); *A61B 17/7056* (2013.01)

(58) Field of Classification Search
USPC .................................. 606/264–275, 300–321
See application file for complete search history.

(56) References Cited

U.S. PATENT DOCUMENTS

| | | | |
|---|---|---|---|
| 5,209,753 A | 5/1993 | Biedermann et al. | |
| 5,291,075 A | 3/1994 | Hollstein et al. | |
| 5,312,404 A | 5/1994 | Asher et al. | |
| 5,352,224 A | 10/1994 | Westermann | |
| 5,360,431 A | 11/1994 | Puno et al. | |
| 5,454,813 A | 10/1995 | Lawes | |
| 5,466,237 A | 11/1995 | Byrd, III et al. | |
| 5,474,555 A | 12/1995 | Puno et al. | |

(Continued)

FOREIGN PATENT DOCUMENTS

| CA | 2289629 A1 | 11/1998 |
|---|---|---|
| DE | 19509332 C1 | 8/1996 |

(Continued)

OTHER PUBLICATIONS

DePuy Spine, Mountaineer OCT Spinal System, Surgical Technique. ā2005 DePuy Spine, Inc.

(Continued)

*Primary Examiner* — Jerry Cumberledge
(74) *Attorney, Agent, or Firm* — Harness, Dickey

(57) ABSTRACT

The present teachings provide one or more surgical implements for repairing damaged tissue, such as in the case of a spinal fixation procedure. A bone anchor is provided. The anchor can include a bone fastener. The bone fastener can include a head and a second end adapted to engage an anatomy. The bone fastener can extend along a longitudinal axis. The anchor can also include a coupling arrangement coupled to the head of the bone fastener so that the bone fastener is rotatable about the longitudinal axis to define a first plane of motion. The anchor can further include a saddle, which can be coupled to the coupling arrangement. The saddle can be movable relative to at least one of the bone fastener and the coupling arrangement to define a second plane of motion.

20 Claims, 58 Drawing Sheets

(56) References Cited

U.S. PATENT DOCUMENTS

| | | | | |
|---|---|---|---|---|
| 5,496,321 | A | 3/1996 | Puno et al. | |
| 5,499,983 | A | 3/1996 | Hughes | |
| 5,584,834 | A | 12/1996 | Errico et al. | |
| 5,669,911 | A | 9/1997 | Errico et al. | |
| 5,683,390 | A | 11/1997 | Metz-Stavenhagen et al. | |
| 5,690,630 | A | 11/1997 | Errico et al. | |
| 5,713,900 | A | 2/1998 | Benzel et al. | |
| 5,743,907 | A | 4/1998 | Asher et al. | |
| 5,876,402 | A | 3/1999 | Errico et al. | |
| 5,879,350 | A | 3/1999 | Sherman et al. | |
| 5,908,422 | A | 6/1999 | Bresina | |
| 5,938,663 | A | 8/1999 | Petreto | |
| 6,010,503 | A | 1/2000 | Richelsoph et al. | |
| 6,053,917 | A | 4/2000 | Sherman et al. | |
| 6,060,111 | A | 5/2000 | Buecher et al. | |
| 6,063,090 | A | 5/2000 | Schlapfer | |
| 6,074,391 | A | 6/2000 | Metz-Stavenhagen et al. | |
| 6,090,111 | A | 7/2000 | Nichols | |
| 6,110,172 | A | 8/2000 | Jackson | |
| 6,248,105 | B1 | 6/2001 | Schlapfer et al. | |
| 6,251,112 | B1 | 6/2001 | Jackson | |
| 6,254,602 | B1 | 7/2001 | Justis | |
| 6,273,888 | B1 | 8/2001 | Justis | |
| 6,280,442 | B1 | 8/2001 | Barker et al. | |
| 6,335,040 | B1 | 1/2002 | Hoier et al. | |
| RE37,665 | E | 4/2002 | Ralph et al. | |
| 6,406,477 | B1 | 6/2002 | Fujiwara | |
| 6,440,132 | B1 | 8/2002 | Jackson | |
| 6,443,953 | B1 | 9/2002 | Perra et al. | |
| 6,443,954 | B1 | 9/2002 | Bramlet et al. | |
| 6,471,705 | B1 | 10/2002 | Biedermann et al. | |
| 6,478,798 | B1 | 11/2002 | Howland | |
| 6,520,963 | B1 | 2/2003 | McKinley | |
| 6,565,565 | B1 | 5/2003 | Yuan et al. | |
| 6,565,566 | B1 | 5/2003 | Wagner et al. | |
| 6,652,526 | B1 | 11/2003 | Arafiles | |
| 6,660,004 | B2 | 12/2003 | Barker et al. | |
| 6,660,005 | B2 | 12/2003 | Toyama et al. | |
| 6,682,529 | B2 | 1/2004 | Stahurski | |
| 6,685,705 | B1 | 2/2004 | Taylor | |
| 6,689,133 | B2 | 2/2004 | Morrison et al. | |
| 6,709,434 | B1 | 3/2004 | Gournay et al. | |
| 6,716,214 | B1 | 4/2004 | Jackson | |
| 6,736,820 | B2 | 5/2004 | Biedermann et al. | |
| 6,755,829 | B1 | 6/2004 | Bono et al. | |
| 6,780,186 | B2 | 8/2004 | Errico et al. | |
| 6,860,884 | B2 | 3/2005 | Shirado et al. | |
| 6,974,460 | B2 | 12/2005 | Carbone et al. | |
| RE39,089 | E | 5/2006 | Ralph et al. | |
| 7,081,116 | B1 | 7/2006 | Carly | |
| 7,081,117 | B2 | 7/2006 | Bono et al. | |
| 7,087,057 | B2 | 8/2006 | Konieczynski et al. | |
| 7,235,075 | B1 | 6/2007 | Metz-Stavenhagen | |
| 7,306,602 | B2 | 12/2007 | Bono et al. | |
| 7,322,981 | B2 | 1/2008 | Jackson | |
| 7,338,491 | B2 | 3/2008 | Baker et al. | |
| 7,445,627 | B2 | 11/2008 | Hawkes et al. | |
| 7,559,943 | B2 | 7/2009 | Mujwid | |
| 7,572,279 | B2 | 8/2009 | Jackson | |
| 7,578,833 | B2 | 8/2009 | Bray | |
| 7,591,839 | B2 | 9/2009 | Biedermann et al. | |
| 7,635,380 | B2 | 12/2009 | Zucherman et al. | |
| 7,691,131 | B2 | 4/2010 | Graf | |
| 7,699,876 | B2 * | 4/2010 | Barry et al. | 606/266 |
| 7,704,270 | B2 * | 4/2010 | De Coninck | 606/264 |
| 7,731,734 | B2 | 6/2010 | Clement et al. | |
| 7,749,258 | B2 | 7/2010 | Biedermann et al. | |
| 7,776,067 | B2 | 8/2010 | Jackson | |
| 7,780,706 | B2 | 8/2010 | Marino et al. | |
| 7,811,310 | B2 | 10/2010 | Baker et al. | |
| 7,850,718 | B2 | 12/2010 | Bette et al. | |
| 7,850,719 | B2 | 12/2010 | Gournay et al. | |
| 7,857,834 | B2 | 12/2010 | Boschert | |
| 7,922,748 | B2 | 4/2011 | Hoffman | |
| 7,955,358 | B2 | 6/2011 | Albert | |
| 7,967,849 | B2 | 6/2011 | Carson et al. | |
| 7,967,850 | B2 | 6/2011 | Jackson | |
| 8,012,183 | B2 | 9/2011 | Alain | |
| 8,034,086 | B2 * | 10/2011 | Iott et al. | 606/267 |
| 8,092,494 | B2 | 1/2012 | Butler et al. | |
| 8,100,945 | B2 * | 1/2012 | Dewey et al. | 606/249 |
| 8,298,275 | B2 * | 10/2012 | Rezach | 606/308 |
| 8,337,530 | B2 * | 12/2012 | Hestad et al. | 606/279 |
| 2001/0001119 | A1 | 5/2001 | Lombardo | |
| 2001/0047173 | A1 | 11/2001 | Schlapfer et al. | |
| 2002/0120272 | A1 | 8/2002 | Yuan et al. | |
| 2002/0183747 | A1 | 12/2002 | Jao et al. | |
| 2003/0167058 | A1 | 9/2003 | Shluzas | |
| 2004/0097933 | A1 | 5/2004 | Lourdel et al. | |
| 2004/0116929 | A1 | 6/2004 | Barker et al. | |
| 2004/0138660 | A1 | 7/2004 | Serhan | |
| 2004/0143265 | A1 | 7/2004 | Landry et al. | |
| 2004/0153068 | A1 | 8/2004 | Janowski et al. | |
| 2004/0158247 | A1 | 8/2004 | Sitiso et al. | |
| 2004/0162558 | A1 | 8/2004 | Hegde et al. | |
| 2004/0204771 | A1 | 10/2004 | Swanson | |
| 2004/0215190 | A1 | 10/2004 | Nguyen et al. | |
| 2004/0236330 | A1 | 11/2004 | Purcell et al. | |
| 2004/0243126 | A1 | 12/2004 | Carbone et al. | |
| 2004/0267264 | A1 | 12/2004 | Konieczynski et al. | |
| 2005/0010221 | A1 | 1/2005 | Dalton | |
| 2005/0025767 | A1 | 2/2005 | Nishihira | |
| 2005/0080415 | A1 * | 4/2005 | Keyer et al. | 606/61 |
| 2005/0080420 | A1 | 4/2005 | Farris et al. | |
| 2005/0131410 | A1 | 6/2005 | Lin | |
| 2005/0154391 | A1 * | 7/2005 | Doherty et al. | 606/61 |
| 2005/0182407 | A1 | 8/2005 | Dalton | |
| 2005/0187548 | A1 | 8/2005 | Butler et al. | |
| 2005/0203515 | A1 | 9/2005 | Doherty et al. | |
| 2005/0203516 | A1 * | 9/2005 | Biedermann et al. | 606/61 |
| 2005/0234451 | A1 | 10/2005 | Markworth | |
| 2005/0261687 | A1 | 11/2005 | Garamszegi et al. | |
| 2006/0025767 | A1 * | 2/2006 | Khalili | 606/61 |
| 2007/0118123 | A1 | 5/2007 | Strausbaugh et al. | |
| 2007/0233063 | A1 | 10/2007 | Rezach | |
| 2008/0004623 | A1 | 1/2008 | Ferrante et al. | |
| 2008/0009682 | A1 | 1/2008 | Hernke | |
| 2008/0009862 | A1 | 1/2008 | Hoffman | |
| 2008/0077138 | A1 | 3/2008 | Cohen et al. | |
| 2008/0108992 | A1 | 5/2008 | Barry et al. | |
| 2008/0119857 | A1 | 5/2008 | Potash et al. | |
| 2008/0125816 | A1 | 5/2008 | Jackson | |
| 2008/0140135 | A1 | 6/2008 | Konieczynski et al. | |
| 2008/0147129 | A1 * | 6/2008 | Biedermann et al. | 606/308 |
| 2008/0154315 | A1 | 6/2008 | Jackson | |
| 2008/0161853 | A1 | 7/2008 | Arnold et al. | |
| 2008/0161863 | A1 | 7/2008 | Arnold et al. | |
| 2008/0177260 | A1 | 7/2008 | McKinley et al. | |
| 2008/0195159 | A1 | 8/2008 | Kloss et al. | |
| 2008/0234761 | A1 | 9/2008 | Jackson | |
| 2008/0243193 | A1 | 10/2008 | Ensign et al. | |
| 2008/0249570 | A1 | 10/2008 | Carson et al. | |
| 2008/0262497 | A1 | 10/2008 | Nijenbanning et al. | |
| 2008/0269809 | A1 | 10/2008 | Garamszegi | |
| 2008/0312655 | A1 | 12/2008 | Kirschman et al. | |
| 2009/0024155 | A1 | 1/2009 | Lee-Sepsick et al. | |
| 2009/0036929 | A1 | 2/2009 | Reglos et al. | |
| 2009/0076552 | A1 | 3/2009 | Tornier | |
| 2009/0105769 | A1 | 4/2009 | Rock et al. | |
| 2009/0182384 | A1 * | 7/2009 | Wilcox et al. | 606/305 |
| 2009/0248025 | A1 | 10/2009 | Haidukewych et al. | |
| 2010/0036426 | A1 | 2/2010 | Mitchell et al. | |
| 2010/0087873 | A1 * | 4/2010 | Null et al. | 606/306 |
| 2010/0100137 | A1 | 4/2010 | Justis et al. | |
| 2010/0198272 | A1 | 8/2010 | Keyer et al. | |
| 2010/0204735 | A1 * | 8/2010 | Gephart et al. | 606/264 |
| 2010/0228293 | A1 | 9/2010 | Courtney et al. | |
| 2010/0241170 | A1 | 9/2010 | Cammisa et al. | |
| 2010/0268279 | A1 | 10/2010 | Gabelberger et al. | |
| 2010/0305621 | A1 | 12/2010 | Wang et al. | |
| 2011/0015677 | A1 * | 1/2011 | Biedermann et al. | 606/264 |
| 2011/0093021 | A1 | 4/2011 | Fanger et al. | |
| 2011/0106173 | A1 | 5/2011 | Lindemann et al. | |
| 2011/0106175 | A1 | 5/2011 | Rezach | |

(56) References Cited

U.S. PATENT DOCUMENTS

| | | | |
|---|---|---|---|
| 2011/0106176 A1 | 5/2011 | Jackson | |
| 2011/0106180 A1 | 5/2011 | Miller et al. | |
| 2011/0112585 A1* | 5/2011 | Biedermann et al. | 606/305 |
| 2011/0137348 A1 | 6/2011 | Jackson | |
| 2012/0095516 A1* | 4/2012 | Dikeman | 606/305 |

FOREIGN PATENT DOCUMENTS

| | | | |
|---|---|---|---|
| DE | 19720782 | A1 | 11/1998 |
| EP | 0441729 | A1 | 8/1991 |
| JP | 2010515552 | A | 5/2010 |
| JP | 2010524637 | A | 7/2010 |
| WO | 9702786 | A1 | 1/1997 |
| WO | 9852482 | A1 | 11/1998 |
| WO | 0115612 | A1 | 3/2001 |
| WO | 2005122929 | A1 | 12/2005 |
| WO | 2006009753 | A1 | 1/2006 |
| WO | 2007047711 | A2 | 4/2007 |
| WO | 2008042948 | A2 | 4/2008 |
| WO | 2008057551 | A2 | 5/2008 |
| WO | 2008089096 | A2 | 7/2008 |
| WO | 2008153723 | A1 | 12/2008 |
| WO | 2009055407 | | 4/2009 |
| WO | WO2009/091686 | | 7/2009 |
| WO | 2010090428 | A2 | 8/2010 |

OTHER PUBLICATIONS

International Search Report and Written Opinion for PCT/US2010/054453 Mailed Jun. 28, 2011.
Burkus, MD, Kenneth, Medtronic, TSRH-3D Spinal System, Surgical Technique, 2009, pp. 32.
EBI Spine, Polaris, Surgical Technique, 2006, pp. 28.
EBI, A Biomet Company, Omega 21 Spinal Fixation System, EBI Spine System, 2001.
Medtronic, Vertex Max, Reconstruction System Surgical Technique Demonstrating Occipital Plate Rod and Occipital Keel Plate, 2009, pp. 1-44.
International Search Report and Written Opinion for Application No. PCT/US2012/036234 mailed Nov. 16, 2012.
Non-Final Office Action for U.S. Appl. No. 12/614,734 Mailed Oct. 28, 2011.
PCT International Preliminary Report on Patentability for related Application No. PCT/US2012/036234; Nov. 21, 2013; 6 pages.
U.S. Appl. No. 13/911,397, filed Jun. 6, 2013, Albert.
Extended European Search Report and European Search Opinion dated Sep. 9, 2013 for PCT Application No. PCT/US2010054453.
ST360° Spinal Fixation System; ©2005 Zimmer Spine, Inc. L1242 Rev. D04/05; 4 Pages.
Office Action for JP Application No. 2014-510361, dated Mar. 3, 2015.

* cited by examiner

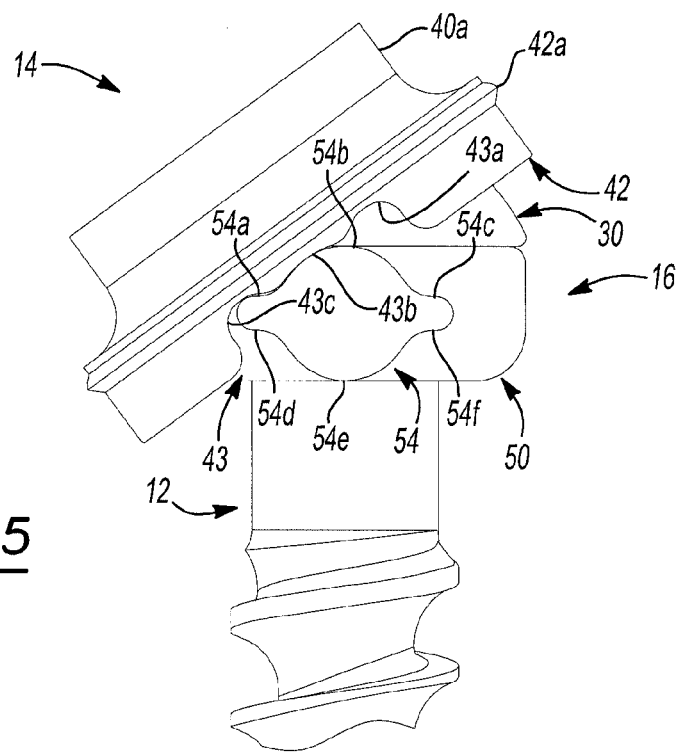
_Fig-5_
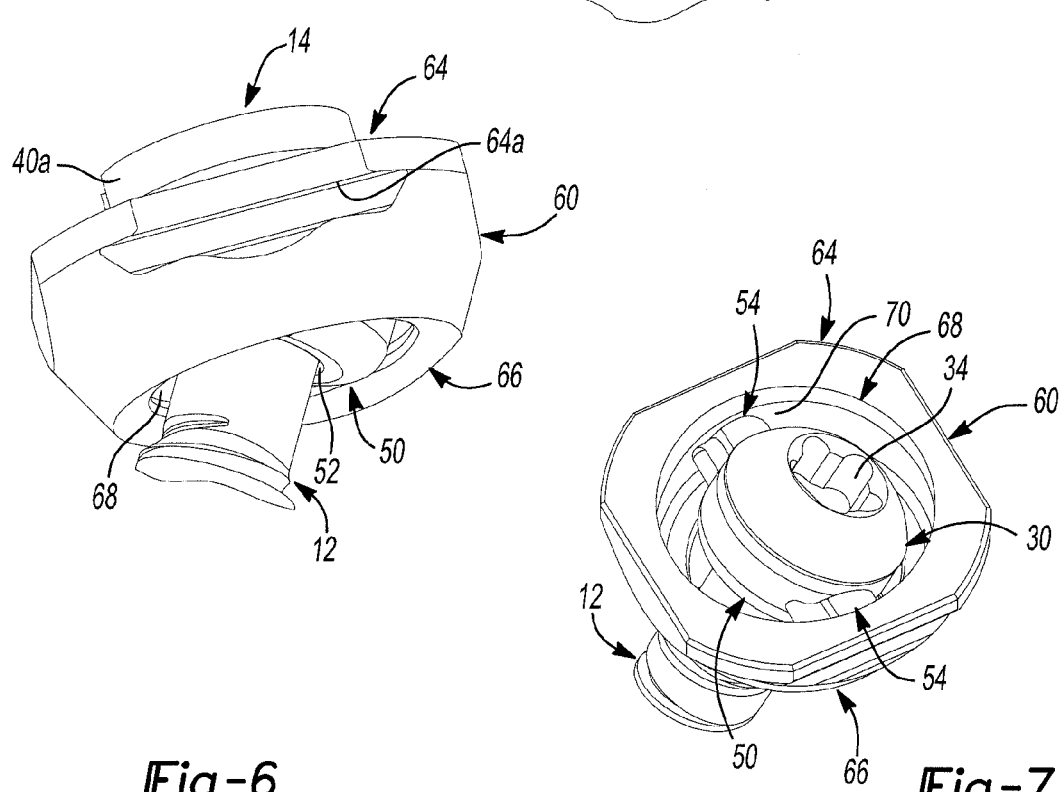
_Fig-6_
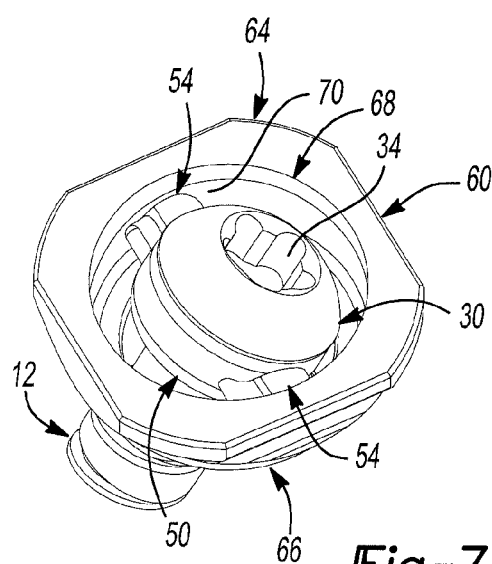
_Fig-7_

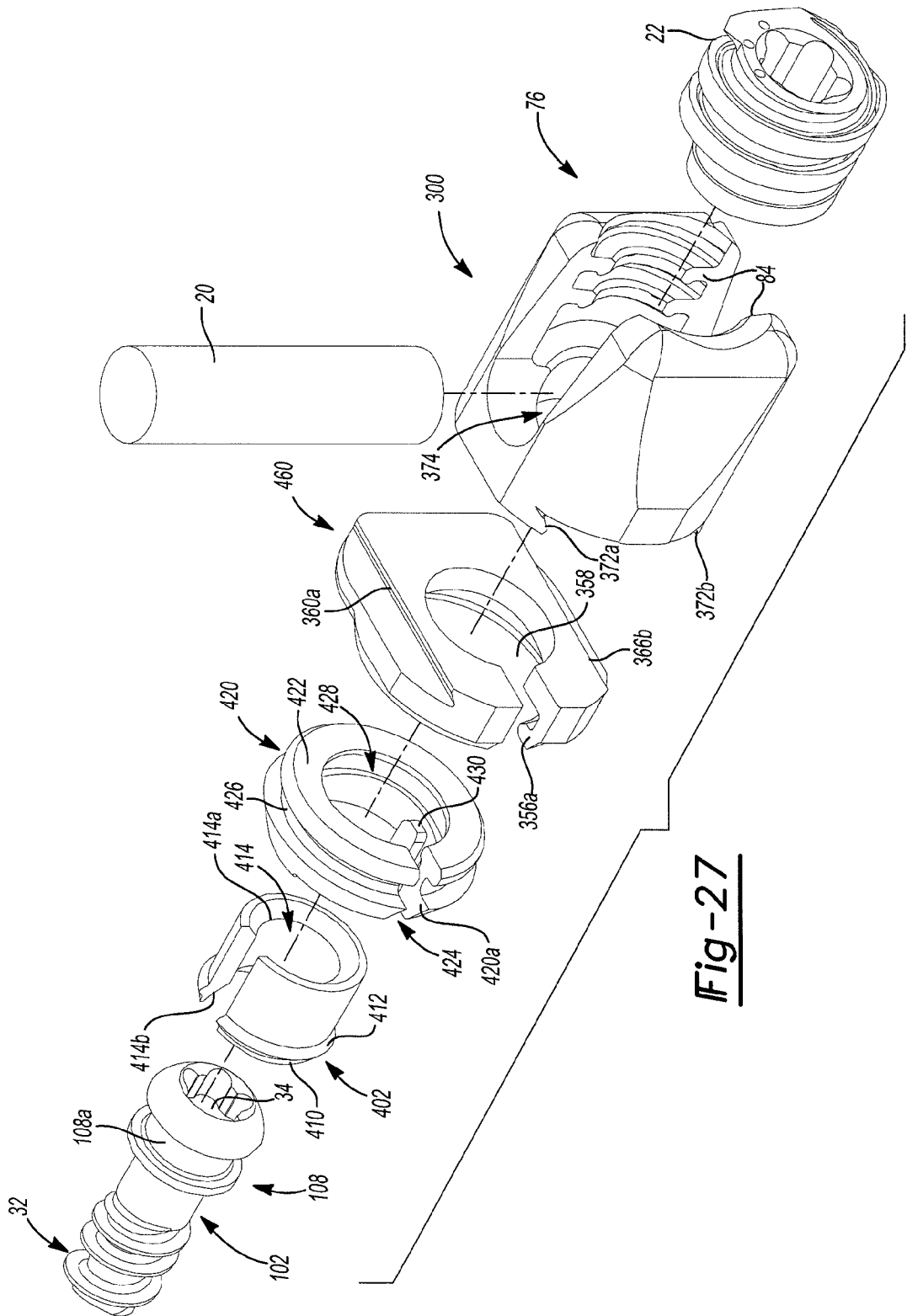

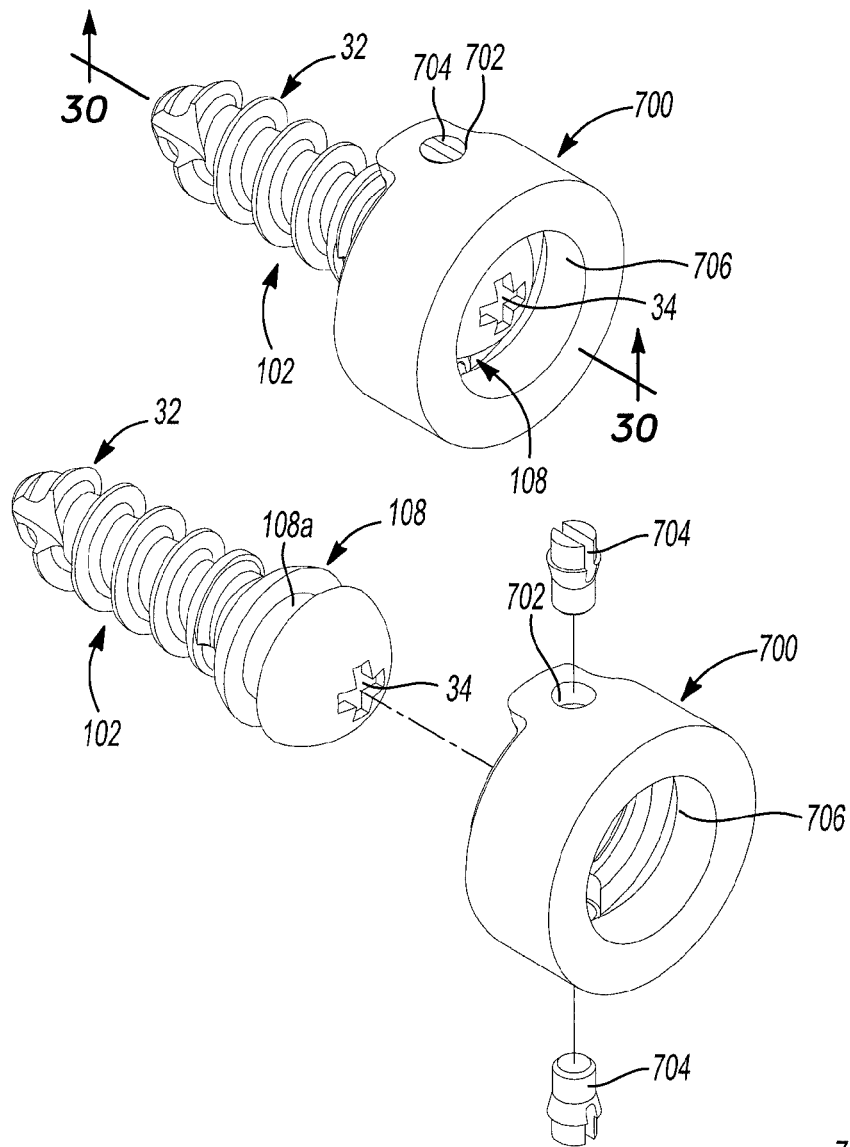
*Fig-28*
*Fig-29*
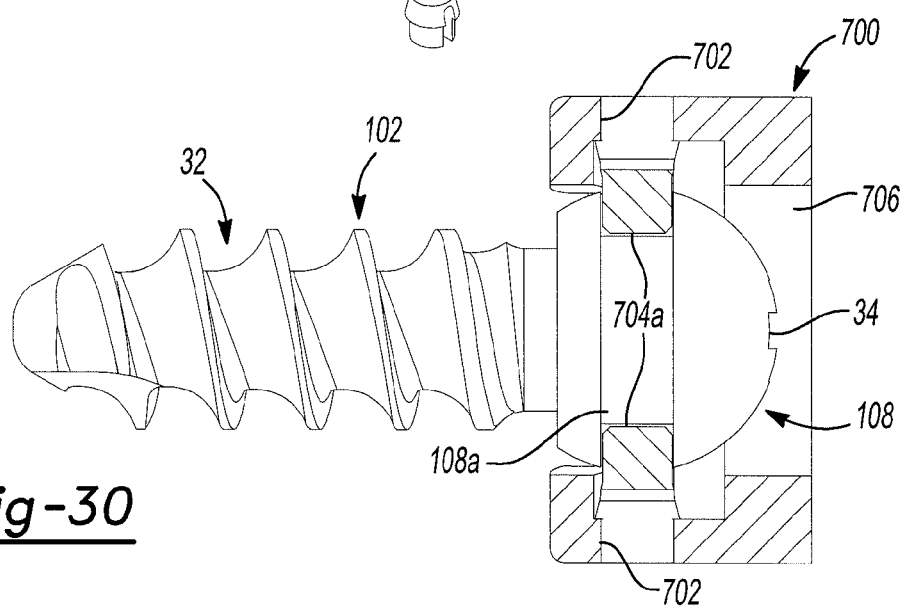
*Fig-30*

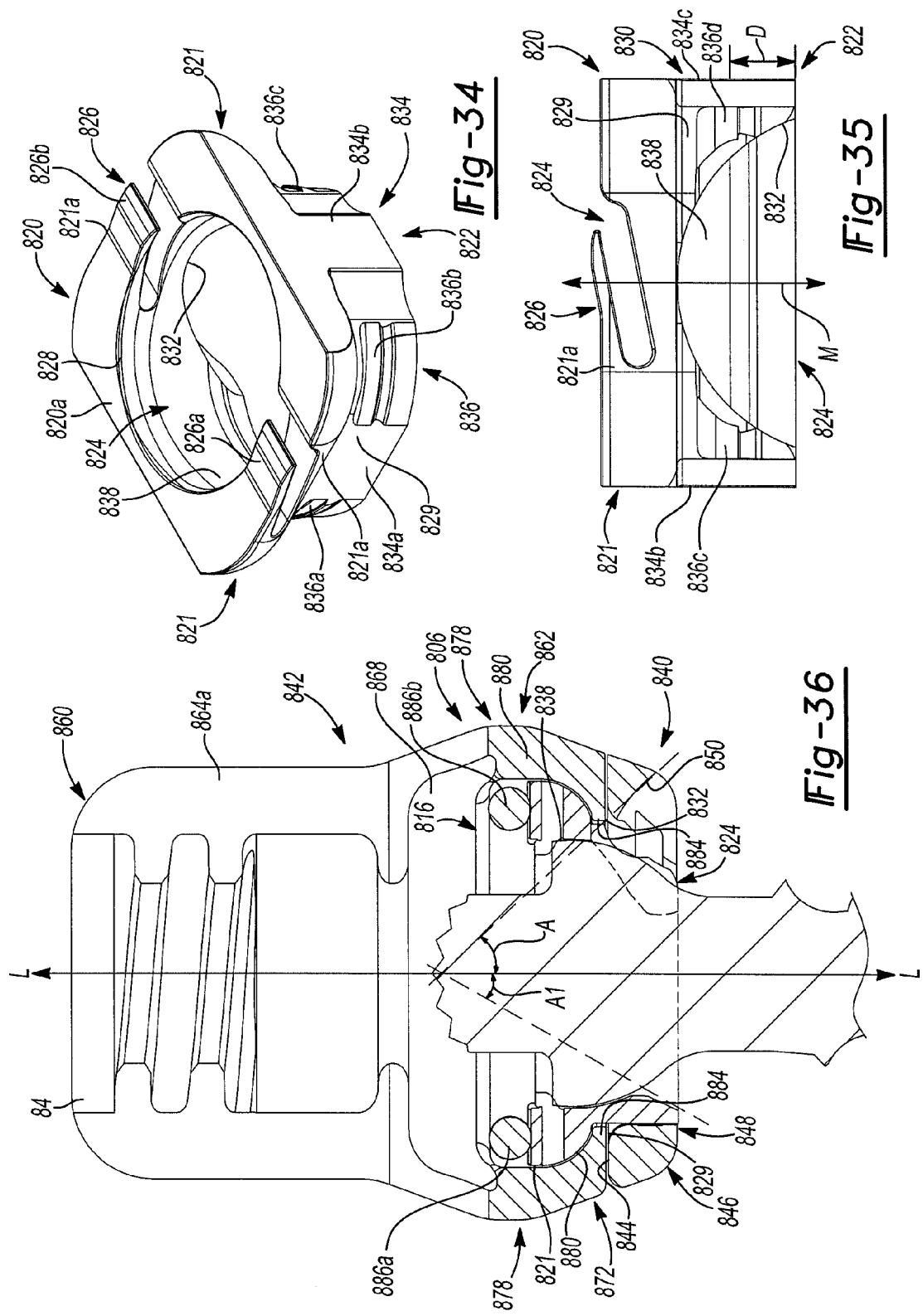

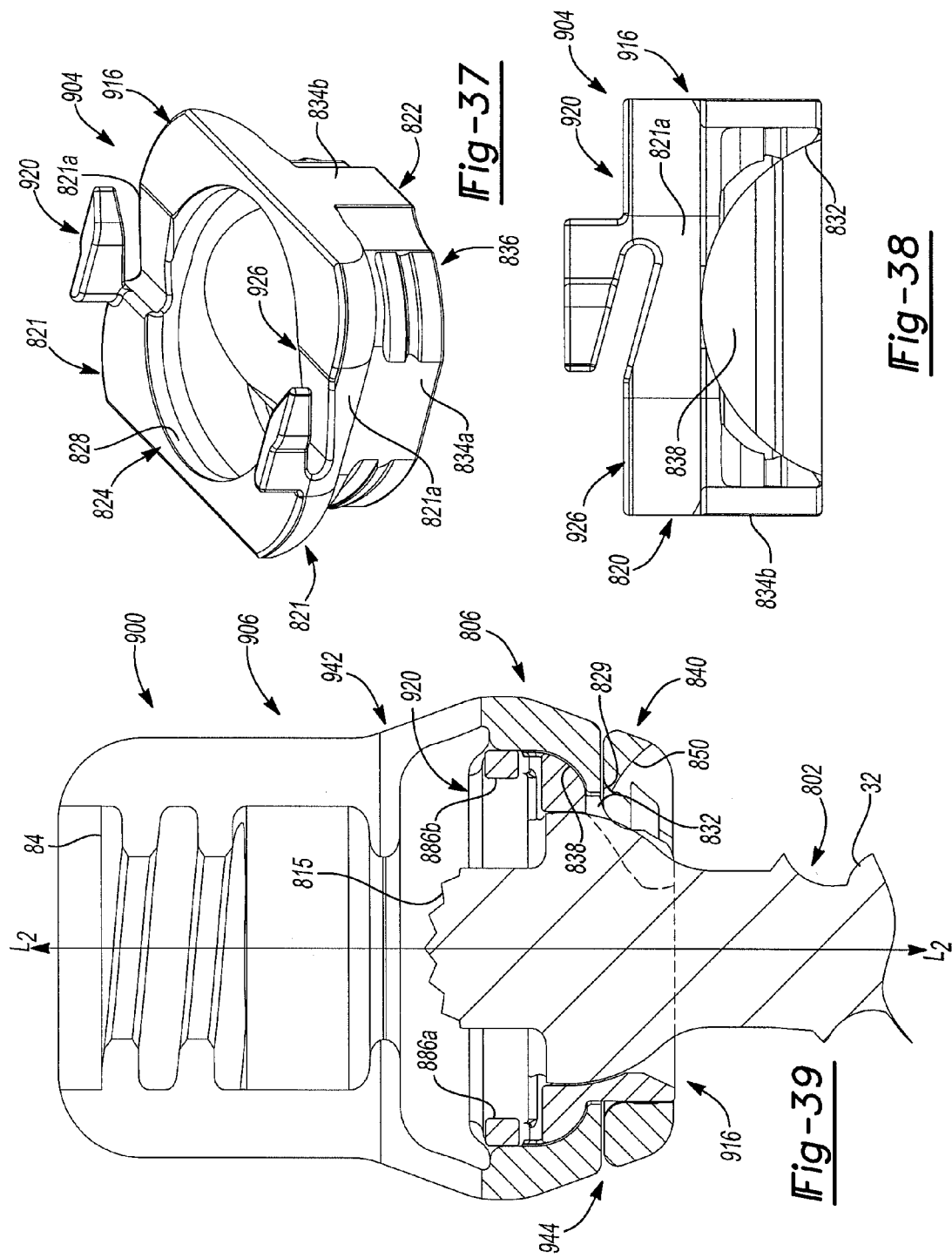

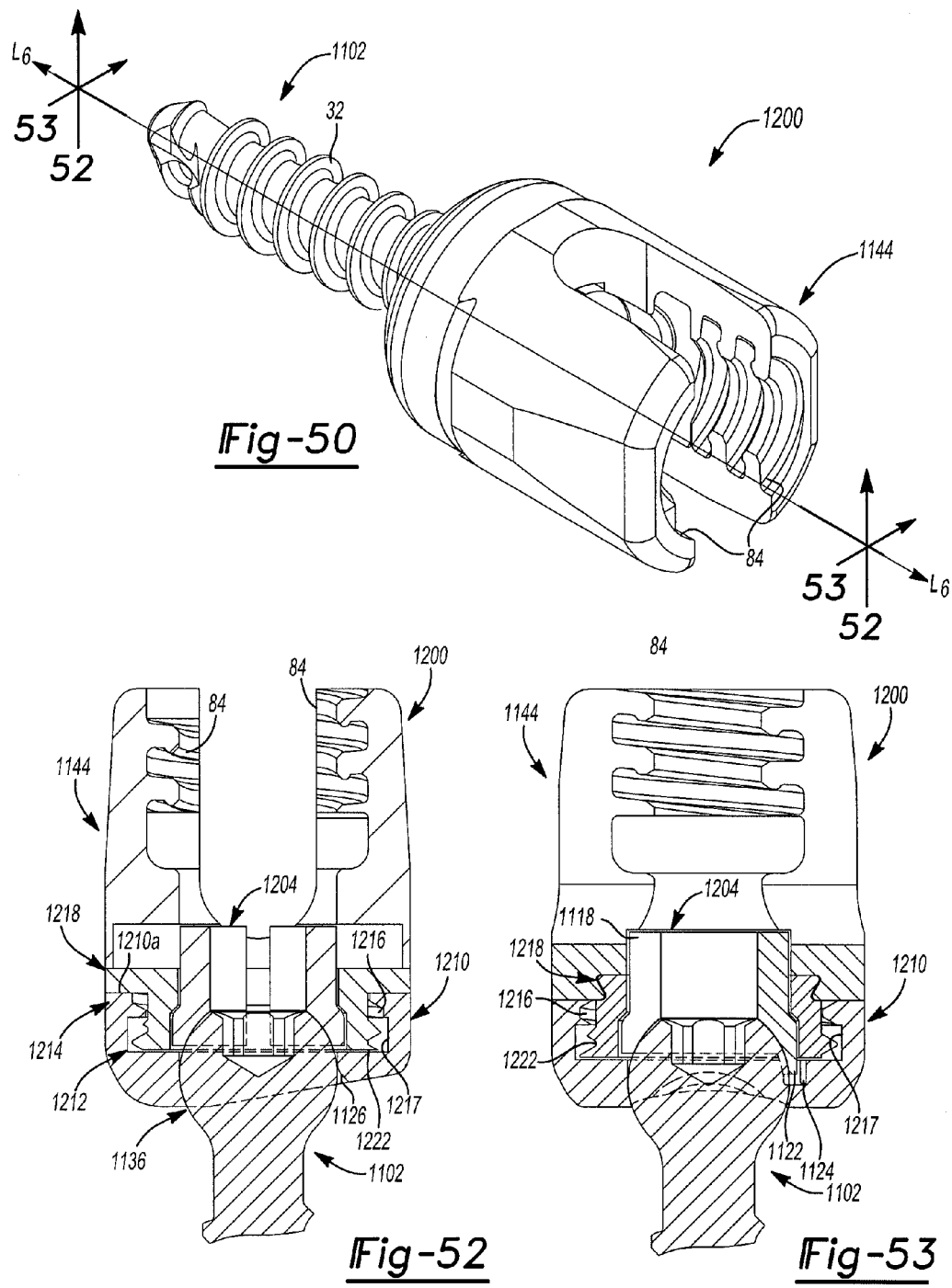

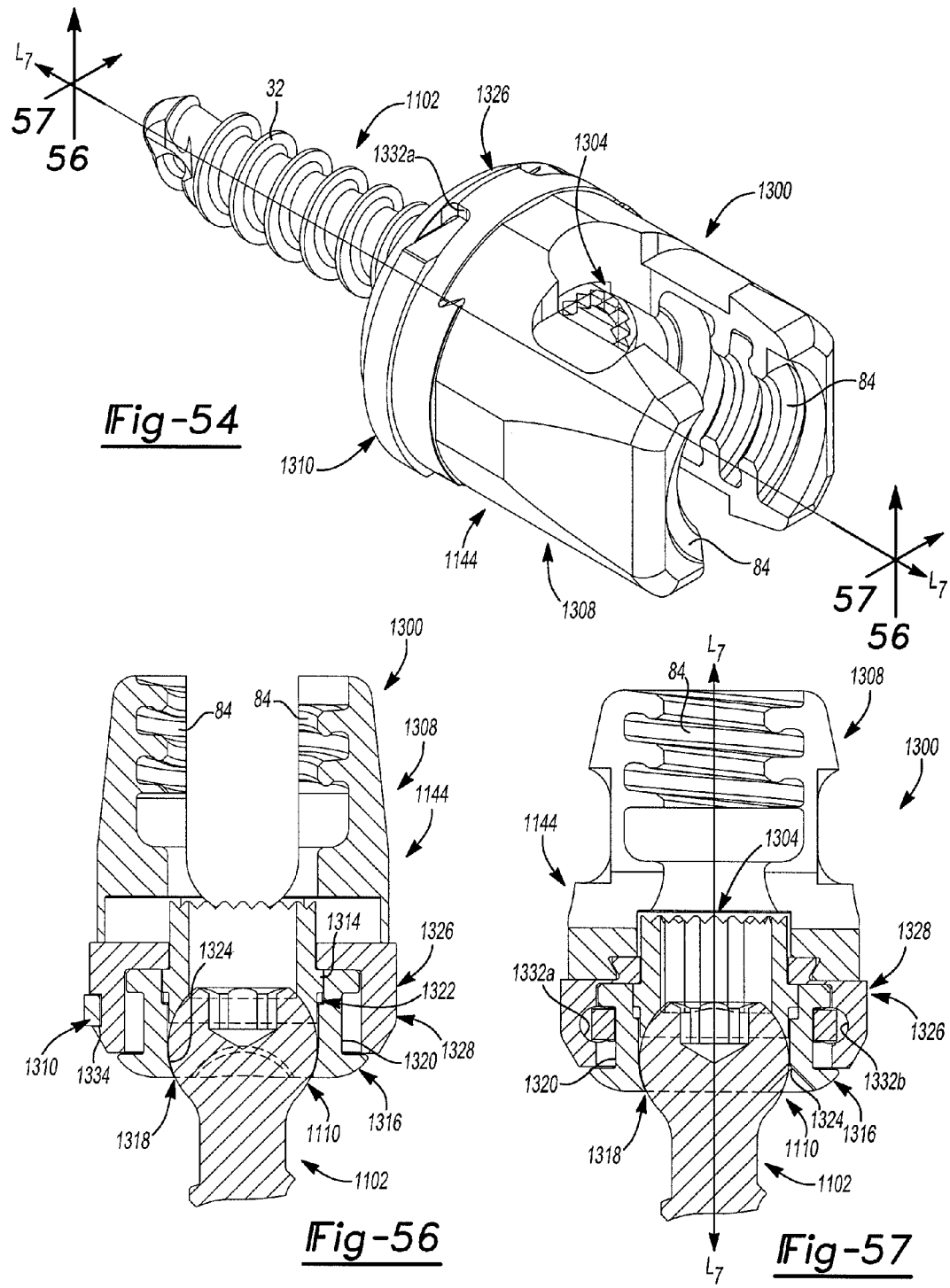

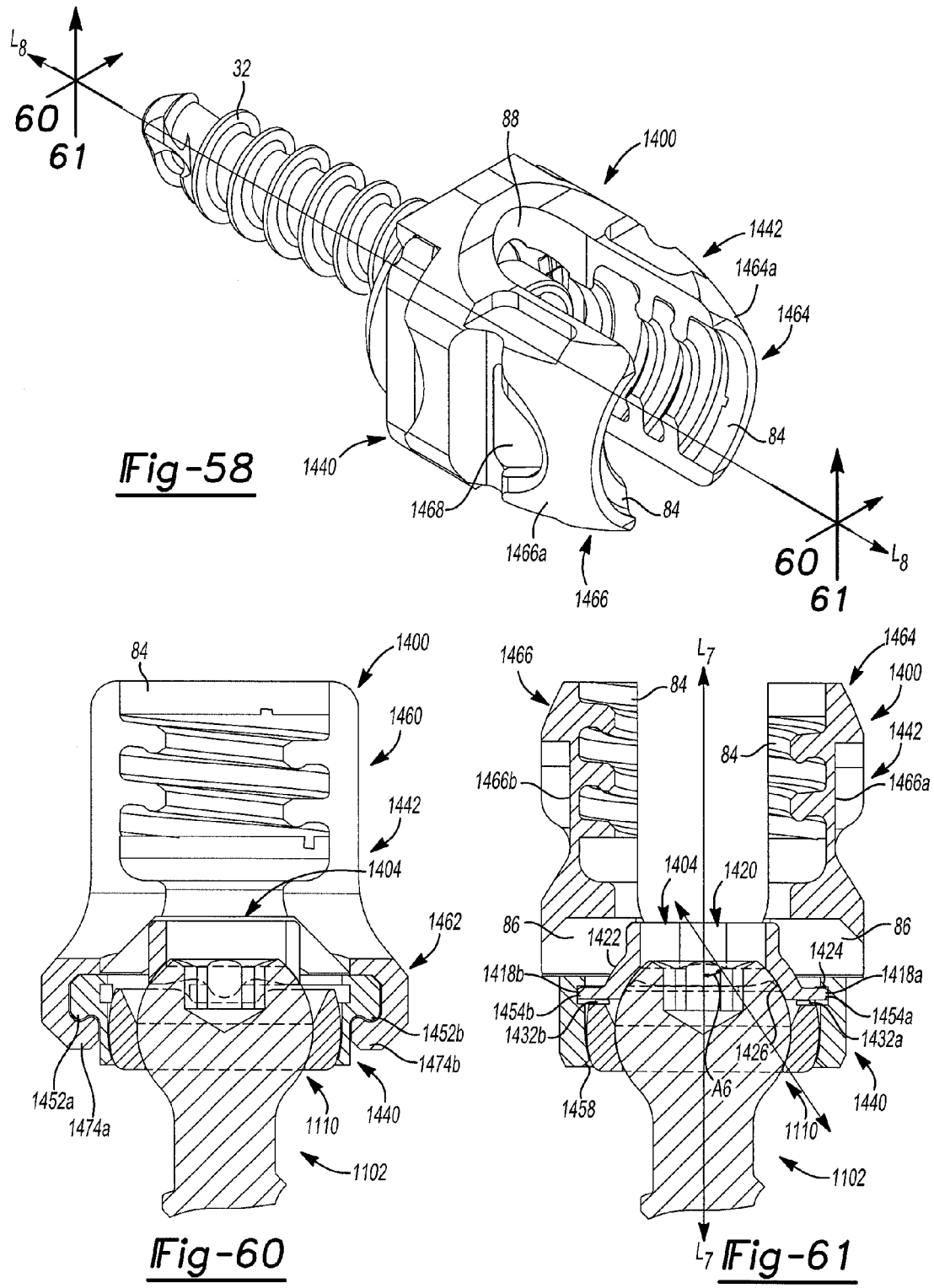

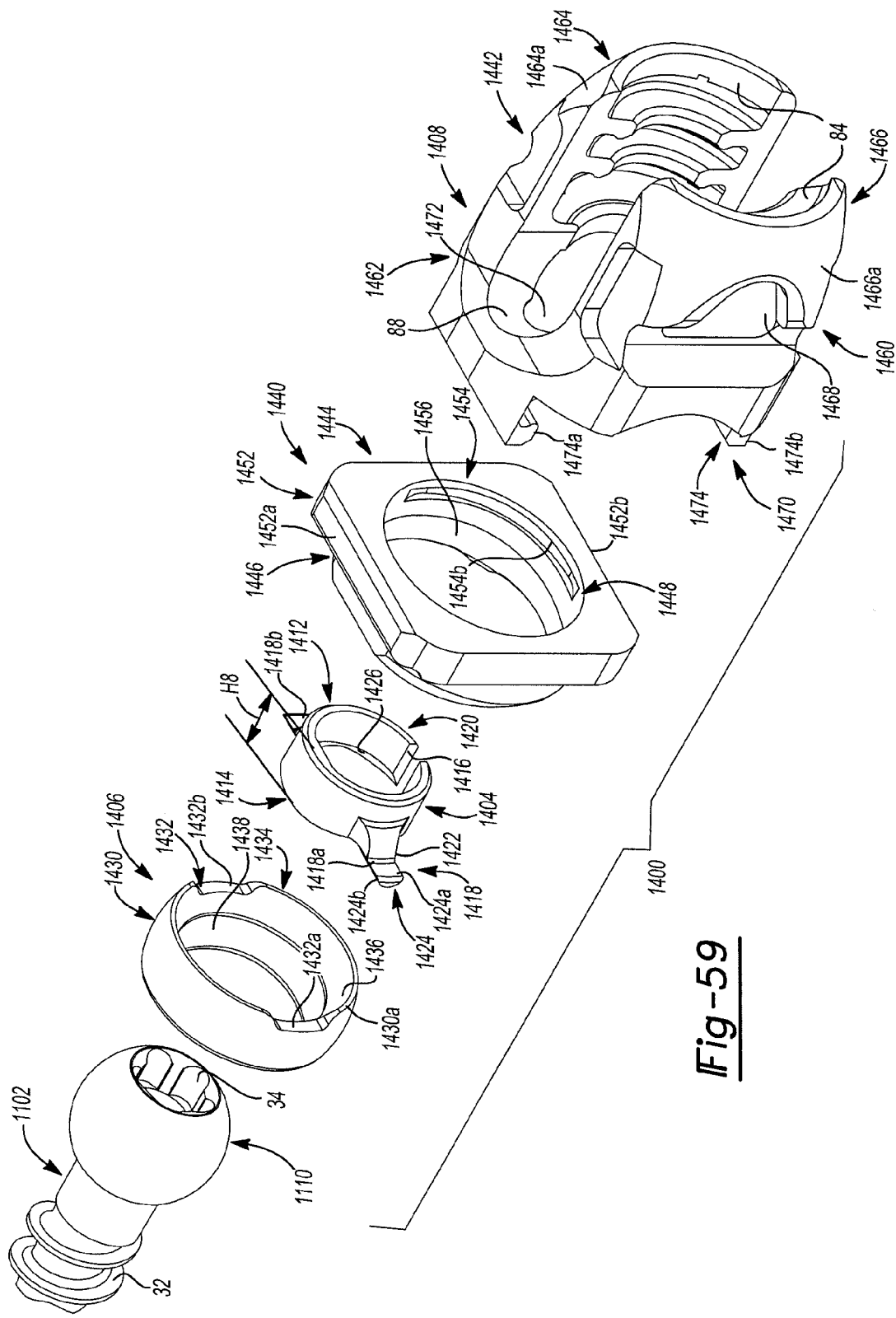

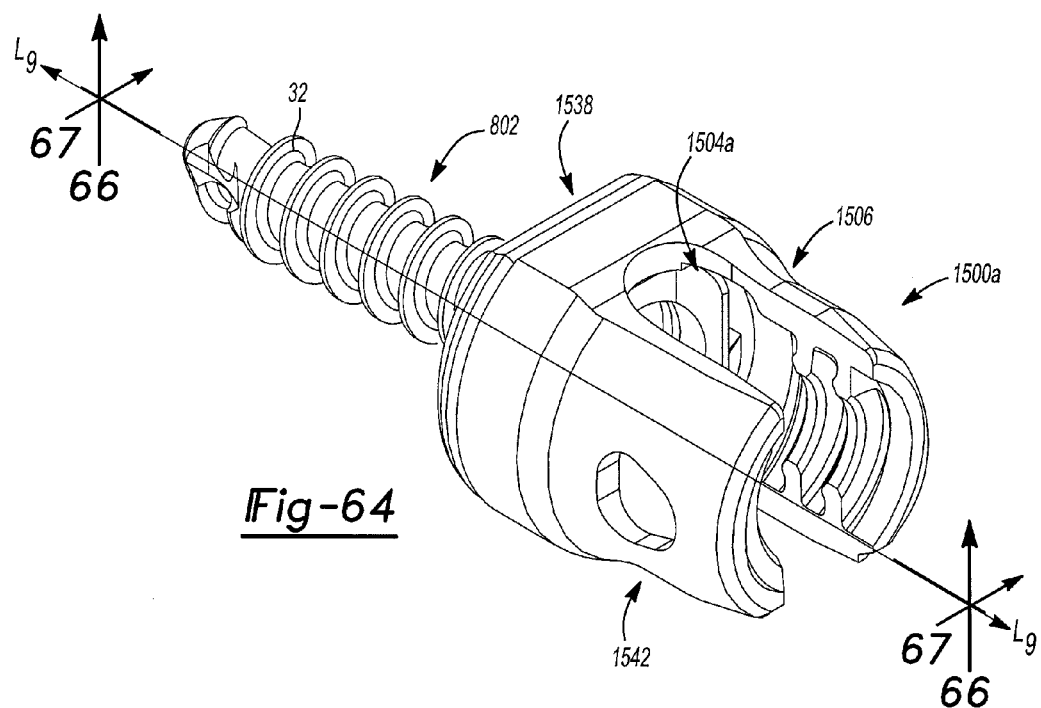
Fig-64
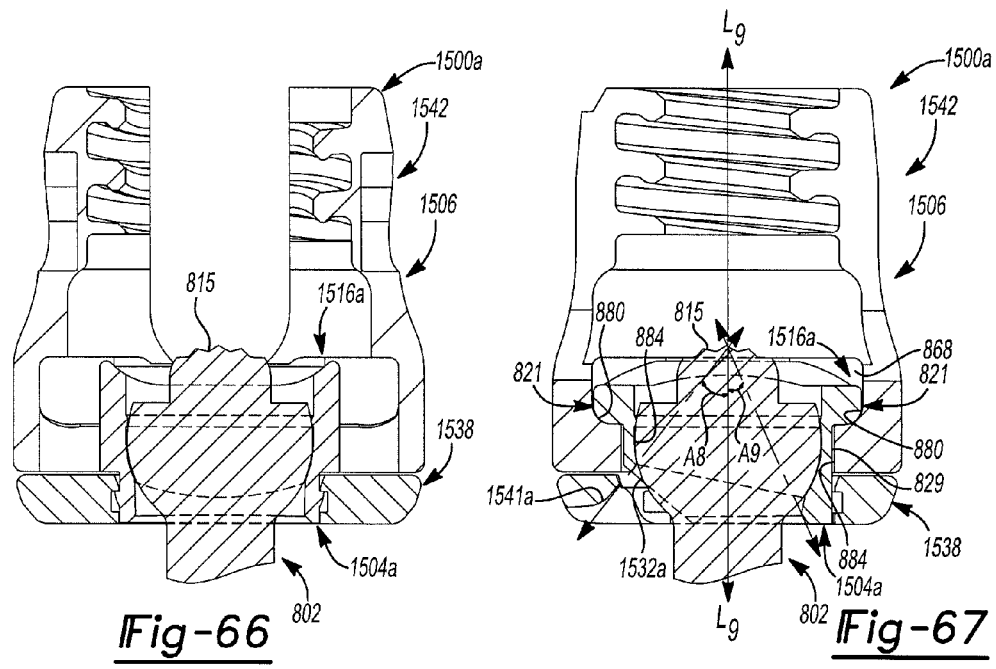
Fig-66
Fig-67

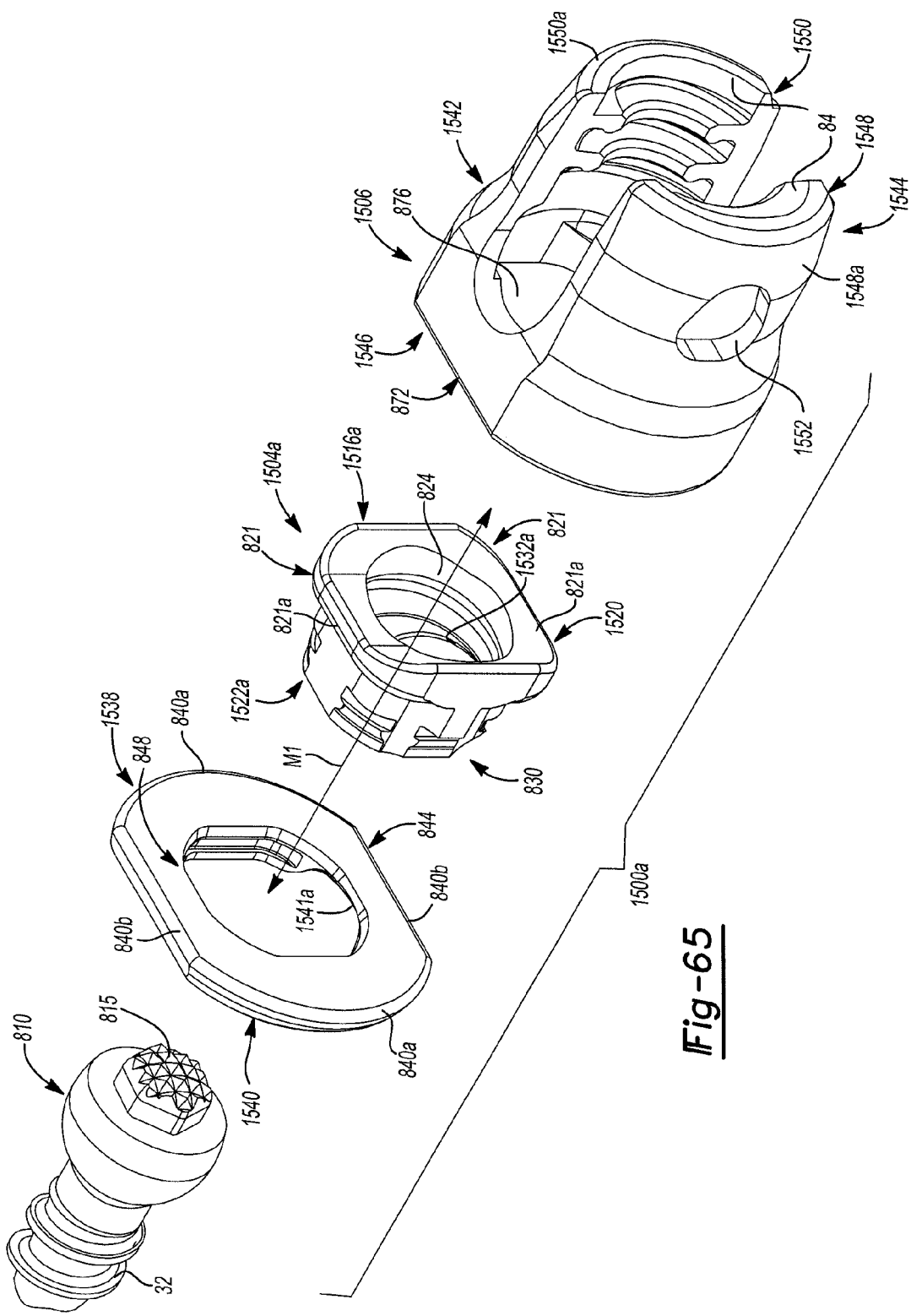

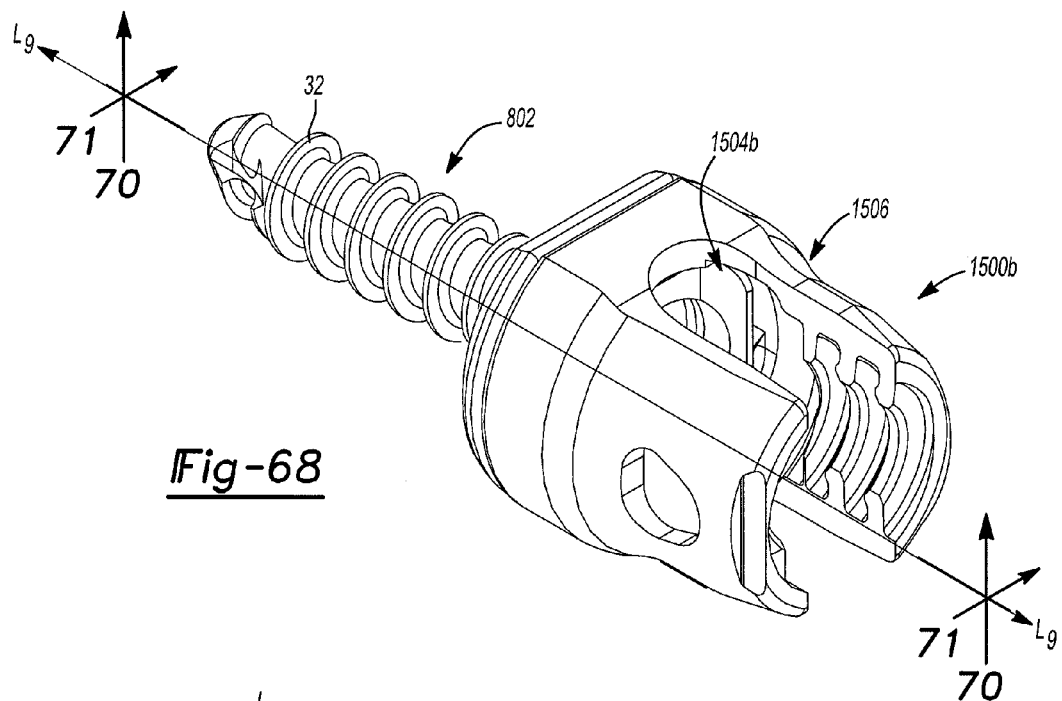
Fig-68
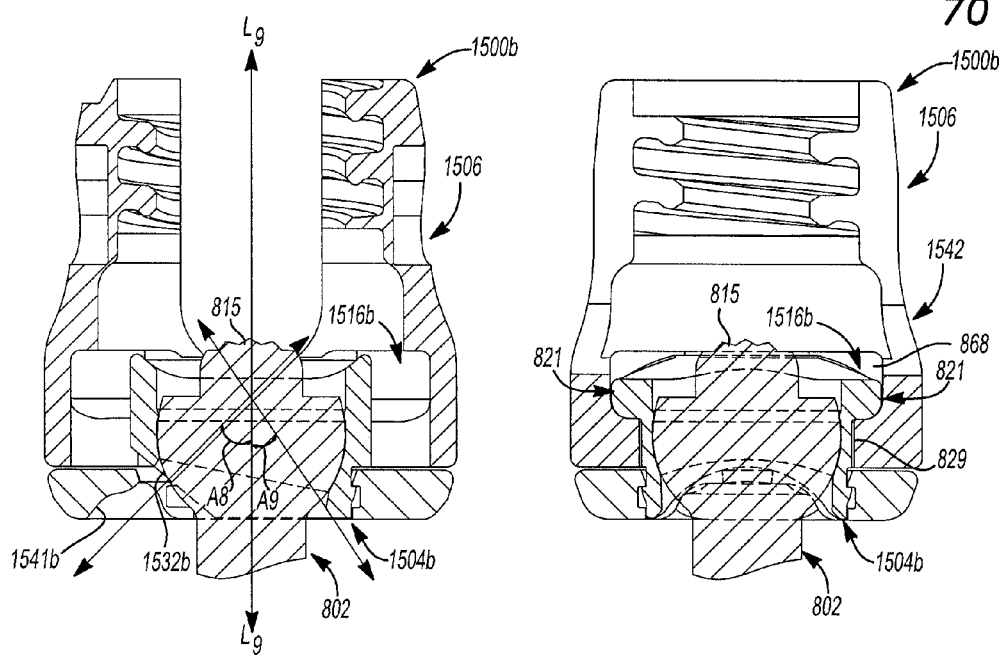
Fig-70
Fig-71

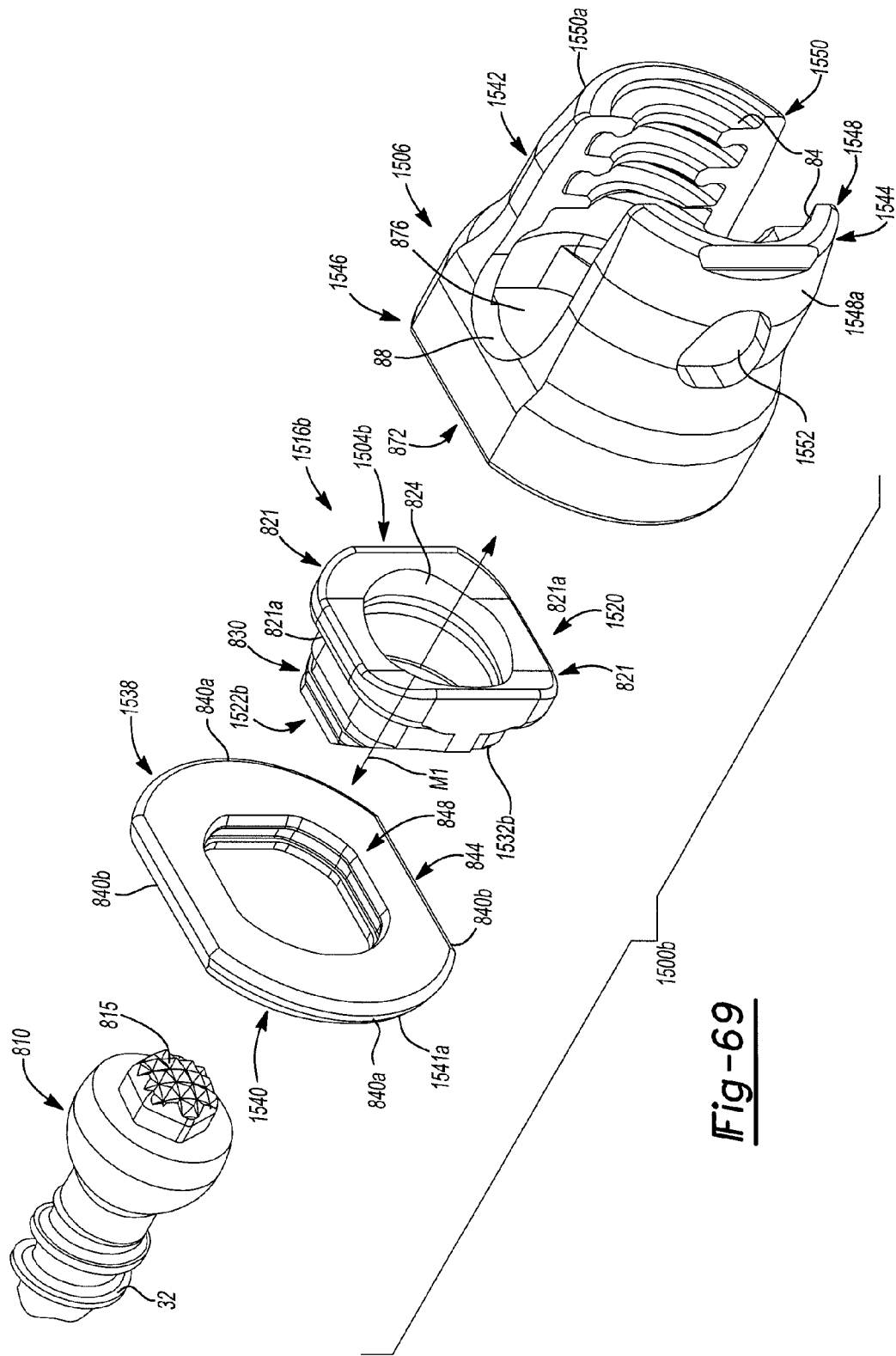

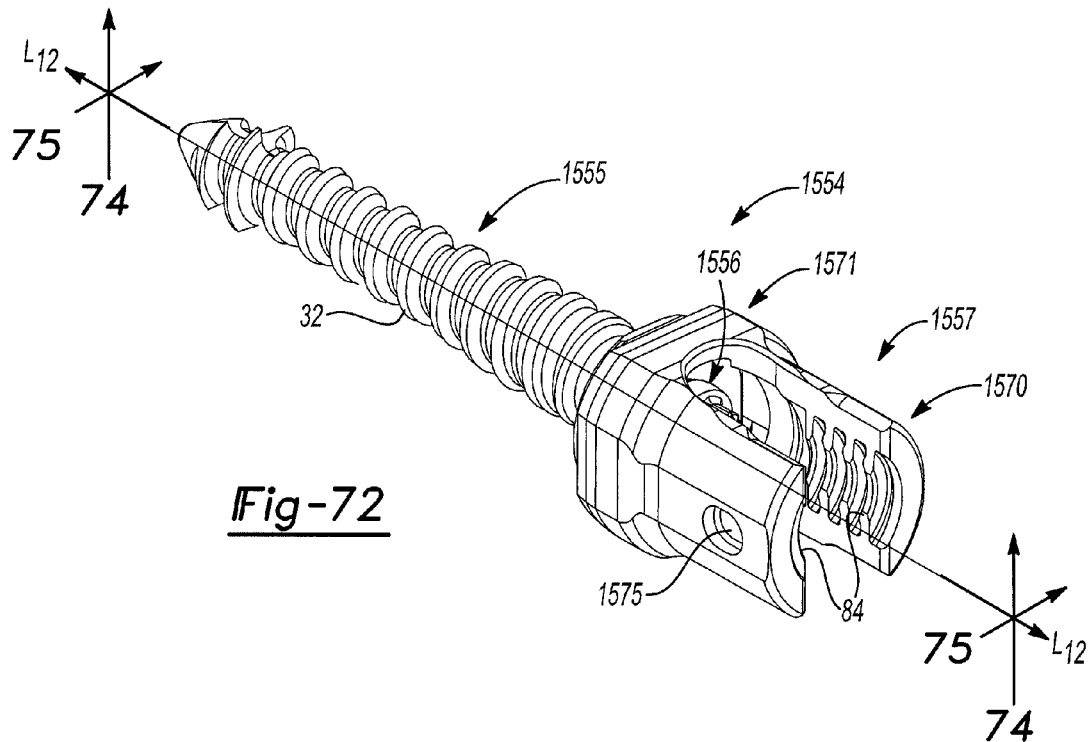
Fig-72
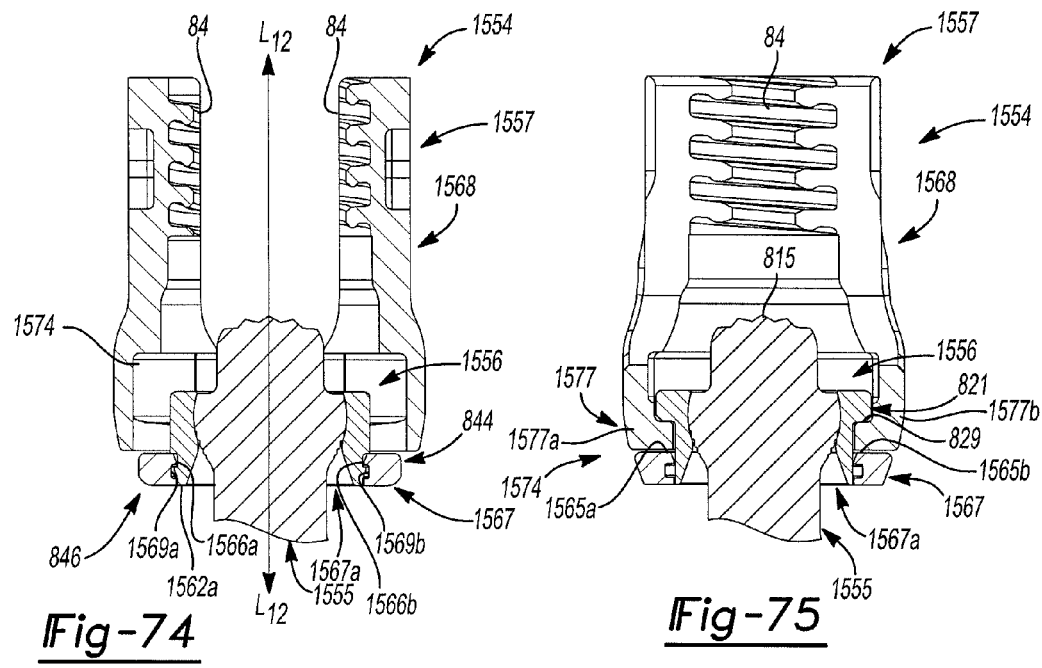
Fig-74
Fig-75

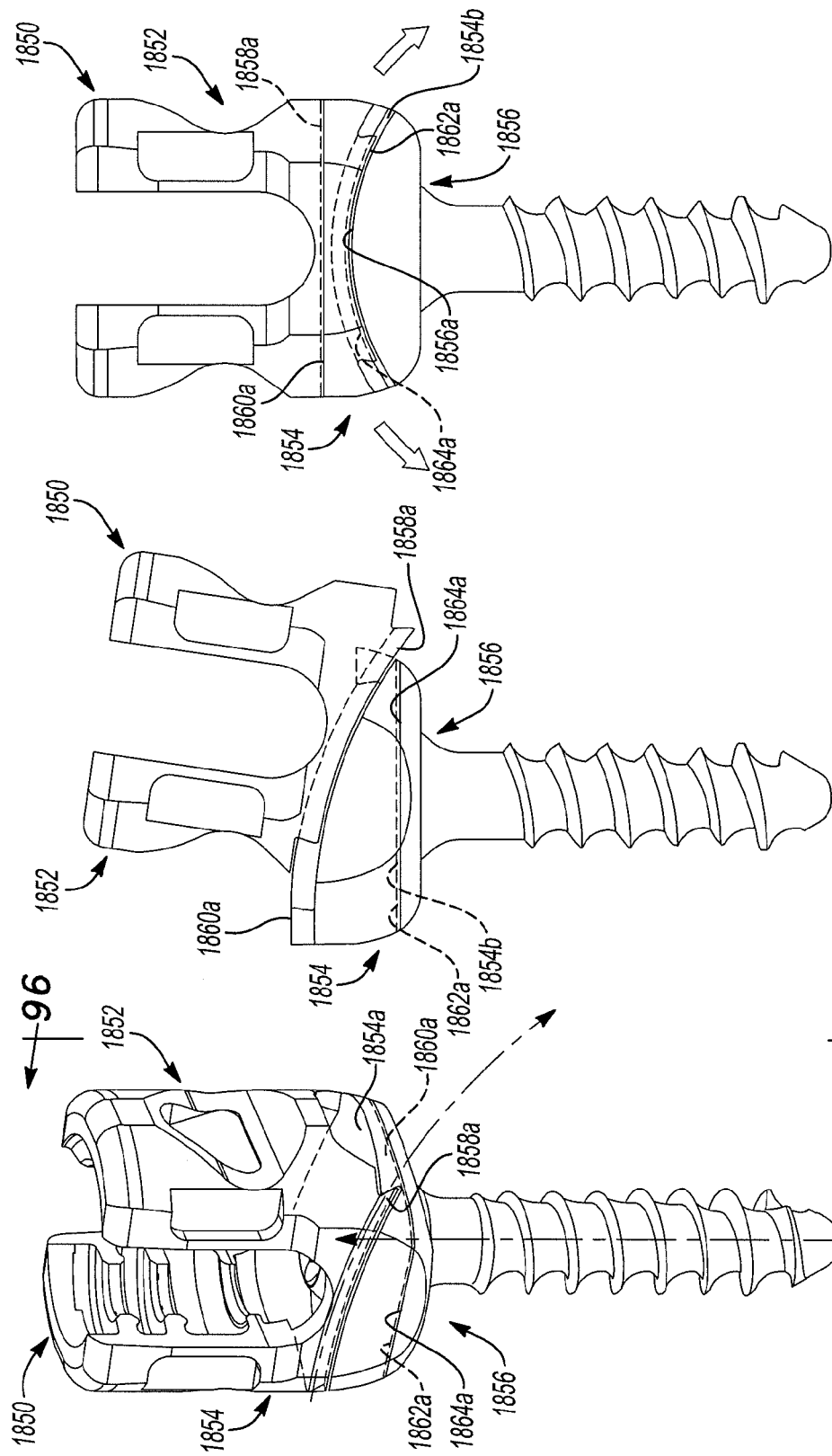

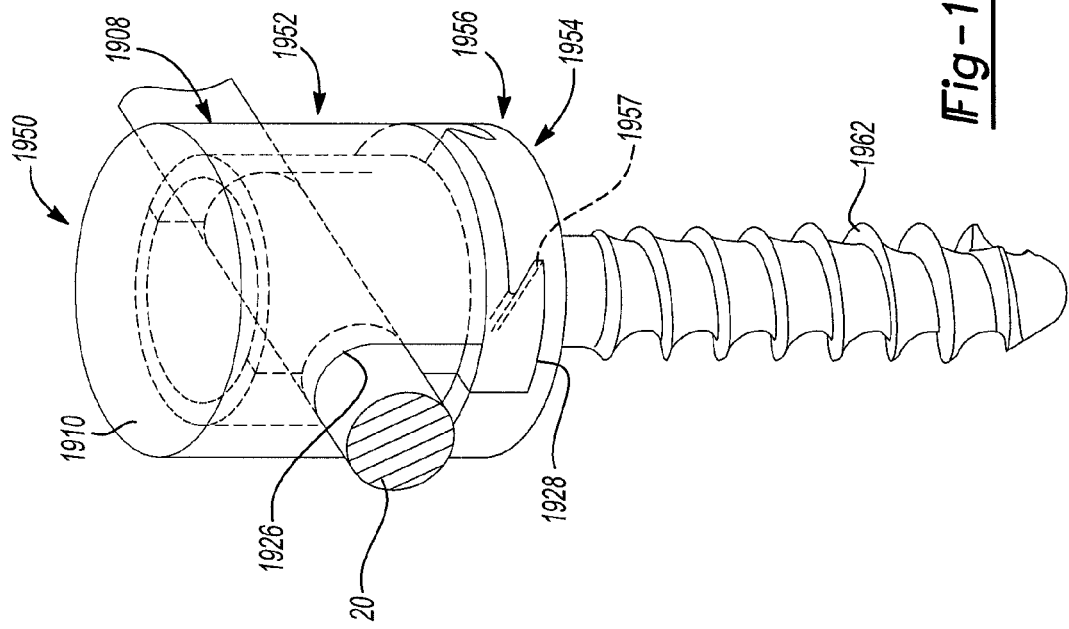
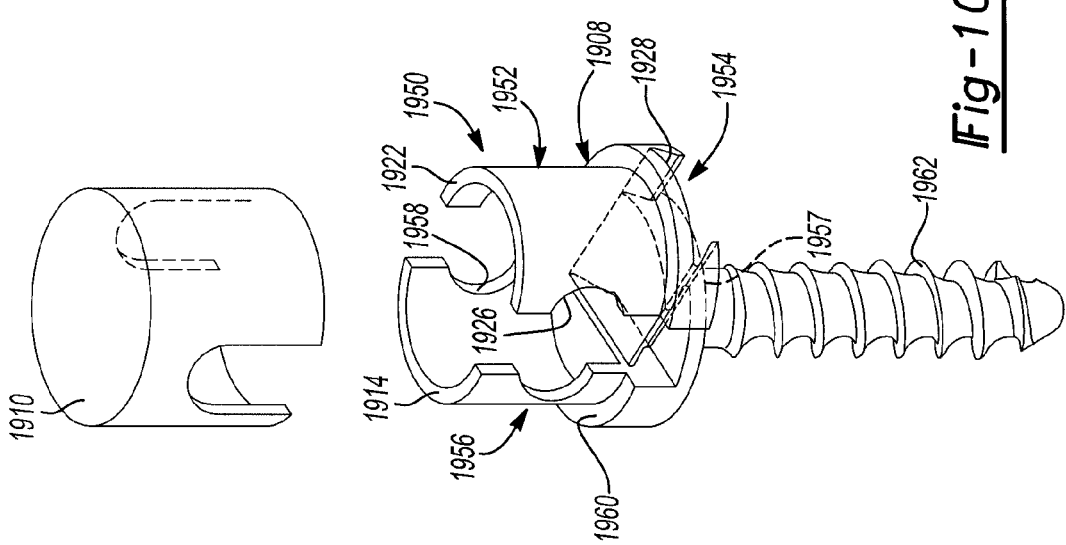

MULTIPLANAR BONE ANCHOR SYSTEM

CROSS-REFERENCE TO RELATED APPLICATIONS

This application is a continuation-in-part of U.S. Pat. No. 8,449,578 issued May 28, 2013. The disclosure of the above application is incorporated herein by reference.

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic prosthesis, such as orthopedic nails, screws, implants, etc., to restore function to the damaged tissue.

Generally, in order to stabilize various boney tissue relative to one another, such as vertebrae of the spine, one or more implants can be coupled to each of the vertebrae and interconnected via a suitable device. In one example, implants or anchors can be coupled to each of the vertebrae, and a connecting device, such as a rod, can be coupled to each of the anchors to stabilize or fix the vertebrae relative to each other. In certain instances, it may be desirable to provide an anchor that can move relative to the connecting device. The present teachings can provide an anchor for use in repairing damaged tissue, such as a bone anchor that can be movable in multiple planes for use in a fixation procedure.

SUMMARY

Provided is a multiplanar bone anchor system for a fixation procedure. The system can include a bone fastener. The bone fastener can include a head and a second end adapted to engage an anatomy. The bone fastener can extend along a longitudinal axis. The system can also include a coupling arrangement coupled to the head of the bone fastener so that the bone fastener is rotatable about the longitudinal axis to define a first plane of motion. The system can further include a saddle, which can be coupled to the coupling arrangement. The saddle can be movable relative to at least one of the bone fastener and the coupling arrangement to define a second plane of motion.

Further provided is a multiplanar bone anchor system for a fixation procedure. The system can include a bone fastener. The bone fastener can include a head and a second end adapted to engage an anatomy. The bone fastener can extend along a longitudinal axis. The system can also include a coupling arrangement, which can be coupled to the head of the bone fastener. The system can include a saddle. The saddle can include a first portion and a second portion. The first portion can be movable relative to the second portion along a first axis. The first axis can be transverse to the longitudinal axis of the bone fastener. The second portion can be coupled to the coupling arrangement such that the bone fastener can pivot relative to the saddle about the head of the bone fastener.

Also provided is a multiplanar bone anchor system for a fixation procedure. The system can include a bone fastener. The bone fastener can include a head and a second end adapted to engage an anatomy. The bone fastener can define a longitudinal axis. The system can also include a ring coupled about the head of the bone fastener. The ring can include at least one wing. The system can include a lock ring, which can have a distal end coupled to the head of the bone fastener. The system can further include a saddle. The saddle can include a first portion and a second portion. The first portion of the saddle can be coupled to the second portion of the saddle so as to be movable relative to the second portion. The second portion of the saddle can be coupled about the head of the bone fastener, the ring and at least a portion of the lock ring. The at least one wing of the ring can cooperate with the lock ring and the second portion of the saddle to enable the bone fastener to pivot about the head of the bone fastener. The at least one wing can also cooperate with the second portion to enable the bone fastener to rotate about the longitudinal axis.

According to various aspects, also provided is a bone anchor. The anchor can include a bone fastener having a head including a first bearing surface. The bone fastener can extend along a longitudinal axis. The anchor can include a connecting arm defining a first bore having a second bearing surface that cooperates with the first bearing surface of the bone fastener to enable the bone fastener to move relative to the connecting arm. The connecting arm can include a first preferred angle slot that defines a preferred angle for the bone fastener to articulate relative to the longitudinal axis. The anchor can include a saddle having a first member and a second member that cooperate to define a second bore that extends along the longitudinal axis. The connecting arm can be received within the second bore such that the first member is movable relative to the second member and the connecting arm in a direction transverse to the longitudinal axis.

Further provided is a bone anchor. The anchor can include a bone fastener having a head including a first bearing surface. The anchor can also include a connecting arm having a first portion, a second portion and a first bore having a second bearing surface. The first portion can include at least one friction surface and the second portion can define a first preferred angle slot in communication with the first bore. The head of the bone fastener can be received within the first bore such that the first bearing surface of the head of the bone fastener cooperates with the second bearing surface of the first bore to enable the bone fastener to move relative to the connecting arm. The anchor can include a saddle having a first member and a second member that cooperate to define a second bore that extends along a longitudinal axis. The connecting arm can be received within the second bore such that the first member is movable relative to the second member over the at least one friction surface.

Additionally, provided is a bone anchor. The anchor can include a bone fastener having a head including a hemispherical bearing surface. The anchor can also include a connecting arm including a first portion, a second portion and defining a first bore having a bearing surface that cooperates with the hemispherical bearing surface of the bone fastener to enable the bone fastener to move relative to the connecting arm. The first portion can have opposed curved features that each including a straight portion. The second portion can include a first preferred angle slot. The anchor can include a saddle having a first member and a second member that cooperate to define a second bore that extends along the longitudinal axis. The first member can be coupled to the first portion of the connecting arm such that the first member moves relative to the connecting arm along the straight portions. The second member can be coupled to the second portion of the connecting arm and can define a second preferred angle slot that cooperates with the first preferred angle slot to define a preferred angle for the bone fastener to articulate relative to the longitudinal axis.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 5 is a perspective view of an exemplary portion of the multiplanar bone anchor system of FIG. 4, which illustrates a first plane of motion;

FIG. 6 is a schematic perspective view of a second exemplary portion of the multiplanar bone anchor system of FIG. 2 moved about one of various planes of motion;

FIG. 7 is a second schematic perspective view of the second exemplary portion of the multiplanar bone anchor system of FIG. 2 moved about one of various planes of motion;

FIG. 27 is a schematic exploded view of another exemplary multiplanar bone anchor system for use with a connecting device in a fixation procedure according to the various teachings;

FIG. 28 is a schematic perspective illustration of an exemplary assembly of a bone fastener and a multiplanar connecting system for use with a multiplanar bone anchor system according to the present teachings;

FIG. 29 is an exploded view of the assembly of FIG. 28;

FIG. 30 is a schematic, cross-sectional illustration of the assembly of FIG. 28, taken along line 30-30 of FIG. 28;

FIG. 34 is a perspective view of an exemplary connecting arm for use with the multiplanar bone anchor system of FIG. 31;

FIG. 35 is a side view of the exemplary connecting arm of FIG. 34;

FIG. 36 is a cross-sectional illustration of the multiplanar bone anchor system of FIG. 31, taken along line 36-36 of FIG. 31;

FIG. 37 is a perspective view of another exemplary connecting arm for use with an exemplary multiplanar bone anchor system similar to the multiplanar bone anchor system of FIG. 31;

FIG. 38 is a side view of the exemplary connecting arm of FIG. 37;

FIG. 39 is a schematic cross-sectional illustration of an exemplary multiplanar bone anchor system incorporating the connecting arm of FIG. 37;

FIG. 50 is a perspective view of another exemplary multiplanar bone anchor system for use with a connecting device in a fixation procedure according to the present teachings;

FIG. 52 is a cross-sectional illustration of the multiplanar bone anchor system of FIG. 50, taken along line 52-52 of FIG. 50;

FIG. 53 is a cross-sectional illustration of the multiplanar bone anchor system of FIG. 50, taken along line 53-53 of FIG. 50;

FIG. 54 is a perspective view of another exemplary multiplanar bone anchor system for use with a connecting device in a fixation procedure according to the present teachings;

FIG. 56 is a cross-sectional illustration of the multiplanar bone anchor system of FIG. 54, taken along line 56-56 of FIG. 54;

FIG. 57 is a cross-sectional illustration of the multiplanar bone anchor system of FIG. 54, taken along line 57-57 of FIG. 54;

FIG. 58 is a perspective view of another exemplary multiplanar bone anchor system for use with a connecting device in a fixation procedure according to the present teachings;

FIG. 59 is an exploded view of the multiplanar bone anchor system of FIG. 58;

FIG. 60 is a cross-sectional illustration of the multiplanar bone anchor system of FIG. 58, taken along line 60-60 of FIG. 58;

FIG. 61 is a cross-sectional illustration of the multiplanar bone anchor system of FIG. 58, taken along line 61-61 of FIG. 58;

FIG. 64 is a perspective view of another exemplary multiplanar bone anchor system for use with a connecting device in a fixation procedure according to the present teachings;

FIG. 65 is an exploded view of the multiplanar bone anchor system of FIG. 64;

FIG. 66 is a cross-sectional illustration of the multiplanar bone anchor system of FIG. 64, taken along line 66-66 of FIG. 64;

FIG. 67 is a cross-sectional illustration of the multiplanar bone anchor system of FIG. 64, taken along line 67-67 of FIG. 64;

FIG. 68 is a perspective view of an exemplary multiplanar bone anchor system for use with a connecting device in a fixation procedure according to the present teachings;

FIG. 69 is an exploded view of the multiplanar bone anchor system of FIG. 68;

FIG. 70 is a cross-sectional illustration of the multiplanar bone anchor system of FIG. 68, taken along line 70-70 of FIG. 68;

FIG. 71 is a cross-sectional illustration of the multiplanar bone anchor system of FIG. 68, taken along line 71-71 of FIG. 68;

FIG. 72 is a perspective view of an exemplary multiplanar bone anchor system for use with a connecting device in a fixation procedure according to the present teachings;

FIG. 74 is a cross-sectional illustration of the multiplanar bone anchor system of FIG. 72, taken along line 74-74 of FIG. 72;

FIG. 75 is a cross-sectional illustration of the multiplanar bone anchor system of FIG. 72, taken along line 75-75 of FIG. 72;

FIG. 95 is a schematic illustration of another multiplanar bone anchor system for use with a connecting device in a fixation procedure according to the present teachings in a first position;

FIG. 96 is a schematic, cross-sectional illustration of the multiplanar bone anchor system of FIG. 95 in a second position, taken along line 96-96 of FIG. 95;

FIG. 97 is a schematic, side illustration of the multiplanar bone anchor system of FIG. 95;

FIG. 100 is a partially exploded schematic illustration of another multiplanar bone anchor system for use with a connecting device in a fixation procedure according to the present teachings;

FIG. 101 is a perspective schematic illustration of the multiplanar bone anchor system of FIG. 100;

DESCRIPTION OF VARIOUS ASPECTS

Figure 1:
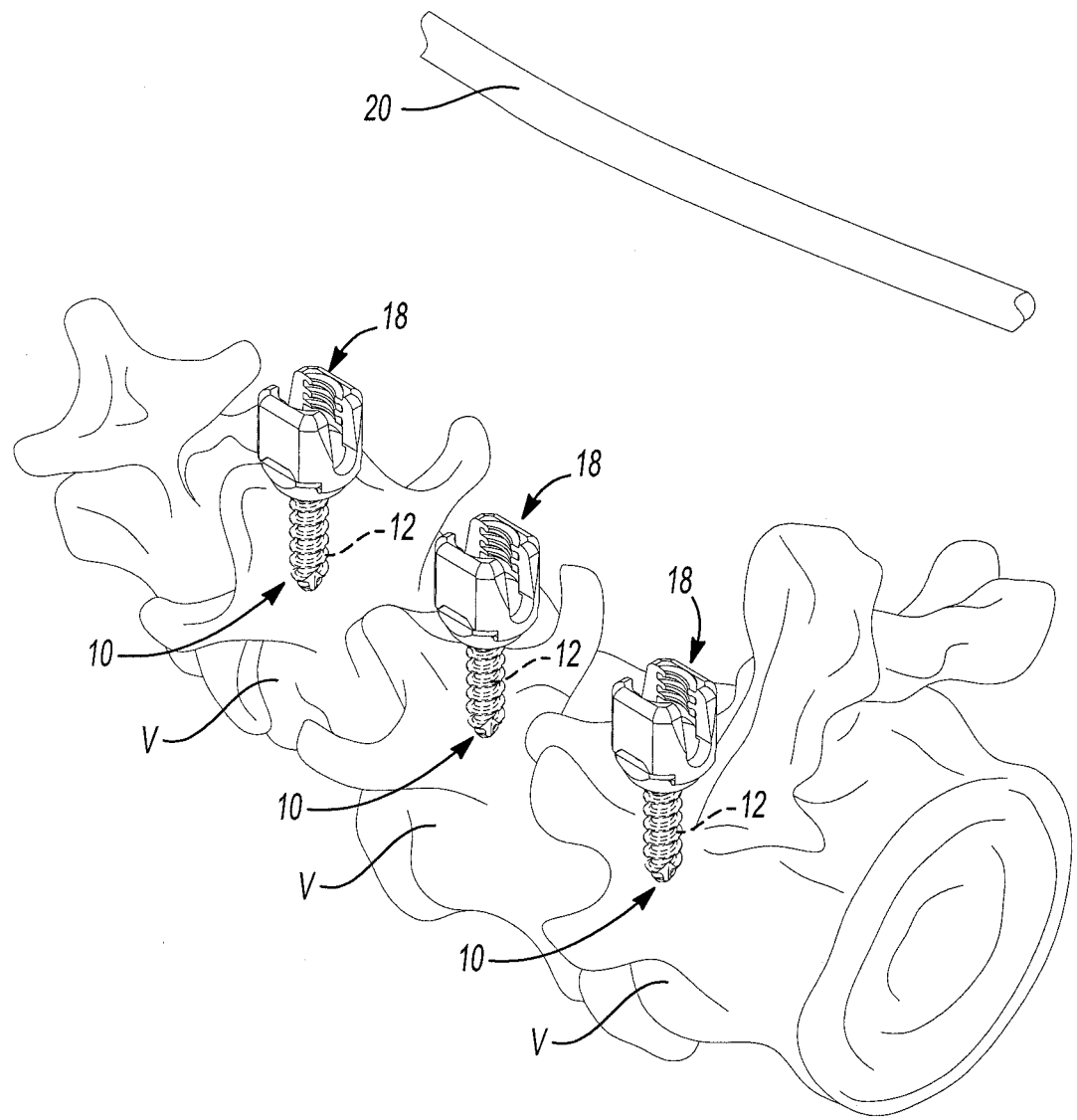
FIG. 1 is a schematic environmental illustration of an exemplary multiplanar bone anchor system for use with a connecting device in a fixation procedure according to the present teachings.

The following description is merely exemplary in nature and is not intended to limit the present teachings, application, or uses. It should be understood that throughout the drawings, corresponding reference numerals indicate like or corresponding parts and features. Although the following description is related generally to a system for use in an anatomy to repair damaged tissue, such as in the case of spinal fusion, static spinal stabilization or dynamic spinal stabilization, it will be understood that the system as described and claimed herein can be used in any appropriate surgical procedure, such as in a minimally invasive orthopedic alignment or fixation procedure. Therefore, it will be understood that the following discussions are not intended to limit the scope of the present teachings and claims herein.

With reference to FIGS. 1-8, a multiplanar bone anchor system 10 is shown. The multiplanar bone anchor system 10 may be particularly adapted for spinal fixation procedures. Various aspects of the present teachings, however, may have application for other procedures. In certain applications, the multiplanar bone anchor system 10 can be coupled to one or more vertebrae or vertebral bodies V (FIG. 1) in a posterior region of the spine. The multiplanar bone anchor system 10 can include a bone engaging member or bone fastener 12, a locking member or lock ring 14 (FIG. 3), a multiplanar coupling arrangement or system 16 (FIG. 3) and a tulip head or saddle 18.

As will be discussed in greater detail herein, the multiplanar coupling system 16 can enable the saddle 18 to move relative to the bone fastener 12 in multiple planes. Generally, the saddle 18 can be configured to receive a connecting device or rod 20, which can be used to interconnect multiple bone anchor systems 10 in an exemplary spinal fixation procedure (FIG. 1). By using the multiplanar coupling system 16, the saddle 18 can be moved relative to the bone fastener 12 in one or more planes to facilitate the connection of the connecting rod 20 to multiple bone anchor systems 10. In this regard, the vertebral bodies V of the patient may be orientated in such a manner that each bone fastener 12, when coupled to a respective vertebral body V, may be slightly offset from one another. By allowing the saddle 18 to move in multiple planes relative to the bone fastener 12, the surgeon can move the saddles 18 into alignment without regard to the placement of the bone fasteners 12. It should be noted, however, that although the multiplanar bone anchor system 10 is generally illustrated and described herein a single assembly for use with a single connecting rod 20, any combination of bone anchor systems 10 and connecting rods 20 can be employed during a surgical procedure.

For example, in a single level spinal fixation procedure, two bone anchor systems 10 can receive a single connecting rod 20. A multiple level spinal fixation procedure, however, will generally require additional bone anchor systems 10. In addition, the multiplanar bone anchor systems 10 need not be coupled to adjacent vertebral bodies V, but rather, the multiplanar bone anchor systems 10 can be positioned so as to skip adjacent vertebral bodies V, if desired.

Figure 2:
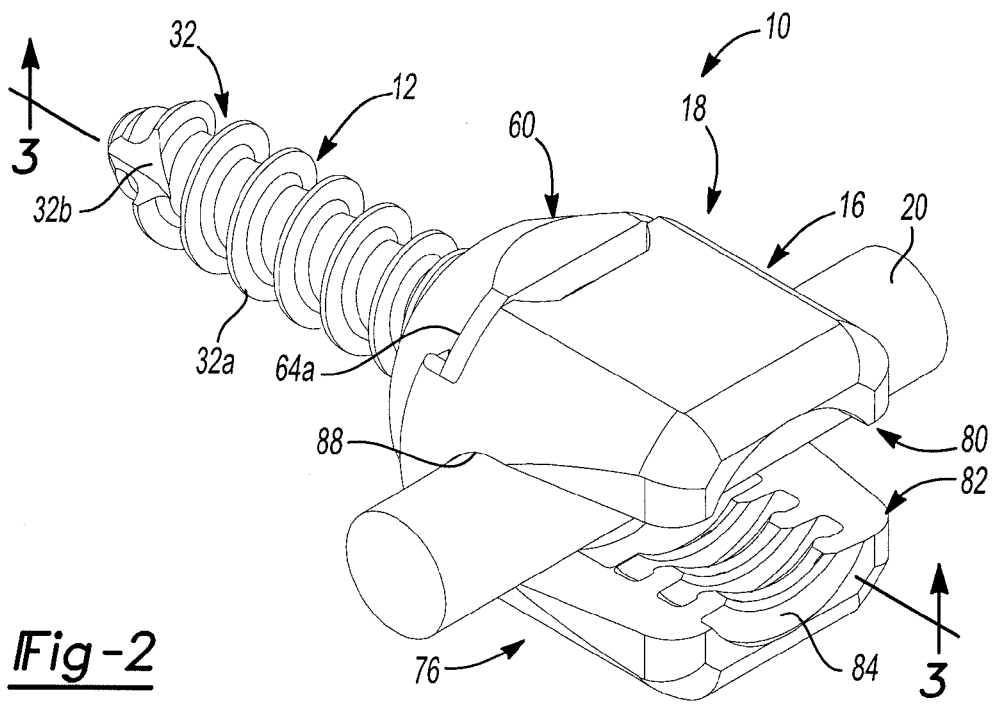
FIG. 2 is a schematic perspective illustration of the multiplanar bone anchor system of FIG. 1.
Figure 3:
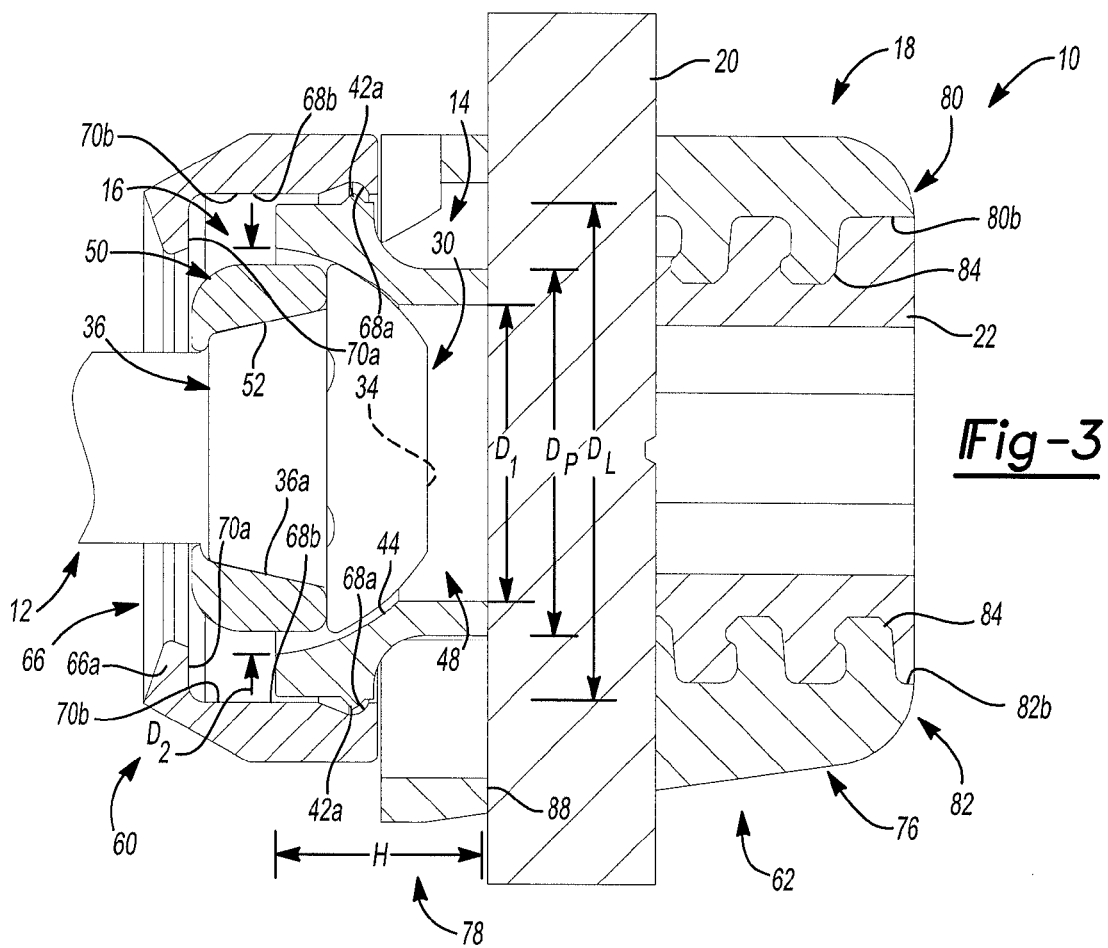
FIG. 3 is a cross-sectional view of the multiplanar bone anchor system of FIG. 2, taken along line 3-3 of FIG. 2.
Figure 4:
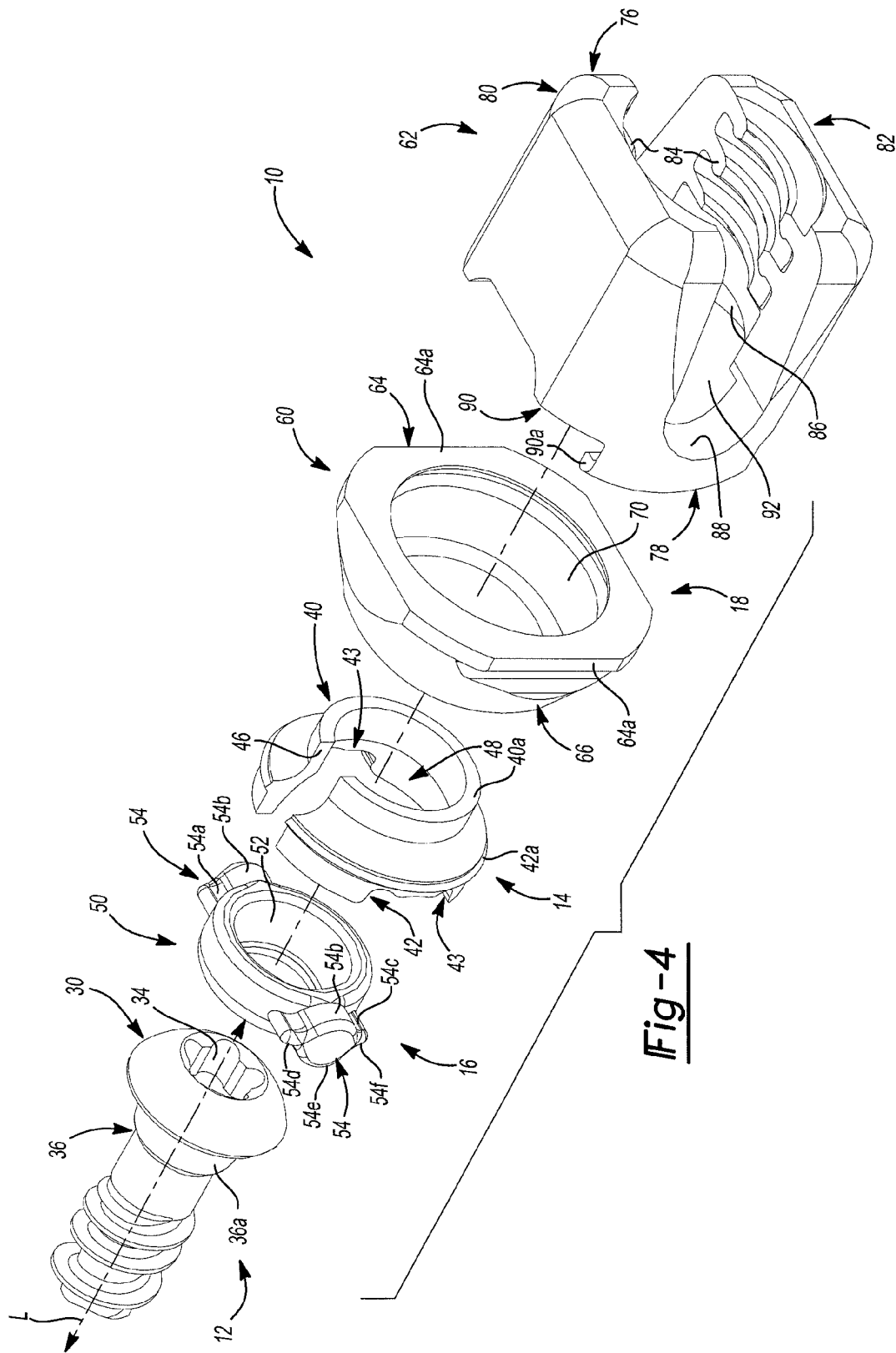
FIG. 4 is an exploded view of the multiplanar bone anchor system of FIG. 1.

With reference to FIGS. 2-4, the bone fastener 12 can be configured to engage the anatomy to couple the multiplanar bone anchor system 10 to the anatomy. The bone fastener 12 can be composed of any suitable biocompatible material, such as titanium, stainless steel, biocompatible polymers, etc. The bone fastener 12 can include a proximal end or head 30 (FIGS. 3 and 4) and a distal end or shank 32 (FIG. 2). With reference to FIGS. 3 and 4, the head 30 can be generally arcuate, and can include a driver connection feature 34 and a channel 36. The driver connection feature 34 can comprise any mating connection interface for a driver, such as a pentalobe, hexalobe, hexagon, torx, Philips, cruciate, straight, etc. Thus, the driver connection feature 34 can enable the application of a torque to drive the bone fastener 12 into the anatomy.

Briefly, it should be noted that particular tools for use with the multiplanar bone anchor system 10 are beyond the scope of the present teachings and need not be described herein. In a conventional manner insofar as the present teachings are concerned, various tools can be used to connect the multiplanar bone anchor system 10 to a respective vertebral body V. Exemplary tools can include those employed in the Polaris™ 5.5 Spinal System, commercially available from Biomet, Inc. of Warsaw, Ind., or the tools disclosed in commonly owned U.S. Patent Publication No. 2008/0077138, filed on Apr. 20, 2007 and incorporated by reference herein.

With continued reference to FIGS. 3 and 4, the channel 36 can be defined about a circumference of the head 30. The channel 36 can receive a portion of the multiplanar coupling system 16 to enable the saddle 18 to rotate about the longitudinal axis L of the bone fastener 12. Thus, the channel 36 can define a first bearing surface 36a. It should be noted that although the bone fastener 12 is illustrated and described herein as including the channel 36, the channel 36 need not be necessary to enable the saddle 18 to rotate about the longitudinal axis L of the bone fastener 12.

With reference to FIG. 2, the shank 32 of the bone fastener 12 can include a plurality of threads 32a and at least one cutting flute 32b. The at least one cutting flute 32b can cooperate with the threads 32a to cut into the anatomy, and thus, the bone fastener 12 does not require a pre-tapped hole. It should be noted that although the bone fastener 12 is illustrated and described herein as including at least one cutting flute 32b, the bone fastener 12 need not include any cutting flutes (requiring a pre-tapped hole), or could include multiple cutting flutes, if desired.

With reference to FIGS. 3 and 4, the lock ring 14 can be positioned about the head 30 of the bone fastener 12. As will be discussed herein, the lock ring 14 can lock at least one of the bone fastener 12 and the multiplanar coupling system 16 relative to the saddle 18 via a force applied by the connecting rod 20. The lock ring 14 can be generally cylindrical, and can have a height H. The height H can be sized to extend above a receiver surface 88 of the saddle 18 so that coupling the connecting rod 20 to the saddle 18 can compress the lock ring 14 onto the head 30 of the bone fastener 12. With reference to FIG. 4, the lock ring 14 can include a proximal end 40, a distal end 42, a bearing surface 44, a slot 46 and a bore 48.

The proximal end 40 can include an annular projection 40a. With reference to FIG. 3, the projection 40a can have a diameter Dp, which is larger than a diameter DI of the lock ring 14. The larger diameter Dp of the projection 40a can be sized to enable the lock ring 14 to move or rotate about the head 30 of the bone fastener 12. With reference to FIGS. 3-5, the distal end 42 can include a ring or flange 42a and at least one cutout 43. The flange 42a can be formed about an exterior surface of the lock ring 14, and can retain the lock ring 14 within the saddle 18, as will be discussed in detail herein. The at least one cutout 43 can be formed along a portion of a circumference of the lock ring 14, and can be sized to cooperate with the multiplanar coupling system 16.

In one example, the lock ring 14 can include two cutouts 43, which can be positioned on opposite sides of the lock ring 14 (FIG. 4). In this example, as best illustrated in FIG. 5, the cutouts 43 can include a first curved recess 43a, a second curved recess 43b and a third curved recess 43c which can be congruent. The cutouts 43 can be generally symmetrical about a longitudinal axis of the lock ring 14. The first curved recess 43a and the third curved recess 43c can be formed from the distal end 42 to the flange 42a. The second curved recess 43b can be formed from the distal end 42 to a location adjacent to the flange 42a. In addition, the second curved recess 43b can have a radius which can be greater than a radius associated with each of the first curved recess 43a and the third curved recess 43c.

With reference to FIGS. 3 and 4, the bearing surface 44 can be formed on an interior surface of the lock ring 14. In one example, the bearing surface 44 can be formed along an interior surface of the projection 40a at the distal end 42 of the lock ring 14. The bearing surface 44 can comprise a generally concave region, which can extend from the circumference of the projection 40a. The bearing surface 44 can contact a portion of the head 30 to enable the lock ring 14 to move or articulate relative to the bone fastener 12. The bearing surface 44 can also enable the lock ring 14 to move or articulate relative to the multiplanar coupling system 16, as will be discussed herein.

With reference to FIG. 4, the lock ring 14 can also include a slot 46. The slot 46 can extend through the projection 40a, the proximal side 40 and the distal end 42. The slot 46 can enable the lock ring 14 to be coupled about the head 30 of the bone fastener 12. Note, that the slot 46 is optional, and the lock ring 14 could be continuous about the circumference of the lock ring 14.

With reference to FIG. 3, the bore 48 can be disposed about a central axis of the lock ring 14. The bore 48 can extend through the projection 40a, the proximal end 40 and the distal end 42. A first diameter D1 of the bore 48 at the projection 40a can be substantially smaller than a second diameter D2 of the bore 48 at the distal end 42 of the lock ring 14. The bearing surface 44 can be formed about the bore 48, and can transition the bore 48 from the first diameter D1 to the second diameter D2. The bore 48 can enable a driver to interface with the driver connection feature 34 formed on the head 30 of the bone fastener 12.

In one example, the multiplanar coupling system 16 can include a ring 50. The ring 50 can be disposed about a head 30 of the bone fastener 12 to enable the bone fastener 12 to move or articulate relative to the saddle 18, as shown in FIG. 3. The ring 50 can be annular, and can be sized to fit within the saddle 18 to enable the bone fastener 12 to articulate relative to the saddle 18, as shown in FIGS. 6 and 7. With reference to FIG. 4, the ring 50 can include a bore 52 and at least one wing 54. The bore 52 can be sized to enable the ring 50 to be coupled to the channel 36 of the bone fastener 12, but can also be sized so as to prevent the ring 50 from migrating above the head 30 of the bone fastener 12, as best shown in FIG. 3.

With reference to FIGS. 4 and 5, at least one wing 54 can extend outwardly from a circumference of the ring 50. In this example, the ring 50 can include two wings 54. The wings 54 can extend outwardly from opposite sides of the ring 50. The wings 54 can cooperate with the saddle 18 to enable the bone fastener 12 to move or articulate relative to the saddle 18 (FIG. 7). The wings 54 can include a first arcuate surface 54a, a second arcuate surface 54b, a third arcuate surface 54c, a fourth arcuate surface 54d, a fifth arcuate surface 54e and a sixth arcuate surface 54f. It should be noted that the shape of the wings 54 described and illustrated herein is merely exemplary, as the wings 54 could have any shape that enables the bone fastener 12 to rotate relative to the saddle 18, such as elliptical, circular, rounded square, rounded rectangular, etc.

The first arcuate surface 54a can be opposite the fourth arcuate surface 54d, the second arcuate surface 54b can be opposite the fifth arcuate surface 54e and the third arcuate surface 54c can be opposite the sixth arcuate surface 54f. Generally, the second arcuate surface 54b and the fifth arcuate surface 54e can be positioned between the first arcuate surface 54a, fourth arcuate surface 54d, third arcuate surface 54c and sixth arcuate surface 54f. The first arcuate surface 54a, second arcuate surface 54b and the third arcuate surface 54c can each contact one of the first curved recess 43a, the second curved recess 43b, third curved recess 43c, respectively, which can enable the lock ring 14 to move or articulate relative to the ring 50, as best shown in FIG. 5. The fourth arcuate surface 54d, fifth arcuate surface 54e and sixth arcuate surface 54f can cooperate with the saddle 18 to enable the bone fastener 12 to move or articulate relative to the saddle 18, as shown in FIGS. 6 and 7.

Figure 8:
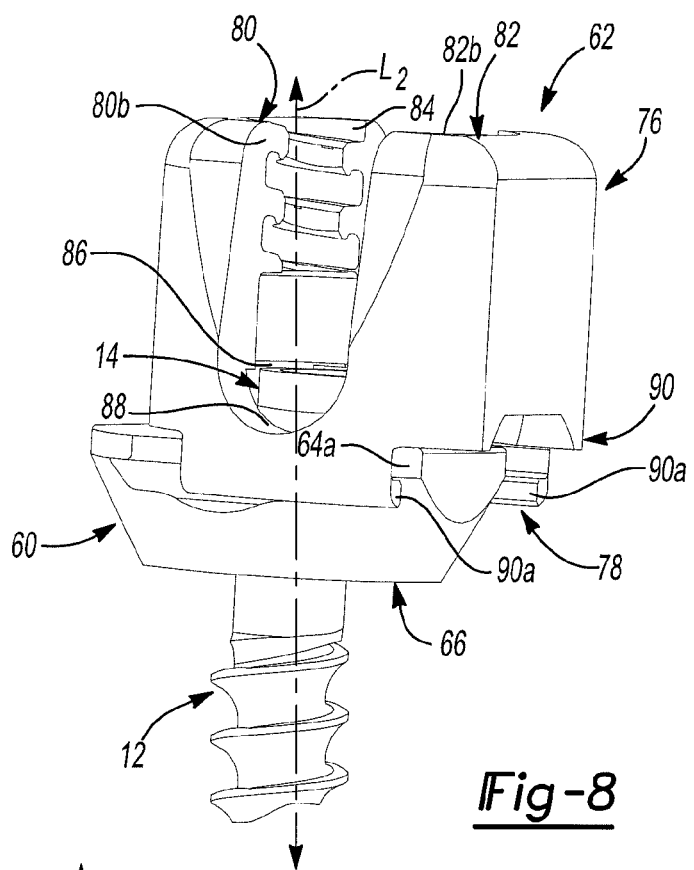
FIG. 8 is a schematic perspective view of the multiplanar bone anchor system of FIG. 2 in which a saddle associated with the multiplanar bone anchor system is moved about one of various planes of motion.

With reference to FIGS. 4 and 6-8, the saddle 18 can include a first portion or bottom portion 60 and a second portion or top portion 62. The top portion 62 can move or translate relative to the bottom portion 60 (FIG. 8). With reference to FIGS. 4 and 6-8, the bottom portion 60 can include a first or proximal end 64, a second or distal end 66, a bore 68 and a bearing surface 70. The proximal end 64 can be generally rectangular, and can include rounded corners. The proximal end 64 can be coupled to the top portion 62 (FIG. 8). The proximal end 64 can define at least one rail 64a. Generally, the top portion 62 can move or translate along the at least one rail 64a (FIG. 8). In one example, the proximal end 64 can define two rails 64a, which can be positioned on opposite sides of the bottom portion 60. As will be discussed, the diameter Dp of the lock ring 14 can define or limit the translation of the top portion 62 relative to the bottom portion 60. The proximal end 64 can taper to the distal end 66.

The distal end 66 can be adjacent to the shank 32 of the bone fastener 12, when the saddle 18 is coupled to the bone fastener 12. As best shown in FIG. 3, the distal end 66 can define a lip or stop 66a on an interior surface. In this example, the stop 66a can extend into the bore 68 of the bottom portion 60. The stop 66a can extend about a circumference of the bore 68, and can limit the motion or articulation of the bone fastener 12 relative to the saddle 18.

The bore 68 can be defined through the bottom portion 60. The bore 68 can be sized to receive the ring 50, the lock ring 14 and the bone fastener 12 therein. With reference to FIG. 3, the bore 68 can include bearing surface 68a and a sidewall 68b. The bearing surface 68a can be configured to receive the flange 42a of the lock ring 14, to couple the lock ring 14 to the saddle 18. In other words, the flange 42a of the lock ring 14 can cooperate with the bearing surface 68a of the bottom portion 60 to prevent the lock ring 14 from migrating out of the saddle 18. The sidewall 68b of the bore 68 can comprise a portion of the bearing surface 70.

The bearing surface 70 can be defined about a circumference of the bore 68. In one example, the bearing surface 70 can be formed on a portion 70a of the stop 66a, and a portion 70b of the sidewall 68b of the bore 68. The bearing surface 70 can generally be shaped so as to cooperate with the ring 50 to enable the ring 50 to move or articulate within the bottom portion 60 of the saddle 18, as best shown in FIG. 7. The relative movement between the ring 50 and the bottom portion 60 can allow the bone fastener 12 to pivot or angulate about a central axis or longitudinal axis of the bone fastener 12.

With reference to FIGS. 3, 4 and 8, the top portion 62 of the saddle 18 can be coupled to the rails 64a of the proximal end 64 of the bottom portion 60 so that the top portion 62 can move relative to the bottom portion 60. The top portion 62 can be substantially U-shaped and symmetrical with respect to a longitudinal axis L2 defined by the multiplanar bone anchor system 10 (FIG. 8). The top portion 62 can include a first or proximal end 76 and a second or distal end 78. In one example, the proximal end 76 can include a first arm 80 and a second arm 82. The first arm 80 and second arm 82 can extend upwardly from the distal end 78 to define the U-shape. Each of the first arm 80 and the second arm 82 can include a mating portion 84 and a cavity 86.

The mating portion 84 can be configured to receive a fastening mechanism to couple the connecting rod 20 to the saddle 18. For example, the mating portion 84 can comprise a plurality of threads, which can be formed on an interior surface 80b, 82b of each of the first arm 80 and second arm 82. In this example, the mating portion 84 can engage threads formed on a set screw 22 to couple the connecting rod 20 to the saddle 18 (FIG. 3). It should be noted, however, that the proximal end 76 can have any suitable configuration to couple the connecting rod 20 to the saddle 18, such as keyed portions, teeth, etc.

The cavity 86 can be defined in each interior surface 80b, 82b of the first arm 80 and second arm 82. The cavity 86 can provide clearance for the movement or articulation of the top portion 62 relative to the bottom portion 60 of the saddle 18. In this regard, the cavity 86 can be defined so as to allow the top portion 62 to move over a portion of the lock ring 14, which can provide a range of motion for the top portion 62 relative to the bottom portion 60. Thus, contact between the lock ring 14 and the cavity 86 can act as a stop to limit the movement or translation of the top portion 62 relative to the bottom portion 60, however, other techniques could be used to stop or limit the movement or translation of the top portion 62 relative to the bottom portion 60.

With reference to FIG. 4, the distal end 78 of the top portion 62 can be generally rectangular, and can include a first or a receiver surface 88, a second or bottom surface 90 and a central bore 92. The receiver surface 88 can receive a portion of the connecting rod 20. In one example, the receiver surface 88 can comprise a generally arcuate, concave surface that forms the U-shape of the saddle 18, however, the receiver surface 88 can comprise any desired shape, such as square, etc.

The bottom surface 90 can include at least one or more guides 90a. In this example, the bottom surface 90 can include two guides 90a. The guides 90a can slidably couple the top portion 62 to the bottom portion 60. In this regard, each guide 90a can cooperate with a respective one of the rails 64a to enable the top portion 62 of the saddle 18 to move or translate relative to the bottom portion 60 of the saddle 18 (FIG. 8). Generally, each guide 90a can comprise a C-shape, and each rail 64a can be received within the guide 90a. It should be understood, however, that any suitable shape could be used to enable the top portion 62 to move or translate relative to the bottom portion 60.

The central bore 92 can be defined through the distal end 78 from the receiver surface 88 to the bottom surface 90. Generally, the central bore 92 can be sized to receive the bone fastener 12, and can cooperate with the multiplanar coupling system 16 to allow the bone fastener 12 to move in the desired planes.

With reference to FIGS. 2 and 3, the connecting rod 20 can be received within the receiver surface 88 of the saddle 18. The connecting rod 20 can be coupled to the saddle 18 via a suitable mechanical fastener, such as the set screw 22. An exemplary connecting rod 20 and set screw 22 can be substantially similar to the connecting rod and set screw employed in the Polaris™ 5.5 Spinal System, commercially available from Biomet, Inc. of Warsaw, Ind., or the connecting element disclosed in commonly owned U.S. Patent Publication No. 2008/0077138, filed on Apr. 20, 2007 and previously incorporated by reference herein. As the connecting rod 20 and the set screw 22 can be generally known, the connecting rod 20 and set screw 22 will not be discussed in great detail herein.

Briefly, however, the connecting rod 20 can comprise an elongated solid cylinder. The connecting rod 20 can also include a slight curvature, which can correspond to the natural curvature of the spine. Typically, the connecting rod 20 can be composed of a suitable biocompatible material having sufficient rigidity to fix the vertebral bodies V relative to each other. The set screw 22 can include threads, which can matingly engage the threads formed on the mating portion 84 of the proximal end 76 of the saddle 18.

With reference to FIGS. 4-8, in order to assemble the multiplanar bone anchor system 10, the ring 50 can be positioned about the channel 36 of the bone fastener 12 (FIG. 5). Then, the bottom portion 60 of the saddle 18 can be positioned about the ring 50 (FIGS. 6 and 7). The lock ring 14 can be coupled to the top portion 62. Next, the top portion 62 of the saddle 18 can be coupled to the bottom portion 60 of the saddle 18 (FIG. 8) Then, the lock ring 14 can be coupled to the head 30 of the bone fastener 12.

Once assembled, the ring 50 can cooperate with the bottom portion 60 to enable movement or rotation of the bone fastener 12 about the central or longitudinal axis of the bone fastener 12 (FIGS. 6 and 7). The lock ring 14 can cooperate with the head 30 of the bone fastener 12 to enable the bone fastener 12 to move or articulate relative to the saddle 18, about the head 30 of the bone fastener 12 (FIG. 5). The top portion 62 of the saddle 18 can cooperate with the bottom portion 60 to enable the top portion 62 of the saddle 18 to move or translate relative to the bottom portion 60 of the saddle 18 (FIG. 8). Thus, when assembled, the multiplanar bone anchor system 10 can have at least three degrees of movement or can be movable in at least three planes. By allowing the multiplanar bone anchor system 10 to move in at least three planes, the surgeon can manipulate the multiplanar bone anchor system 10 as necessary to conform to the anatomy of the patient.

With the bone fastener 12 coupled to the saddle 18 via the multiplanar coupling system 16, surgical access can be made through the skin S adjacent to the vertebral bodies V of interest (FIG. 1). The specific surgical access approaches are beyond the scope of the present application, but for example, surgical access can be obtained via a minimally invasive surgical procedure such as that used with the Polaris™ 5.5 Spinal System, commercially available from Biomet, Inc. of Warsaw, Ind., or the minimally invasive surgical procedure disclosed in commonly owned U.S. Patent Publication No. 2008/0077138, filed on Apr. 20, 2007 and previously incorporated by reference herein.

Next, one or more multiplanar bone anchor systems 10 can be coupled to a respective vertebral body V via the bone fastener 12 (FIG. 1). Various techniques can be used to couple the multiplanar bone anchor systems 10 to the anatomy, such as those described in commonly owned U.S. Patent Publication No. 2008/0077138, filed on Apr. 20, 2007, previously incorporated by reference herein. In one example, if each bone fastener 12 includes the driver connection feature 34 defined in the head 30, a suitable tool can be coupled to the driver connection feature 34 to drive the bone fastener 12 into the anatomy in a conventional manner. Once the multiplanar bone anchor systems 10 are coupled to the anatomy, the connecting rod 20 can be inserted into the saddle 18 of each of the multiplanar bone anchor systems 10. Generally, the connecting rod 20 can be inserted such that the connecting rod 20 rests on the receiver surface 88 of the distal end 78 of the saddle 18 (FIG. 2).

With the connecting rod 20 positioned in the saddles 18 of the multiplanar bone anchor systems 10, the set screw 22 can be coupled to each mating portion 84 of each saddle 18 (FIG. 3). The coupling of the set screw 22 can apply a force to the lock ring 14 to fixedly couple or lock the position of the bone fastener 12 relative to the saddle 18. In this regard, the lock ring 14 can apply a force to the head 30 of the bone fastener 12, which in turn, can provide a force on the ring 50. Additionally, the lock ring 14 can apply a force directly to the ring 50. The force on the ring 50, can in turn be applied to the bottom portion 60 of the saddle 18 to thereby fix the position of the bone fastener 12 relative to the saddle 18.

Figure 9:
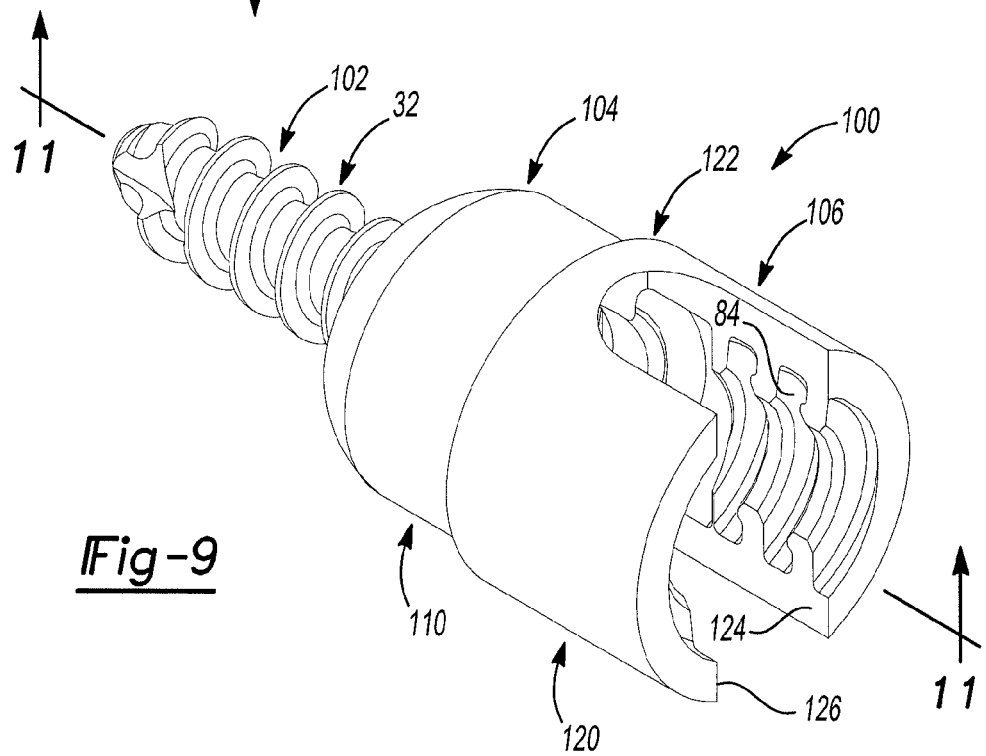
FIG. 9 is a schematic perspective illustration of another exemplary multiplanar bone anchor system for use with a connecting device in a fixation procedure according to the present teachings.
Figure 10:
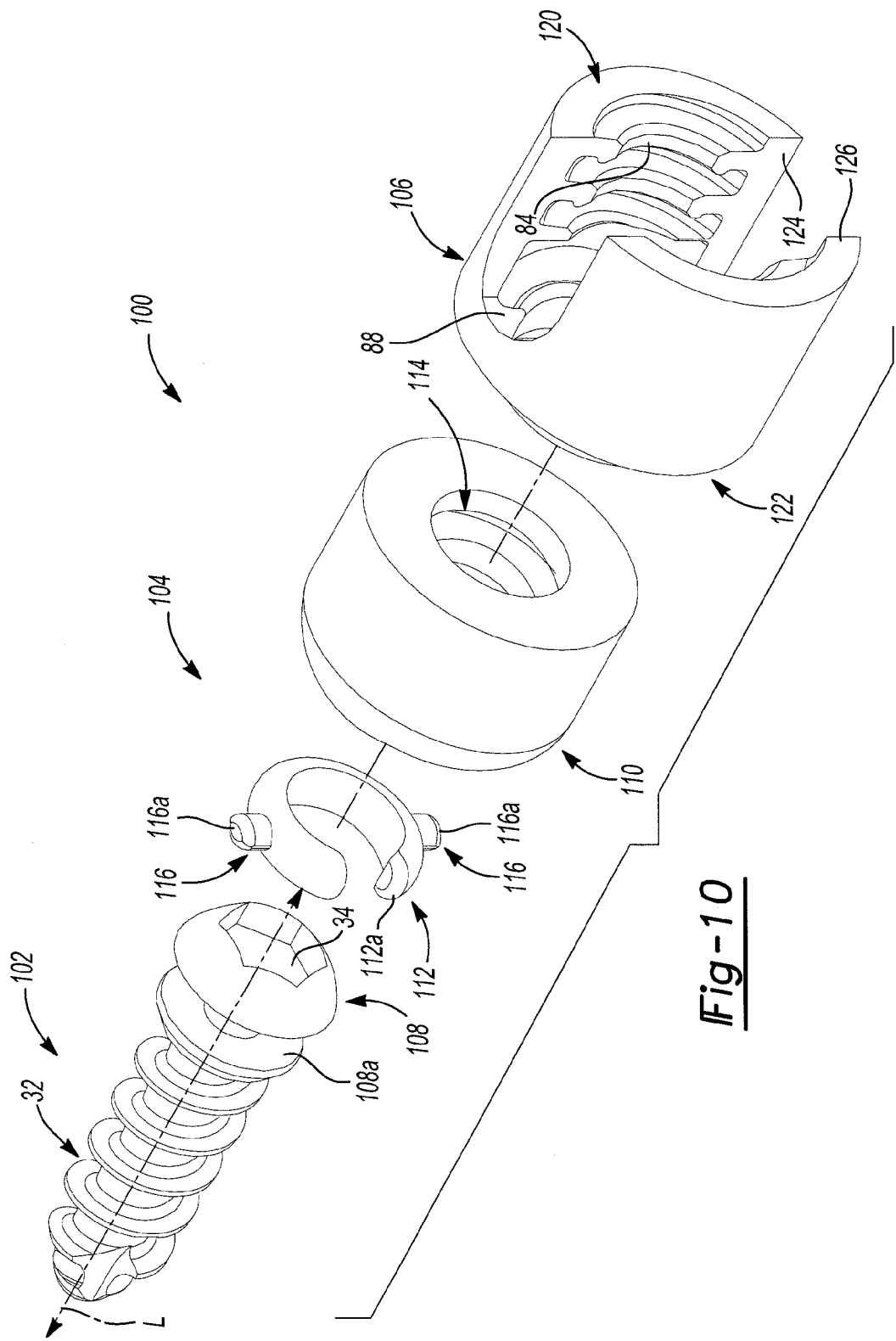
FIG. 10 is an exploded view of the multiplanar bone anchor system of FIG. 9.
Figure 11:
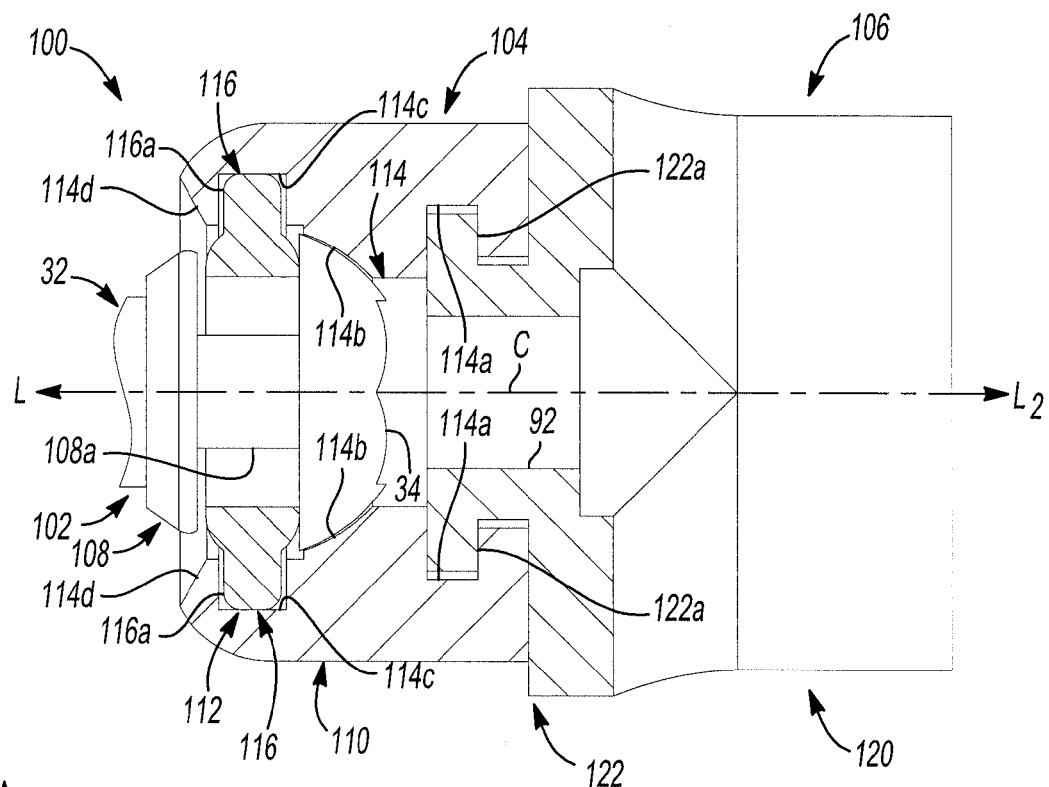
FIG. 11 is a schematic, cross-sectional illustration of the multiplanar bone anchor system of FIG. 9, taken along line 11-11 of FIG. 9.

With reference now to FIGS. 9-11, in one example, a multiplanar bone anchor system 100 can be employed with the connecting rod 20 to repair a damaged portion of an anatomy. As the multiplanar bone anchor system 100 can be similar to the multiplanar bone anchor system 10 described with reference to FIGS. 1-8, only the differences between the multiplanar bone anchor system 10 and the multiplanar bone anchor system 100 will be discussed in great detail herein, and the same reference numerals will be used to denote the same or similar components. The multiplanar bone anchor system 100 can include a bone fastener 102, a multiplanar coupling arrangement or system 104 and a saddle 106. It should be noted, that although the multiplanar bone anchor system 100 is described and illustrated herein as not including a lock ring 14, a suitable lock ring 14 could be employed with the multiplanar bone anchor system 100, if desired.

With continued reference to FIGS. 9-11, the bone fastener 102 can be configured to engage the anatomy to couple the multiplanar bone anchor system 100 to the anatomy. The bone fastener 102 can be composed of any suitable biocompatible material, such as titanium, stainless steel, biocompatible polymers, etc. The bone fastener 102 can include a head 108 and the shank 32. The head 108 can be generally arcuate, and can include the driver connection feature 34 and a channel 108a.

The channel 108a can be defined about a circumference of the head 108, generally between the head 108 and the shank 32. The channel 108a can receive a portion of the multiplanar coupling system 104 to enable the saddle 106 to rotate about the longitudinal axis L of the bone fastener 102 (FIG. 10). Thus, the channel 108a can define a first bearing surface. It should be noted that although the bone fastener 102 is illustrated and described herein as including the channel 108a, the channel 108a need not be necessary to enable the saddle 106 to rotate about the longitudinal axis L of the bone fastener 102.

In one example, with continued reference to FIGS. 9-11, the multiplanar coupling system 104 can include a connecting arm 110 and a bearing member or ring 112. The connecting arm 110 and the ring 112 can cooperate with the bone fastener 102 to enable the bone fastener 102 to move relative to the saddle 106. The connecting arm 110 can be disposed about a head 108 of the bone fastener 102 to enable the bone fastener 102 to move or articulate relative to the saddle 106 as shown in FIG. 11. In this example, the connecting arm 110 can be annular, and can be coupled to the saddle 106. The connecting arm 110 can include a bore 114. The bore 114 can be formed about a central axis C of the connecting arm 110. As best shown in FIG. 11, the bore 114 can include a mating portion 114a, a recess 114b, a coupling portion 114c and a tapered portion 114d.

The mating portion 114a can couple the connecting arm 110 to the saddle 106. It should be noted that the mating portion 114a can be configured so that the saddle 106 can move or translate relative to the connecting arm 110. For example, the mating portion 114a can comprise opposing guides or slots formed through a portion of the connecting arm 110 that can slidably receive a portion of the saddle 106. It should be noted, however, any suitable method or configuration can be used to slidably couple the saddle 106 to the connecting arm 110, such as a dovetail, rails, etc.

The recess 114b can be defined between the mating portion 114a and the at least one coupling portion 114c. Generally, the recess 114b can be arcuate, and in one example, can be hemispherical. The recess 114b can provide at least clearance for the rotation of the head 108 of the bone fastener 102 within and relative to the connecting arm 110. In this regard, the recess 114b can be sized to enable at least rotation about the longitudinal axis L of the bone fastener 102, and can also be sized to enable rotation of the connecting arm 110 relative to the head 108 of the bone fastener 102, if desired.

The coupling portion 114c can be defined between the recess 114b and the tapered portion 114d. In one example, the coupling portion 114c can comprise a channel defined about the circumference of the connecting arm 110. Generally, the coupling portion 114c can be configured to receive the ring 112, which can movably or rotatably couple the bone fastener 102 to the connecting arm 110, as will be discussed herein.

The tapered portion 114d can be defined at a distal most end of the bore 114. The tapered portion 114d can provide clearance for the angular movement of the bone fastener 102 relative to the saddle 106. In this regard, the tapered portion 114d can be formed about a circumference of the bore 114, and the shank 32 of the bone fastener 102 can contact the tapered portion 114d to limit the angular motion of the bone fastener relative to the connecting arm 110. Thus, the tapered portion 114d can provide a stop or limit for the angular movement of the bone fastener 102 relative to the saddle 106.

With reference to FIGS. 10 and 11, the ring 112 can be coupled to the channel 108a of the head 108 of the bone fastener 102, and can cooperate with the bore 114 to enable the bone fastener 102 to move or rotate relative to the connecting arm 110. In one example, the ring 112 can comprise a generally C-shape body, and can have a slot 112a. The ring 112 can be at least partially received within the channel 108a of the head 108. Generally, the ring 112 can be snap-fit into the channel 108a of the bone fastener 102. In one example, the ring 112 can have an inner diameter which can be greater than an outer diameter of the channel 108a of the head 108 to prevent separation of the ring 112 from about the head 108 of the bone fastener 102. It should be noted, however, that the ring 112 could have a continuous annular body, such as an O-shape, and in this case, the ring 112 could be threaded over the shank 32 into the channel 36.

With reference to FIG. 10, the ring 112 can include at least one wing 116. The at least one wing 116 can extend outward from the body of the ring 112 to engage the coupling portion 114c of the bore 114. In this example, the ring 112 can include two wings 116, which can each be received within and slidably coupled to the coupling portion 114c of the bore 114 of the connecting arm 110. The wings 116 can comprise bearing surfaces, which can cooperate with the coupling portion 114c to enable the rotation of the bone fastener 102 about the connecting arm 110. Thus, the wings 116 can have any shape, which can enable the wings 116 to move or slide within the coupling portion 114c of the bore 114, such as elliptical, spherical, rounded, annular, rounded square, rounded rectangular, etc. The wings 116 can also include at least one tapered surface 116a, which can enable the connecting arm 110 to move or pivot relative to the bone fastener 102. In this example, the wings 116 can include two opposed tapered surfaces 116a, which can cooperate with the coupling portion 114c to enable the connecting arm 110 to move or pivot about the head 108 of the bone fastener 102.

With reference to FIGS. 9-11, the saddle 106 can be coupled to the multiplanar coupling system 104 via the connecting arm 110. Generally, the saddle 106 can be coupled to the connecting arm 110 so that the saddle 106 can move or translate relative to the multiplanar coupling system 104 and the bone fastener 102. The saddle 106 can be substantially U-shaped and symmetrical with respect to a longitudinal axis L defined by the multiplanar bone anchor system 100. In one example, the saddle 106 can include a first or proximal end 120 and a second or distal end 122. In one example, the proximal end 120 can include a first arm 124 and a second arm 126. The first arm 124 and second arm 126 can extend upwardly from the distal end 122 to define the U-shape. Each of the first arm 124 and the second arm 126 can include the mating portion 84.

With reference to FIGS. 10 and 11, the distal end 122 can be generally rectangular, and can include the receiver surface 88 (FIG. 10), at least one rail 122a (FIG. 11) and the central bore 92 (FIG. 11). In one example, the distal end 122 can include two rails 122a. Generally, the rails 122a can be formed on opposite sides of the bore 92, and can extend outwardly from the bore 92. The rails 122a can slidably couple the saddle 106 to the connecting arm 110. In this regard, each rail 122a can cooperate with a respective one of the guides or slots of the mating portion 114a to enable the saddle 106 to move or translate relative to the connecting arm 110 and bone fastener 102. It should be understood, however, that any suitable mechanism could be used to enable the saddle 106 to move or translate relative to the connecting arm 110, such as a dovetail assembly, etc. Further, the distal end 122 could include only one rail 122a, if desired. It should also be understood that the saddle 106 could include the mating portion 114a and the rails 122a could be formed on the connecting arm 110 to enable the relative motion between the saddle 106 and the connecting arm 110, if desired.

With reference to FIGS. 10 and 11, in order to assemble the multiplanar bone anchor system 100, the ring 112 can be coupled to the channel 108a of the bone fastener 102. Then, the connecting arm 110 can be coupled to the ring 112 such that the wings 116 of the ring 112 are received within the coupling portion 114c of the connecting arm 110. The saddle 106 can be positioned so that the rails 122a are slidably coupled to the mating portion 114a of the connecting arm 110.

Once assembled, the connecting arm 110 can cooperate with the ring 112 to enable movement or rotation of the bone fastener 102 about the central or longitudinal axis of the bone fastener 102, which provides a first plane of motion. In addition, the tapered surfaces 116a of the wings 116 can cooperate with the coupling portion 114c of the connecting arm 110 to enable the connecting arm 110 to move or pivot relative to the bone fastener 102, about the head 108 of the bone fastener 102, thereby providing a second plane of motion. The saddle 106 can also cooperate with the connecting arm 110 to enable the saddle 106 to move or translate relative to the connecting arm 110, which can provide a third plane of motion. Thus, when assembled, the multiplanar bone anchor system 100 can have at least three planes or degrees of motion. By allowing the multiplanar bone anchor system 100 to move in at least three planes, the surgeon can manipulate the multiplanar bone anchor system 100 as necessary to conform to the anatomy of the patient.

As the surgical insertion and use of the multiplanar bone anchor system 100 in a fixation procedure can be similar to the surgical insertion and insertion of the multiplanar bone anchor system 10 in a fixation procedure, the surgical insertion and use of the multiplanar bone anchor system 100 will not be discussed in great detail herein. Briefly, however, once the multiplanar bone anchor system 100 is secured to the anatomy, the multiplanar coupling system 104 and the saddle 106 can be moved, pivoted or rotated relative to the bone fastener 102 into the desired alignment for the fixation procedure. Once the aligned, the connecting rod 20 can be coupled to a desired number of multiplanar bone anchor systems 100.

Figure 12:
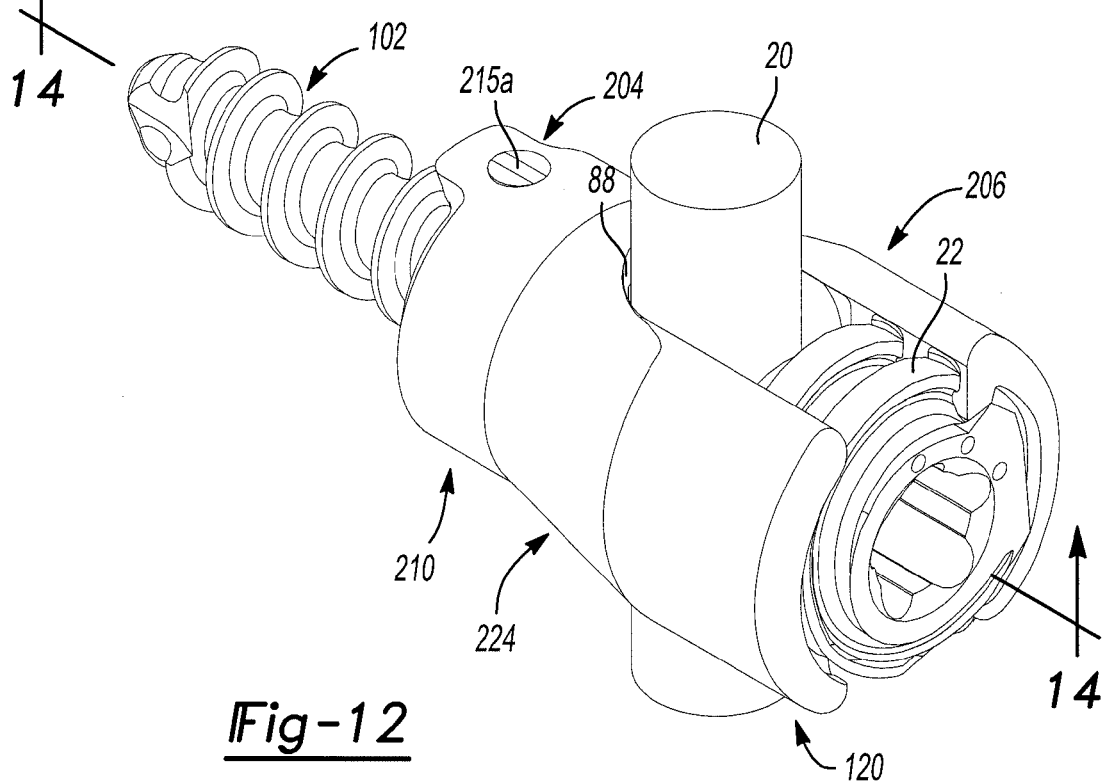
FIG. 12 is a schematic perspective illustration of another exemplary multiplanar bone anchor system for use with a connecting device in a fixation procedure according to the present teachings.
Figure 13:
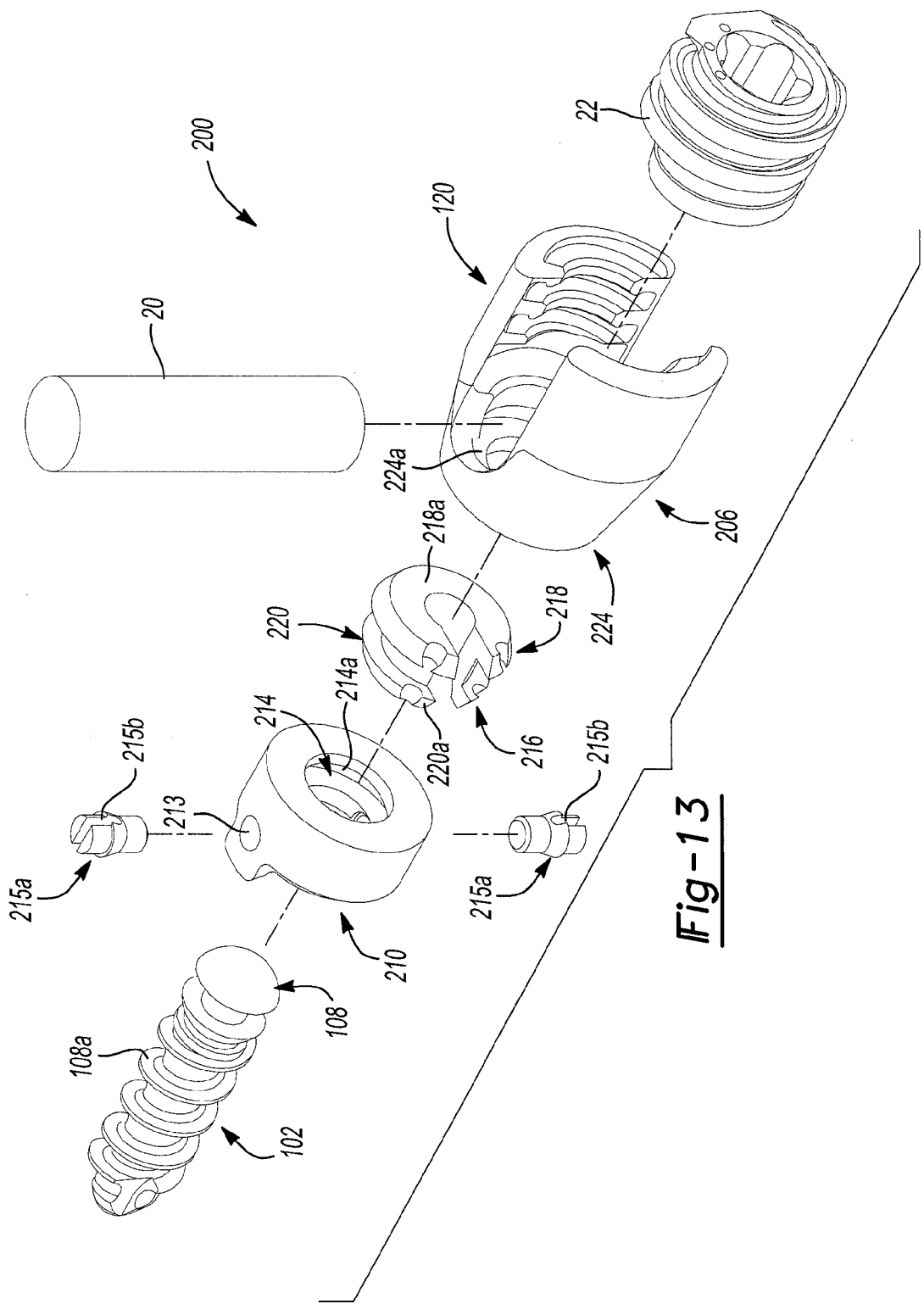
FIG. 13 is an exploded view of the multiplanar bone anchor system of FIG. 12.
Figure 14:
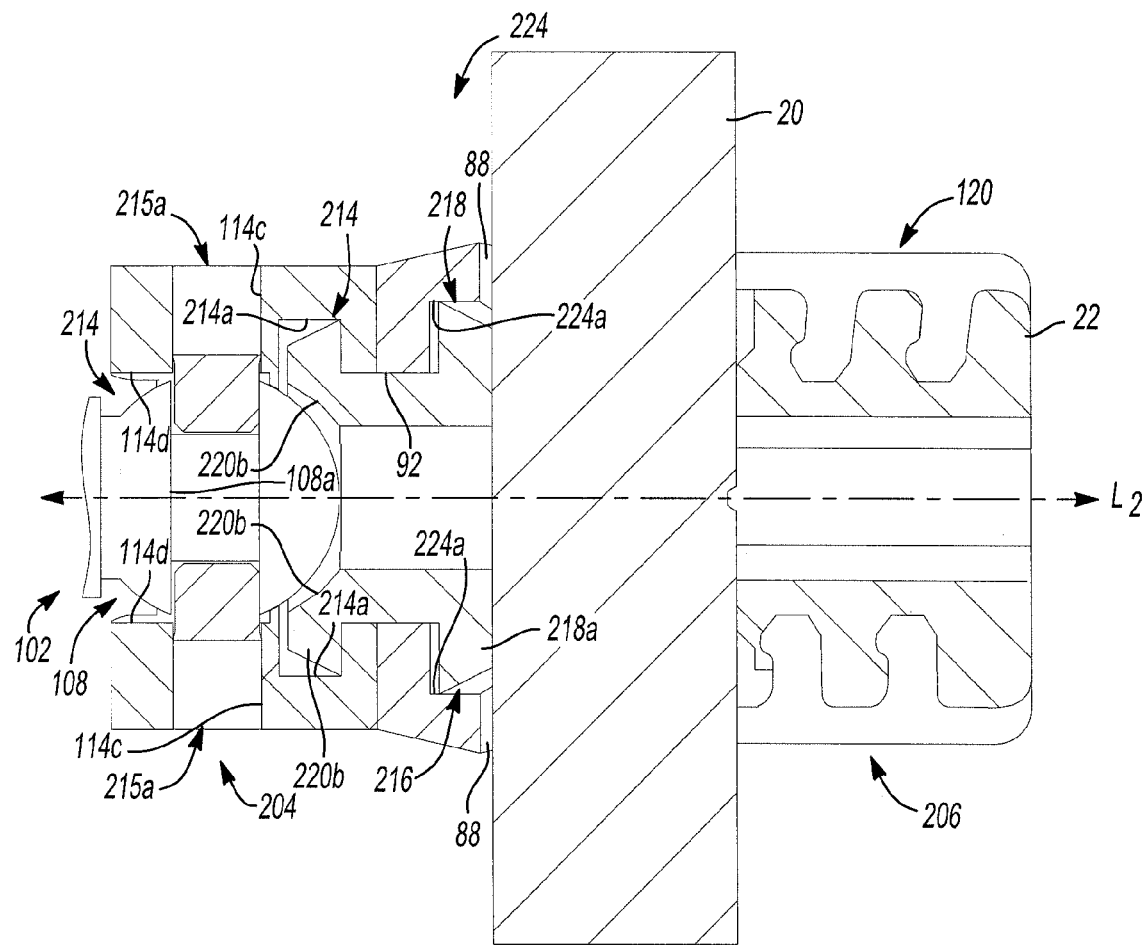
FIG. 14 is a schematic, cross-sectional illustration of the multiplanar bone anchor system of FIG. 12, taken along line 14-14 of FIG. 12.

With reference now to FIGS. 12-14, in one example, a multiplanar bone anchor system 200 can be employed with the connecting rod 20 to repair a damaged portion of an anatomy. As the multiplanar bone anchor system 200 can be similar to the multiplanar bone anchor system 100 described with reference to FIGS. 9-11, only the differences between the multiplanar bone anchor system 100 and the multiplanar bone anchor system 200 will be discussed in great detail herein, and the same reference numerals will be used to denote the same or similar components. The multiplanar bone anchor system 200 can include the bone fastener 102, a multiplanar coupling arrangement or system 204 and a saddle 206.

With reference to FIGS. 12-14, the multiplanar coupling system 204 can include a connecting arm 210, at least one plug 215 and a retaining ring 216. The connecting arm 210 can cooperate with the bone fastener 102 to enable the bone fastener 102 to move relative to the saddle 206. The connecting arm 210 can be disposed about a head 108 of the bone fastener 102 to enable the bone fastener 102 to move or articulate relative to the saddle 206. In this example, the connecting arm 210 can be annular, and can be coupled to the saddle 206. The connecting arm 210 can include at least one coupling feature 213 and a bore 214. The at least one coupling feature 213 can comprise two coupling features 213. In this example, the coupling features 213 can comprise bores, which can be defined through opposite sides of the connecting arm 210 to the bore 214. The bore 214 can be formed about a central axis C of the connecting arm 210. As best shown in FIG. 14, the bore 214 can include a mating portion 214a, the coupling portion 114c and the tapered portion 114d.

The mating portion 214a can cooperate with the retaining ring 216 to couple the connecting arm 210 to the saddle 206. Generally, the mating portion 214a can be configured so that the saddle 206 can move relative to the connecting arm about via the retaining ring 216. In this example, the mating portion 214a can comprise opposing guides or slots formed through a portion of the connecting arm 210, which can slidably receive a portion of the retaining ring 216. It should be noted, however, any suitable method or configuration can be used to movably couple the saddle 206 to the connecting arm 210, such as a dovetail, rails, etc.

With reference to FIG. 13, in one example, the at least one plug 215a can comprise two plugs 215a. The plugs 215a can engage the coupling portion 114c of the bore 214. In this example, each of the plugs 215a can be received within and slidably coupled to the coupling portion 114c of the bore 214 of the connecting arm 210. The plugs 215a can comprise bearing surfaces, which can cooperate with the coupling portion 114c to enable the rotation of the bone fastener 102 about the connecting arm 210. Thus, the plugs 215a can have any shape, which can enable the plugs 215a to move or slide within the coupling portion 114c of the bore 114, such as elliptical, spherical, rounded, annular, rounded square, rounded rectangular, etc. In one example, the plugs 215a can each include a cut out (or similar features) 215b, which can enable the plugs 215a to be snap-fit or press-fit into the connecting arm 210. It should be understood, however, that the plugs 215a could be integrally formed with the connecting arm 210, if desired. The plugs 215a can cooperate with the coupling portion 114c to enable the connecting arm 210 to move or pivot about the head 108 of the bone fastener 102.

As best shown in FIG. 14, the retaining ring 216 can couple the saddle 206 to the connecting arm 210. In this regard, the retaining ring 216 can include a first or proximal end 218 and a second or distal end 220. The proximal end 218 can be coupled to a portion of the saddle 206, as will be discussed, and the distal end 220 can be coupled to the mating portion 214a of the connecting arm 210. The retaining ring 216 can comprise any suitable structure, such as an annular ring, which may or may not include a continuous, uninterrupted circumference. In this example, the retaining ring 216 can comprise a C-shaped ring, however, it should be understood that the retaining ring 216 could also comprise a non-annular structure, such as a rectangular structure, square structure, etc.

The proximal end 218 of the retaining ring 216 can include a projection 218a, which can couple the proximal end 218 to the saddle 206. The distal end 220 can also include a projection 220a, which can couple the distal end 220 to the mating portion 214a. The projection 220a of the distal end 220 can also include a recess 220b, as best shown in FIG. 14. The recess 220b can allow the head 108 of the bone fastener 102 to rotate about the connecting arm 210 without contacting the retaining ring 216.

The saddle 206 can be coupled to the connecting arm 210 via the retaining ring 216. Generally, the saddle 206 can be coupled to the connecting arm 210 so that the saddle 206 can move or rotate relative to the multiplanar coupling system 204 and the bone fastener 102. The saddle 206 can be substantially U-shaped and symmetrical with respect to a longitudinal axis L defined by the multiplanar bone anchor system 200 (FIG. 14). In one example, the saddle 206 can include the first or proximal end 120 and a second or distal end 224.

With reference to FIG. 14, the distal end 224 can be generally annular, and can include the receiver surface 88, at least one channel 224a and the central bore 92. In this example, the distal end 224 can include two channels 224a. Generally, the channels 224a can be formed on opposite sides of the bore 92. The channels 224a can couple the saddle 206 to the connecting arm 210. In this regard, the channels 224a can receive the projection 220a of the distal end 220 of the retaining ring 216 to couple the saddle 206 to the connecting arm 210 and bone fastener 102.

With reference to FIGS. 13 and 14, in order to assemble the multiplanar bone anchor system 200, the retaining ring 216 can be coupled to the channels 224a of the saddle 206. With the retaining ring 216 coupled to the saddle 206, the distal end 220 of the retaining ring 216 can be pushed into the connecting arm 210, such that the projection 220a of the retaining ring 216 fits within the mating portion 214a of the connecting arm 210. Then, the connecting arm 210 can be positioned over the bone fastener 102, and the plugs 215a can be coupled to the connecting arm 210 so that the plugs 215a are received through the coupling features 213 of the connecting arm 210.

Once assembled, the connecting arm 210 can cooperate with the plugs 215a to enable movement or rotation of the bone fastener 102 about the central or longitudinal axis of the bone fastener 102, which provides a first plane of motion. In addition, the plugs 215a can cooperate with the coupling portion 114c of the connecting arm 210 to enable the connecting arm 210 to move or pivot relative to the bone fastener 102, about the head 108 of the bone fastener 102, thereby providing a second plane of motion. The saddle 206 can also cooperate with the connecting arm 210 via the retaining ring 216 to enable the saddle 206 to move or rotate relative to the connecting arm 210, which can provide a third plane of motion. Thus, when assembled, the multiplanar bone anchor system 200 can have at least three planes or degrees of motion. By allowing the multiplanar bone anchor system 200 to move in at least three planes, the surgeon can manipulate the multiplanar bone anchor system 200 as necessary to conform to the anatomy of the patient.

As the surgical insertion and use of the multiplanar bone anchor system 200 in a fixation procedure can be similar to the surgical insertion and insertion of the multiplanar bone anchor system 100 in a fixation procedure, the surgical insertion and use of the multiplanar bone anchor system 200 will not be discussed in great detail herein. Briefly, however, once the multiplanar bone anchor system 200 is secured to the anatomy, the multiplanar coupling system 204 and the saddle 206 can be moved, pivoted or rotated relative to the bone fastener 102 into the desired alignment for the fixation procedure. Once the aligned, the connecting rod 20 can be coupled to a desired number of multiplanar bone anchor systems 200.

Figure 15:
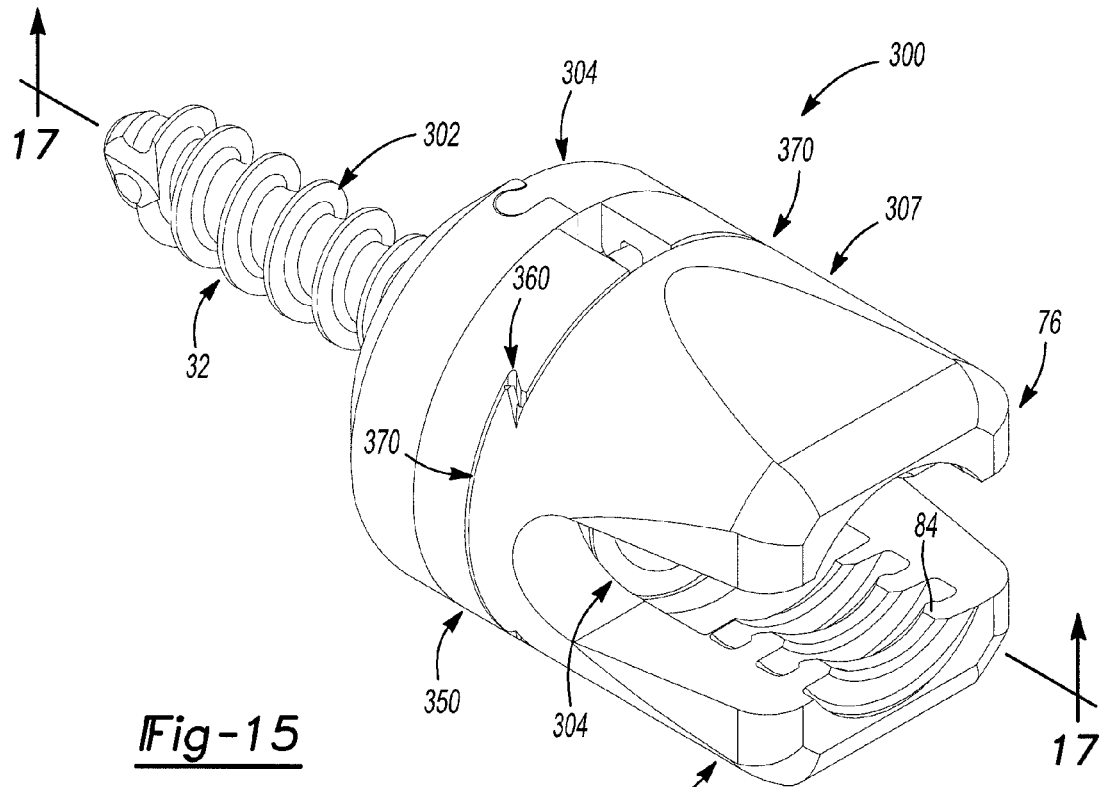
FIG. 15 is a schematic perspective illustration of another exemplary multiplanar bone anchor system for use with a connecting device in a fixation procedure according to the present teachings.
Figure 17:
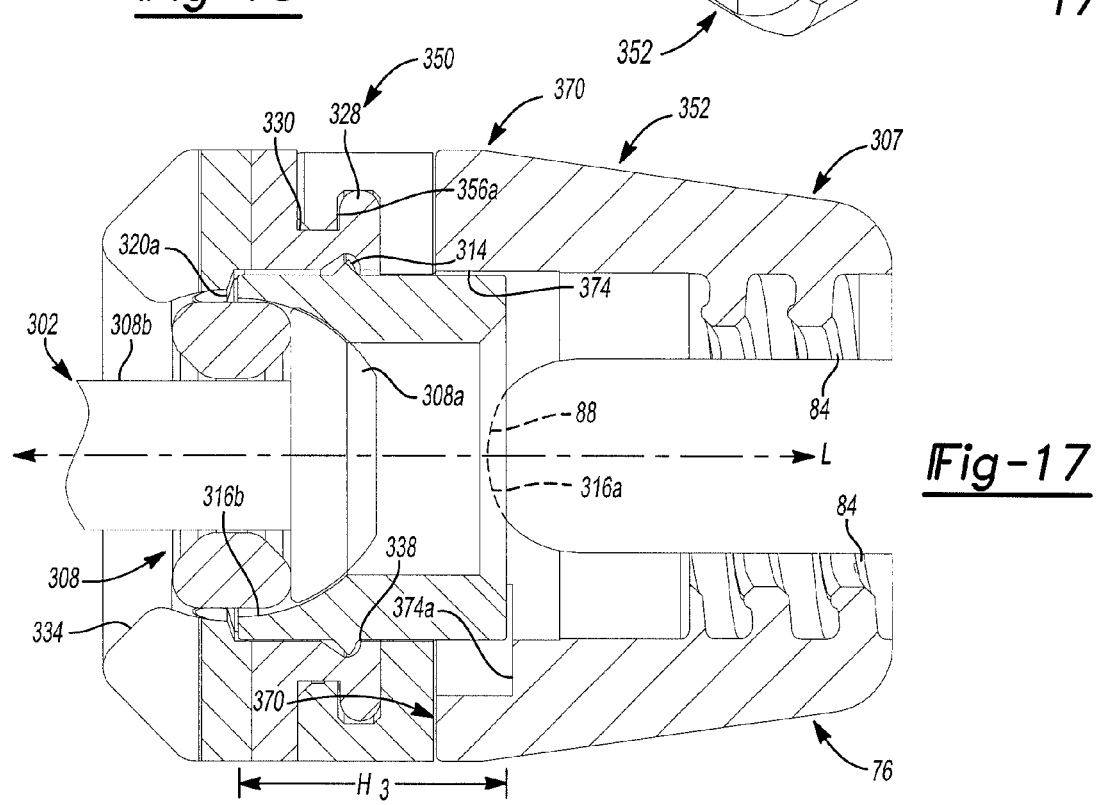
FIG. 17 is a schematic, cross-sectional illustration of the multiplanar bone anchor system of FIG. 15, taken along line 17-17 of FIG. 15.
Figure 16:
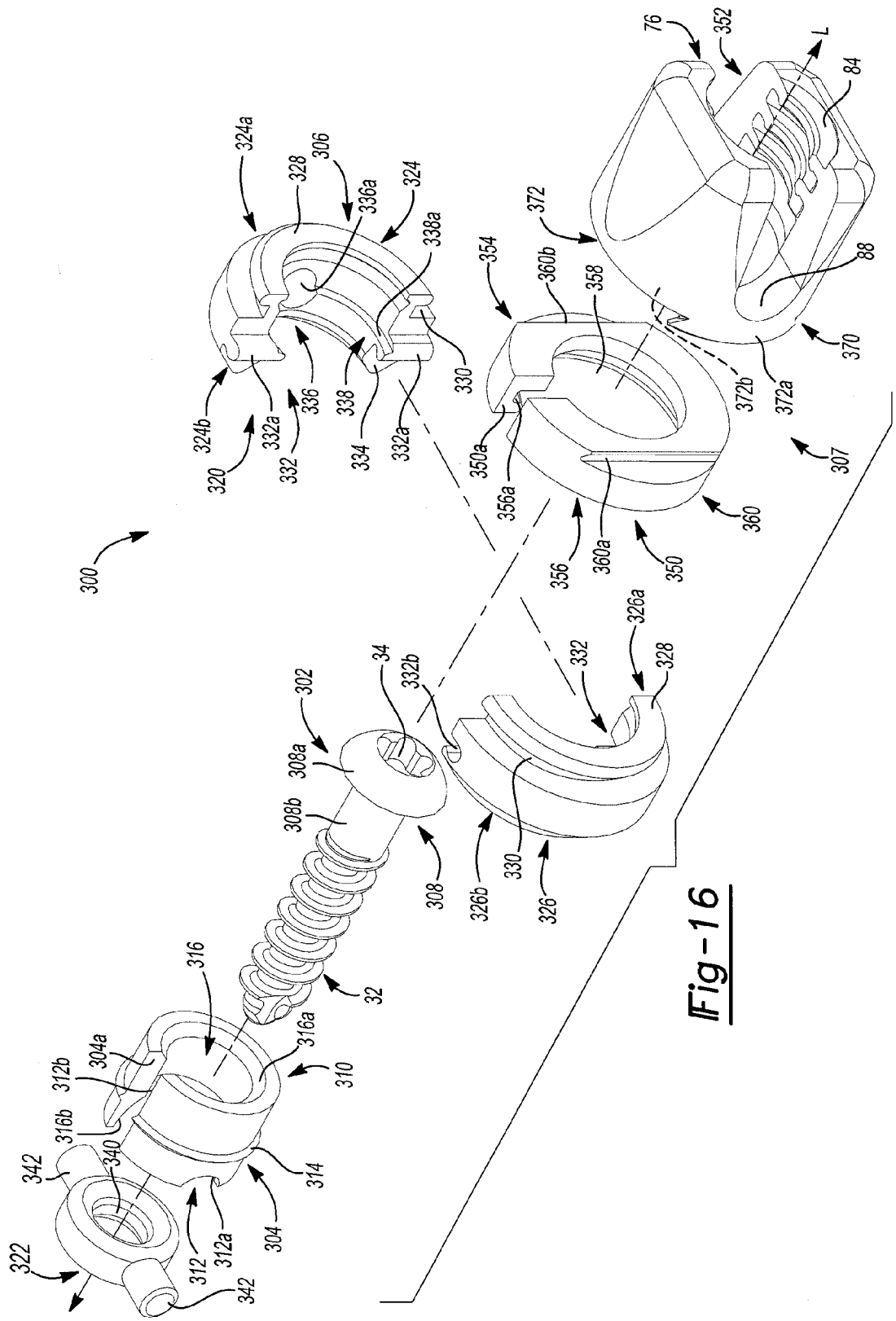
FIG. 16 is an exploded view of the multiplanar bone anchor system of FIG. 15.

With reference now to FIGS. 15-17, in one example, a multiplanar bone anchor system 300 can be employed with the connecting rod 20 to repair a damaged portion of an anatomy. As the multiplanar bone anchor system 300 can be similar to the multiplanar bone anchor system 10 described with reference to FIGS. 1-9, only the differences between the multiplanar bone anchor system 300 and the multiplanar bone anchor system 10 will be discussed in great detail herein, and the same reference numerals will be used to denote the same or similar components. The multiplanar bone anchor system 300 can include a bone fastener 302, a lock ring 304, a multiplanar coupling arrangement or system 306 and a saddle 307.

With reference to FIGS. 15 and 16, the bone fastener 302 can be configured to engage the anatomy to couple the multiplanar bone anchor system 300 to the anatomy. The bone fastener 302 can be composed of any suitable biocompatible material, such as titanium, stainless steel, biocompatible polymers, etc. The bone fastener 302 can include a proximal end or head 308 and the distal end or shank 32. The head 308 can include a generally arcuate or hemispherical portion 308a coupled to the shank 32 via a shaft 308b. The hemispherical portion 308a can include the driver connection feature 34. The hemispherical portion 308a can be coupled to the lock ring 304 when the multiplanar bone anchor system 300 is assembled. The shaft 308b can be generally cylindrical, and can extend distally from the hemispherical portion 308a. The shaft 308b can receive a portion of the multiplanar coupling system 306 to couple the multiplanar coupling system 306 to the bone fastener 302.

The lock ring 304 can be positioned about the head 308 of the bone fastener 302, as best shown in FIG. 17. The lock ring 304 can couple or lock the bone fastener 302 relative to the multiplanar coupling system 306 via a force applied by the connecting rod 20, as will be discussed herein. The lock ring 304 can be generally cylindrical, and can have a height H3. The height H3 can be sized to extend above or about equal to a receiver surface 88 of the saddle 307 so that coupling the connecting rod 20 to the saddle 307 can compress the lock ring 304 onto the head 308 of the bone fastener 302. In this example, as shown in FIG. 16, the lock ring 304 can include a cut out 304a, which can facilitate positioning the lock ring 304 about the head 308 of the bone fastener 302. It should be understood, however, that the cut out 304a can be optional, as the lock ring 304 can have a continuous, uninterrupted cylindrical body. In addition, the lock ring 304 can include a proximal end 310, a distal end 312, a flange 314 and a bore 316.

The proximal end 310 can extend above the receiver surface 88 of the saddle 307 when the multiplanar bone anchor system 300 is assembled. The proximal end 310 can contact at least a portion of the connecting rod 20 when the connecting rod 20 is coupled to the multiplanar bone anchor system 300. The distal end 312 can be coupled to the hemispherical portion 308a of the head 308 of the bone fastener 302 when the lock ring 304 is coupled to bone fastener 302. The distal end 312 can include at least one cut-out or recess 312a. In one example, the distal end 312 can include two recesses 312a, 312b. The recesses 312a and 312b can provide clearance for a portion of the multiplanar coupling system 306. Optionally, the recesses 312a and 312b can enable the bone fastener 302 to move or pivot about the head 308 of the bone fastener 302, as discussed with regard to FIGS. 1-9.

The flange 314 can be formed between the proximal end 310 and the distal end 312, and can extend outwardly about an exterior circumference of the lock ring 304. The flange 314 can cooperate with a portion of the multiplanar coupling system 306 to couple or retain the lock ring 304 within the multiplanar coupling system 306.

The bore 316 can be disposed about a central axis of the lock ring 304. The bore 316 can extend from the proximal end 310 to the distal end 312. The bore 316 can include a first countersink 316a formed near or at the proximal end 310 and a second countersink 316b formed near or at the distal end 312. The first countersink 316a can be configured to at least partially receive a portion of the connecting rod 20 when the connecting rod 20 is coupled to the multiplanar bone anchor system 300. The second countersink 316b can comprise a bearing surface, which can be slidably coupled to the head 308 of the bone fastener 302. Generally, the second countersink 316b can enable the head 308 to move, rotate and/or pivot relative to the lock ring 304.

The multiplanar coupling system 306 can include a connecting arm 320 and a ring 322. The connecting arm 320 can cooperate with the bone fastener 302 to enable the bone fastener 302 to move relative to the saddle 307. It should be noted that although the multiplanar coupling system 306 is described and illustrated herein as including the connecting arm 320 and the ring 322, the multiplanar coupling system 306 could include only a ring or only a connecting arm, if desired. In this example, the connecting arm 320 can have a first shell half 324 and a second shell half 326, which can cooperate to form a substantially continuous annular or cylindrical body having a bore 320a when assembled together (FIG. 17). Each of the first shell half 324 and the second shell half 326 can include a flange 328, a channel 330, at least one mating feature 332, a stop 334, a ring retaining portion 336 and a lock ring retaining portion 338. Generally, each of the flange 328 and the channel 330 can be formed on an exterior surface of each of the first shell half 324 and the second shell half 326, while the stop 334, the ring coupling portion 336 and the lock ring retaining portion 338 can be formed on an interior surface of the first shell half 324 and the second shell half 326.

With reference to FIG. 16, the flange 328 can be defined at a proximal end 324a, 326a of the first shell half 324 and the second shell half 326. The flange 328 can have a smaller diameter than the body of the first shell half 324 and the second shell half 326. The flange 328 can cooperate with the channel 330 to couple a portion of the saddle 307 to the connecting arm 320. The channel 330 can be defined adjacent to the flange 328. The channel 330 can have a diameter that can be smaller than the flange 328. As will be discussed, the flange 328 and the channel 330 can cooperate to rotatably couple a portion of the saddle 307 to the connecting arm 320.

With continued reference to FIG. 16, the at least one mating feature 332 can couple the first shell half 324 and the second shell half 326 together. In one example, the at least one mating feature 332 can comprise two mating features 332, however, it should be understood that any number of mating features could be employed to couple the first shell half 324 to the second shell half 326. For example, a mating portion 332a of the first shell half 324 can comprise a plug, and a mating portion 332b of the second shell half 326 can comprise a receiver. It should be noted that the use of a plug and a receiver is merely exemplary as any suitable technique could be used to couple the first shell half 324 to the second shell half 326, such as adhesives, mechanical fasteners, welding, etc. When the first shell half 324 and the second shell half 326 are coupled together via the mating portions 332, the first shell half 324 and the second shell half 326 can define the bore 320a. The stop 334, the ring coupling portion 336 and the lock ring coupling portion 338 can generally be defined within the bore 320a.

The stop 334 can comprise a tapered portion, which can be formed near or at a distal end 324b, 326b of the first shell half 324 and the second shell half 326. The stop 334 can serve to limit the range of motion of the bone fastener 302 relative to the connecting arm 320. The ring coupling portion 336 can be defined between the proximal end 324a, 326a and the distal end 324b, 326b. In one example, the ring coupling portion 336 can comprise a bore 336a. The bore 336a of the ring coupling portion 336 can receive a portion of the ring 322 to couple the ring 322 to the connecting arm 320, as will be discussed in detail further herein.

The lock ring retaining portion 338 can be defined between the proximal end 324a, 326a and the ring coupling portion 336 of the first shell half 324 and the second shell half 326. The lock ring retaining portion 338 can include a bearing surface 338a. The bearing surface 338a can be defined radially about the interior of the first shell half 324 and the second shell half 326, such that when the first shell half 324 is coupled to the second shell half 326, the bearing surface 338a can extend circumferentially about the bore 320a. The bearing surface 338a can be configured to receive at least a portion of the flange 314 of the lock ring 304 to couple the lock ring 304 to the connecting arm 320.

The ring 322 can be coupled to the connecting arm 320 via the ring coupling portion 336. The ring 322 can be disposed about the head 308 of the bone fastener 302 to enable the bone fastener 302 to move or rotate relative to the saddle 307. The ring 322 can be annular, and can be sized to fit within the connecting arm 320 to enable the connecting arm 320 to move or rotate with the bone fastener 302 relative to the saddle 307. The ring 322 can include a bore 340 and at least one wing 342. The bore 340 can be sized to enable the ring 322 to be coupled about the shaft 308b of the bone fastener 302, but can also be sized so as to prevent the ring 322 from migrating onto the hemispherical portion 308a of the head 308 of the bone fastener 302.

The at least one wing 342 can extend outwardly from a circumference of the ring 322. In this example, the at least one wing 342 can comprise two wings 342. The wings 342 can extend outwardly from generally opposite sides of the ring 322. The wings 342 can be generally cylindrical in shape, and can be sized to be coupled to or received within the bore 336a of the ring coupling portion 336. It should be noted that the shape of the wings 342 described and illustrated herein is merely exemplary, as the wings 342 could have any shape that enables the bone fastener 302 to be coupled to the connecting arm 320, such as elliptical, circular, rounded square, rounded rectangular, etc. The wings 342 can couple the ring 322 to the connecting arm 320 so that the connecting arm 320 can rotate with the bone fastener 302 relative to the saddle 307.

With reference to FIGS. 16 and 17, the saddle 307 can be coupled to the multiplanar coupling system 306 via the connecting arm 320. Generally, the saddle 307 can be coupled to the connecting arm 320 so that the connecting arm 320 can move or rotate relative to the saddle 307, and so that the saddle 307 can move or translate relative to the multiplanar coupling system 306 and the bone fastener 302.

The saddle 307 can be substantially U-shaped and symmetrical with respect to a longitudinal axis L defined by the multiplanar bone anchor system 300 (FIG. 17). The saddle 307 can include a first portion or bottom portion 350, and a second portion or top portion 352. The top portion 352 can move or translate relative to the bottom portion 350.

In this regard, with reference to FIGS. 16 and 17, the bottom portion 350 of the saddle 307 can be generally annular or cylindrical in shape, and can comprise a proximal end 354, a distal end 356 and a bore 358. The bottom portion 350 can also include a cut out 350a, if desired, which can facilitate coupling the bottom portion 350 to the connecting arm 320. It should be noted, that the cut out 350a is optional, as the bottom portion 350 could be coupled to the connecting arm 320 via other techniques, such as a snap-fit, press-fit, etc. The proximal end 354 can be coupled to the top portion 352 of the saddle 307, while the distal end 356 can be coupled to the connecting arm 320. The bore 358 can be sized to allow at least a portion of the proximal end 310 of the lock ring 304 to pass therethrough. As will be discussed, the bore 358 can also be configured to receive a portion of the connecting arm 320 therein, when the connecting arm 320 is coupled to the bottom portion 350.

In one example, the proximal end 354 of the bottom portion 350 can define at least one rail 360, which can cooperate with the top portion 352 of the saddle 307 to enable the saddle 307 to move or translate relative to the connecting arm 320. In this example, the proximal end 354 can define two rails 360a, 360b, which can be disposed on generally opposite sides of the bore 358. In on example, the rails 360a, 360b can extend along a plane generally perpendicular to the longitudinal axis L of the multiplanar bone anchor system 300, however, it should be understood that the rails 360a, 360b can extend in any desired plane or in multiple planes. The rails 360a, 360b can enable the saddle 307 to move, translate or slide along the proximal end 354 of the bottom portion 350.

The distal end 356 of the bottom portion 350 can define a lip 356a. The lip 356a can extend about the circumference of the bottom portion 350. The lip 356a can project into the bore 358, and can couple the distal end 356 of the bottom portion 350 to the connecting arm 320. In this regard, the lip 356a can be configured to be coupled to the flange 328 of the connecting arm 320. The engagement of the lip 356a with the flange 328 can allow the connecting arm 320 to move or rotate with the bone fastener 302, relative to at least the top portion 352 of the saddle 307, as will be discussed further herein.

The top portion 352 of the saddle 307 can be coupled to the rails 360a, 360b of the proximal end 354 of the bottom portion 350 so that the top portion 352 can move relative to the bottom portion 350. The top portion 352 can be substantially U-shaped and symmetrical with respect to a longitudinal axis L defined by the multiplanar bone anchor system 300. The top portion 352 can include the first or proximal end 76 and a second or distal end 370.

With reference to FIG. 17, the distal end 370 of the top portion 352 can be generally rectangular, and can include the first or receiver surface 88, a second or bottom surface 372 and a central bore 374. The bottom surface 372 can include at least one or more guides 372a. In this example, the bottom surface 90 can include two guides 372a, 372b. The guides 372a, 372b can slidably couple the top portion 352 to the bottom portion 350. In this regard, each guide 372a, 372b can cooperate with a respective one of the rails 360a, 360b to enable the top portion 352 of the saddle 307 to move or translate relative to the bottom portion 350 of the saddle 307. Generally, each guide 372a, 372b can comprise a dovetail shape.

It should be understood, however, that although the top portion 352 and the bottom portion 350 are illustrated and described herein as including rails and guides to enable the relative motion, any suitable device or mechanism could be used to enable the relative motion between the top portion 352 and the bottom portion 350, such as a monorail assembly, bearing, cam surface, etc. It should also be understood that the rails 360a, 360b of the bottom portion 350 could be interchanged with the guides 372a, 372b of the top portion 352, if desired.

With reference to FIGS. 15-17, in order to assemble the multiplanar bone anchor system 300, the ring 322 can be coupled to the shaft 308b of the bone fastener 302. Then, the lock ring 304 can be positioned on the head 308 of the bone fastener 302. Next, the first shell half 324 and the second shell half 326 of the connecting arm 320 can be coupled to the ring 322 and the lock ring 304. The bottom portion 350 of the saddle 307 can then be coupled to the connecting arm 320, such that the connecting arm 320 can move or rotate relative to the bottom portion 350 of the saddle 307. Next, the top portion 352 of the saddle 307 can be coupled to the bottom portion 350 so that the guides 372a, 372b are movably or slidably coupled to the guides 372a, 372b of the connecting arm 320. Note that the movement of the top portion 352 relative to the bottom portion 350 can be limited by contact between the recess 374a of the central bore 374 and the lock ring 304.

Once assembled, the connecting arm 320 can cooperate with the bone fastener 302 to enable movement or rotation of the bone fastener 302 about the central or longitudinal axis of the bone fastener 302, which provides a first plane of motion. The bottom portion 350 of the saddle 307 can also rotate relative to the bone fastener 302, and thus, the top portion 352 of the saddle 307 can rotate relative to the bone fastener 302 to thereby define a second plane of motion. In addition, the top portion 352 can also move or translate relative to the bottom portion 350, which can thereby define a third plane of motion. Therefore, when assembled, the multiplanar bone anchor system 300 can have at least three degrees or planes of motion. By allowing the multiplanar bone anchor system 300 to move in at least three planes, the surgeon can manipulate the multiplanar bone anchor system 300 as necessary to conform to the anatomy of the patient.

As the surgical insertion and use of the multiplanar bone anchor system 300 in a fixation procedure can be similar to the surgical insertion and insertion of the multiplanar bone anchor system 10 in a fixation procedure, the surgical insertion and use of the multiplanar bone anchor system 300 will not be discussed in great detail herein. Briefly, however, once the multiplanar bone anchor system 300 is secured to the anatomy, the multiplanar coupling system 306 and the saddle 307 can be moved, rotated or translated relative to the bone fastener 302 into the desired alignment for the fixation procedure. Once the aligned, the connecting rod 20 can be coupled to a desired number of multiplanar bone anchor systems 300.

Figure 18:
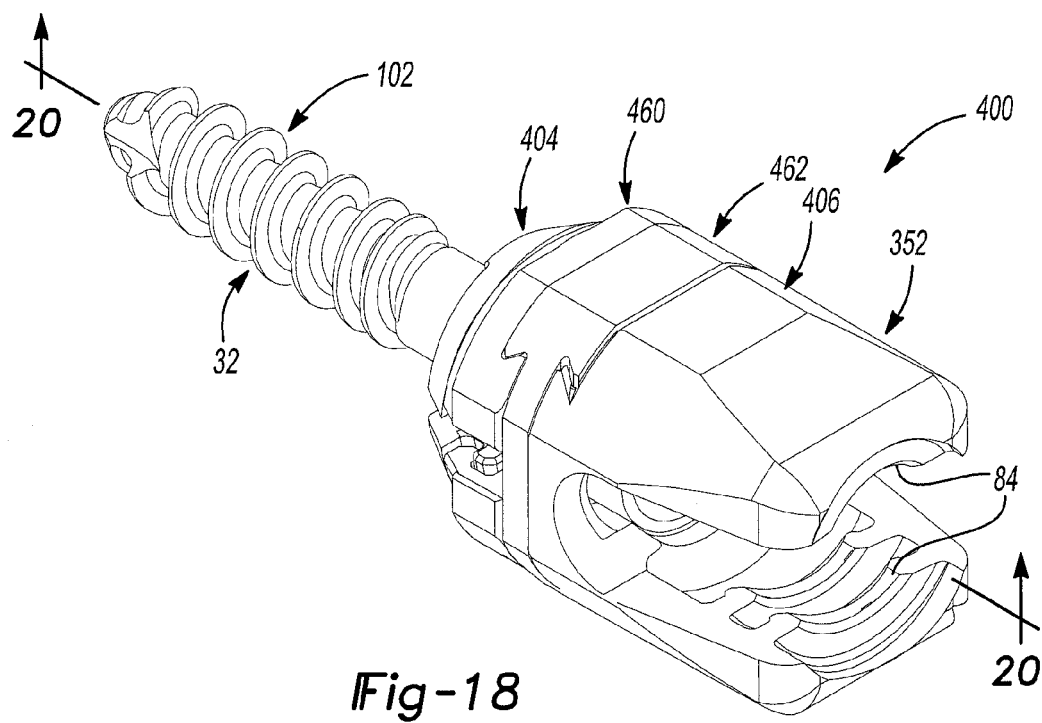
FIG. 18 is a schematic perspective illustration of another exemplary multiplanar bone anchor system for use with a connecting device in a fixation procedure according to the present teachings.
Figure 20:
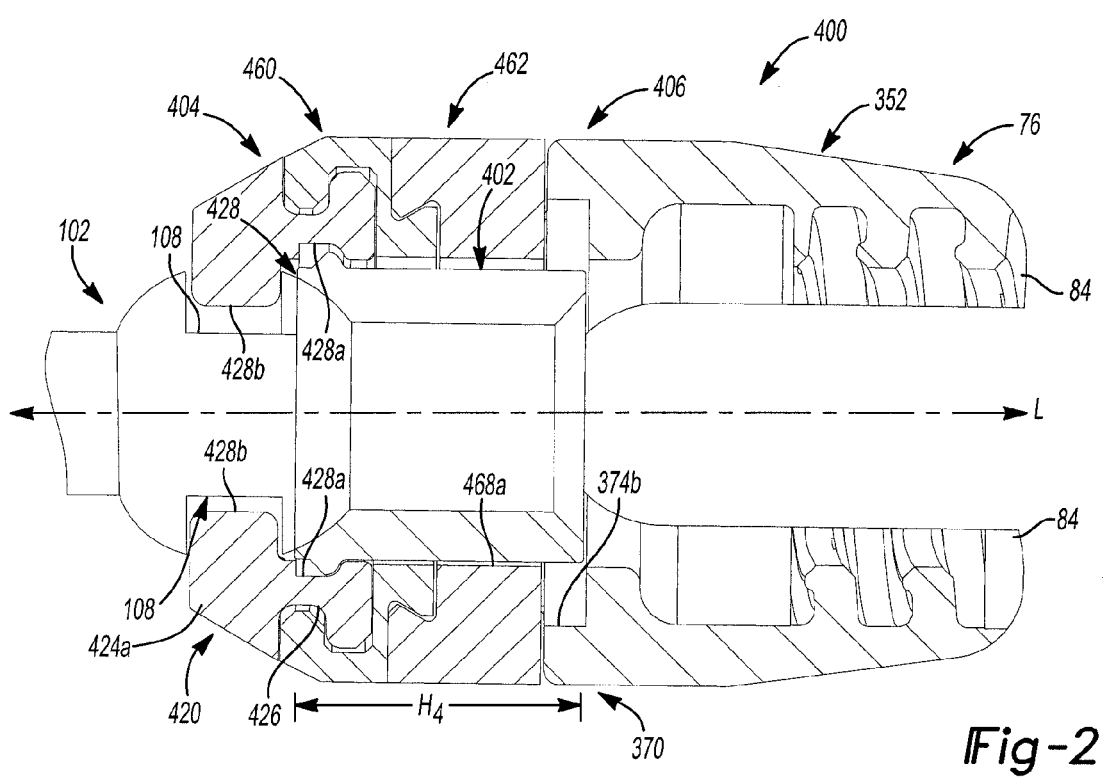
FIG. 20 is a schematic, cross-sectional illustration of the multiplanar bone anchor system of FIG. 18, taken along line 20-20 of FIG. 18.
Figure 19:
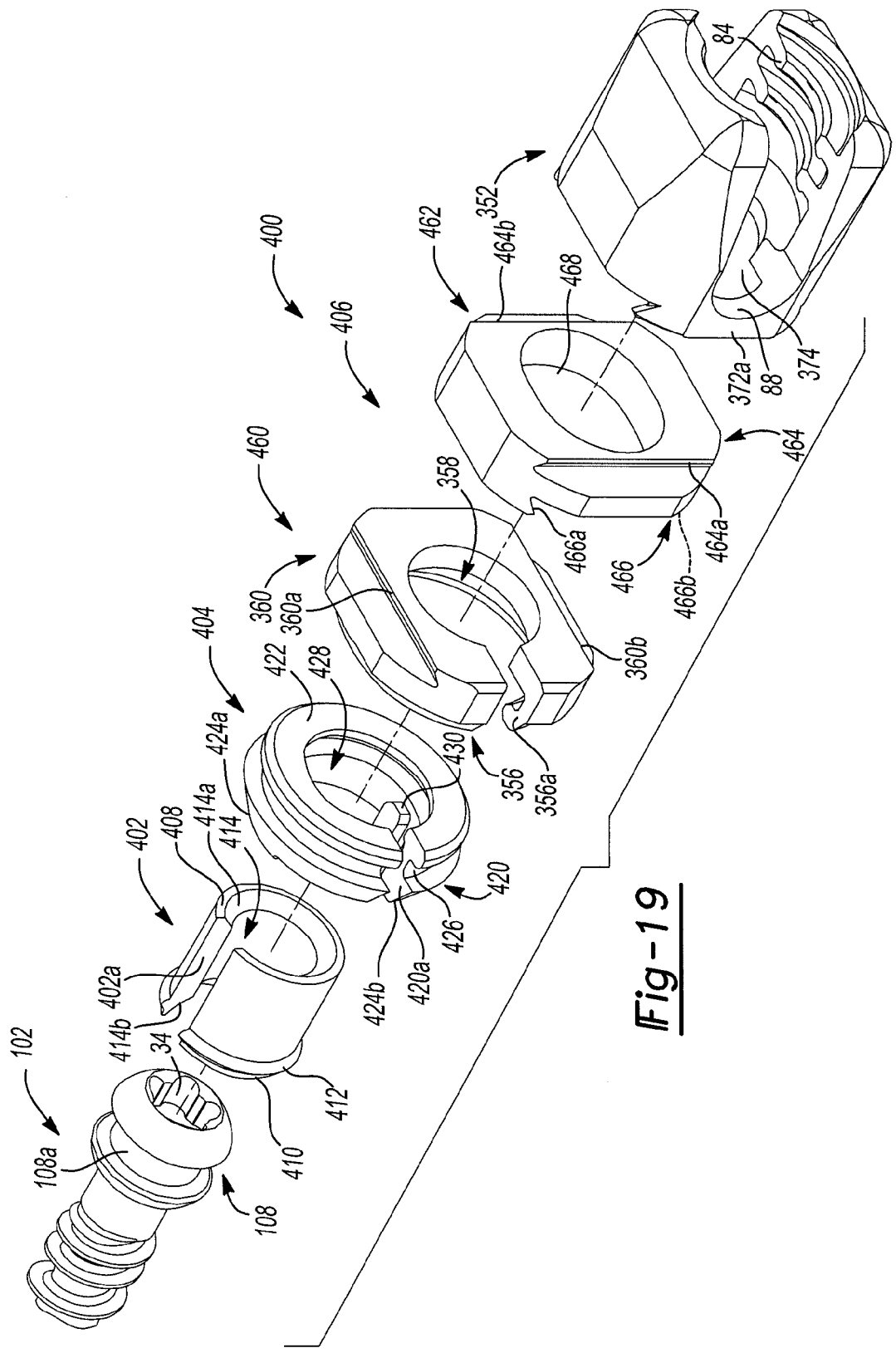
FIG. 19 is an exploded view of the multiplanar bone anchor system of FIG. 18.

With reference now to FIGS. 18-20, in one example, a multiplanar bone anchor system 400 can be employed with the connecting rod 20 to repair a damaged portion of an anatomy. As the multiplanar bone anchor system 400 can be similar to the multiplanar bone anchor system 100, 300 described with reference to FIGS. 9-11 and 15-17, only the differences between the multiplanar bone anchor system 100, 300 and the multiplanar bone anchor system 400 will be discussed in great detail herein, and the same reference numerals will be used to denote the same or similar components. The multiplanar bone anchor system 400 can include the bone fastener 102, a lock ring 402, a multiplanar coupling arrangement or system 404 and a saddle 406.

The lock ring 402 can be positioned about the head 108 of the bone fastener 102. The lock ring 402 can couple or lock the bone fastener 102 relative to the multiplanar coupling system 404 via a force applied by the connecting rod 20, as will be discussed herein. As best shown in FIG. 20, the lock ring 402 can be generally cylindrical, and can have a height H4. The height H4 be sized to extend above or about equal to the receiver surface 88 of the saddle 406 so that coupling the connecting rod 20 to the saddle 406 can compress the lock ring 402 onto the head 108 of the bone fastener 102. In this example, with reference to FIG. 19, the lock ring 402 can include a cut out 402a, which can facilitate positioning the lock ring 402 about the head 108 of the bone fastener 102. It should be understood, however, that the cut out 402a can be optional, as the lock ring 402 can have a continuous, uninterrupted cylindrical body. In addition, the lock ring 402 can include a proximal end 408, a distal end 410, a flange 412 and a bore 414.

The proximal end 408 can extend above or at the receiver surface 88 of the saddle 406 when the multiplanar bone anchor system 400 is assembled. The proximal end 408 can contact at least a portion of the connecting rod 20 when the connecting rod 20 is coupled to the multiplanar bone anchor system 400. The distal end 410 can be coupled to the head 108 of the bone fastener 102 when the lock ring 402 is coupled to bone fastener 102. The flange 412 can be formed near or at the distal end 410, and can extend outwardly about an exterior circumference of the lock ring 402. The flange 412 can cooperate with a portion of the multiplanar coupling system 404 to couple or retain the lock ring 402 within the multiplanar coupling system 404.

The bore 414 can be disposed about a central axis of the lock ring 402. The bore 414 can extend from the proximal end 408 to the distal end 410. The bore 414 can include a first countersink 414a formed near or at the proximal end 408 and a second countersink 414b formed near or at the distal end 410. The first countersink 414a can be configured to at least partially receive a portion of the connecting rod 20 when the connecting rod 20 is coupled to the multiplanar bone anchor system 400. The second countersink 414b can comprise a bearing surface, which can be slidably coupled to the head 108 of the bone fastener 102. Generally, the second countersink 414b can enable the head 108 to move, rotate and/or pivot relative to the lock ring 402.

The multiplanar coupling system 404 can include a connecting arm 420. The connecting arm 420 can cooperate with the bone fastener 102 to enable the bone fastener 102 to move relative to the saddle 406. It should be noted that although the multiplanar coupling system 404 is described and illustrated herein as including only a connecting arm 420, the multiplanar coupling system 404 could include a ring, if desired. In this example, the connecting arm 420 can have a cylindrical body, which can include a cut out 420a. The cut out 420a can facilitate the coupling of the connecting arm 420 to the head 108 of the bone fastener 302. For example, the cut out 420a can enable the connecting arm 420 to be snap-fit around the head 108 of the bone fastener 102. It should be noted, however, that the cut out 410a can be optional, as the connecting arm 420 could have a continuous, uninterrupted cylindrical body. In the case of a continuous, uninterrupted cylindrical body, the connecting arm 420 could be threaded over the shank 32 of the bone fastener 102 into engagement with the head 108 of the bone fastener 102.

In this example, the connecting arm 420 can further comprise a first or proximal end 422, a second or distal end 424, a channel 426, a bore 428 and a coupling feature 430. The proximal end 422 can have a generally smooth surface, which can be positioned adjacent to a portion of the saddle 406 when the multiplanar bone anchor system 400 is assembled. The distal end 424 can be positioned opposite the proximal end 422, and generally, the distal end 424 can comprise a taper 424a. The taper 424a can provide the connecting arm 420 with atraumatic edges.

The channel 426 can be defined between the proximal end 422 and the distal end 424. The channel 426 can extend about an exterior circumference of the cylindrical body of the connecting arm 420. The channel 426 can receive a portion of the saddle 406 to couple the connecting arm 420 to the saddle 406, as will be discussed in detail further herein.

The bore 428 can be defined about a central axis of the connecting arm 420. The bore 428 can receive at least a portion of the lock ring 402 and at least a portion of the bone fastener 102 therein to couple each of the lock ring 402 and the bone fastener 102 to the connecting arm 420. In this regard, with reference to FIG. 20, the bore 428 can include a lock ring coupling portion 428a and a bone fastener coupling portion 428b. In one example, the lock ring coupling portion 428a can comprise a recess, which can be configured to engage the flange 412 of the lock ring 402. The engagement of the flange 412 of the lock ring 402 with the lock ring coupling portion 428a can couple or retain the lock ring 402 within the connecting arm 420. The bone fastener coupling portion 428b can comprise an annular or circumferential projection, which can extend about a circumference of the bore 428. Generally, the bone fastener coupling portion 428b can be sized so as to engage the channel 108a formed in the head 108 of the bone fastener 102 so that the bone fastener 102 can move or rotate relative to the connecting arm 420. Thus, the bone fastener coupling portion 428b can comprise a bearing surface, which can enable the bone fastener 102 to move or rotate relative to the connecting arm 420.

The coupling feature 430 can be formed adjacent to the cut out 420a, and generally, can be formed to engage the channel 108a of the bone fastener 102. The engagement of the coupling feature 430 with the channel 108a can enable the multiplanar coupling system 404 to move (rotate and pivot) relative to the bone fastener 102. It should be noted, however, that the coupling feature 430 can be optional, as any suitable device or technique could be used to allow the multiplanar coupling system 404 to move (rotate and pivot) relative to the bone fastener 102, such as a ring with wings, as discussed previously herein.

The saddle 406 can be coupled to the multiplanar coupling system 404 via the connecting arm 420. Generally, the saddle 406 can be coupled to the connecting arm 420 so that the connecting arm 420 can move or rotate relative to the saddle 406, and so that the saddle 406 can move or translate relative to the multiplanar coupling system 404 and the bone fastener 102.

The saddle 406 can be substantially U-shaped and symmetrical with respect to a longitudinal axis L defined by the multiplanar bone anchor system 400 (FIG. 20). The saddle 406 can include a first portion or bottom portion 460, the second portion or top portion 352 and a third portion or middle portion 462. The top portion 352 can move or translate relative to the middle portion 462.

With reference to FIG. 19, the bottom portion 460 of the saddle 406 can be substantially similar to the bottom portion 350 of the saddle 307 described with reference to FIGS. 15-17, and thus, only the differences between the bottom portion 460 of the saddle 406 and the bottom portion 350 of the saddle 307 will be discussed in great detail herein. In this regard, the bottom portion 460 of the saddle 406 can have a substantially different geometric shape than the bottom portion 350 of the saddle 307. For example, the bottom portion 460 can be generally octagonal, such that the rails 360a, 360b associated with the first or proximal end 354 of the bottom portion 460 can be generally rectangular or dovetail in shape. By having a generally rectangular or dovetail shape, the rails 360a, 360b of the bottom portion 460 can have a substantially larger length than the rails 360a, 360b of the bottom portion 350. This can enable the saddle 406 to move or translate for a greater distance than the saddle 307. It should be understood, however, that the bottom portion 460 can have the same shape as the bottom portion 350, if desired. The bottom portion 460 of the saddle 406 can be coupled to the connecting arm 420 so that the connecting arm 420 can move or rotate relative to the saddle 406.

In this regard, the channel 426 of the connecting arm 420 can be coupled to the annular lip 356a of the bottom portion 460 such that the annular lip 356a rests in the channel 426 to retain the connecting arm 420 to the bottom portion 460 of the saddle 406. The engagement between the channel 426 and the annular lip 346a can allow the connecting arm 420 to move or rotate with the bone fastener 102, relative to at least the top portion 352 of the saddle 406, as will be discussed further herein.

With reference to FIG. 20, the bottom portion 460 can also include a bore 358, which can be sized to enable at least a portion of the lock ring 402 to pass through the bore 348. In addition, as discussed, the bore 348 can be configured to receive a portion of the connecting arm 420 therein, when the connecting arm 420 is coupled to the bottom portion 460.

With continued reference to FIG. 20, the top portion 352 of the saddle 307 can be coupled to the middle portion 462 so that the top portion 352 can move relative to at least one of the bottom portion 460 and the middle portion 462, as will be discussed in greater detail herein. The middle portion 462 can be coupled between the top portion 352 and the bottom portion 460. Generally, the middle portion 462 can be movable or translatable relative to each of the top portion 352 and the bottom portion 460. The middle portion 462 can be generally octagonal in shape. It should be noted that the shape of the middle portion 462 is merely exemplary, as any suitable shape could be used, such as cylindrical, rectangular, etc. The middle portion 462 can include a first or rail surface 464 opposite a second or guide surface 466 and a bore 468. The bore 468 can be defined about a central axis of the middle portion 462, and can coaxially aligned with the bore 358 of the bottom portion 460 and the central bore 374 of the top portion 352. The bore 468 can be sized to enable a portion of the lock ring 402 to extend through the middle portion 462.

The rail surface 464 can include at least one rail 464a. Generally, the rail surface 464 can include two rails 464a, 464b, which can be configured to movably or slidably engage the guides 372a, 372b of the top portion 352. The engagement between the rails 464a, 464b and the guides 372a, 372b can enable the top portion 352 of the saddle 406 to move or translate relative to the middle portion 462 of the saddle 406.

The guide surface 466 can include at least one guide 466a. Generally, the guide surface 466 can include two guides 466a, 466b, which can be configured to movably or slidably engage the rails 360a, 360b of the bottom portion 460 of the saddle 406. The engagement between the guides 466a, 466b and the rails 360a, 360b can enable the bottom portion 460 of the saddle 406 to move or translate relative to the middle portion 462 of the saddle 406.

It should be understood, however, that although the top portion 352, the middle portion 462 and the bottom portion 460 are illustrated and described herein as including rails and guides to enable the relative motion, any suitable device or mechanism could be used to enable the relative motion between the top portion 352, the middle portion 462 and the bottom portion 460, such as a monorail assembly, etc. It should also be understood that the guides 372a, 372b, 466a, 466b of the top portion 352 and the middle portion 462 could be interchanged with the rails 360a, 360b, 464a, 464b of the bottom portion 350 and the middle portion 462, if desired.

With reference to FIGS. 19 and 20, in order to assemble the multiplanar bone anchor system 400, the connecting arm 420 can be coupled to the channel 108a of the bone fastener 102. Then, the lock ring 402 can be coupled to the connecting arm 420. Next, the bottom portion 460 of the saddle 406 can be coupled to the connecting arm 420, such that the connecting arm 420 can move or rotate relative to the bottom portion 460 of the saddle 406. The middle portion 462 can be coupled to the rails 360a, 360b of the bottom portion 460 of the saddle 406 to enable the middle portion 462 to move or translate relative to the bottom portion 460. Note that the movement of the middle portion 462 relative to the bottom portion 460 can be limited by contact between a sidewall 468a of the bore 468 of the middle portion 462 and the lock ring 402 (FIG. 20). Then, the top portion 352 of the saddle 406 can be coupled to the middle portion 462 so that the guides 372a, 372b are slidably coupled to the rails 464a, 464b of the connecting arm 420. Note that the movement of the top portion 352 relative to the middle portion 462 can be limited by contact between a sidewall 374b of the bore 374 of the top portion 352 and the lock ring 402 (FIG. 20).

Once assembled, the connecting arm 420 can cooperate with the bone fastener 102 to enable movement or rotation of the bone fastener 102 about the central or longitudinal axis of the bone fastener 102, which provides a first plane of motion. The bottom portion 460 of the saddle 406 can also rotate relative to the bone fastener 102, and thus, the top portion 352 of the saddle 406 can rotate relative to the bone fastener 102 to thereby define a second plane of motion. In addition, the middle portion 462 can move or translate relative to the connecting arm 420, thereby defining a third plane of motion. As the top portion 352 can also move or translate relative to the middle portion 462, the multiplanar bone anchor system 400 can define a fourth plane of motion. Therefore, when assembled, the multiplanar bone anchor system 400 can have at least four degrees or planes of motion. By allowing the multiplanar bone anchor system 400 to move in at least four planes, the surgeon can manipulate the multiplanar bone anchor system 400 as necessary to conform to the anatomy of the patient.

As the surgical insertion and use of the multiplanar bone anchor system 400 in a fixation procedure can be similar to the surgical insertion and insertion of the multiplanar bone anchor system 300 in a fixation procedure, the surgical insertion and use of the multiplanar bone anchor system 400 will not be discussed in great detail herein. Briefly, however, once the multiplanar bone anchor system 400 is secured to the anatomy, the multiplanar coupling system 404 and the saddle 406 can be moved, rotated or translated relative to the bone fastener 102 into the desired alignment for the fixation procedure. Once the aligned, the connecting rod 20 can be coupled to a desired number of multiplanar bone anchor systems 400.

Figure 21:
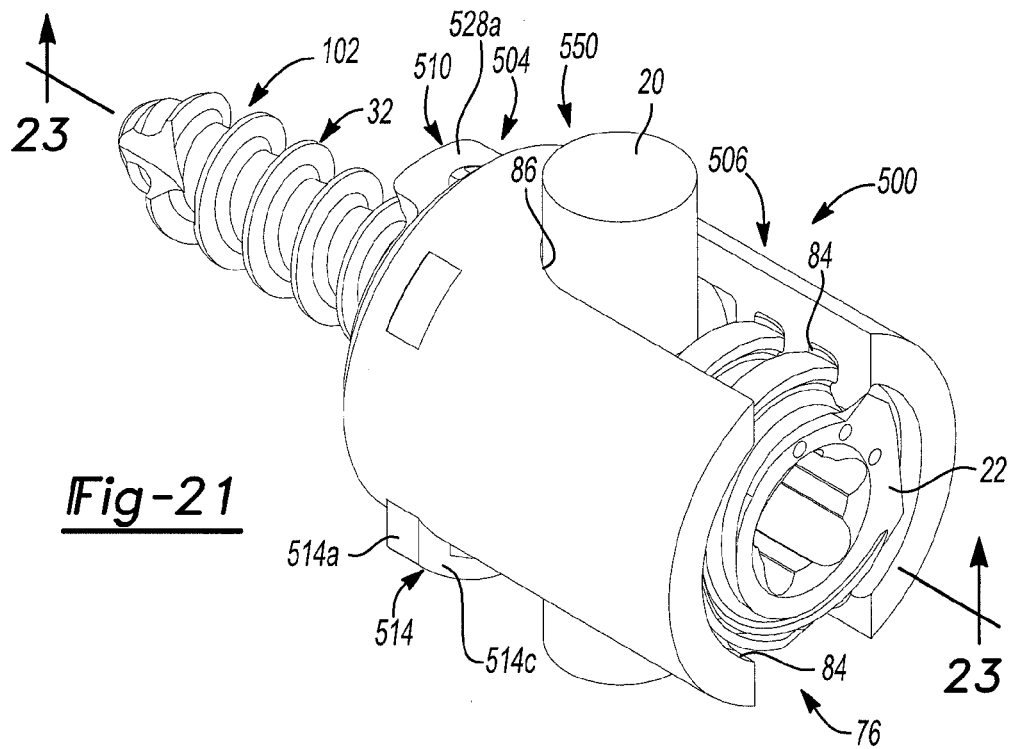
FIG. 21 is a schematic perspective illustration of another exemplary multiplanar bone anchor system for use with a connecting device in a fixation procedure according to the present teachings.
Figure 23:
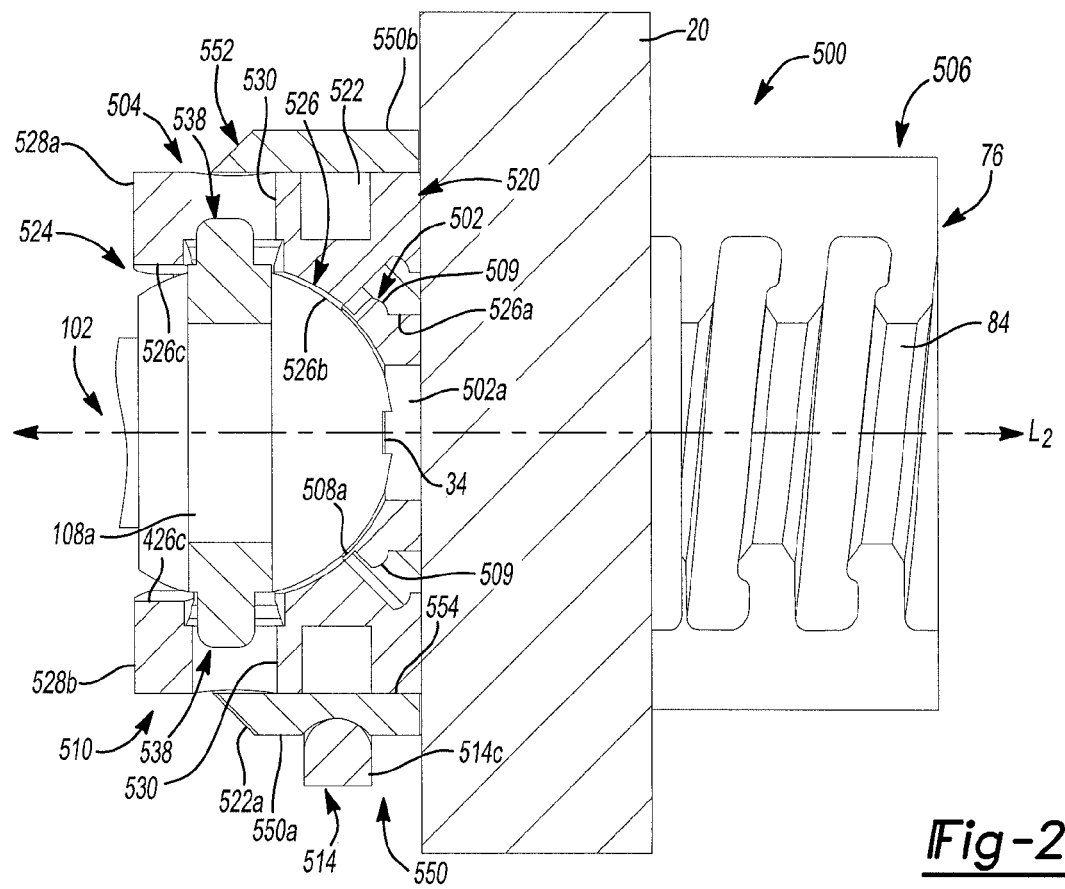
FIG. 23 is a schematic, cross-sectional illustration of the multiplanar bone anchor system of FIG. 21, taken along line 23-23 of FIG. 21.
Figure 22:
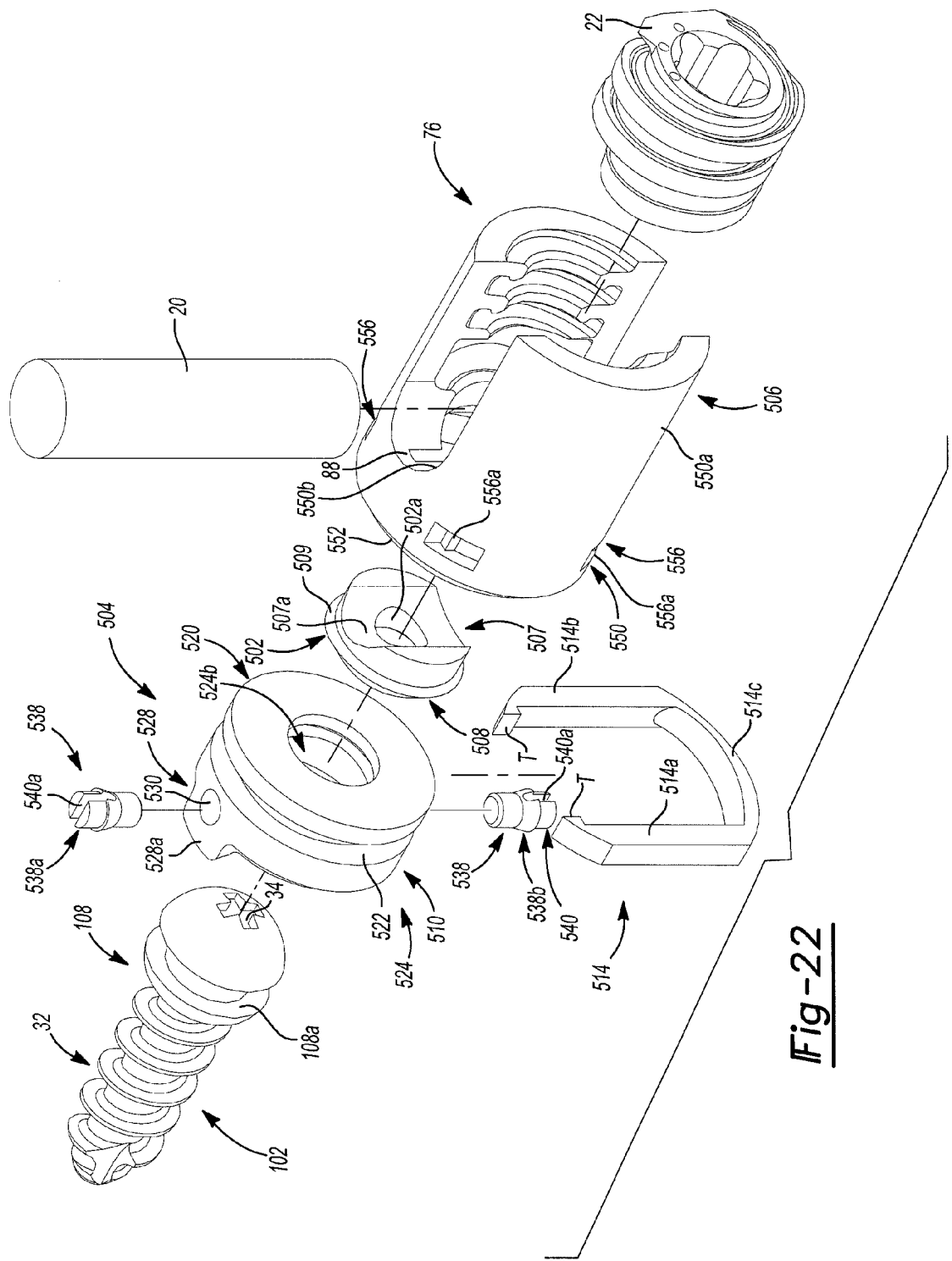
FIG. 22 is an exploded view of the multiplanar bone anchor system of FIG. 21.

With reference now to FIGS. 21-23, in one example, a multiplanar bone anchor system 500 can be employed with the connecting rod 20 to repair a damaged portion of an anatomy. As the multiplanar bone anchor system 500 can be similar to the multiplanar bone anchor system 100, 200 described with reference to FIGS. 9-15, only the differences between the multiplanar bone anchor system 100, 200 and the multiplanar bone anchor system 500 will be discussed in great detail herein, and the same reference numerals will be used to denote the same or similar components. The multiplanar bone anchor system 500 can include the bone fastener 102, a lock ring 502, a multiplanar coupling arrangement or system 504 and a saddle 506. It should be noted that although the multiplanar bone anchor system 500 is described and illustrated herein as including the lock ring 502, it should be understood that the multiplanar bone anchor system 500 need not include the lock ring 502. Furthermore, the multiplanar bone anchor system 500 could employ the lock ring 14 instead of the lock ring 502, if desired.

The lock ring 502 can be received within the saddle 506, and can cooperate the multiplanar coupling system 504 and the saddle 506 to fixedly couple or lock the bone fastener 102 into a desired angular position (FIG. 23). In one example, with reference to FIG. 22, the lock ring 502 can include a continuous cylindrical body, which can be formed out of any suitable biocompatible material, such as a biocompatible metal, ceramic, metal alloy, polymer or combinations thereof. The lock ring 502 can include a first or proximal end 507, a second or distal end 508 and a flange 509. In addition, the lock ring 502 can include a bore 502a, which can enable a tool to engage the driver interface feature 34 of the bone fastener 102.

The proximal end 507 of the lock ring 502 can define a first concave surface 507a, which can have a curvature configured to mate with the connecting rod 20. In this regard, the lock ring 502 can support a portion of the connecting rod 20 when the connecting rod 20 is coupled to the multiplanar bone anchor system 500. In this example, the force applied by the set screw 22 to couple the connecting rod 20 to the multiplanar bone anchor system 500 can apply a force to the lock ring 502 to fixedly couple or lock the bone fastener 102 in the desired angular position.

The distal end 508 of the lock ring 502 can apply a force to the head 108 of the bone fastener 102 to fixedly couple or lock the bone fastener 102 in the desired angular position. With reference to FIG. 23, the distal end 508 can define a second concave surface 508a. The concave surface 508a can be configured to mate with the head 108 of the bone fastener 102 to fixedly couple or lock the bone fastener 102 in the desired angular position when the force is applied to the lock ring 502.

The flange 509 can extend about a circumference of the lock ring 502, and can be positioned between the proximal end 507 and the distal end 508 of the lock ring 502. The flange 509 can be integrally formed with the lock ring 502, or could be coupled to the circumference of the lock ring 502 through any suitable manufacturing technique, such as overmolding, adhesives, etc. The flange 509 can be configured to engage a portion of the multiplanar coupling system 504 to couple the lock ring 502 to the multiplanar coupling system 504, as will be discussed in greater detail herein.

With reference to FIGS. 21-23, the multiplanar coupling system 504 can include a connecting arm 510, at least one plug 538 and a retaining clip 514. In one example, the multiplanar coupling system 504 can include two plugs 538. The connecting arm 510 and the plugs 538 can cooperate with the bone fastener 102 to enable the bone fastener 102 to move relative to the saddle 506. The connecting arm 510 can be disposed about a head 30 of the bone fastener 102 to enable the bone fastener 102 to move or articulate relative to the saddle 506. In this example, the connecting arm 510 can be cylindrical, and can be coupled to the saddle 506 via the retaining clip 514, as will be discussed (FIG. 23). The connecting arm 510 can include a first or proximal end 520, a channel 522, a second or distal end 524 and a bore 526.

The proximal end 520 can be received within the saddle 506, when the saddle 506 is coupled to the connecting arm 510 (FIG. 23). The channel 522 can be disposed between the proximal end 520 and the distal end 524. The channel 522 can be received within the saddle 506 and can cooperate with the saddle 506 and the retaining clip 514 to couple the connecting arm 510 to the saddle 506, as will be discussed. A majority of the distal end 524 can be disposed outside of the saddle 506 when the connecting arm 510 is coupled to the saddle 506 (FIG. 23). The distal end 524 can include at least one flange 528.

In one example, with continued reference to FIG. 23, the distal end 524 can include two flanges 528a, 528b. Generally, the flanges 528 can be positioned opposite each other, and can each extend for a length beyond the distal end 524 of the connecting arm 510, as shown in FIG. 22. With reference back to FIG. 23, each of the flanges 528 can include a bore 530. Each of the bores 530 can receive a portion of one of the plugs 538 to couple the bone fastener 102 to the connecting arm 510, as will be discussed in greater detail herein. In one example, the bores 530 can be defined through the circumference of the flanges 528 such that the bores 530 are in communication with the bore 526.

The bore 526 can be defined from the proximal end 520 to the distal end 524. The bore 526 can be formed about a central axis of the connecting arm 510. The bore 526 can receive at least a portion of the lock ring 502 when the multiplanar bone anchor system 500 is assembled. In this regard, with reference to FIG. 23, the bore 526 can include a lock ring coupling portion 526a, a bearing portion 526b and a limiting portion 526c.

The lock ring coupling portion 526a can be formed near or at the proximal end 520. The lock ring coupling portion 526a can be configured to engage the flange 509 of the lock ring 502 to couple the lock ring 502 to the connecting arm 510. In one example, the lock ring coupling portion 526a can comprise a portion of the bore 526 that has a contour that mates with an exterior contour of the lock ring 502, however, it should be understood that the lock ring coupling portion 526a can have any desired configuration operable to retain the lock ring 502 within the connecting arm 510. In this example, the lock ring coupling portion 526a can be formed such that the proximal end 507 of the lock ring 502 extends beyond the proximal end 520 of the connecting arm 510 so that the connecting rod 20 can be received within the concave surface 507a of the lock ring 502.

The bearing portion 526b can be formed adjacent to the proximal end 520 of the connecting arm 510. The bearing portion 526b can be generally concave, and can be configured to mate with at least a portion of the hemispherical head 30 of the bone fastener 102. The bearing portion 526b can enable the bone fastener 102 to move, rotate or articulate relative to the connecting arm 510. The limiting portion 526c can be defined adjacent to the distal end 524 of the connecting arm 510. Although not illustrated herein, the limiting portion 526c can include a taper, if desired. Generally, the limiting portion 526c can limit the range of motion or articulation of the bone fastener 102.

With reference to FIG. 22, the plugs 538 can cooperate with the connecting arm 510 to enable the bone fastener 102 to move or rotate about the longitudinal axis L2 of the bone fastener 102. The plugs 538 can couple the bone fastener 102 to the connecting arm 510. Each of the plugs 538 can include a coupling end 540. The coupling end 540 can couple the plug 538 to the connecting arm 510. The coupling end 540 can include a fastening feature 540a, which can be accessible when the plugs 538 are coupled to the connecting arm 510. The fastening feature 540a can comprise any suitable feature, such as a slot, cut-out or other feature engagable by a tool. Generally, the fastening feature 540a can enable a tool, such as a driver, to couple the plug 538 to the connecting arm 510 and the head 30 of the bone fastener 12. In addition, if desired, the plugs 538 could be integrally formed with the connecting arm 510. It should be noted that the shape of the plugs 538 is merely exemplary, as the plugs 538 could have any desired shape, such as elliptical, spherical, rounded, annular, cylindrical, rounded square, rounded rectangular, etc. In addition, although not illustrated herein, the plugs 538 can include one or more tapered surfaces, which can enable the bone fastener 102 to move or pivot relative to the connecting arm 510, if desired.

With reference to FIGS. 22 and 23, the retaining clip 514 can couple the saddle 506 to the connecting arm 510. The retaining clip 514 can comprise a substantially U-shaped clip, such as Dutchman clip, for example. As a Dutchman clip can be generally known, the retaining clip 514 will not be discussed in great detail herein. Briefly, however, the retaining clip 514 can define a first arm 514a and a second arm 514b, which can be coupled together via a connector 514c. Each of the first arm 514a and the second arm 514b can include a locking tang T. Generally, the first arm 514a and the second arm 514b can be flexible, so that the retaining clip 514 can be biased into engagement with the saddle 506 and the connecting arm 510. As will be discussed, the retaining clip 514 can be received through a portion of the saddle 506 and through the channel 522 of the connecting arm 510 to movably or rotatably couple the saddle 506 to the connecting arm 510.

The saddle 506 can include the first or proximal end 76 and a second or distal end 550. The distal end 550 can be generally cylindrical, and can include the first or a receiver surface 88, a second or bottom surface 552, a central bore 554 and at least one slot 556.

As best shown in FIG. 23, the bottom surface 552 can include a taper 552a. The taper 552a can provide the bottom surface 552 with atraumatic edges. The central bore 554 can be defined from the receiver surface 88 through to the bottom surface 552 of the saddle 506. The central bore 554 can be configured to receive at least a portion of the connecting arm 510 rotatably therein. Thus, the central bore 554 can have a diameter, which can be slightly greater than a diameter of the connecting arm 510, so that the connecting arm 510 can rotate relative to the saddle 506.

The at least one slot 556 can be defined through a portion of the distal end 550 of the saddle 506. In one example, the at least one slot 556 can comprised two slots 556. The two slots 556 can be formed opposite each other, and can generally be formed a distance apart, with the distance between the two slots 556 about equal to a length of the connector 514c of the retaining clip 514.

The slots 556 can be defined from a first side 550a to a second side 550b of the distal end 550 of the saddle 506. The slots 556 can have a length from the first side 550a to the second side 550b, which can be about equal to a length of the first arm 514a and the second arm 514b. Given the length of the slots 556, the connector 514c of the retaining clip 514 can generally be disposed adjacent to an exterior surface of the distal end 550 of the saddle 506 (FIG. 23). It should be noted, however, that the saddle 506 could be configured so that the connector 514c is received within the saddle 506 when the retaining clip 514 is coupled to the saddle 506 and connecting arm 510.

The slots 556 can each include a tab 556a, which can be formed near the second side 550b of the distal end 550. The tab 556a can cooperate with the tang T of the first arm 514a and the second arm 514b to couple the retaining clip 514 to the saddle 506. By coupling the retaining clip 514 to the saddle 506, the connecting arm 510 can also be coupled to the saddle 506.

In this regard, with reference to FIGS. 22 and 23, in order to assemble the multiplanar bone anchor system 500, the lock ring 502 can be positioned within the bore 526 and coupled to the lock ring coupling portion 526a via the flange 509 of the lock ring 502. With the lock ring 502 coupled to the connecting arm 510, the distal end 550 of the saddle 506 can be positioned onto the proximal end 520 of the connecting arm 510. Next, the bone fastener 102 can be coupled to the connecting arm 510 by snap-fitting, press-fitting or threading the plugs 538 into engagement with the bores 530 of the connecting arm 510 so that the bone fastener 102 can move (rotate and pivot) relative to the connecting arm 510.

With the distal end 550 of the saddle 506 positioned about at least the proximal end 520 of the connecting arm 510, the retaining clip 514 can be inserted into the slots 556 so that the tangs T of the first arm 514a and the second arm 514b can engage the tabs 556a of the slots 556. The first arm 514a and the second arm 514b can be inserted such that the first arm 514a and the second arm 514b can be at least partially retained within the channel 522 of the connecting arm 510. Thus, the retaining clip 514 can be employed to couple the connecting arm 510 and bone fastener 102 to the saddle 506.

Once assembled, the plugs 538 can cooperate with the channel 108a of the bone fastener 102 to enable movement or rotation of the bone fastener 102 about the central or longitudinal axis of the bone fastener 102, thereby providing a first plane of motion. In addition, the retaining clip 514 can enable the connecting arm 510 to move or rotate relative to the saddle 506, thereby defining a second plane of motion. Thus, when assembled, the multiplanar bone anchor system 500 can have at least two planes or degrees of motion. By allowing the multiplanar bone anchor system 500 to move in at least two planes, the surgeon can manipulate the multiplanar bone anchor system 500 as necessary to conform to the anatomy of the patient.

As the surgical insertion and use of the multiplanar bone anchor system 500 in a fixation procedure can be similar to the surgical insertion and insertion of the multiplanar bone anchor system 100, 200 in a fixation procedure, the surgical insertion and use of the multiplanar bone anchor system 500 will not be discussed in great detail herein. Briefly, however, once the multiplanar bone anchor system 500 is secured to the anatomy, the bone fastener 102, the multiplanar coupling system 504 and/or the saddle 506 can be moved or rotated relative to one another until the multiplanar bone anchor system 500 is in the desired alignment for the fixation procedure. Once the aligned, the connecting rod 20 can be coupled to a desired number of multiplanar bone anchor systems 500.

Figure 24:
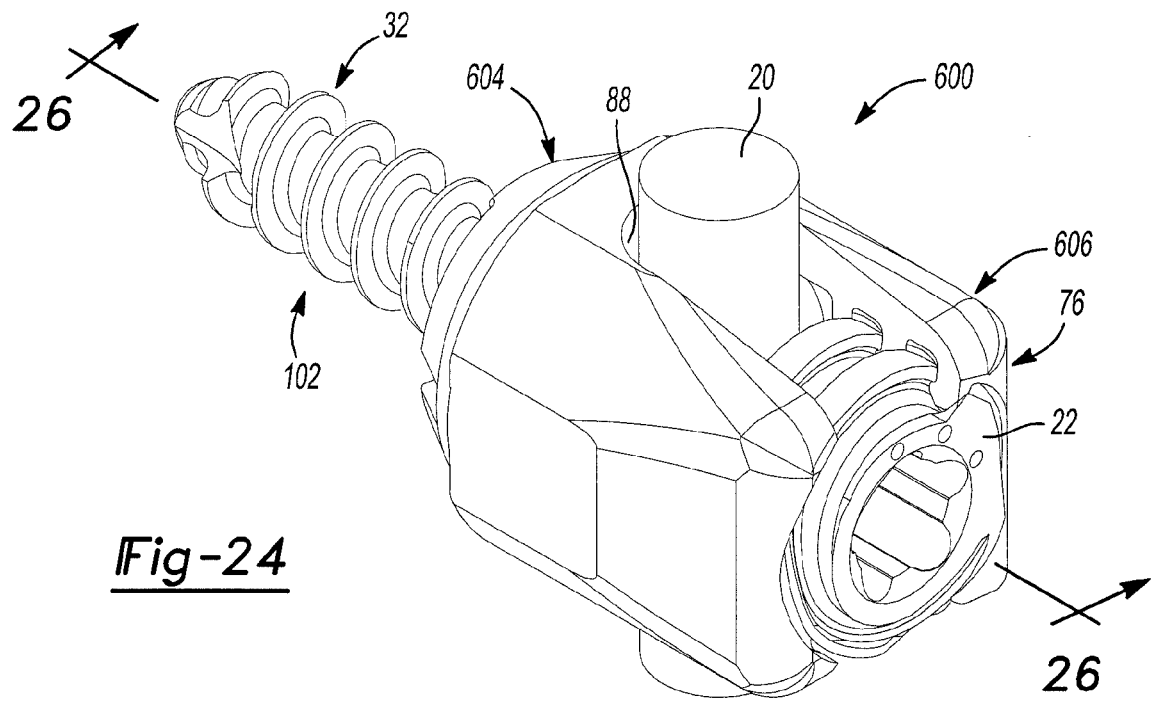
FIG. 24 is a schematic perspective illustration of another exemplary multiplanar bone anchor system for use with a connecting device in a fixation procedure according to the present teachings.
Figure 26:
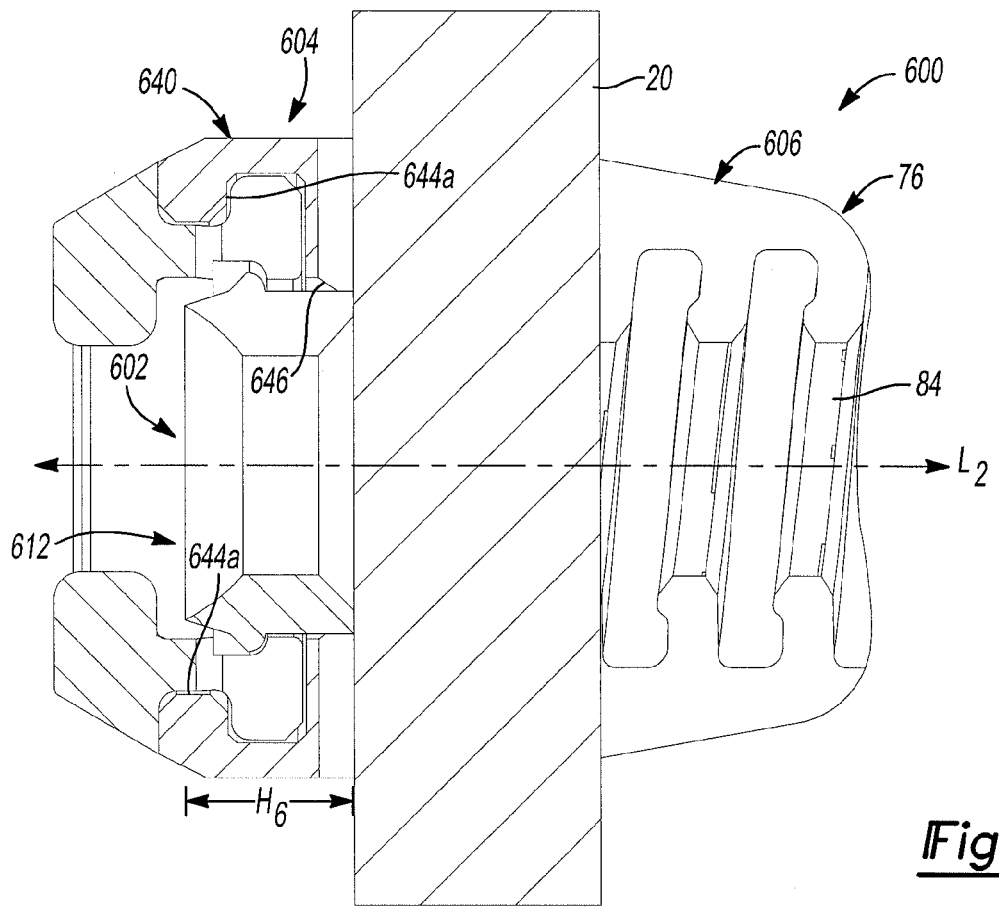
FIG. 26 is a schematic, cross-sectional illustration of the multiplanar bone anchor system of FIG. 24, taken along line 26-26 of FIG. 24.
Figure 25:
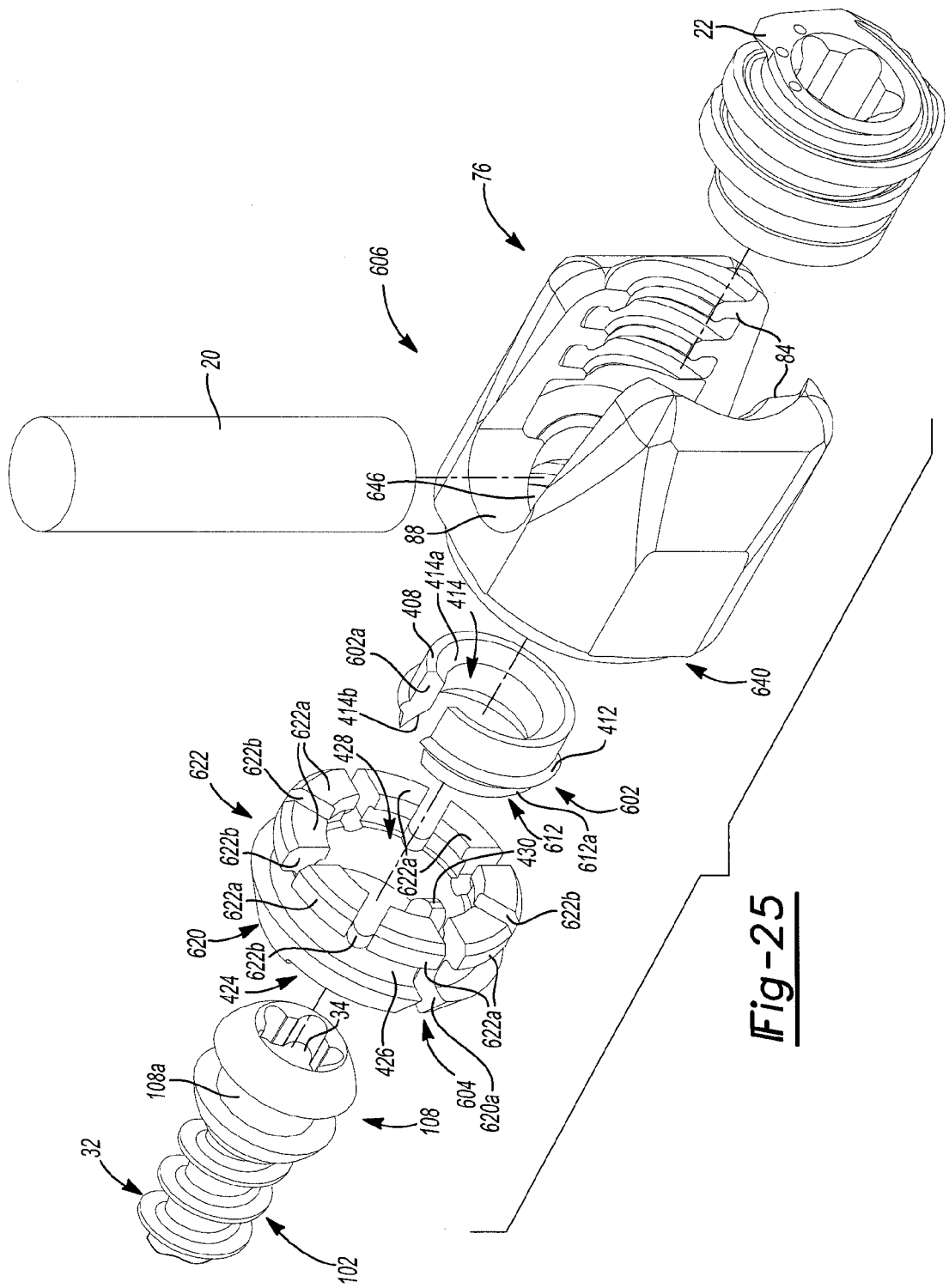
FIG. 25 is an exploded view of the multiplanar bone anchor system of FIG. 24.

With reference now to FIGS. 24-26, in one example, a multiplanar bone anchor system 600 can be employed with the connecting rod 20 to repair a damaged portion of an anatomy. As the multiplanar bone anchor system 600 can be similar to the multiplanar bone anchor system 400 described with reference to FIGS. 18-20, only the differences between the multiplanar bone anchor system 400 and the multiplanar bone anchor system 600 will be discussed in great detail herein, and the same reference numerals will be used to denote the same or similar components. The multiplanar bone anchor system 600 can include the bone fastener 102, a lock ring 602, a multiplanar coupling arrangement or system 604 and a saddle 606.

The lock ring 602 can be positioned about the head 108 of the bone fastener 102. The lock ring 602 can couple or lock the bone fastener 102 relative to the multiplanar coupling system 604 via a force applied by the connecting rod 20, as will be discussed herein. With reference to FIG. 26, the lock ring 602 can be generally cylindrical, and can have a height H6. The height H6 be sized to extend above or about equal to a receiver surface 88 of the saddle 606 so that coupling the connecting rod 20 to the saddle 606 can compress the lock ring 602 onto the head 108 of the bone fastener 102. In this example, the lock ring 602 can include a cut out 602a, which can facilitate positioning the lock ring 602 about the head 108 of the bone fastener 102. It should be understood, however, that the cut out 602a can be optional, as the lock ring 602 can have a continuous, uninterrupted cylindrical body. In addition, the lock ring 602 can include the proximal end 408, a distal end 610, the flange 412 and the bore 414. With reference to FIGS. 25 and 26, the distal end 610 can be coupled to the head 108 of the bone fastener 102 when the lock ring 602 is coupled to bone fastener 102.

The multiplanar coupling system 604 can include a connecting arm 620. The connecting arm 620 can cooperate with the bone fastener 102 to enable the bone fastener 102 to move relative to the saddle 606. It should be noted that although the multiplanar coupling system 604 is described and illustrated herein as including only a connecting arm 620, the multiplanar coupling system 604 could include a ring, such as the ring 322 illustrated in FIG. 16, if desired. In this example, the connecting arm 620 can have a cylindrical body, which can include a cut out 620a. The cut out 620a can facilitate the coupling of the connecting arm 620 to the head 108 of the bone fastener 102. For example, the cut out 620a can enable the connecting arm 620 to be snap-fit around the head 108 of the bone fastener 102. It should be noted, however, that the cut out 620a can be optional, as the connecting arm 620 could have a continuous, uninterrupted cylindrical body. In the case of a continuous, uninterrupted cylindrical body, the connecting arm 620 could be threaded over the shank 32 of the bone fastener 102 into engagement with the head 108 of the bone fastener 102.

In this example, the connecting arm 620 can further comprise a first or proximal end 622, the second or distal end 424, the channel 426, the bore 428 and the coupling feature 430. The proximal end 622 can include a plurality of arcuate members 622a, which can each be separated by one or more spaces 622b. The plurality of arcuate members 622a can generally be formed about a circumference of the proximal end 622. The plurality of arcuate members 622a can cooperate with the channel 426 to couple the connecting arm 620 to the saddle 606. The one or more spaces 622b can enable the plurality of arcuate members 622a to be flexible, such that the plurality of arcuate members 622a can be snap-fit into engagement with the saddle 606.

Generally, with reference to FIGS. 25 and 26, the saddle 606 can be coupled to the connecting arm 620 so that the connecting arm 620 can move or rotate relative to the saddle 606. The saddle 606 can be substantially U-shaped and symmetrical with respect to a longitudinal axis L2 defined by the multiplanar bone anchor system 600. The saddle 606 can include the first or proximal end 76 and a second or distal end 640.

With reference to FIG. 25, the distal end 640 of the saddle 606 can be generally rectangular, and can include the first or a receiver surface 88, a second or bottom surface 644 and a bore 646. With reference to FIG. 26, the bottom surface 644 can include a lip 644a. The lip 644a can extend downwardly from the bottom surface 644 about the perimeter of the bottom surface 644. The lip 644a can be configured to be received in the channel 426 so that a portion of the bore 646 can surround the plurality of arcuate members 622a to couple the saddle 606 to the connecting arm 620. This can also enable the saddle 606 to move or rotate relative to the connecting arm 620.

With reference to FIGS. 25 and 26, in order to assemble the multiplanar bone anchor system 600, the connecting arm 620 can be coupled to the channel 108a of the bone fastener 102. Then, the lock ring 602 can be coupled to the connecting arm 620. Next, the distal end 640 of the saddle 606 can be coupled to the connecting arm 620, such that the connecting arm 620 can move or rotate relative to the saddle 606.

Once assembled, the connecting arm 620 can cooperate with the bone fastener 102 to enable movement or rotation of the bone fastener 102 about the central or longitudinal axis of the bone fastener 102, which can provide a first plane of motion. The saddle 606 can also rotate relative to the connecting arm 620, which can thereby define a second plane of motion. In addition, the saddle 606 can rotate relative to the bone fastener 102 to thereby define a third plane of motion. Therefore, when assembled, the multiplanar bone anchor system 600 can have at least three degrees or planes of motion. By allowing the multiplanar bone anchor system 600 to move in at least three planes, the surgeon can manipulate the multiplanar bone anchor system 600 as necessary to conform to the anatomy of the patient.

As the surgical insertion and use of the multiplanar bone anchor system 600 in a fixation procedure can be similar to the surgical insertion and insertion of the multiplanar bone anchor system 400 in a fixation procedure, the surgical insertion and use of the multiplanar bone anchor system 600 will not be discussed in great detail herein. Briefly, however, once the multiplanar bone anchor system 600 is secured to the anatomy, the multiplanar coupling system 604 and the saddle 606 can be moved or rotated relative to the bone fastener 102 into the desired alignment for the fixation procedure. Once the aligned, the connecting rod 20 can be coupled to a desired number of multiplanar bone anchor systems 600.

With reference to FIG. 27, while the multiplanar bone anchor system 300 has been described herein with reference to FIGS. 15-17 as including the bone fastener 302, the lock ring 304, the connecting arm 320, the ring 322 and the bottom portion 350, those of skill in the art will appreciate that the present disclosure, in its broadest aspects, may be constructed somewhat differently. In this regard, a multiplanar bone anchor system 300' could include the bone fastener 102, the lock ring 402, the connecting arm 420 and the bottom portion 460 associated with the multiplanar bone anchor system 400. In this example, the multiplanar bone anchor system 300' can provide multiple planes of motion while requiring fewer components, which may be desirable for manufacturing purposes.

As a further example, with reference to FIGS. 28-30, while the multiplanar bone anchor system 10, 100, 200, 500 has been described herein as having a ring 50, 112, 322, those of skill in the art will appreciate that the present disclosure, in its broadest aspects, may be constructed somewhat differently. In this regard, a connecting arm 700 could be employed in place of the ring 50, 112, 322. The connecting arm 700 can cooperate with the bone fastener 102, and can include at least one bore 702 and at least one plug 704. The connecting arm 700 can also define a throughbore 706, which can receive the head 108 of the bone fastener 102 therein. The at least one plug 704 can be coupled to the at least one bore 702 of the connecting arm 700 to enable the bone fastener 102 to rotate relative to the connecting arm 700. In this example, the at least one plug 704 can include two plugs 704, which can be received within two opposite bores 702. Each of the plugs 704 can be press fit into the bores 702 so that a bearing surface 704a formed on the plugs 704 can rotate about the channel 108a of the bone fastener 102.

Figures 31, 32:
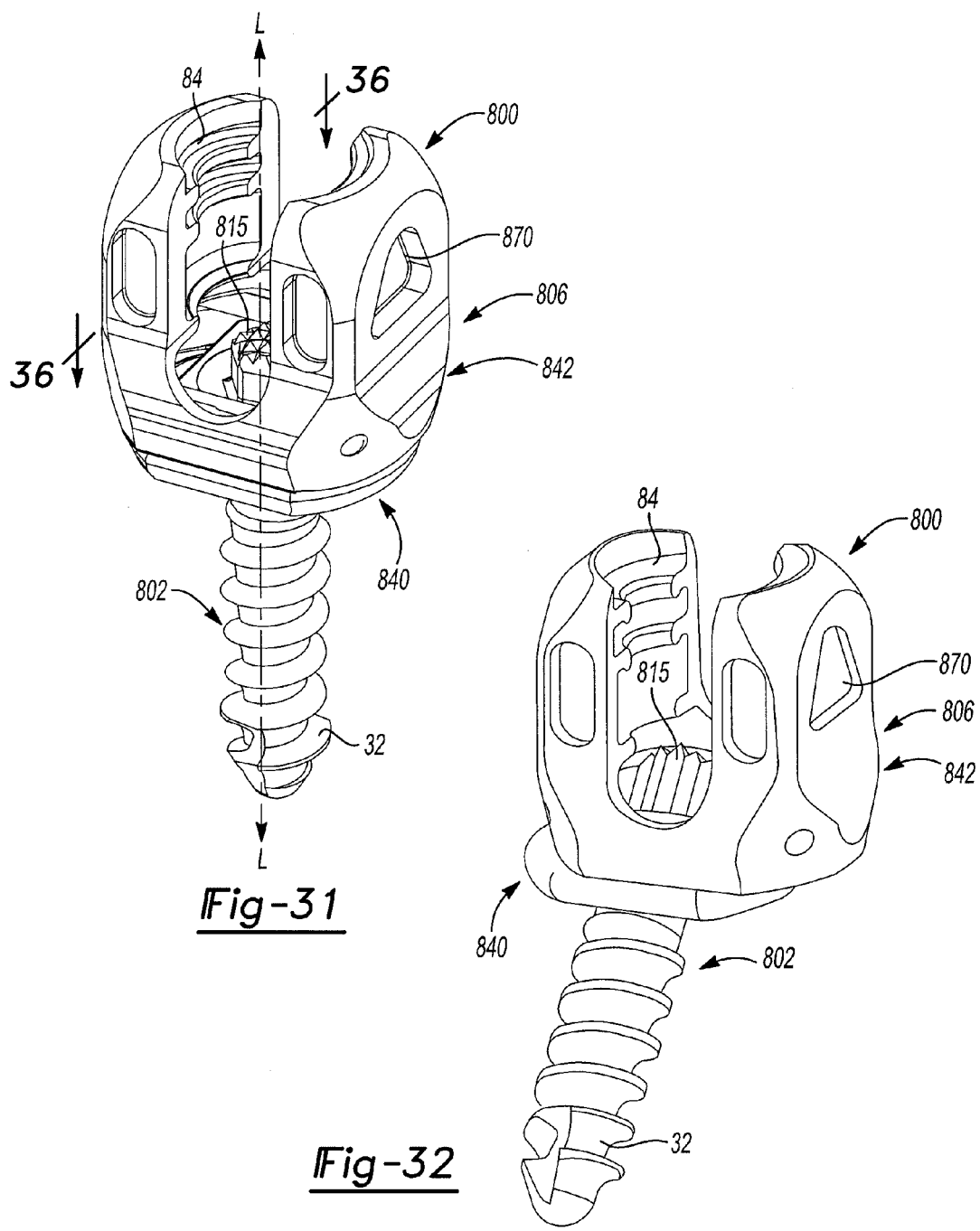
FIG. 31 is a perspective view of another exemplary multiplanar bone anchor system for use with a connecting device in a fixation procedure according to the present teachings.
FIG. 32 is a schematic illustration of the exemplary multiplanar bone anchor system of FIG. 31 in one of various positions.

With reference now to FIGS. 31-36, in one example, a multiplanar bone anchor system 800 can be employed with the connecting rod 20 to repair a damaged portion of an anatomy. As the multiplanar bone anchor system 800 can be similar to the multiplanar bone anchor system 10 described with reference to FIGS. 1-8, only the differences between the multiplanar bone anchor system 10 and the multiplanar bone anchor system 800 will be discussed in great detail herein, and the same reference numerals will be used to denote the same or similar components. The multiplanar bone anchor system 800 can include a bone fastener 802, a multiplanar coupling arrangement or system 804 (FIG. 33) and a saddle 806 (FIG. 31). The multiplanar bone anchor system 800 can define a longitudinal axis L, and the multiplanar bone anchor system 800 can be configured such that the bone fastener 802 and the saddle 806 can move relative to the longitudinal axis L in multiple planes.

As will be discussed in greater detail herein, the multiplanar coupling system 804 can enable the saddle 806 to move relative to the bone fastener 802 in multiple planes. Generally, the saddle 806 can be configured to receive the connecting device or rod 20, which can be used to interconnect multiple bone anchor systems 800 in an exemplary spinal fixation procedure (similar to that illustrated in FIG. 1). By using the multiplanar coupling system 804, the saddle 806 can be moved relative to the bone fastener 802 in one or more planes to facilitate the connection of the connecting rod 20 to multiple bone anchor systems 800. In this regard, the vertebral bodies V of the patient may be orientated in such a manner that each bone fastener 802, when coupled to a respective vertebral body V, may be slightly offset from one another. By allowing the saddle 806 to move in multiple planes relative to the bone fastener 802, the surgeon can move the saddles 806 into alignment without regard to the placement of the bone fasteners 802. It should be noted, however, that although the multiplanar bone anchor system 800 is generally illustrated and described herein a single assembly for use with a single connecting rod 20, any combination of bone anchor systems 800 and connecting rods 20 can be employed during a surgical procedure.

For example, in a single level spinal fixation procedure, two bone anchor systems 800 can receive a single connecting rod 20. A multiple level spinal fixation procedure, however, will generally require additional bone anchor systems 800. In addition, the multiplanar bone anchor systems 800 need not be coupled to adjacent vertebral bodies V, but rather, the multiplanar bone anchor systems 800 can be positioned so as to skip adjacent vertebral bodies V, if desired.

Figure 33:
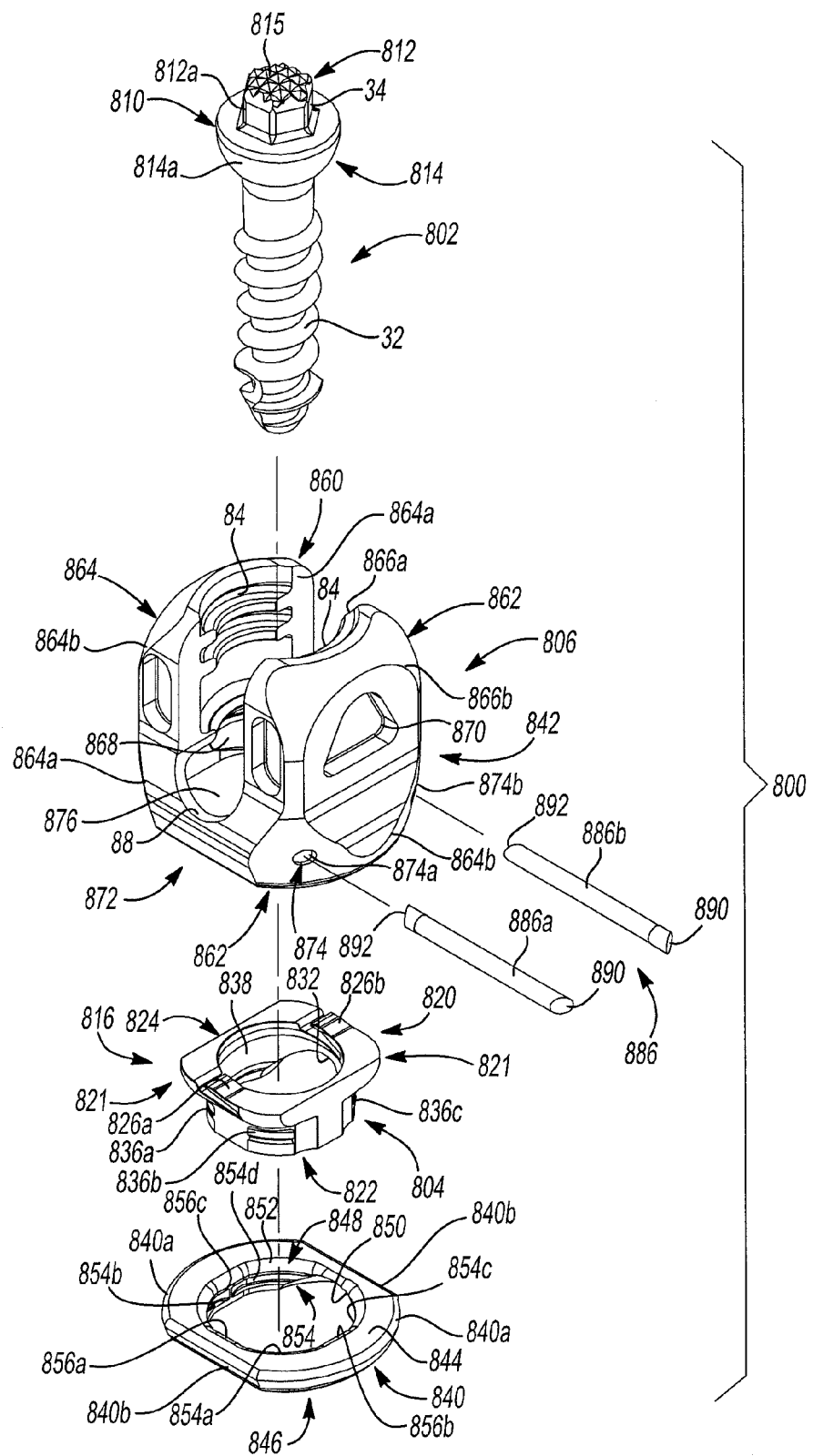
FIG. 33 is an exploded view of the multiplanar bone anchor system of FIG. 31.

With reference to FIG. 33, the bone fastener 802 can be configured to engage the anatomy to couple the multiplanar bone anchor system 800 to the anatomy. The bone fastener 802 can be composed of any suitable biocompatible material, such as titanium, stainless steel, biocompatible metals, metal alloys, polymers, etc. The bone fastener 802 can include a proximal end or head 810 and the distal end or shank 32. The head 810 can include a first or upper portion 812 and a second or lower portion 814.

The upper portion 812 can include a contact surface 815 and the driver connection feature 34. The contact surface 815 can be adjacent to the connecting rod 20 when the connecting rod 20 is received within the saddle 806. As will be discussed greater herein, in one example, when the set screw 22 is coupled to the saddle 806 to lock the connecting rod 20 to the multiplanar bone anchor system 800, the connecting rod 20 can be pushed or forced into engagement with the contact surface 815. The contact between the contact surface 815 and the connecting rod 20 can frictionally lock the bone fastener 802 relative to the saddle 806, thereby preventing further movement of the bone fastener 802. It should be noted, however, that depending upon the angulation of the bone fastener 802, the lower portion 814 could also be in contact with the connecting rod 20.

In one example, the contact surface 815 can be formed on the driver connection feature 34, and can comprise, for example, a roughened or knurled surface formed along a proximalmost surface 812a of the driver connection feature 34. It should be noted that the contact surface 815 is merely exemplary, and the upper portion 812 could comprise a smooth surface, if desired.

Briefly, it should be noted that particular tools for use with the multiplanar bone anchor system 10 are beyond the scope of the present teachings and need not be described herein. In a conventional manner insofar as the present teachings are concerned, various tools can be used to connect the multiplanar bone anchor system 10 to a respective vertebral body V. Exemplary tools can include those employed in the Polaris™ 5.5 Spinal System, commercially available from Biomet, Inc. of Warsaw, Ind., or the tools disclosed in commonly owned U.S. Patent Publication No. 2008/0077138, filed on Apr. 20, 2007 and incorporated by reference herein.

The lower portion 814 of the head 810 can be generally hemispherical or conical. The lower portion 814 can provide a bearing surface 814a, which can cooperate with the multiplanar coupling system 804 to enable the movement (rotation, articulation) of the bone fastener 802 within the saddle 806, as will be discussed in greater detail herein. Generally, the bone fastener 802 can rotate about the longitudinal axis L and can also pivot in a single plane or multiple planes relative to the longitudinal axis L, as will be discussed herein. In addition, a proximalmost surface of the lower portion 814 can cooperate with a portion of the multiplanar coupling system 804 to provide a frictional fit between the bone fastener 802 and the multiplanar coupling system 804.

In one example, the multiplanar coupling system 804 can include a connecting arm 816. The connecting arm 816 can be composed of any suitable biocompatible material, such as a biocompatible metal, metal alloy, ceramic or polymer. The connecting arm 816 can be disposed about the head 810 of the bone fastener 802 to allow relative movement between the bone fastener 802 and the saddle 806, as shown in FIG. 32. The connecting arm 816 can be sized to fit within the saddle 806, and can also allow a portion of the saddle 806 to move or translate relative to another portion of the saddle 806, as will be discussed in greater detail herein. With reference to FIGS. 33-35, the connecting arm 816 can include a first or upper portion 820, a second or lower portion 822 and a bore 824.

The upper portion 820 can be shaped to be received within a portion of the saddle 806, and can be generally rectangular with rounded corners. In one example, the upper portion 820 can have opposite curved features 821. The opposite curved features 821 can include a generally straight portion 821a. As will be discussed in greater detail herein, the straight portion 821a can cooperate with the saddle 806 to enable the saddle 806 to move or translate relative to the upper portion 820 of the connecting arm 816. The opposite curved features 821 can project outwardly from or extend outwardly away from the lower portion 822 of the connecting arm 816 and can aid in retaining a portion of the saddle 806 on the connecting arm 816, as will be discussed in greater detail herein. With reference to FIG. 34, the upper portion 820 can include at least one friction surface 826, a retention surface 828 and a rail 829.

The at least one friction surface 826 can be formed on opposite sides of the bore 824 along an exterior surface of the connecting arm 816. In one example, the at least one friction surface 826 can comprise a first leaf spring 826a and a second leaf spring 826b. It should be noted that although the at least one friction surface 826 is described and illustrated herein as comprising two leaf springs, the at least one friction surface 826 could comprise a single leaf spring, a frictional coating or other interference, which can control the movement of a portion of the saddle 806 relative to the connecting arm 816 and another portion of the saddle 806, as will be discussed in greater detail herein.

The retention surface 828 can be formed on the upper portion 820 near an end 820a of the upper portion 820. The retention surface 828 can extend slightly into the bore 824 so as to form a lip to retain the bone fastener 802 within the connecting arm 816. Generally, the retention surface 828 can extend about a majority of a circumference of the bore 824, but the retention surface 828 could be formed about the entire circumference of the bore 824 if desired. Further, it should be noted that the use of a retention surface 828 is merely exemplary, as any suitable feature could be used to retain the bone fastener 802 within the connecting arm 816 such as one or more protrusions extending into the bore 824.

The rail 829 can be formed below each of the opposite curved features 821, and can provide a contact surface for a portion of the saddle 806 to move or translate relative to the connecting arm 816 (FIG. 36). The rail 829 can be positioned adjacent to the lower portion 822.

With reference to FIGS. 34 and 35, the lower portion 822 can include a connection surface 830 and a preferred angle slot 832. The connection surface 830 can comprise at least one flat surface 834 and at least one rib 836. The at least one flat surface 834 and at least one rib 836 can cooperate with a portion of the saddle 806 to couple that portion of the saddle 806 immovably to the connecting arm 816. In one example, the connecting surface 830 can comprise three flat surfaces 834a-834c and four ribs 836a-836d. The flat surfaces 834a-834c can generally alternate with the ribs 836a-836d about an exterior surface of the lower portion 822. The flat surfaces 834a-834d can prevent the connecting arm 816 from rotating relative to the portion of the saddle 806. The ribs 836a-836d can be formed along arcuate surfaces of the lower portion 822 and can be positioned a distance D from a bottommost surface 822a of the lower portion 822 (FIG. 35). The ribs 836a-836d can create an overlap interference or snap fit between the portion of the saddle 806 and the lower portion 822, as will be discussed in greater detail herein. It should be noted, however that the use the ribs 836a-836d is merely exemplary, as any suitable mechanism could be employed to couple the portion of the saddle 806 to the lower portion 822, such as pins, threads, etc.

The preferred angle slot 832 can enable the bone fastener 802 to articulate to a greater angle A relative to a longitudinal axis L of the multiplanar bone anchor system 800. In this regard, with reference to FIG. 36, the bone fastener 802 can generally articulate to an angle A1 relative to the longitudinal axis L along the portion of the connecting arm 816 that does not include the preferred angle slot 832. At the location of the preferred angle slot 832, the bone fastener 802 can generally articulate to the greater angle A relative to the longitudinal axis L. In one example, the angle A1 can be generally about less than the greater angle A, and the greater angle A can be between about 15 degrees and about 90 degrees. The preferred angle slot 832 can comprise an arcuate cut-out defined through the lower portion 822 of the connecting arm 816, which can be in communication with the bore 824. The arcuate cut-out of the preferred angle slot 832 can enable the bone fastener 802 to move or articulate to the greater angle A relative to the longitudinal axis L.

It should be noted that although only one preferred angle slot 832 is illustrated in the drawings, the connecting arm 816 can include any number of preferred angle slots 832 at any location along the connecting arm 816 to enable the bone fastener 802 to articulate in any selected direction. It should also be noted that the shape of the cut-out that forms the preferred angle slot 832 can be modified to reduce or increase the greater angle A of the articulation of the bone fastener 802 relative to the longitudinal axis L. Alternatively, the connecting arm 816 could be devoid of a preferred angle slot, if desired.

With reference to FIGS. 33-36, in one example, the bore 824 of the connecting arm 816 can be formed along the longitudinal axis L and can extend through an interior surface of the connecting arm 816 from the upper portion 820 to the lower portion 822. The bore 824 can be sized to receive the bone fastener 802, and can include a bearing surface 838. The bearing surface 838 can allow the bone fastener 802 to articulate within the connecting arm 816. The bearing surface 838 can be disposed about a portion of the bore 824 of the connecting arm 816, and can have a curve configured to mate with the bearing surface 814a of the bone fastener 802.

With reference to FIGS. 31-33, the saddle 806 can be coupled to the connecting arm 816 and can move or translate relative to the connecting arm 816. In this regard, the saddle 806 can include a first portion or bottom portion 840 and a second portion or top portion 842. The bottom portion 840 can be immovably coupled to the connecting arm 816, and the top portion 842 can move or translate relative to the bottom portion 840 and the connecting arm 816 (FIG. 32). It should be noted that the bottom portion 840 can be optional, if desired.

In one example, with reference to FIG. 33, the bottom portion 840 can include opposed generally arcuate surfaces 840a, which can be interconnected by generally straight or flat surfaces 840b. The shape of the bottom portion 840 can cooperate with the shape of the connecting arm 816 so that the bottom portion 840 can be coupled to the connecting arm 816. The bottom portion 840 can include a first or proximal end 844, a second or distal end 846 and a bore 848.

The proximal end 844 can be positioned adjacent to the top portion 842 when the saddle 806 is coupled to the connecting arm 816. The distal end 846 can include a preferred angle slot 850. The preferred angle slot 850 can be defined through the distal end 846 so as to be in communication with the bore 848. The preferred angle slot 850 of the bottom portion 840 can be positioned in substantially the same location relative to the connecting arm 816 such that when the bottom portion 840 is coupled to the connecting arm 816, the preferred angle slot 850 of the bottom portion 840 is aligned with the preferred angle slot 832 of the connecting arm 816. The alignment between the preferred angle slot 832 and the preferred angle slot 850 can enable the bone fastener 802 to move or articulate to the greater angle A (FIG. 36).

With reference to FIG. 36, in one example, the bore 848 can be formed along the longitudinal axis L from the proximal end 844 to the distal end 846. With reference to FIG. 33, the bore 848 can be sized and configured to be immovably coupled about the connecting arm 816. The bore 848 can include a rounded or chamfered edge 852, at least one groove 854 and at least one flat surface 856. The chamfered edge 852 can be formed at the proximal end 844. The chamfered edge 852 can provide a lead-in for coupling the bottom portion 840 to the connecting arm 816. It should be noted that the chamfered edge 852 can be optional.

The at least one groove 854 and the at least one flat surface 856 of the bottom portion 840 can cooperate with the at least one flat surface 834 and the at least one rib 836 of the connecting arm 816 to couple the bottom portion 840 to the connecting arm 816. In one example, the bore 848 can include four grooves 854a-854d and three flat surfaces 856a-856c. A respective one of each of the grooves 854a-854d can engage a respective one of each of the ribs 836a-836d. The grooves 854a-854d can be positioned about the bore 848 so that the grooves 854a-854d alternate with the flat surfaces 856a-856c. The flat surfaces 856a-856c can cooperate with the flat surfaces 834a-834c of the connecting arm 816 to resist relative rotation between the connecting arm 816 and the bottom portion 840.

With reference to FIG. 36, the top portion 842 of the saddle 806 can be disposed about the curved features 821 of the connecting arm 816. The top portion 842 can move or translate relative the connecting arm 816, and thus, move or translate relative to the bottom portion 840. The top portion 842 can be substantially U-shaped and symmetrical with respect to a longitudinal axis L defined by the multiplanar bone anchor system 800. The top portion 842 can include a first or proximal end 860 and a second or distal end 862. In one example, with reference to FIG. 33, the proximal end 860 can include a first arm 864 and a second arm 866. The first arm 864 and second arm 866 can extend upwardly from the distal end 862 to define the U-shape. Each of the first arm 864 and the second arm 866 can include the mating portion 84, a cavity 868 and a connector feature 870.

With reference to FIGS. 33 and 36, the cavity 868 can be defined in each interior surface 864a, 866a of the first arm 864 and the second arm 866. The cavity 868 can provide clearance for the movement or articulation of the top portion 842 relative to the bottom portion 840 of the saddle 806. In this regard, the cavity 868 can be defined so as to allow the top portion 842 to move over the head 810 of the bone fastener 802, which can provide a range of motion for the top portion 842 relative to the bottom portion 840. If desired, the cavity 868 could be configured such that contact between the head 810 of the bone fastener 802 and the cavity 868 can act as a stop to limit the movement or translation of the top portion 842 relative to the bottom portion 840. Further, other techniques could be used to stop or limit the movement or translation of the top portion 842 relative to the bottom portion 840, such as features formed on the connecting arm 816.

With reference to FIG. 33, the connector feature 870 can be defined in an exterior surface 864b, 866b of the first arm 864 and the second arm 866. The connector feature 870 can enable the multiplanar bone anchor system 800 to be coupled to instrumentation, such as rod reduction instruments or to a suitable cross-connector device in a spinal fixation procedure. The connector feature 870 is illustrated herein as comprising a triangular recess with rounded corners formed in each of the first arm 864 and the second arm 866, however, it should be noted that the connector feature 870 can have any selected shape and dimension to cooperate with a selected cross-connector device or instrument.

With reference to FIG. 33, the distal end 862 of the top portion 842 can be generally rectangular, and can include rounded corners to correspond with the shape of the bottom portion 840. It should be noted that the shape of the bottom portion 840 does not have to be generally rectangular, but could be generally square, cylindrical, oval, etc. The distal end 862 can include the first or receiver surface 88, a second or bottom surface 872, at least one bore 874 and a central bore 876.

With reference to FIG. 36, the bottom surface 872 of the distal end 862 can include at least one guide 878. In one example, the bottom surface 872 of the distal end 862 can include two guides 878a, 878b, which can be positioned opposite each other and adjacent to a respective receiver surface 88. The guides 878a, 878b, can have a curved surface 880 and a lip 884. The curved surface 880 can be shaped to cooperate with the curved features 821 of the connecting arm 816. The cooperation between the curved surface 880 and the curved features 821 can allow the top portion 842 to move or translate relative to the connecting arm 816. The lip 884 can retain the top portion 842 on the connecting arm 816. The lip 884 can also contact the rail 829 on the connecting arm 816 to aid in guiding the movement of the top portion 842 relative to the connecting arm 816.

With reference to FIG. 36, the at least one bore 874 can receive at least one pin 886 to enable frictional movement between the top portion 842 and the connecting arm 816. In one example, the distal end 862 can include two bores 874a, 874b and two pins 886a, 886b. The bores 874a, 874b can be defined on the distal end 862 can define passageways for receipt of the pins 886a, 886b. Generally, the bores 874a, 874b can be formed so that the passageways extend transverse to the longitudinal axis L. In one example, the passageways can be defined by the bores 874a, 874b, so as to extend adjacent to the receiver surface 88 from a first side 864a of the distal end 862 to a second side 864b of the distal end 862.

A respective one of the pins 886a, 886b can be received in a respective one of the bores 874a, 874b. The pins 886a, 886b can be fixed relative to the top portion 842. When the top portion 842 moves relative to the connecting arm 816, the biasing force from the friction element 826 can resist the movement of the top portion 842, which can allow for controlled movement of the top portion 842 relative to the connecting arm 816. This can enable the surgeon to place the top portion 842 in a selected position and the friction between the pins 886a, 886b and the connecting arm 816 can allow the top portion 842 to remain in that selected position.

The pins 886a, 886b, can be elongated and can include a first end 890 and a second end 892. In one example, the pins 886a, 886b can have a uniform cross-section, however, the pins 886a, 886b could have varying cross-sections to increase the friction between the top portion 842 and the connecting arm 816. The cross-section of the pins 886a, 886b is illustrated herein as being circular, but the pins 886a, 886b could have any desired cross-section, such as oval, rectangular, square, triangular, trapezoidal, etc. The first end 890 and the second end 892 of the pins 886a, 886b can include a taper which can allow the first end 890 and second end 892 of the pins 886a, 886b to be contained generally wholly within the top portion 842.

The central bore 876 can be defined through the distal end 862 from the receiver surface 88 to the bottom surface 872. Generally, the central bore 876 can be sized to receive the connecting arm 816 and the bone fastener 802 (FIG. 36).

With reference to FIG. 34, in order to assemble the multiplanar bone anchor system 800 according to one exemplary method, the bone fastener 802 can be inserted through the bore 824 of the connecting arm 816 and passed through the retention surface 828 so that the bone fastener 802 is retained within and can articulate within the connecting arm 816. Then, the connecting arm 816 can be inserted into the top portion 842 of the saddle 806. Generally, the connecting arm 816 can be rotated about 90° around a main axis M of the connecting arm 816 in order to insert the connecting arm 816 through the top portion 842 (FIG. 35). The connecting arm 816 can be rotated back about 90° around the axis M until the curved features 821 and straight portions 821a of the connecting arm 816 are engaged with the curved surface 884 and flat surface 886 of the top portion 842. Alternatively, the bone fastener 802 can be inserted into the bore 824 of the connecting arm 816 after the connecting arm 816 is coupled to the saddle 806.

Next, with reference to FIG. 33, the pins 886a, 886b, can be pressed into the bores 874a, 874b of the top portion 842. The bottom portion 840 can then be snap fit about the connecting arm 816 such that the grooves 854a-854d of the bottom portion 840 engage the ribs 836a-836d of the connecting arm 816. It should be noted that the use of the bottom portion 840 is merely exemplary, as the pins 886a, 886b can solely retain the connecting arm 816 within the top portion 842.

Once assembled, the connecting arm 816 can enable the bone fastener 802 to move or rotate within the bore 824 of the connecting arm 816. With reference to FIG. 36, the connecting arm 816 can also allow the bone fastener 802 to move or angulate relative to the longitudinal axis L of the multiplanar bone anchor system 800. The preferred angle slot 832 of the connecting arm 816 can cooperate with the preferred angle slot 850 of the bottom portion 840 to enable the bone fastener 802 to move or articulate to the greater angle A. The top portion 842 of the saddle 806 can move or translate relative to the bottom portion 840 and connecting arm 816 to a selected position. The friction between the pins 886a, 886b and the friction surface 826 of the connecting arm 816 can allow the top portion 842 to stay in the selected position once moved to the selected position. Thus, when assembled, the multiplanar bone anchor system 800 can have at least three degrees of movement or can be movable in at least three planes. For example, the bone fastener 802 can rotate about the longitudinal axis L. The bone fastener 802 can also pivot relative to the longitudinal axis L in at least a first direction and a second direction. The saddle 806 can translate relative to the longitudinal axis L. By allowing the multiplanar bone anchor system 800 to move in at least three planes, the surgeon can manipulate the multiplanar bone anchor system 800 as necessary to conform to the anatomy of the patient.

As the surgical insertion and use of the multiplanar bone anchor system 800 in a fixation procedure can be similar to the surgical insertion and insertion of the multiplanar bone anchor system 10 in a fixation procedure, the surgical insertion and use of the multiplanar bone anchor system 800 will not be discussed in great detail herein. Briefly, however, once the multiplanar bone anchor system 800 is secured to the anatomy, the multiplanar coupling system 804 and the saddle 806 can be moved, pivoted or rotated relative to the bone fastener 802 into the desired alignment for the fixation procedure. Once the aligned, the connecting rod 20 can be inserted into a desired number of multiplanar bone anchor systems 800.

With the connecting rod 20 positioned in the saddles 806 of the multiplanar bone anchor systems 800, the set screw 22 can be coupled to each mating portion 84 of each saddle 806. The coupling of the set screw 22 can apply a force to the head 810 of the bone fastener 802 to fixedly couple or lock the position of the bone fastener 802 relative to the saddle 806.

With reference now to FIGS. 37-39, in one example, a multiplanar bone anchor system 900 can be employed with the connecting rod 20 to repair a damaged portion of an anatomy. As the multiplanar bone anchor system 900 can be similar to the multiplanar bone anchor system 800 described with reference to FIGS. 31-36, only the differences between the multiplanar bone anchor system 800 and the multiplanar bone anchor system 900 will be discussed in great detail herein, and the same reference numerals will be used to denote the same or similar components. The multiplanar bone anchor system 900 can include the bone fastener 802, a multiplanar coupling arrangement or system 904 and a saddle 906. The multiplanar bone anchor system 900 can define a longitudinal axis L2, and the multiplanar bone anchor system 900 can be configured such that the bone fastener 902 and the saddle 906 can move relative to the longitudinal axis L2 in multiple planes (FIG. 39).

The multiplanar coupling system 904 can include a connecting arm 916. The connecting arm 916 can be composed of any suitable biocompatible material, such as a biocompatible metal, metal alloy, ceramic or polymer. The connecting arm 916 can be disposed about the head 810 of the bone fastener 802 to allow relative movement between the bone fastener 802 and the saddle 906. The connecting arm 916 can be sized to fit within the saddle 906, and can also allow a portion of the saddle 906 to move or translate relative to another portion of the saddle 906, as will be discussed in greater detail herein. The connecting arm 916 can include a first or upper portion 920, the second or lower portion 822 and the bore 824.

The upper portion 920 can be shaped to be received within a portion of the saddle 906, and can be generally rectangular with rounded corners. In one example, the upper portion 820 can have opposite curved features 821. The opposite curved features 821 can include the generally straight portion 821a. As will be discussed in greater detail herein, the straight portion 821a can cooperate with the saddle 906 to enable the saddle 906 to move or translate relative to the upper portion 820 of the connecting arm 916. The upper portion 920 can include at least one friction surface 926, the retention surface 828 and the rail 829.

With reference to FIG. 37, the at least one friction surface 926 can be formed on opposite sides of the bore 824. In one example, the at least one friction surface 926 can comprise a first vertical spring 926a and a second vertical spring 926b. It should be noted that although the at least one friction surface 926 is described and illustrated herein as comprising two vertical springs, the at least one friction surface 926 could comprise a single vertical spring, a frictional coating or other interference, which can control the movement of a portion of the saddle 906 relative to the connecting arm 916 and another portion of the saddle 906, as will be discussed in greater detail herein. The first vertical spring 926a and the second vertical spring 926b can be biased against the saddle 906 to enable the saddle 906 to be moved in a controlled fashion.

With reference to FIGS. 37-39, the saddle 906 can be coupled to the connecting arm 916 and can move or translate relative to the connecting arm 916. In this regard, the saddle 906 can include the first portion or bottom portion 840 and a second portion or top portion 942. The bottom portion 840 can be immovably coupled to the connecting arm 916, and the top portion 942 can move or translate relative to the bottom portion 840 and the connecting arm 916. When the top portion 942 moves relative to the connecting arm 916, the biasing force from the friction element 926 can resist the movement of the top portion 942, which can allow for controlled movement of the top portion 942 relative to the connecting arm 916. This can enable the surgeon to place the top portion 942 in a selected position and the friction from the connecting arm 916 can allow the top portion 942 to remain in that selected position. The top portion 942 can be substantially U-shaped and symmetrical with respect to a longitudinal axis L2 defined by the multiplanar bone anchor system 900. The top portion 942 can include the first or proximal end 860 and a second or distal end 944. The distal end 944 of the top portion 942 can be generally rectangular, and can include rounded corners to correspond with the shape of the bottom portion 940. The distal end 944 can include the first or receiver surface 88, the second or bottom surface 872 and the central bore 876.

With reference to FIG. 34, in order to assemble the multiplanar bone anchor system 900 according to one exemplary method, the bone fastener 802 can be inserted through the bore 824 of the connecting arm 916 and passed through the retention surface 828 so that the bone fastener 802 is retained within and can articulate within the connecting arm 916. Then, the connecting arm 916 can be inserted into the top portion 842 of the saddle 906. Generally, the connecting arm 916 can be rotated about 90° around a main axis of the connecting arm 916 in order to insert the connecting arm 916 through the top portion 942. The connecting arm 916 can be rotated back about 90° around the main axis until the curved features 821 and straight portions 821a of the connecting arm 916 are engaged with the curved surface 884 and flat surface 886 of the top portion 942. Alternatively, the bone fastener 802 can be inserted into the bore 824 of the connecting arm 916 after the connecting arm 916 is coupled to the saddle 806.

Next, the bottom portion 840 can then be snap fit about the connecting arm 916 such that the grooves 854a-854d of the bottom portion 840 engage the ribs 836a-836d of the connecting arm 916.

Once assembled, the connecting arm 916 can enable the bone fastener 802 to move or rotate within the bore 824 of the connecting arm 916. With reference to FIG. 39, the connecting arm 916 can also allow the bone fastener 802 to move or angulate relative to the longitudinal axis L2 of the multiplanar bone anchor system 900. The preferred angle slot 832 of the connecting arm 916 can cooperate with the preferred angle slot 850 of the bottom portion 840 to enable the bone fastener 802 to move or articulate to the greater angle A. The top portion 942 of the saddle 906 can move or translate relative to the bottom portion 840 and connecting arm 916 to a selected position. The friction from the friction surface 926 of the connecting arm 916 can allow the top portion 942 to stay in the selected position once moved to the selected position. Thus, when assembled, the multiplanar bone anchor system 900 can have at least three degrees of movement or can be movable in at least three planes. For example, the bone fastener 802 can rotate about the longitudinal axis L2. The bone fastener 802 can also pivot relative to the longitudinal axis L2 in at least a first direction and a second direction. The saddle 806 can translate relative to the longitudinal axis L2. By allowing the multiplanar bone anchor system 900 to move in at least three planes, the surgeon can manipulate the multiplanar bone anchor system 900 as necessary to conform to the anatomy of the patient.

As the surgical insertion and use of the multiplanar bone anchor system 900 in a fixation procedure can be similar to the surgical insertion and insertion of the multiplanar bone anchor system 10 in a fixation procedure, the surgical insertion and use of the multiplanar bone anchor system 900 will not be discussed in great detail herein. Briefly, however, once the multiplanar bone anchor system 900 is secured to the anatomy, the multiplanar coupling system 904 and the saddle 906 can be moved, pivoted or rotated relative to the bone fastener 802 into the desired alignment for the fixation procedure. Once the aligned, the connecting rod 20 can be inserted into a desired number of multiplanar bone anchor systems 900.

With the connecting rod 20 positioned in the saddles 906 of the multiplanar bone anchor systems 900, the set screw 22 can be coupled to each mating portion 84 of each saddle 906. The coupling of the set screw 22 to the saddle 906 can apply a force to the head 810 of the bone fastener 802 to fixedly couple or lock the position of the bone fastener 802 relative to the saddle 906.

Figures 40, 41:
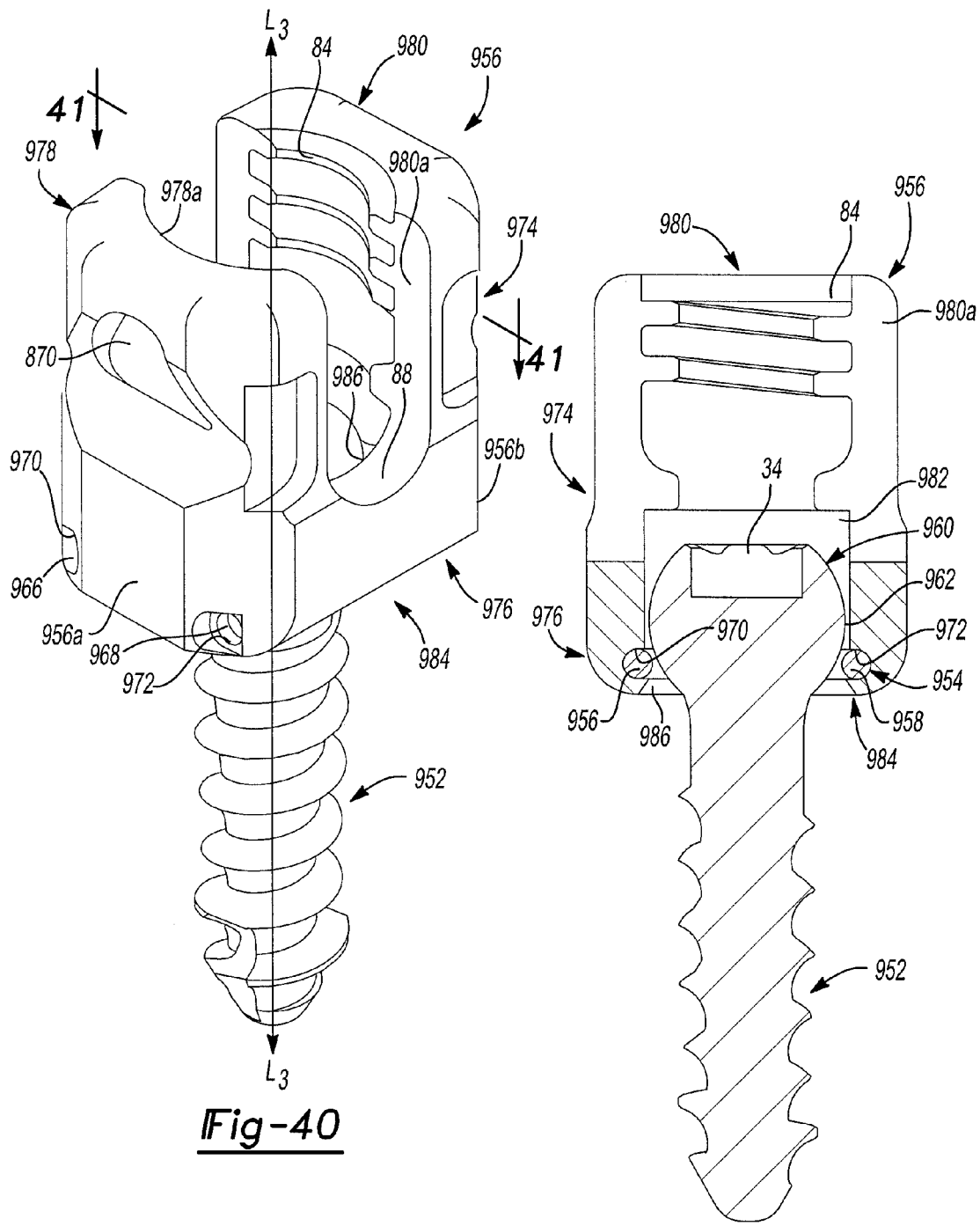
FIG. 40 is a perspective view of an exemplary multiplanar bone anchor system for use with a connecting device in a fixation procedure according to the present teachings.
FIG. 41 is a cross-sectional illustration of the multiplanar bone anchor system of FIG. 40, taken along line 41-41 of FIG. 40.

With reference now to FIGS. 40 and 41, in one example, a multiplanar bone anchor system 950 can be employed with the connecting rod 20 to repair a damaged portion of an anatomy. As the multiplanar bone anchor system 950 can be similar to the multiplanar bone anchor system 800 described with reference to FIGS. 31-36, only the differences between the multiplanar bone anchor system 800 and the multiplanar bone anchor system 950 will be discussed in great detail herein, and the same reference numerals will be used to denote the same or similar components. The multiplanar bone anchor system 950 can include a bone fastener 952, a multiplanar coupling arrangement or system 954 and a saddle 956. The multiplanar bone anchor system 950 can define a longitudinal axis L3, and the multiplanar bone anchor system 950 can be configured such that the bone fastener 952 and the saddle 956 can move relative to the longitudinal axis L3 in multiple planes. It should be noted that although the multiplanar bone anchor system 950 is described and illustrated herein as not including a lock ring, a lock ring could be employed with the multiplanar bone anchor system 950, if desired.

The bone fastener 952 can be configured to engage the anatomy to couple the multiplanar bone anchor system 900 to the anatomy. The bone fastener 952 can be composed of any suitable biocompatible material, such as titanium, stainless steel, biocompatible metals, metal alloys, polymers, etc. The bone fastener 952 can include a proximal end or head 960 (FIG. 41) and the distal end or shank 32. The head 960 can be substantially spherical, and can define a bearing surface 962 and the driver connection feature 34.

The bearing surface 962 can be formed adjacent to the shank 32 of the bone fastener 952. The bearing surface 962 can contact the multiplanar coupling system 954 to enable the bone fastener 952 to move or angulate relative to the longitudinal axis L3. The bearing surface 962 can also cooperate with the multiplanar coupling system 954 to enable the bone fastener 952 to move or rotate relative to the saddle 956 and can also allow the saddle 956 to move relative to the bone fastener 952, as will be discussed in greater detail herein.

In one example, the multiplanar coupling system 954 can include a first pin 966 and a second pin 968. The first pin 966 can be positioned substantially opposite the second pin 968 within the saddle 956. The first pin 966 and the second pin 968 can define rails or guides for the saddle 956 to move relative to the bone fastener 952, while also allowing the bone fastener 952 to freely rotate and articulate relative to the saddle 956. The first pin 966 and the second pin 968 can also serve to couple the bone fastener 952 to the saddle 956 and retain the bone fastener 952 within the saddle 956. The first pin 966 and the second pin 968 can be composed of any suitable biocompatible material, such as a biocompatible metal. Generally, the first pin 966 and the second pin 968 can be press-fit into the saddle 956, and thus, the first pin 966 and the second pin 968 can have a diameter that is substantially equal or slightly larger than a diameter of a first pin bore 970 and a second pin bore 972 defined in the saddle 956. Alternatively, the first pin 966 and the second pin 968 can be coupled to the saddle 956 through any suitable technique, such as welding, swaging, etc. In addition, it should be noted that although the multiplanar coupling system 954 is described and illustrated herein as including the first pin 966 and the second pin 968, only one pin could be employed, if desired.

The saddle 956 can move or translate relative the bone fastener 952 along the first pin 966 and the second pin 968. The saddle 956 can be substantially U-shaped and symmetrical with respect to the longitudinal axis L3 defined by the multiplanar bone anchor system 950 (FIG. 40). The saddle 956 can include a first or proximal end 974 and a second or distal end 976. In one example, the proximal end 974 can include a first arm 978 and a second arm 980. The first arm 978 and second arm 980 can extend upwardly from the distal end 976 to define the U-shape. Each of the first arm 978 and the second arm 980 can include the mating portion 84, a cavity 982 and the connector feature 870.

The cavity 982 can be defined in each interior surface 978a, 980a of the first arm 978 and the second arm 980. The cavity 982 can provide clearance for the movement or articulation of the saddle 956 relative to the bone fastener 952. In this regard, the cavity 982 can be configured so as to allow the saddle 956 to move over the head 960 of the bone fastener 952, which can provide a range of motion for the saddle 956 relative to the bone fastener 952. Thus, contact between the head 960 of the bone fastener 952 and the cavity 982 can act as a stop to limit the movement or translation of the saddle 956 relative to the bone fastener 952, however, other techniques could be used to stop or limit the movement or translation of the saddle 956 relative to the bone fastener 952, such as features formed on the first pin 966 and/or the second pin 968.

With reference to FIG. 40, the distal end 976 of the saddle 956 can be generally rectangular, and can include rounded corners. It should be noted that the shape of the distal end 976 of the saddle 956 does not have to be generally rectangular, but could be generally square, cylindrical, oval, etc. The distal end 976 can include the first or receiver surface 88, a second or bottom surface 984 and a central bore 986. The bottom surface 984 can include the first pin bore 970 and the second pin bore 972. The first pin bore 970 and the second pin bore 972 can be defined on substantially opposite sides of the saddle 956 and can extend along an axis substantially transverse to the longitudinal axis L3. In one example, the first pin bore 970 and the second pin bore 972 can be defined to extend from a first side 956a of the saddle 956 to a second side 956b of the saddle 956. The first pin bore 970 and the second pin bore 972 can have a diameter that can be substantially equal or less than the diameter of the first pin 966 and the second pin 968 to enable the first pin 966 and the second pin 968 to be press-fit into the saddle 956, but allow the saddle 956 to move or translate relative to the bone fastener 952 on the first pin 966 and the second pin 968. In one example, the first pin bore 970 and the second pin bore 972 can have an open periphery over a length of the first pin bore 970. The open periphery of the first pin bore 970 and the second pin bore 972 can enable the bone fastener 952 to contact the first pin 966 and the second pin 968 to move about the first pin 966 and the second pin 968, while allowing the first pin 966 and the second pin 968 to retain the bone fastener 952 within the saddle 956.

The central bore 986 can be defined through the distal end 976 from the receiver surface 88 to the bottom surface 984. Generally, the central bore 986 can be sized to receive the bone fastener 952 and to allow the bone fastener 952 to move, rotate or articulate about the central bore 986.

With continued reference to FIGS. 40 and 41, in order to assemble the multiplanar bone anchor system 950 according to one exemplary method, the bone fastener 952 can be inserted through the central bore 986 of the saddle 956. Then, the first pin 966 and the second pin 968 can be pressed into the first pin bore 970 and the second pin bore 972 to retain the bone fastener 952 within the saddle 956. The first pin 966 and the second pin 968 can allow the bone fastener 952 to move, rotate and articulate about the longitudinal axis L3, and can allow the saddle 956 to move or translate relative to the bone fastener 952. Thus, when assembled, the multiplanar bone anchor system 950 can have at least three degrees of movement or can be movable in at least three planes. For example, the bone fastener 952 can rotate about the longitudinal axis L3. The bone fastener 952 can also pivot relative to the longitudinal axis L3 in at least a first direction and a second direction. The saddle 956 can translate relative to the longitudinal axis L3. By allowing the multiplanar bone anchor system 950 to move in at least three planes, the surgeon can manipulate the multiplanar bone anchor system 950 as necessary to conform to the anatomy of the patient.

As the surgical insertion and use of the multiplanar bone anchor system 950 in a fixation procedure can be similar to the surgical insertion and insertion of the multiplanar bone anchor system 10 in a fixation procedure, the surgical insertion and use of the multiplanar bone anchor system 950 will not be discussed in great detail herein. Briefly, however, once the bone fastener 952 is secured to the anatomy, the saddle 956 can be moved, pivoted or rotated relative to the bone fastener 952 into the desired alignment for the fixation procedure. Once the aligned, the connecting rod 20 can be inserted into a desired number of multiplanar bone anchor systems 950.

With the connecting rod 20 positioned in the saddles 956 of the multiplanar bone anchor systems 950, the set screw 22 can be coupled to each mating portion 84 of each saddle 956. The coupling of the set screw 22 to the saddle 956 can apply a force to the head 960 of the bone fastener 952 to fixedly couple or lock the position of the bone fastener 952 relative to the saddle 956.

With reference now to FIGS. 42-45, in one example, a multiplanar bone anchor system 1000 can be employed with the connecting rod 20 to repair a damaged portion of an anatomy. As the multiplanar bone anchor system 1000 can be similar to the multiplanar bone anchor system 10 described with reference to FIGS. 1-8, only the differences between the multiplanar bone anchor system 10 and the multiplanar bone anchor system 1000 will be discussed in great detail herein, and the same reference numerals will be used to denote the same or similar components. The multiplanar bone anchor system 1000 can include a bone fastener 1002, a lock ring 1004 and a saddle 1006. The multiplanar bone anchor system 1000 can define a longitudinal axis L4, and the multiplanar bone anchor system 1000 can be configured such that the bone fastener 1002 and the saddle 1006 can move relative to the longitudinal axis L4 in multiple planes.

Figures 42, 44:
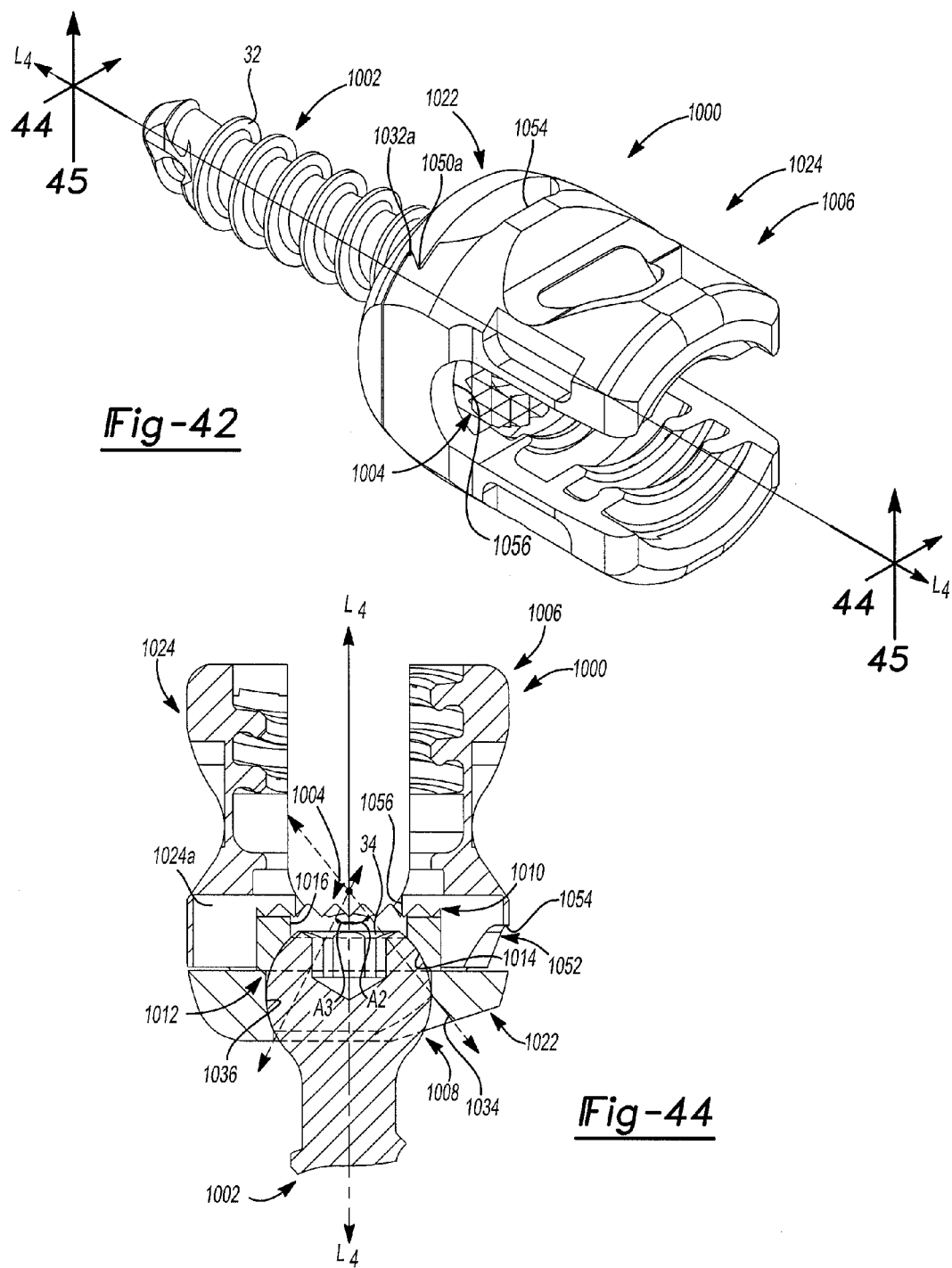
FIG. 42 is a perspective view of an exemplary multiplanar bone anchor system for use with a connecting device in a fixation procedure according to the present teachings.
FIG. 44 is a cross-sectional illustration of the multiplanar bone anchor system of FIG. 42, taken along line 44-44 of FIG. 42.
Figure 43:
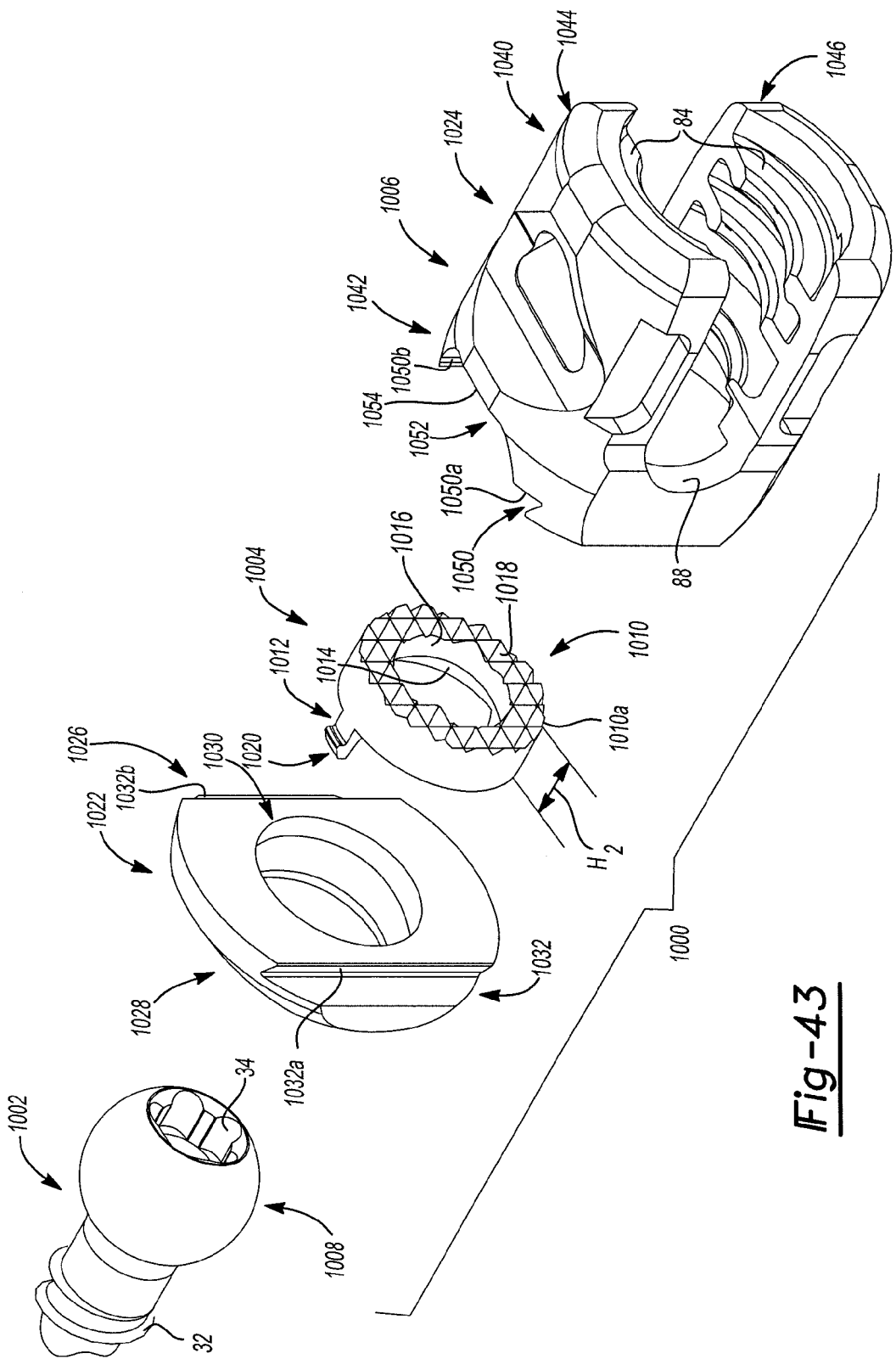
FIG. 43 is an exploded view of the multiplanar bone anchor system of FIG. 42.
Figure 45:
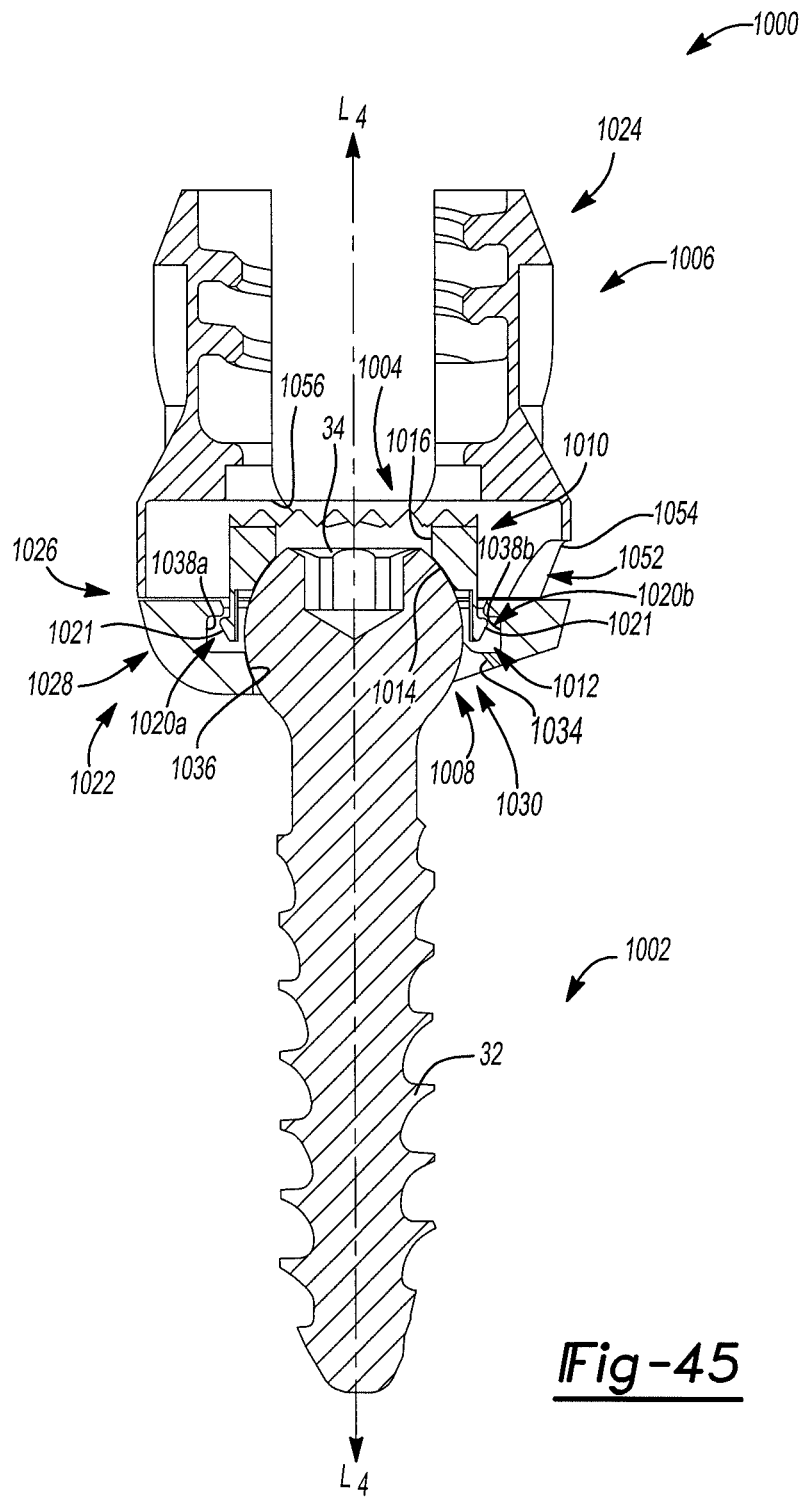
FIG. 45 is a cross-sectional illustration of the multiplanar bone anchor system of FIG. 42, taken along line 45-45 of FIG. 42.

With continued reference to FIGS. 42-45, the bone fastener 1002 can be configured to engage the anatomy to couple the multiplanar bone anchor system 1000 to the anatomy. The bone fastener 1002 can be composed of any suitable biocompatible material, such as titanium, stainless steel, biocompatible polymers, etc. The bone fastener 1002 can include a proximal end or head 1008 (FIGS. 44 and 45) and the distal end or shank 32 (FIG. 45). With reference to FIGS. 43-45, the head 1008 can be generally spherical, and can include the driver connection feature 34.

With reference to FIGS. 43-45, the lock ring 1004 can be positioned about the head 1008 of the bone fastener 1002 and coupled to the saddle 1006. The lock ring 1004 can lock the bone fastener 1002 relative to the saddle 1006 via a force applied by the connecting rod 20. With reference to FIG. 43, the lock ring 1004 can be generally cylindrical, and can have a height H1. The height H1 can be sized to extend above the receiver surface 88 of the saddle 1006, as illustrated in FIG. 42, so that coupling the connecting rod 20 to the saddle 1006 can compress the lock ring 1004 onto the head 1008 of the bone fastener 1002. With reference to FIGS. 43-45, the lock ring 1004 can include a proximal end 1010, a distal end 1012, a bearing surface 1014 and a bore 1016.

With reference to FIG. 43, the proximal end 1010 can include one or more projections or teeth 1018. The teeth 1018 can be formed along a proximalmost surface 1010a of the proximal end 1010. The teeth 1018 can engage the connecting rod 20 to assist in coupling the connecting rod 20 to the saddle 1006. The distal end 1012 can include at least one tab 1020. In one example, with reference to FIG. 45, the at least one tab 1020 can comprise two tabs 1020a, 1020b. The tabs 1020a, 1020b can extend from the distal end 1012 and can be spaced about 180° apart from each other about a circumference of the lock ring 1004. The tabs 1020a, 1020b can include a locking tab 1021, which can engage a portion of the saddle 1006 to couple the lock ring 1004 to the saddle 1006. The tabs 1020a, 1020b can also couple a portion of the saddle 1006 to another portion of the saddle 1006.

The bearing surface 1014 can be formed adjacent to the distal end 1012 of the lock ring 1004 along a portion of the bore 1016. In one example, the bearing surface 1014 can comprise an arcuate ring defined about the bore 1016, which is configured to enable the head 1008 of the bone fastener 1002 to move, rotate and articulate relative to the lock ring 1004.

With reference to FIGS. 43-45, the bore 1016 can be disposed about a central axis of the lock ring 1004. The bore 1016 can extend from the proximal end 1010 to the distal end 1012. The bearing surface 1014 can be formed about the bore 1016. The bore 1016 can enable a driver to interface with the driver connection feature 34 formed on the head 1008 of the bone fastener 1002.

With reference to FIGS. 42-45, the saddle 1006 can include a first portion or bottom portion 1022 and a second portion or top portion 1024. The top portion 1024 can move or translate relative to the bottom portion 1022. With reference to FIG. 43, the bottom portion 1022 can include a first or proximal end 1026, a second or distal end 1028 and a bore 1030.

The proximal end 1026 can be generally rectangular, and can include rounded corners. The proximal end 1026 can be coupled to the top portion 1024 (FIG. 42). The proximal end 1026 can define at least one rail 1032. Generally, the top portion 1024 can move or translate along the at least one rail 1032. In one example, the proximal end 1026 can define two rails 1032a, 1032b, which can be positioned on opposite sides of the bore 1030. As will be discussed, the lock ring 1004 can define or limit the translation of the top portion 1024 relative to the bottom portion 1022.

With reference to FIGS. 44 and 45, the distal end 1028 can include a preferred angle slot 1034. The preferred angle slot 1034 can be formed through at least one side of the distal end 1028 and can be in communication with the bore 1030. The preferred angle slot 1034 can be defined through the bottom portion 1022 at any desired location. With reference to FIG. 44, the preferred angle slot 1034 can enable the bone fastener 1002 to articulate to a greater angle A2 relative to the longitudinal axis L4. In this regard, the bone fastener 1002 can articulate to an angle A3 relative to the longitudinal axis L4 in an area of the bottom portion 1022 that does not include the preferred angle slot 1034. The angle A3 can be less than the greater angle A2. Alternatively, the distal end 1028 could be devoid of the preferred angle slot, if desired.

With reference to FIG. 45, the bore 1030 can be defined through the bottom portion 1022 from the proximal end 1026 to the distal end 1028. The bore 1030 can be sized to receive the lock ring 1004 and the bone fastener 1002 therein. The bore 1030 can include a bearing surface 1036 and at least one groove 1038. The bearing surface 1036 can be configured to contact the head 1008 of the bone fastener 1002 to enable the bone fastener 1002 to move, rotate or articulate relative to the bottom portion 1022. Thus, the bearing surface 1036 can be generally arcuate. The at least one groove 1038 can be formed in a sidewall of the bore 1030, and can mate with the at least one tab 1020. In one example, the at least one groove 1038 can comprise two grooves 1038*a*, 1038*b*. The grooves 1038*a*, 1038*b* can be spaced about 180° apart from each other about a circumference of the bore 1030. A respective one of the tabs 1020*a*, 1020*b* can engage a respective one of the grooves 1038*a*, 1038*b* to secure the lock ring 1004 to the saddle 1006, and to secure the bottom portion 1022 to the top portion 1024.

With reference to FIG. 42, the top portion 1024 of the saddle 1006 can be coupled to the at least one rail 1032 of the proximal end 1026 of the bottom portion 1022 so that the top portion 1024 can move relative to the bottom portion 1022. The top portion 1024 can be substantially U-shaped and symmetrical with respect to a longitudinal axis L4 defined by the multiplanar bone anchor system 1000. With reference to FIG. 43, the top portion 1024 can include a first or proximal end 1040 and a second or distal end 1042. In one example, the proximal end 1040 can include a first arm 1044 and a second arm 1046. The first arm 1044 and second arm 1046 can extend upwardly from the distal end 1042 to define the U-shape. Each of the first arm 1044 and the second arm 1046 can include the mating portion 84.

With reference to FIG. 43, the distal end 1042 of the top portion 1024 can be generally rectangular, and can include the receiver surface 88, at least one guide 1050, an assembly slot 1052, an assembly aperture 1054 and a central bore 1056. It should be noted that the shape of the distal end 1042 does not have to be generally rectangular, but could be generally square, cylindrical, oval, etc. The at least one guide 1050 can cooperate with the at least one rail 1032 to enable the top portion 1024 to move relative to the bottom portion 1022. In one example, the at least one guide 1050 can comprise two guides 1050*a*, 1050*b*. The guides 1050*a*, 1050*b* can allow the top portion 1024 to move along the rails 1032*a*, 1032*b* to enable the top portion 1024 to move or translate relative to the bottom portion 1022. It should be noted that while the guides 1050*a*, 1050*b* and the rails 1032*a*, 1032*b* are illustrated herein as comprising a dovetail arrangement (FIG. 42), any type of arrangement can be used to enable the top portion 1024 to move relative to the bottom portion 1022.

With reference to FIG. 44, the assembly slot 1052 can be defined from the assembly aperture 1054 to an opposite side 1024*a* of the top portion 1024. The assembly slot 1052 can be sized to enable the top portion 1024 to pass over the bottom portion 1022 to couple the top portion 1024 to the bottom portion 1022, as will be discussed herein. It should be noted that although one assembly slot 1052 is described and illustrated herein, more than one assembly slot 1052 could be defined in the distal end 1042.

The assembly aperture 1054 can be defined through a sidewall 1024*b* of the top portion 1024. The assembly aperture 1054 can have a width, which can be less than a width of the assembly slot 1052. Generally, the width of the assembly aperture 1054 can be sized to enable the top portion 1024 to pass over the head 1008 of the bone fastener 1002, but can contact the lock ring 1004 when the lock ring 1004 is assembled within the saddle 1006 to prevent the disassembly of the top portion 1024 and the bottom portion 1022. As will be discussed, the assembly aperture 1054 can cooperate with the assembly slot 1052 to enable the top portion 1024 to be coupled to the bottom portion 1022.

The central bore 1056 can be defined through the distal end 1042 from the receiver surface 88 to the guides 1050*a*, 1050*b*. Generally, the central bore 1056 can be sized to receive the bone fastener 1002 and the tabs 1020*a*, 1020*b* of the lock ring 1004.

With reference to FIGS. 42-45, in order to assemble the multiplanar bone anchor system 1000 according to one exemplary method, the bone fastener 1002 can be inserted through the bore 1030 of the bottom portion 1022 of the saddle 1006. Initially, the bone fastener 1002 can rest within a pocket defined by the bearing surface 1036 of the bore 1030 (FIG. 44). Then, the lock ring 1004 can be inserted into the central bore 1056 of the top portion 1024 of the saddle 1006 and can be pushed into the central bore 1056 from the distal end 1042. With the lock ring 1004 positioned within the top portion 1024, the top portion 1024 can be slid onto the bottom portion 1022 with the rails 1032*a*, 1032*b* engaging the grooves 1050*a*, 1050*b*. In one example, the top portion 1024 can be slid onto the bottom portion 1022 in the direction of the assembly slot 1052 such that the assembly slot 1052 contacts the bottom portion 1022 first. The assembly slot 1052 can be sized to enable the top portion 1024 to pass over the head 1008 of the bone fastener 1002. Once the top portion 1024 is assembled onto the bottom portion 1022, the lock ring 1004 can be pushed down until the tabs 1020*a*, 1020*b* of the lock ring 1004 engage the grooves 1050*a*, 1050*b* of the bottom portion 1022 (FIG. 45).

When assembled, the multiplanar bone anchor system 1000 can have at least three degrees of movement or can be movable in at least three planes. In this regard, the bone fastener 1002 can move or rotate about the longitudinal axis L4 and can also move or articulate relative to the longitudinal axis L4. The top portion 1024 can move or translate relative to the bottom portion 1022 in a direction transverse to the longitudinal axis L4. By allowing the multiplanar bone anchor system 1000 to move in at least three planes, the surgeon can manipulate the multiplanar bone anchor system 1000 as necessary to conform to the anatomy of the patient.

As the surgical insertion and use of the multiplanar bone anchor system 1000 in a fixation procedure can be similar to the surgical insertion and insertion of the multiplanar bone anchor system 10 in a fixation procedure, the surgical insertion and use of the multiplanar bone anchor system 1000 will not be discussed in great detail herein. Briefly, however, once the bone fastener 1002 is secured to the anatomy, the saddle 1006 can be moved, pivoted or rotated relative to the bone fastener 1002 into the desired alignment for the fixation procedure. Once the aligned, the connecting rod 20 can be inserted into a desired number of multiplanar bone anchor systems 1000.

With the connecting rod 20 positioned in the saddles 1006 of the multiplanar bone anchor systems 1000, the set screw 22 can be coupled to each mating portion 84 of each saddle 1006. The coupling of the set screw 22 to the saddle 1006 can apply a force to the head 1008 of the bone fastener 1002 to fixedly couple or lock the position of the bone fastener 1002 relative to the saddle 1006.

With reference now to FIGS. 46-49, in one example, a multiplanar bone anchor system 1100 can be employed with the connecting rod 20 to repair a damaged portion of an anatomy. As the multiplanar bone anchor system 1100 can be similar to the multiplanar bone anchor system 10 described with reference to FIGS. 1-8, only the differences between the multiplanar bone anchor system 10 and the multiplanar bone anchor system 1100 will be discussed in great detail herein, and the same reference numerals will be used to denote the same or similar components. The multiplanar bone anchor system 1100 can include a bone fastener 1102, a lock ring 1104, a multiplanar coupling arrangement or system 1106 and a saddle 1108. The multiplanar bone anchor system 1100 can define a longitudinal axis L5, and the multiplanar bone anchor system 1100 can be configured such that the bone fastener 1102 and the saddle 1108 can move relative to the longitudinal axis L5 in multiple planes.

Figures 46, 48, 49:
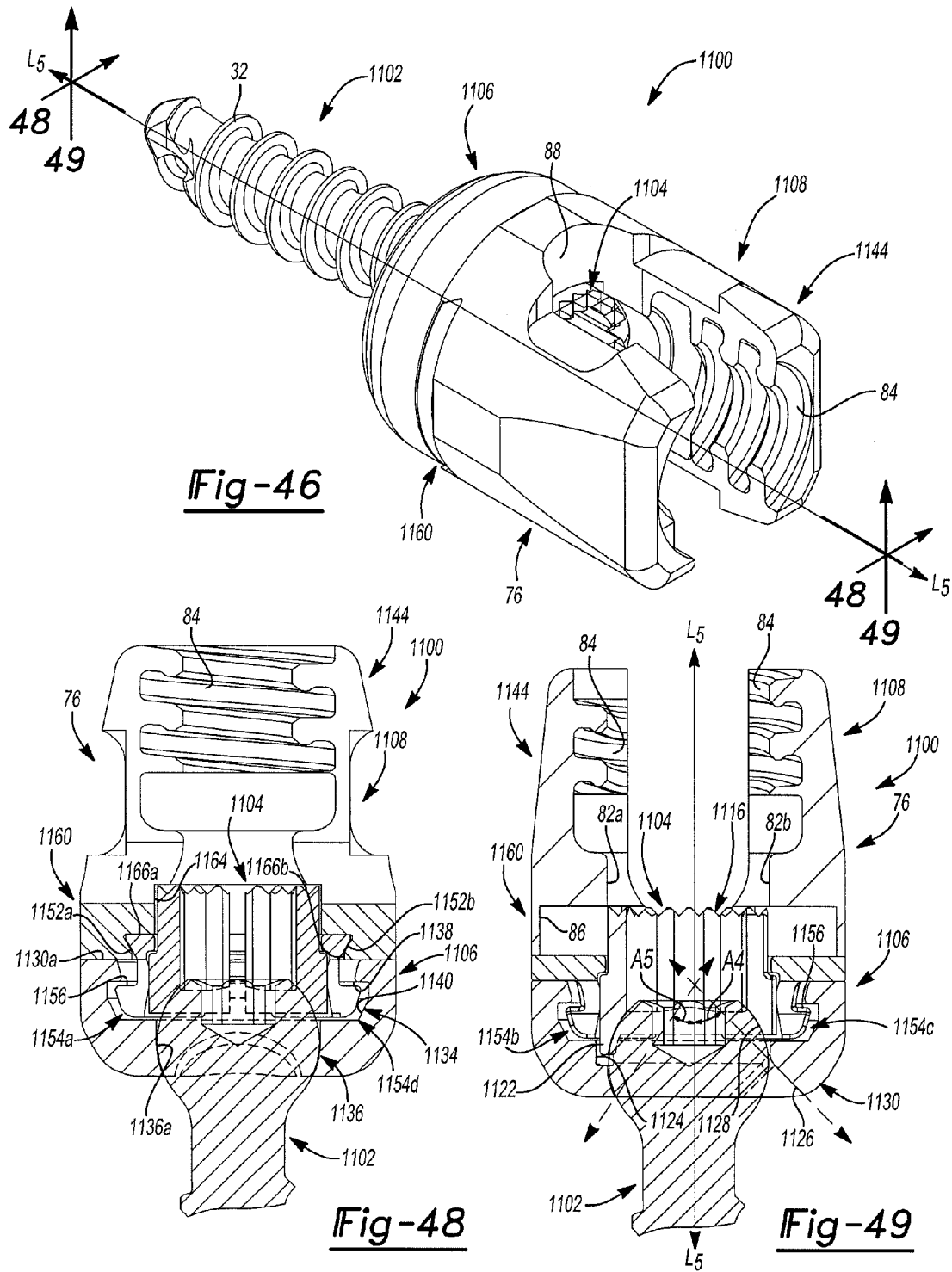
FIG. 46 is a perspective view of another exemplary multiplanar bone anchor system for use with a connecting device in a fixation procedure according to the present teachings.
FIG. 48 is a cross-sectional illustration of the multiplanar bone anchor system of FIG. 46, taken along line 48-48 of FIG. 46.
FIG. 49 is a cross-sectional illustration of the multiplanar bone anchor system of FIG. 46, taken along line 49-49 of FIG. 46.
Figure 47:
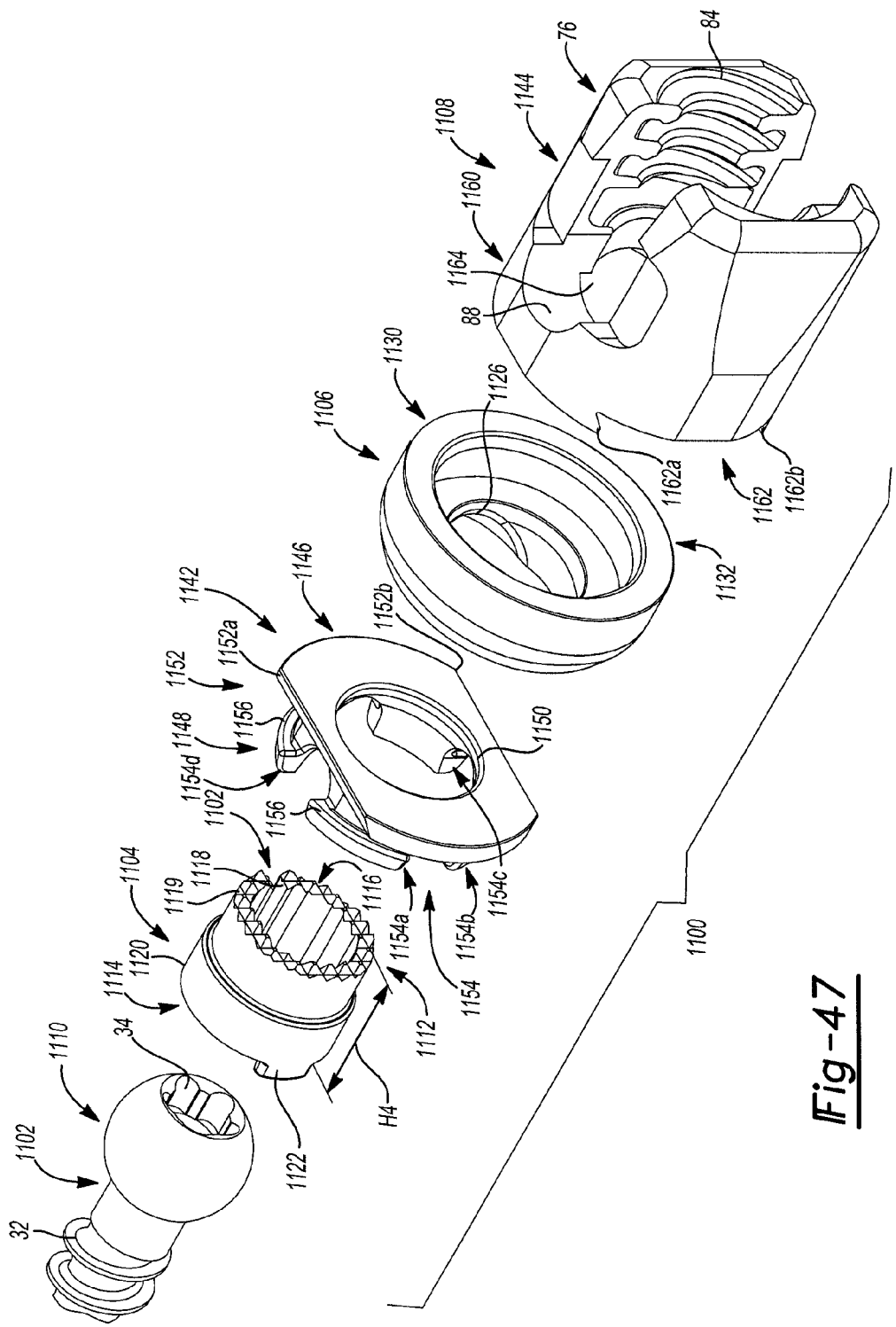
FIG. 47 is an exploded view of the multiplanar bone anchor system of FIG. 46.

With reference to FIGS. 46 and 47, the bone fastener 1102 can be configured to engage the anatomy to couple the multiplanar bone anchor system 1100 to the anatomy. The bone fastener 1102 can be composed of any suitable biocompatible material, such as titanium, stainless steel, biocompatible polymers, etc. The bone fastener 1102 can include a proximal end or head 1110 (FIG. 47) and the distal end or shank 32 (FIG. 46). With reference to FIG. 47, the head 1110 can be generally spherical, and can include the driver connection feature 34.

With reference to FIGS. 47-49, the lock ring 1104 can be positioned about the head 1110 of the bone fastener 1102. As will be discussed herein, the lock ring 1104 can lock at least one of the bone fastener 1102 and the multiplanar coupling system 1106 relative to the saddle 1108 via a force applied by the connecting rod 20. The lock ring 1104 can be generally cylindrical, and can have a height H4. The height H4 can be sized to extend above the receiver surface 88 of the saddle 1108 so that coupling the connecting rod 20 to the saddle 1108 can compress the lock ring 1104 onto the head 1110 of the bone fastener 1102 (FIG. 46). With reference to FIG. 47, the lock ring 1104 can include a proximal end 1112, a distal end 1114 and a bore 1116.

The proximal end 1112 can bear against the connecting rod 20 when the connecting rod 20 is coupled to the saddle 1108. The proximal end 1112 can include a slot 1118 and a plurality of teeth 1119. The slot 1118 can enable a tool to engage the lock ring 1104 to move the lock ring 1104 within the saddle 1108. As will be discussed, the movement of the lock ring 1104 within the saddle 1108 can enable the user to select a position for the bone fastener 1102 to articulate to a greater angle. The teeth 1119 can engage or bite into the connecting rod 20 to assist in coupling the connecting rod 20 to the saddle 1108.

The distal end 1114 can include a collar 1120 and a preferred tab 1122. The collar 1120 can extend about a circumference of the lock ring 1104 and can contact a portion of the saddle 1108 to assist in coupling the portion of the saddle 1108 to the connecting arm 1130. As illustrated in FIG. 49, the preferred tab 1122 can be keyed to mate with a preferred slot 1124 defined in a connecting arm 1130. The engagement of the preferred tab 1122 with the preferred slot 1124 can enable the lock ring 1104 to move in concert with the connecting arm 1130. The coordinated movement of the lock ring 1104 and the connecting arm 1130 can allow the user to move the lock ring 1104 to adjust a position of a preferred angle slot 1126 defined in the connecting arm 1130, as will be discussed herein.

With reference to FIG. 49, the bore 1116 can be defined from the proximal end 1112 to the distal end 1114. The bore 1116 can enable an instrument to engage the driver connection feature 34 when the multiplanar bone anchor system 1100 is assembled. It should be noted that the use of the driver connection feature 34 is merely exemplary, as a tool could engage the lock ring 1104 couple the bone fastener 1102 to the anatomy. The bore 1116 can include a bearing surface 1128. The bearing surface 1128 can generally be formed adjacent to the distal end 1114. The bearing surface 1128 can be arcuate and generally concave to slidably engage the spherical head 1110 of the bone fastener 1102. The bearing surface 1128 can also enable the lock ring 1104 to move or articulate relative to the multiplanar coupling system 1106, as will be discussed herein.

In one example, with reference to FIG. 47, the multiplanar coupling system 1106 can include a connecting arm 1130. The connecting arm 1130 can be disposed about a head 1110 of the bone fastener 1102 to enable the bone fastener 1102 to move or articulate relative to the saddle 1108, as shown in FIG. 48. The connecting arm 1130 can be annular, and can be sized to receive a portion of the saddle 1108 and the lock ring 1104. With reference to FIGS. 47 and 49, the connecting arm 1130 can include the preferred slot 1124 (FIG. 49), the preferred angle slot 1126 and a bore 1132.

With reference to FIG. 49, the preferred slot 1124 can be defined near the preferred angle slot 1126. The preferred slot 1124 can be configured to receive the preferred tab 1122 to enable the operator to control the location of the preferred angle slot 1126. The preferred angle slot 1126 can enable the bone fastener 1102 to articulate to a greater angle A4 relative to the longitudinal axis L5. In one example, the preferred angle slot 1126 can comprise a cut-out in a portion of the connecting arm 1130, which can be in communication with the bore 1132 to enable the bone fastener 1102 to articulate to the greater angle A4. In this regard, the bone fastener 1102 can articulate to an angle A5 relative to the longitudinal axis L5 in an area of the connecting arm 1130 that does not include the preferred angle slot 1126. The angle A5 can be less than the greater angle A4.

With reference to FIG. 48, the bore 1132 can have a first portion 1134 and a second portion 1136. The first portion 1134 can include a lip 1138 and a recess 1140 for coupling a portion of the saddle 1108 to the connecting arm 1130. The lip 1138 can be formed adjacent to a proximalmost end 1130*a* of the connecting arm 1130. The lip 1138 can cooperate with a portion of the saddle 1108 to couple the saddle 1108 to the connecting arm 1130. The recess 1140 can be sized to receive a portion of the saddle 1108, a portion of the lock ring 1104 and the head 1110 of the bone fastener 1102.

The second portion 1136 of the bore 1132 can be sized to receive the head 1110 of the bone fastener 1102. The second portion 1136 can include a bearing surface 1136*a*. The bearing surface 1136*a* can contact the head 1110 of the bone fastener 1102 to enable the bone fastener 1102 to move, rotate or articulate relative to the connecting arm 1130.

With reference to FIG. 47, the saddle 1108 can include a first portion or bottom portion 1142 and a second portion or top portion 1144. The top portion 1144 can move or translate relative to the bottom portion 1142. The bottom portion 1142 can include a first or proximal end 1146, a second or distal end 1148 and a bore 1150. The bore 1150 can be defined through the bottom portion 1142. The bore 1150 can be sized to receive the lock ring 1104 therein (FIG. 48).

The proximal end 1146 can define at least one rail 1152. In one example, the proximal end 1146 can include two rails 1152*a*, 1152*b*, which can be positioned on substantially opposite sides of the bottom portion 1142. Generally, the top portion 1144 can move or translate along the rails 1152*a*, 1152*b*.

The distal end 1148 can include at least one locking tab 1154. In one example, the distal end 1148 can include four locking tabs 1154*a*-1154*d*, which can be spaced about a circumference of the bottom portion 1142. The locking tabs 1154*a*-1154*d* can include an edge 1156, which can engage the lip 1138 of the connecting arm 1130 to couple the bottom portion 1142 to the connecting arm 1130 (FIGS. 48 and 49).

With reference to FIGS. 47 and 48, the top portion 1144 of the saddle 1108 can be coupled to the rails 1152a, 1152b of the proximal end 1146 of the bottom portion 1142 so that the top portion 1144 can move relative to the bottom portion 1142. The top portion 1144 can be substantially U-shaped and symmetrical with respect to a longitudinal axis L5 defined by the multiplanar bone anchor system 1100 (FIG. 46). The top portion 1144 can include the first or proximal end 76 and a second or distal end 1160.

With reference to FIG. 47, the distal end 1160 of the top portion 1144 can be generally rectangular, and can include the first or a receiver surface 88, a second or bottom surface 1162 and a central bore 1164. It should be noted that the shape of the distal end 1160 does not have to be generally rectangular, but could be generally square, cylindrical, oval, etc. The central bore 1164 can be defined through the distal end 1160 from the receiver surface 88 to the bottom surface 1162. Generally, the central bore 1164 can be sized to receive the lock ring 1104 (FIG. 48).

With reference to FIGS. 47 and 48, the bottom surface 1162 can include at least one or more guides 1166. In this example, the bottom surface 1162 can include two guides 1166a, 1166b. The guides 1166a, 1166b can slidably couple the top portion 1144 to the bottom portion 1142. In this regard, each guides 1166a, 1166b can cooperate with a respective one of the rails 1152a, 1152b to enable the top portion 1144 of the saddle 1108 to move or translate relative to the bottom portion 1142 of the saddle 1108. Generally, the guides 1166a, 1166b can cooperate with the rails 1152a, 1152b to create a dovetail relationship. It should be understood, however, that any suitable relationship or technique could be used to enable the top portion 1144 to move or translate relative to the bottom portion 1142.

In addition, it should be noted that the lock ring 1104 can define or limit the translation of the top portion 1144 relative to the bottom portion 1142. In this regard, with reference to FIG. 49, the cavity 86 can be defined in each interior surface 80b, 82b of the first arm 80 and second arm 82 of the top portion 1144 of the saddle 1108. The cavity 86 can provide clearance for the movement or articulation of the top portion 1144 relative to the bottom portion 1142 of the saddle 1108. Generally, the cavity 86 can be defined so as to allow the top portion 1144 to move over a portion of the lock ring 1104, which can provide a range of motion for the top portion 1144 relative to the bottom portion 1142. Thus, contact between the lock ring 1104 and the cavity 86 can act as a stop to limit the movement or translation of the top portion 1144 relative to the bottom portion 1142, however, other techniques could be used to stop or limit the movement or translation of the top portion 1144 relative to the bottom portion 1142.

With reference to FIG. 47, in order to assemble the multiplanar bone anchor system 1100 according to one exemplary method, the bone fastener 1102 can be inserted through the bore 1132 of the connecting arm 1130. Then, the bottom portion 1142 of the saddle 1108 can be snap-fit into the connecting arm 1130 with the lock ring 1104 inserted into the bottom portion 1142 and positioned such that the preferred tab 1122 engages the preferred slot 1124 of the connecting arm 1130 so that the edge 1156 of the locking tabs 1154a-1154d engage the lip 1138 of the connecting arm 1130 (FIG. 48). The guides 1162a, 1162b of the top portion 1144 can be slid onto the rails 1152a, 1152b of the bottom portion 1142 to couple the top portion 1144 to the bottom portion 1142.

When assembled, the multiplanar bone anchor system 1100 can have at least three degrees of movement or can be movable in at least three planes. In this regard, the bone fastener 1102 can move or rotate about the longitudinal axis L5 and can also move or articulate relative to the longitudinal axis L5. The top portion 1144 can move or translate relative to the bottom portion 1142 in a direction transverse to the longitudinal axis L5. By allowing the multiplanar bone anchor system 1100 to move in at least three planes, the surgeon can manipulate the multiplanar bone anchor system 1100 as necessary to conform to the anatomy of the patient.

As the surgical insertion and use of the multiplanar bone anchor system 1100 in a fixation procedure can be similar to the surgical insertion and insertion of the multiplanar bone anchor system 10 in a fixation procedure, the surgical insertion and use of the multiplanar bone anchor system 1100 will not be discussed in great detail herein. Briefly, however, once the bone fastener 1102 is secured to the anatomy, the saddle 1108 can be moved, pivoted or rotated relative to the bone fastener 1102 into the desired alignment for the fixation procedure. Once the aligned, the connecting rod 20 can be inserted into a desired number of multiplanar bone anchor systems 1100.

With the connecting rod 20 positioned in the saddles 1108 of the multiplanar bone anchor systems 1100, the set screw 22 can be coupled to each mating portion 84 of each saddle 1108. The coupling of the set screw 22 to the saddle 1108 can apply a force to the lock ring 1104 to fixedly couple or lock the position of the bone fastener 1102 relative to the saddle 1108.

With reference now to FIGS. 50-53, in one example, a multiplanar bone anchor system 1200 can be employed with the connecting rod 20 to repair a damaged portion of an anatomy. As the multiplanar bone anchor system 1200 can be similar to the multiplanar bone anchor system 1100 described with reference to FIGS. 46-49, only the differences between the multiplanar bone anchor system 1100 and the multiplanar bone anchor system 1200 will be discussed in great detail herein, and the same reference numerals will be used to denote the same or similar components. The multiplanar bone anchor system 1200 can include the bone fastener 1102, a lock ring 1204, a multiplanar coupling arrangement or system 1206 and a saddle 1208. The multiplanar bone anchor system 1200 can define a longitudinal axis L6, and the multiplanar bone anchor system 1200 can be configured such that the bone fastener 1102 and the saddle 1208 can move relative to the longitudinal axis L6 in multiple planes.

Figure 51:
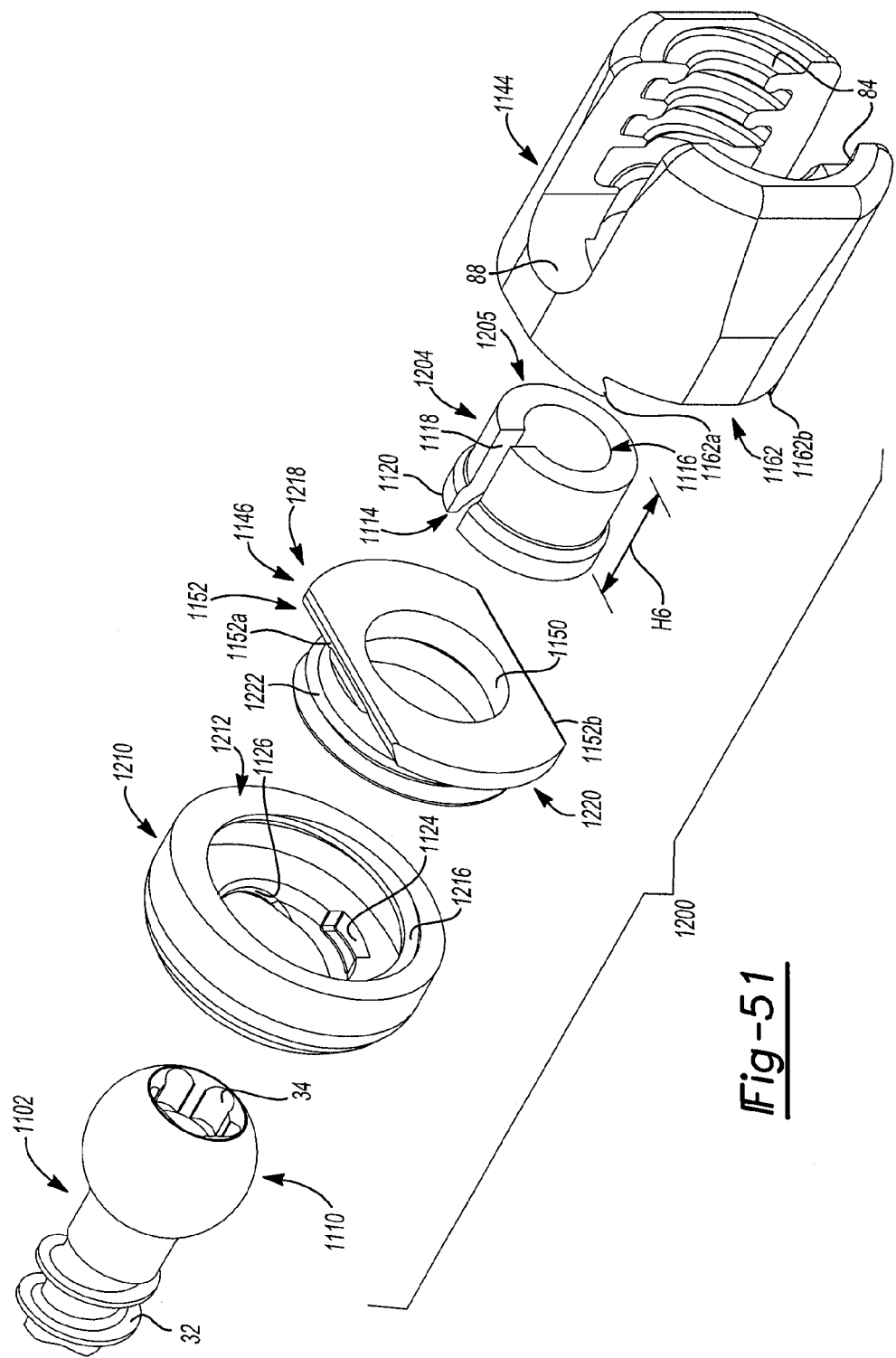
FIG. 51 is an exploded view of the multiplanar bone anchor system of FIG. 50.

With reference to FIGS. 51-53, the lock ring 1204 can be positioned about the head 1110 of the bone fastener 1102. As will be discussed herein, the lock ring 1204 can lock at least one of the bone fastener 1102 and the multiplanar coupling system 1206 relative to the saddle 1208 via a force applied by the connecting rod 20. The lock ring 1204 can be generally cylindrical, and can have a height H6. The height H6 can be sized to extend above the receiver surface 88 of the saddle 1208 so that coupling the connecting rod 20 to the saddle 1208 can compress the lock ring 1204 onto the head 1110 of the bone fastener 1102. With reference to FIG. 51, the lock ring 1204 can include a proximal end 1205, the distal end 1114 and the bore 1116. The proximal end 1205 can bear against the connecting rod 20 when the connecting rod 20 is coupled to the saddle 1208. The proximal end 1205 can include the slot 1118. Although not illustrated herein, the lock ring 1204 can include teeth formed along the proximal end 1205, if desired.

In one example, the multiplanar coupling system 1206 can include a connecting arm 1210. The connecting arm 1210 can be disposed about the head 1110 of the bone fastener 1102 to enable the bone fastener 1102 to move or articulate relative to the saddle 1208. The connecting arm 1210 can be annular, and can be sized to receive a portion of the saddle 1208 and the lock ring 1104 (FIG. 52). With reference to FIG. 51, the connecting arm 1210 can include the preferred slot 1124, the preferred angle slot 1126 and a bore 1212.

With reference to FIG. 52, the bore 1212 can have a first portion 1214 and the second portion 1136. The first portion 1214 can include a plurality of threads 1216 and a recess 1217 for coupling a portion of the saddle 1208 to the connecting arm 1210. The threads 1216 can be formed adjacent to a proximalmost end 1210a of the connecting arm 1210 and can extend about a circumference of the connecting arm 1210. The threads 1216 can cooperate with a portion of the saddle 1208 to couple the saddle 1208 to the connecting arm 1210.

With reference to FIGS. 51-53, the saddle 1208 can include a first portion or bottom portion 1218 and the second portion or top portion 1144. The top portion 1144 can move or translate relative to the bottom portion 1218. With reference to FIG. 51, the bottom portion 1218 can include the first or proximal end 1146, a second or distal end 1220 and the bore 1150.

The distal end 1220 can include a plurality of threads 1222 formed about an exterior of the bottom portion 1218. The plurality of threads 1222 can extend from the proximal end 1146 to the distal end 1220 and can engage the threads 1216 of the connecting arm 1210 to couple the bottom portion 1218 to the connecting arm 1210, as illustrated in FIGS. 52 and 53.

With reference to FIG. 51, in order to assemble the multiplanar bone anchor system 1200 according to one exemplary method, the bone fastener 1102 can be inserted through the bore 1132 of the connecting arm 1210. Then, the threads 1222 of the bottom portion 1218 of the saddle 1208 can be threaded into the threads 1216 of the connecting arm 1210 to couple the bottom portion 1218 to the connecting arm 1210 with the lock ring 1204 assembled to the bottom portion 1218 and the preferred tab 1122 aligned with the preferred slot 1124 of the connecting arm 1210 (FIG. 52). The guides 1162a, 1162b of the top portion 1144 can be slid onto the rails 1152a, 1152b of the bottom portion 1218 to couple the top portion 1144 to the bottom portion 1218 (FIG. 53).

When assembled, the multiplanar bone anchor system 1200 can have at least three degrees of movement or can be movable in at least three planes. In this regard, the bone fastener 1102 can move or rotate about the longitudinal axis L6 and can also move or articulate relative to the longitudinal axis L6. The top portion 1144 can move or translate relative to the bottom portion 1218 in a direction transverse to the longitudinal axis L6. By allowing the multiplanar bone anchor system 1200 to move in at least three planes, the surgeon can manipulate the multiplanar bone anchor system 1200 as necessary to conform to the anatomy of the patient.

As the surgical insertion and use of the multiplanar bone anchor system 1200 in a fixation procedure can be similar to the surgical insertion and insertion of the multiplanar bone anchor system 1100 in a fixation procedure, the surgical insertion and use of the multiplanar bone anchor system 1200 will not be discussed in great detail herein. Briefly, however, once the bone fastener 1102 is secured to the anatomy, the saddle 1208 can be moved, pivoted or rotated relative to the bone fastener 1102 into the desired alignment for the fixation procedure. Once the aligned, the connecting rod 20 can be inserted into a desired number of multiplanar bone anchor systems 1200.

With the connecting rod 20 positioned in the saddles 1208 of the multiplanar bone anchor systems 1200, the set screw 22 can be coupled to each mating portion 84 of each saddle 1208. The coupling of the set screw 22 to the saddle 1208 can apply a force to the lock ring 1104 to fixedly couple or lock the position of the bone fastener 1102 relative to the saddle 1208.

With reference now to FIGS. 54-57, in one example, a multiplanar bone anchor system 1300 can be employed with the connecting rod 20 to repair a damaged portion of an anatomy. As the multiplanar bone anchor system 1300 can be similar to the multiplanar bone anchor system 1100 described with reference to FIGS. 46-49, only the differences between the multiplanar bone anchor system 1100 and the multiplanar bone anchor system 1300 will be discussed in great detail herein, and the same reference numerals will be used to denote the same or similar components. The multiplanar bone anchor system 1300 can include the bone fastener 1102, a lock ring 1304, a multiplanar coupling arrangement or system 1306, a saddle 1308 and a coupling device 1310. The multiplanar bone anchor system 1300 can define a longitudinal axis L7, and the multiplanar bone anchor system 1300 can be configured such that the bone fastener 1102 and the saddle 1308 can move relative to the longitudinal axis L7 in multiple planes.

Figure 55:
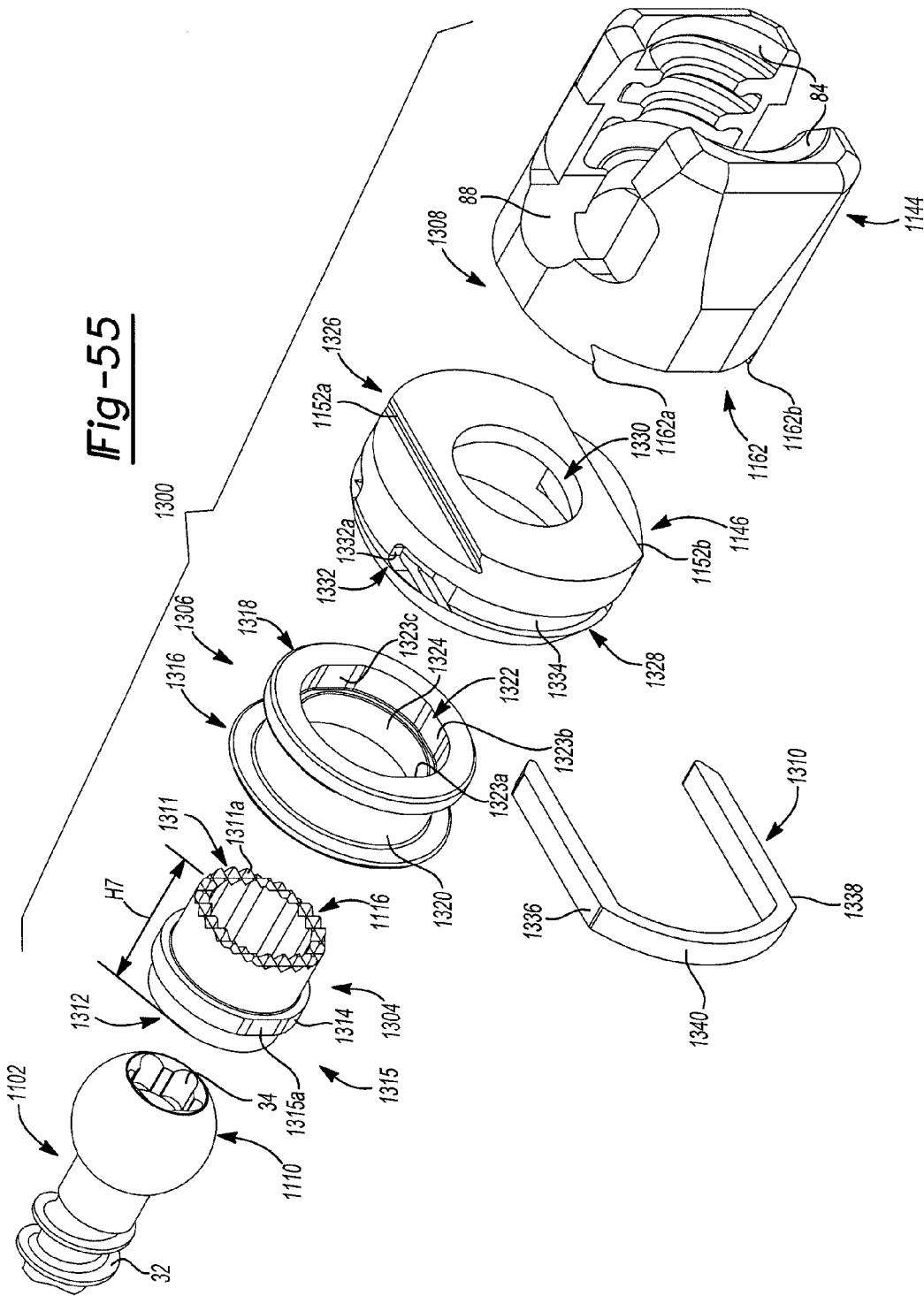
FIG. 55 is an exploded view of the multiplanar bone anchor system of FIG. 54.

With reference to FIGS. 55-57, the lock ring 1304 can be positioned about the head 1110 of the bone fastener 1102. As will be discussed herein, the lock ring 1304 can lock at least one of the bone fastener 1302 and the multiplanar coupling system 1306 relative to the saddle 1308 via a force applied by the connecting rod 20. The lock ring 1304 can be generally cylindrical, and can have a height H6. The height H6 can be sized to extend above the receiver surface 88 of the saddle 1308 so that coupling the connecting rod 20 to the saddle 1308 can compress the lock ring 1304 onto the head 1110 of the bone fastener 1102 (FIG. 54). With reference to FIG. 55, the lock ring 1304 can include a proximal end 1311, a distal end 1312 and the bore 1116.

The proximal end 1311 can bear against the connecting rod 20 when the connecting rod 20 is coupled to the saddle 1308. The proximal end 1311 can include a plurality of teeth 1311a. The teeth 1311a can engage or bite into the connecting rod 20 to assist in coupling the connecting rod 20 to the saddle 1308. It should be noted, that the teeth 1311a are optional.

The distal end 1312 can include a collar 1314. The collar 1314 can extend about a circumference of the lock ring 1304 and can be positioned a distance above a distalmost surface 1304a of the lock ring 1304. The collar 1314 can be in contact with the connecting arm 1316 and a portion of the saddle 1308. The collar 1314 can include at least one flat surface 1315.

The at least one flat surface 1315 can contact the connecting arm 1316 to assist in coupling the lock ring 1304 to the connecting arm 1316. In one example the at least one flat surface 1315 can comprise three flat surfaces 1315a-1315c, which can be spaced about a perimeter of the collar 1314 of the lock ring 1304. The flat surfaces 1315a-1315c can cooperate with the connecting arm 1316 to enable the user to manipulate the lock ring 1304 and the connecting arm 1316 to select a preferred angle, as will be described further herein. It should be noted that although not illustrated herein, the lock ring 1304 could include the preferred angle tab to mate with a preferred angle slot as described with regard to the multiplanar bone anchor system 1100.

With reference to FIGS. 55-57, the multiplanar coupling system 1306 can include a connecting arm 1316. The connecting arm 1316 can be disposed about the head 1110 of the bone fastener 1102 to enable the bone fastener 1102 to move or articulate relative to the saddle 1308. The connecting arm 1316 can be annular, and can be sized to receive a portion of the saddle 1308 and the lock ring 1304. With reference to FIG. 55, the connecting arm 1316 can include a bore 1318 and an annular recess 1320. The annular recess 1320 can receive a portion of the saddle 1308 and the coupling device 1310 to couple the portion of the saddle 1308 to the connecting arm 1316.

The bore 1318 can have a counterbored portion 1322 and a bearing surface 1324. The counterbored portion 1322 can be formed near a proximalmost end 1316a of the connecting arm 1316. The counterbored portion 1322 can receive the collar 1314 of the lock ring 1304. The counterbored portion 1322 can include at least one flat surface 1323. In one example, the counterbored portion 1322 can include three flat surfaces 1323a-1323c, which can cooperate with the flat surfaces 1315a-1315c of the lock ring 1304 to couple the lock ring 1304 to the connecting arm 1316. The bearing surface 1324 can contact the head 1110 of the bone fastener 1102 to enable the bone fastener 1102 to move, rotate or articulate relative to the connecting arm 1316.

With reference to FIGS. 54-57, the saddle 1308 can include a first portion or bottom portion 1326 and a second portion or top portion 1144. The top portion 1144 can move or translate relative to the bottom portion 1326. With reference to FIG. 55, the bottom portion 1326 can include the first or proximal end 1146, a second or distal end 1328 and a bore 1330.

The distal end 1328 can include at least one coupling bore 1332 and a coupling recess 1334. In one example, the at least one coupling bore 1332 can comprise two coupling bores 1332a, 1332b, as best illustrated in FIG. 57. The coupling bores 1332a, 1332b can receive the coupling device 1310 to couple the connecting arm 1316 to the bottom portion 1326. The coupling bores 1332a, 1332b can be positioned substantially opposite each other, and can generally extend in a direction transverse to the longitudinal axis L7. A portion of each of the coupling bores 1332a, 1332b can be defined by the annular recess 1320 of the connecting arm 1316. With reference to FIGS. 55 and 56, the coupling recess 1334 can be formed through a portion of the distal end 1328 and can be generally elongate. The coupling recess 1334 can be positioned between the coupling bores 1332a, 1332b. The coupling recess 1334 can receive a portion of the coupling device 1310 to enable the coupling device 1310 to be substantially flush with a surface of the bottom portion 1326 (FIG. 54).

The bore 1330 can be defined through the bottom portion 1326. The bore 1330 can be sized to receive a portion of the lock ring 1304 and the connecting arm 1316 therein (FIG. 56). The bore 1330 can have a first diameter at the proximal end 1146 and second diameter at a distal end 1328. The diameter can be sized to receive the lock ring 1304 therethrough, while the diameter can be sized to receive the bone fastener 1102, the lock ring 1304 and the connecting arm 1316.

With reference to FIG. 55, the coupling device 1310 can be received through the coupling bores 1332a, 1332b and the coupling recess 1334. In one example, the coupling device 1310 can comprise a clip, such as a Dutchman clip, however, any suitable device or technique could be used to couple the connecting arm 1316 to the bottom portion 1326, such as pins, adhesives, mechanical fasteners, etc. The coupling device 1310 can be substantially U-shaped, with a first arm 1336 and an opposed second arm 1338. The first arm 1336 can be coupled to the second arm 1338 via a body 1340. The first arm 1336 and the second arm 1338 can include a flange at a distalmost end, if desired, which can engage a portion of the bottom portion 1326 to further secure the coupling device 1310 within the bottom portion 1326 of the saddle 1308. The first arm 1336 and the second arm 1338 can each be received through a respective one of the coupling bores 1332a, 1332b until the body 1340 is received within and in contact with the coupling recess 1334 (FIG. 54).

With reference to FIG. 55, in order to assemble the multiplanar bone anchor system 1300 according to one exemplary method, the bone fastener 1102 can be inserted through the bore 1318 of the connecting arm 1316. Then, the bottom portion 1326 of the saddle 1308 can be positioned over the connecting arm 1316 with the lock ring 1304 positioned over the head 1110 of the bone fastener 1102 such that the connecting arm 1316 is received within the bore 1330 of the bottom portion 1326. The guides 1162a, 1162b of the top portion 1144 can be slid onto the rails 1152a, 1152b of the bottom portion 1326 to couple the top portion 1144 to the bottom portion 1326. Next, the coupling device 1310 can be inserted through the coupling bores 1332a, 1332b until the body 1340 of the coupling device 1310 is received within the coupling recess 1334 (FIG. 54).

When assembled, the multiplanar bone anchor system 1300 can have at least three degrees of movement or can be movable in at least three planes. In this regard, the bone fastener 1102 can move or rotate about the longitudinal axis L7 and can also move or articulate relative to the longitudinal axis L7. The top portion 1144 can move or translate relative to the bottom portion 1326 in a direction transverse to the longitudinal axis L7. By allowing the multiplanar bone anchor system 1300 to move in at least three planes, the surgeon can manipulate the multiplanar bone anchor system 1300 as necessary to conform to the anatomy of the patient.

As the surgical insertion and use of the multiplanar bone anchor system 1300 in a fixation procedure can be similar to the surgical insertion and insertion of the multiplanar bone anchor system 10 in a fixation procedure, the surgical insertion and use of the multiplanar bone anchor system 1300 will not be discussed in great detail herein. Briefly, however, once the bone fastener 1102 is secured to the anatomy, the saddle 1308 can be moved, pivoted or rotated relative to the bone fastener 1102 into the desired alignment for the fixation procedure. Once the aligned, the connecting rod 20 can be inserted into a desired number of multiplanar bone anchor systems 1300.

With the connecting rod 20 positioned in the saddles 1308 of the multiplanar bone anchor systems 1300, the set screw 22 can be coupled to each mating portion 84 of each saddle 1308. The coupling of the set screw 22 to the saddle 1308 can apply a force to the lock ring 1304 to fixedly couple or lock the position of the bone fastener 1102 relative to the saddle 1308.

With reference now to FIGS. 58-63, in one example, a multiplanar bone anchor system 1400 can be employed with the connecting rod 20 to repair a damaged portion of an anatomy. As the multiplanar bone anchor system 1400 can be similar to the multiplanar bone anchor system 1100 described with reference to FIGS. 46-49, only the differences between the multiplanar bone anchor system 1100 and the multiplanar bone anchor system 1400 will be discussed in great detail herein, and the same reference numerals will be used to denote the same or similar components. The multiplanar bone anchor system 1400 can include the bone fastener 1102, a lock ring 1404, a multiplanar coupling arrangement or system 1406 and a saddle 1408. The multiplanar bone anchor system 1400 can define a longitudinal axis L8, and the multiplanar bone anchor system 1400 can be configured such that the bone fastener 1102 and the saddle 1408 can move relative to the longitudinal axis L8 in multiple planes (FIG. 58).

With reference to FIGS. 59-61, the lock ring 1404 can be positioned about the head 1110 of the bone fastener 1102. As will be discussed herein, the lock ring 1404 can lock at least one of the bone fastener 1102 and the multiplanar coupling system 1406 relative to the saddle 1408 via a force applied by the connecting rod 20. The lock ring 1404 can be generally cylindrical, and can have a height H8. The height H8 can be sized to extend above the receiver surface 88 of the saddle 1408 so that coupling the connecting rod 20 to the saddle 1408 can compress the lock ring 1404 onto the head 1110 of the bone fastener 1102 (FIG. 58). The lock ring 1404 can contact a portion of the saddle 1408 to limit the motion of the saddle 1408, as will be discussed in greater detail herein. With reference to FIG. 59, the lock ring 1404 can include a proximal end 1412, a distal end 1414, a slot 1416, at least one wing 1418 and a bore 1420.

The proximal end 1412 can bear against the connecting rod 20 when the connecting rod 20 is coupled to the saddle 1408. The distal end 1414 can be adjacent to and in contact with the head 1110 of the bone fastener 1102. The slot 1416 can extend from the proximal end 1412 to the distal end 1414. The slot 1416 can enable the lock ring 1404 to flex. The at least one wing 1418 can engage a portion of the saddle 1408. In one example, the at least one wing 1418 can comprise two wings 1418a, 1418b. The wings 1418a, 1418b can be positioned about 180° apart about the circumference of the lock ring 1404. Each of the wings 1418a, 1418b can include a base 1422 and an arm 1424. The base 1422 can couple the arm 1424 to the lock ring 1404. The base 1422 can be coupled between the proximal end 1412 and the distal end 1414, and the arm 1424 can extend from the base 1422 so as to be at or below a plane defined by the distal end 1414. The arm 1424 can have a flat portion 1424a opposite a curved portion 1424b.

Figure 62:
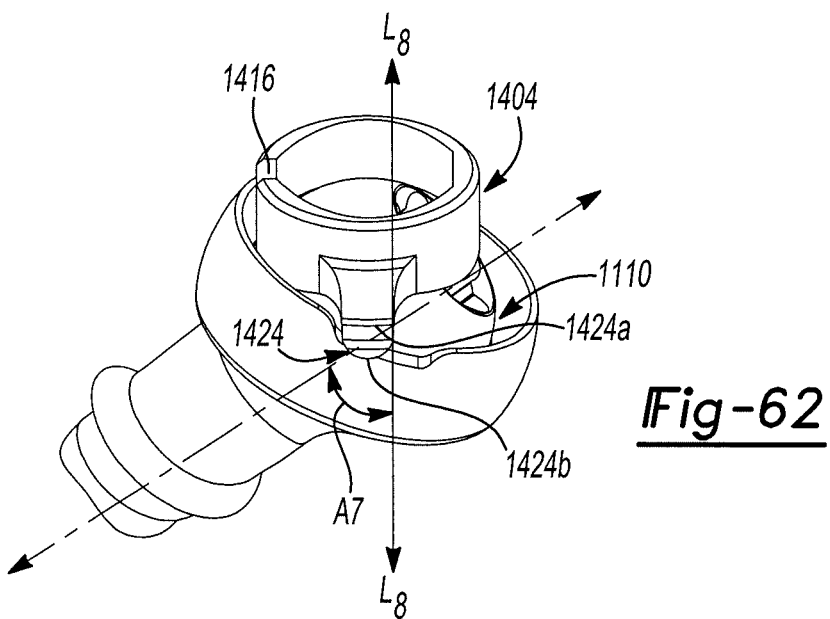
FIG. 62 is a schematic partial illustration of the multiplanar bone anchor system of FIG. 58, illustrating an articulation of a bone fastener to a first greater angle.

The flat portion 1424a can aid in keeping the wings 1418a, 1418b in contact with the connecting arm 1430 and within a portion of the saddle 1408, as illustrated in FIG. 61. With reference to FIG. 62, the curved portion 1424b can enable the lock ring 1404 to move or articulate relative the connecting arm 1430 and the saddle 1408, which can thereby allow the bone fastener 1102 to move or articulate relative the connecting arm 1430 and the saddle 1408, as will be discussed further herein.

With reference to FIG. 59, the bore 1420 can be defined from the proximal end 1412 to the distal end 1414. The bore 1420 can enable an instrument to engage the driver connection feature 34 when the multiplanar bone anchor system 1400 is assembled. The bore 1420 can include a bearing surface 1426. The bearing surface 1426 can generally be formed adjacent to the distal end 1414. The bearing surface 1426 can be arcuate and generally concave to slidably engage the spherical head 1110 of the bone fastener 1102 (FIG. 61).

Figure 63:
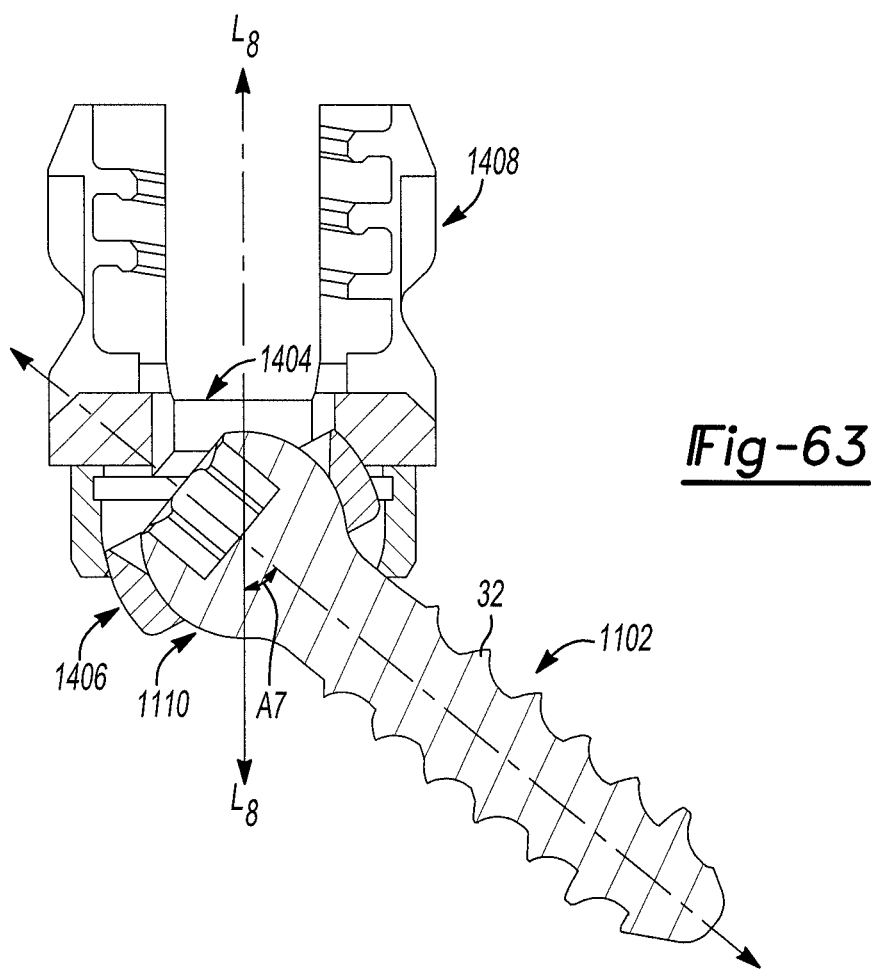
FIG. 63 is a schematic cross-sectional illustration of the multiplanar bone anchor system of FIG. 58, illustrating an articulation of the bone fastener to a second greater angle.

In one example, with reference to FIG. 59, the multiplanar coupling system 1406 can include a connecting arm 1430. The connecting arm 1430 can be disposed about the head 1110 of the bone fastener 1102 to enable the bone fastener 1102 to move or articulate relative to the saddle 1408, as shown in FIG. 63. The connecting arm 1430 can be annular, and can be sized to be received within a portion of the saddle 1408. With reference to FIG. 59, the connecting arm 1430 can include at least one pocket 1432 and a bore 1434.

The at least one pocket 1432 can be defined in a proximalmost end 1430a of the connecting arm 1430. In one example, the at least one pocket 1432 can comprise two pockets 1432a, 1432b. The pockets 1432a, 1432b can be positioned about 180° apart about the circumference of the connecting arm 1430. The pockets 1432a, 1432b can be sized to receive a respective one of the wings 1418a, 1418b. The pockets 1432a, 1432b can each define cut-outs, which extend for about 5° to about 25° around the circumference of the connecting arm 1430. The pockets 1432a, 1432b can have a depth sized to receive the arm 1425 of the wings 1418a, 1418b. The depth can also be sized to enable the lock ring 1404 to move, pivot or rotate relative to the connecting arm 1430, as will be discussed herein.

The bore 1434 can be defined through the connecting arm 1430, and can have a chamfered surface 1436 and a bearing surface 1438. The chamfered surface 1436 can provide clearance for the movement of the lock ring 1404. The bearing surface 1438 can be defined adjacent to the chamfered surface 1436. The bearing surface 1438 can be generally concave. The bearing surface 1438 can contact the head 1110 of the bone fastener 1102 to enable the bone fastener 1102 to move, rotate or articulate relative to the connecting arm 1430.

With reference to FIGS. 58-61, the saddle 1408 can include a first portion or bottom portion 1440 and a second portion or top portion 1442. The top portion 1442 can move or translate relative to the bottom portion 1440. With reference to FIG. 59, the bottom portion 1440 can include a first or proximal end 1444, a second or distal end 1446 and a bore 1448. The proximal end 1444 can be generally rectangular, and can include rounded corners. It should be noted that the shape of the proximal end 1444 is merely exemplary, and the proximal end 1444 could have any selected shape, such as generally square, cylindrical, oval, etc. The proximal end 1444 can be coupled to the top portion 1442 (FIG. 60). The proximal end 1444 can define at least one rail 1452. Generally, the top portion 1442 can move or translate along the at least one rail 1452. In one example, the proximal end 1444 can define two rails 1452a, 1452b, which can be positioned on opposite sides of the bottom portion 1440. As will be discussed, the height H8 and/or diameter of the lock ring 1404 can define or limit the translation of the top portion 1442 relative to the bottom portion 1440. The distal end 1446 can be adjacent to the shank 32 of the bone fastener 1102, when the saddle 1408 is coupled to the bone fastener 1102. The bore 1448 can be defined from the proximal end 1444 to the distal end 1446.

The bore 1448 can be sized to receive the connecting arm 1430 and the bone fastener 1102 therein. With reference to FIGS. 59 and 61, the bore 1448 can include at least one groove 1454, a bearing surface 1456 and a tapered surface 1458. The at least one groove 1454 can be defined under a proximalmost surface 1444a of the bottom portion 1440. In one example, the at least one groove 1454 can comprise two grooves 1454a, 1454b. The two grooves 1454a, 1454b can each extend for about 90° about a circumference of the bore 1448, and can be positioned generally 180° apart from each other about the bore 1448. The grooves 1454a, 1454b can receive the wings 1418a, 1418b of the lock ring 1404 to enable the lock ring 1404 to move, rotate or pivot relative to the connecting arm 1430 and bottom portion 1440.

The bearing surface 1456 can be configured to receive the connecting arm 1430 and can enable the connecting arm 1430 to move, rotate or pivot relative to the bottom portion 1440. As best illustrated in FIG. 61, the tapered surface 1458 can provide clearance for the movement or articulation of the bone fastener 1102 relative to the connecting arm 1430 and the saddle 1408.

With reference to FIGS. 59 and 60, the top portion 1442 of the saddle 1408 can be coupled to the rails 1452a, 1452b of the proximal end 1444 of the bottom portion 1440 so that the top portion 1442 can move relative to the bottom portion 1440. The top portion 1442 can be substantially U-shaped and symmetrical with respect to the longitudinal axis L8 defined by the multiplanar bone anchor system 1400 (FIG. 58). The top portion 1442 can include a first or proximal end 1460 and a second or distal end 1462. In one example, the proximal end 1460 can include a first arm 1464 and a second arm 1466. The first arm 1464 and second arm 1466 can extend upwardly from the distal end 1462 to define the U-shape. Each of the first arm 1464 and the second arm 1466 can include the mating portion 84, the cavity 86 and a connector feature 1468.

The connector feature 1468 can be defined in an exterior surface 1464a, 1466a of the first arm 1464 and the second arm 1466. The connector feature 1468 can enable the multiplanar bone anchor system 1400 to be coupled to instrumentation, such as rod reduction instruments or to a suitable cross-connector device in a spinal fixation procedure. The connector feature 1468 is illustrated herein as comprising a triangular recess formed in each of the first arm 1464 and the second arm 1466, however, it should be noted that the connector feature 1468 can have any selected shape and dimension to cooperate with a selected cross-connector device or instrument.

It should be noted that the lock ring 1404 can define or limit the translation of the top portion 1442 relative to the bottom portion 1440. In this regard, the cavity 86 can be defined in each interior surface 1464b, 1466b of the first arm 1464 and second arm 1466 of the top portion 1442 of the saddle 1408. The cavity 86 can provide clearance for the movement or articulation of the top portion 1442 relative to the bottom portion 1440 of the saddle 1408. Generally, the cavity 86 can be defined so as to allow the top portion 1442 to move over a portion of the lock ring 1404, which can provide a range of motion for the top portion 1442 relative to the bottom portion 1440. Thus, contact between the lock ring 1404 and the cavity 86 can act as a stop to limit the movement or translation of the top portion 1442 relative to the bottom portion 1440, however, other techniques could be used to stop or limit the movement or translation of the top portion 1442 relative to the bottom portion 1440.

With reference to FIG. 59, the distal end 1462 of the top portion 1442 can be generally rectangular, and can include the first or a receiver surface 88, a second or bottom surface 1470 and a central bore 1472. It should be noted that the shape of the distal end 1442 does not have to be generally rectangular, but could be generally square, cylindrical, oval, etc. The central bore 1472 can be defined through the distal end 1462 from the receiver surface 88 to the bottom surface 1470.

The bottom surface 1470 can include at least one or more guides 1474. In this example, the bottom surface 1470 can include two guides 1474a, 1474b. The guides 1474a, 1474b can slidably couple the top portion 1442 to the bottom portion 1440. In this regard, each guide 1474a, 1474b can cooperate with a respective one of the rails 1452a, 1452b to enable the top portion 1442 of the saddle 1408 to move or translate relative to the bottom portion 1440 of the saddle 1408 (FIG. 60). Generally, each guide 1474a, 1474b can comprise a C-shape, and each rail 1452a, 1452b can be received within a center of a respective guide 1474a, 1474b. It should be understood, however, that any suitable shape could be used to enable the top portion 1442 to move or translate relative to the bottom portion 1440.

With reference to FIG. 59, in order to assemble the multiplanar bone anchor system 1400 according to one exemplary method, the bone fastener 1102 can be inserted through the bore 1434 of the connecting arm 1430 until the bone fastener 1102 is seated within the connecting arm 1430. Then, bone fastener 1102 and the connecting arm 1430 can be inserted into the bottom portion 1440 of the saddle 1408. The lock ring 1404 can be inserted into the central bore 1472 of the top portion 1442. The rails 1452a, 1452b of the top portion 1442 can be slid onto the guides 1452a, 1452b of the bottom portion 1440 (FIG. 60). Then, the lock ring 1404 can be pushed downward and compressed until the wings 1418a, 1418b are received within the grooves 1454a, 1454b of the bottom portion 1440 and the pockets 1432a, 1432b of the connecting arm 1430 (FIG. 61).

When assembled, the multiplanar bone anchor system 1400 can have at least three degrees of movement or can be movable in at least three planes. The bone fastener 1102 can move or rotate about the longitudinal axis L8 and can also move or articulate relative to the longitudinal axis L8. In this regard, with reference to FIGS. 62 and 63, the multiplanar bone anchor system 1400 can enable the bone fastener 1102 to articulate to a first preferred angle A6 (FIG. 61) and a second preferred angle A7 (FIGS. 62 and 63) relative to the longitudinal axis L8. The second preferred angle A7 can be greater than the second preferred angle A6. The first preferred angle A6 can be defined by the articulation of the bone fastener 1102 relative to the connecting arm 1430 (FIG. 61). The second preferred angle A7 can be defined by the articulation of the connecting arm 1430 within the bottom portion 1440 (FIGS. 62 and 63). It should be noted that the multiplanar bone anchor system 1400 need not include one or more preferred angles, if desired.

In this regard, the wings 1418a, 1418b of the lock ring 1404 can prevent the articulation of the connecting arm 1430 within the bottom portion 1440. In a plane perpendicular to the wings 1418a, 1418b, however, the connecting arm 1430 can be free to articulate relative to the bottom portion 1440. This articulation of the connecting arm 1430 within the bottom portion 1440 in the plane can define the second preferred angle A7. In addition, as the lock ring 1404 can move within the saddle 1408, the operator can move the lock ring 1404 to a desired location to enable the selection of the location for the second preferred angle A5.

The top portion 1442 can also move or translate relative to the bottom portion 1440 in a direction transverse to the longitudinal axis L8. By allowing the multiplanar bone anchor system 1400 to move in at least three planes, the surgeon can manipulate the multiplanar bone anchor system 1400 as necessary to conform to the anatomy of the patient.

As the surgical insertion and use of the multiplanar bone anchor system 1400 in a fixation procedure can be similar to the surgical insertion and insertion of the multiplanar bone anchor system 10 in a fixation procedure, the surgical insertion and use of the multiplanar bone anchor system 1400 will not be discussed in great detail herein. Briefly, however, once the bone fastener 1102 is secured to the anatomy, the saddle 1408 can be moved, pivoted or rotated relative to the bone fastener 1102 into the desired alignment for the fixation procedure. Once the aligned, the connecting rod 20 can be inserted into a desired number of multiplanar bone anchor systems 1400.

With the connecting rod 20 positioned in the saddles 1408 of the multiplanar bone anchor systems 1400, the set screw 22 can be coupled to each mating portion 84 of each saddle 1408. The coupling of the set screw 22 to the saddle 1408 can apply a force to the lock ring 1404 to fixedly couple or lock the position of the bone fastener 1102 relative to the saddle 1408.

With reference now to FIGS. 64-71, in one example, multiplanar bone anchor systems 1500a, 1500b can be employed with the connecting rod 20 to repair a damaged portion of an anatomy. As the multiplanar bone anchor systems 1500a, 1500b can be similar to the multiplanar bone anchor system 800 described with reference to FIGS. 31-36, only the differences between the multiplanar bone anchor system 800 and the multiplanar bone anchor systems 1500a, 1500b will be discussed in great detail herein, and the same reference numerals will be used to denote the same or similar components. The multiplanar bone anchor systems 1500a, 1500b can include the bone fastener 802, a multiplanar coupling arrangement or system 1504*a*, 1504*b* and a saddle 1506. The multiplanar bone anchor system 1500 can define a longitudinal axis L9, and the multiplanar bone anchor system 1500 can be configured such that the bone fastener 802 and the saddle 1506 can move relative to the longitudinal axis L9 in multiple planes.

In one example, with reference to FIGS. 65 and 69, the multiplanar coupling system 1504*a*, 1504*b* can include a connecting arm 1516*a*, 1516*b*. The connecting arm 1516*a*, 1516*b* can be composed of any suitable biocompatible material, such as a biocompatible metal, metal alloy, ceramic or polymer. The connecting arm 1516*a*, 1516*b* can be disposed about the head 810 of the bone fastener 802 to allow relative movement between the bone fastener 802 and the saddle 806. The connecting arm 1516*a*, 1516*b* can be sized to fit within the saddle 1506, and can also allow a portion of the saddle 1506 to move or translate relative to another portion of the saddle 1506, as will be discussed in greater detail herein. The connecting arm 1516*a*, 1516*b* can include a first or upper portion 1520, a second or lower portion 1522*a*, 1522*b* and the bore 824.

The upper portion 1520 can be shaped to be received within a portion of the saddle 1506, and can be generally rectangular with rounded corners. In one example, the upper portion 1520 can have opposite curved features 821. The opposite curved features 821 can include generally straight portions 821*a*. The straight portion 821*a* can cooperate with the saddle 1506 to enable the saddle 806 to move or translate relative to the upper portion 1520 of the connecting arm 1516*a*, 1516*b*. The upper portion 1520 can include the rail 829 as illustrated in FIGS. 67 and 71.

With reference to FIGS. 65 and 69, the lower portion 1522*a*, 1522*b* can include the connection surface 830 and a preferred angle slot 1532*a* or preferred angle slot 1532*b*, respectively. Each of the preferred angle slots 1532*a*, 1532*b* can enable the bone fastener 802 to articulate to a greater angle A8 relative to a longitudinal axis L9 of the multiplanar bone anchor system 800. In this regard, with reference to FIGS. 67 and 70, the bone fastener 802 can generally articulate to an angle A9 relative to the longitudinal axis L9 along the portion of the connecting arm 1516*a*, 1516*b* that does not include the preferred angle slot 1532*a*, 1532*b*. At the location of the preferred angle slot 1532*a*, 1532*b*, the bone fastener 802 can generally articulate to the greater angle A8 relative to the longitudinal axis L9. In one example, the angle A9 can be about less than the greater angle A8, and the greater angle A8 can be between about 15 degrees and about 90 degrees. The preferred angle slot 1532*a*, 1532*b* can comprise an arcuate cut-out defined through the lower portion 1522 of the connecting arm 1516*a*, 1516*b*, which can be in communication with the bore 824. The arcuate cut-out of the preferred angle slot 1532*a*, 1532*b* can enable the bone fastener 802 to move or articulate to the greater angle A8 relative to the longitudinal axis L9.

In one example, as illustrated in FIGS. 64-67, the preferred angle slot 1532*a* can be defined to enable the bone fastener 802 to articulate to the greater angle A8 in a cephalad-caudal direction. In another example, as illustrated in FIGS. 68-71, the preferred angle slot 1532*b* can be defined to enable the bone fastener 802 to articulate to the greater angle A8 in a medial-lateral direction.

Further, it should be noted that although only one preferred angle slot 1532*a*, 1532*b* is illustrated in the drawings for the multiplanar bone anchor systems 1500*a*, 1500*b*, the connecting arm 1516*a*, 1516*b* can include any number of preferred angle slots 1532 at any location along the connecting arm 1516*a*, 1516*b* to enable the bone fastener 802 to articulate in any selected direction. It should also be noted that the shape of the cut-out that forms the preferred angle slot 1532 can be modified to reduce or increase the greater angle A8 of the articulation of the bone fastener 802 relative to the longitudinal axis L9. In addition, it should be noted that the multiplanar bone anchor systems 1500*a*, 1500*b* need not include one or more preferred angle slots, if desired.

With reference to FIGS. 65 and 69, the saddle 1506 can be coupled to the connecting arm 1516*a*, 1516*b* and can move or translate relative to the connecting arm 1516*a*, 1516*b*. In this regard, the saddle 1506 can include a first portion or bottom portion 1538 and a second portion or top portion 1542. The bottom portion 1538 can be immovably coupled to the connecting arm 1516*a*, 1516*b* and the top portion 1542 can move or translate relative to the bottom portion 1538 and the connecting arm 1516*a*, 1516*b*. In one example, the bottom portion 1538 can include the opposed generally arcuate surfaces 840*a*, which can be interconnected by generally straight or flat surfaces 840*b*. It should be noted that any suitable geometry could be employed to enable the top portion 1542 to move or translate relative to the bottom portion 1538. The shape of the bottom portion 1538 can correlate with the shape of the connecting arm 1516*a*, 1516*b*. The bottom portion 1538 can include the first or proximal end 844, a second or distal end 1540 and the bore 848.

The distal end 1540 can include a preferred angle slot 1541*a*, 1541*b*. The preferred angle slot 1541*a*, 1541*b* can be defined through the distal end 1540 so as to be in communication with the bore 848. In one example, as illustrated in FIGS. 64-67, the preferred angle slot 1541*a* can be defined to enable the bone fastener 802 to articulate to the greater angle A8 in the cephalad-caudal direction. In another example, as illustrated in FIGS. 68-71, the preferred angle slot 1541*b* can be defined to enable the bone fastener 802 to articulate to the greater angle A8 in the medial-lateral direction. The preferred angle slot 1541*a*, 1541*b* of the bottom portion 1538 can be positioned in substantially the same location relative to the connecting arm 1516*a*, 1516*b* such that when the bottom portion 1538 is coupled to the connecting arm 1516*a*, 1516*b*, a respective one of the preferred angle slot 1541*a*, 1541*b* of the bottom portion 1538 is aligned with a respective one of the preferred angle slot 1532*a*, 1532*b* of the connecting arm 1516*a*, 1516*b*. The alignment between the preferred angle slot 1532*a*, 1532*b* and the preferred angle slot 1541*a*, 1541*b* can enable the bone fastener 802 to move or articulate to the greater angle A8.

With reference to FIGS. 67 and 71, the top portion 1542 of the saddle 1506 can be disposed about the curved features 821 of the connecting arm 1516*a*, 1516*b*. The top portion 1542 can move or translate relative the connecting arm 1516*a*, 1516*b*, and thus, move or translate relative to the bottom portion 1538. The top portion 1542 can be substantially U-shaped and symmetrical with respect to a longitudinal axis L9 defined by the multiplanar bone anchor system 1500*a*, 1500*b* (FIGS. 64 and 68). With reference to FIGS. 65 and 69, the top portion 1542 can include a first or proximal end 1544 and a second or distal end 1546. In one example, the proximal end 1544 can include a first arm 1548 and a second arm 1550. The first arm 1548 and second arm 1550 can extend upwardly from the distal end 1546 to define the U-shape. Each of the first arm 1548 and the second arm 1550 can include the mating portion 84, the cavity 868 (FIGS. 67 and 71) and a connector feature 1552.

With reference to FIGS. 65 and 69, the connector feature 1552 can be defined in an exterior surface 1548*a*, 1550*a* of the first arm 1548 and the second arm 1550. The connector feature 1552 can enable the multiplanar bone anchor system 1500a, 1500b to be coupled to instrumentation, such as rod reduction instruments or to a suitable cross-connector device in a spinal fixation procedure. The connector feature 1552 is illustrated herein as comprising a recess formed in each of the first arm 1548 and the second arm 1550, it should be noted that the connector feature 1552 can have any selected shape and dimension to cooperate with a selected cross-connector device or instrument.

With reference to FIGS. 65 and 69, the distal end 1546 of the top portion 1542 can be generally rectangular, and can include rounded corners to correspond with the shape of the bottom portion 1538. It should be noted that the shape of the distal end 1546 does not have to be generally rectangular, but rather could be generally square, cylindrical, oval, etc. The distal end 1546 can include the first or receiver surface 88, the second or bottom surface 872 and the central bore 876.

With reference to FIGS. 65 and 69, in order to assemble the multiplanar bone anchor system 1500a, 1500b according to one exemplary method, the bone fastener 802 can be inserted into the bore 824 of the connecting arm 1516a, 1516b so that the bone fastener 802 is retained within and can articulate within the connecting arm 1516a, 1516b. Then, the connecting arm 1516a, 1516b can be inserted into the top portion 1542 of the saddle 1506. Generally, the connecting arm 1516a, 1516b can be rotated about 90° around the main axis M1 of the connecting arm 1516a, 1516b in order to insert the connecting arm 1516a, 1516b through the top portion 1542. The connecting arm 1516a, 1516b can be rotated back about 90° around the axis M1 until the curved features 821 and straight portions 821a of the connecting arm 1516a, 1516b are engaged with the curved features 880 and straight features 882 of the top portion 1542. Then, the bottom portion 1538 can be coupled to the connecting arm 1516a, 1516b.

It should be noted that this assembly technique is merely exemplary, as the multiplanar bone anchor systems 1500a, 1500b could be assembled according to various methods. For example, the connecting arm 1516a, 1516b could be inserted into the saddle 1506, and then the bone fastener 802 could be inserted into connecting arm 1516a, 1516b. Then, the bottom portion 1538 can be coupled to the connecting arm 1516a, 1516b.

Once assembled, the connecting arm 1516a, 1516b can enable the bone fastener 802 to move or rotate within the bore 824 of the connecting arm 1516a, 1516b. The connecting arm 1516a, 1516b can also allow the bone fastener 802 to move or angulate relative to the longitudinal axis L9 of the multiplanar bone anchor system 1500a, 1500b.

In one example, the preferred angle slot 1532a of the connecting arm 1516a can cooperate with the preferred angle slot 1540a of the bottom portion 1538 to enable the bone fastener 802 to move or articulate to the greater angle A8 in the calphalad-caudal direction. In another example, the preferred angle slot 1532b of the connecting arm 1516b can cooperate with the preferred angle slot 1540b of the bottom portion 1538 to enable the bone fastener 802 to move or articulate to the greater angle A8 in the medial-lateral direction. In either example, the top portion 1542 of the saddle 1506 can move or translate relative to the bottom portion 1538 and connecting arm 1516a, 1516b to a selected position.

Thus, when assembled, the multiplanar bone anchor system 1500a, 1500b can have at least three degrees of movement or can be movable in at least three planes. For example, the bone fastener 802 can rotate about the longitudinal axis L9. The bone fastener 802 can also pivot relative to the longitudinal axis L9 in at least a first direction and a second direction. The saddle 1506 can translate relative to the longitudinal axis L9. By allowing the multiplanar bone anchor system 1500a, 1500b to move in at least three planes, the surgeon can manipulate the multiplanar bone anchor system 1500a, 1500b as necessary to conform to the anatomy of the patient.

As the surgical insertion and use of the multiplanar bone anchor system 1500a, 1500b in a fixation procedure can be similar to the surgical insertion and insertion of the multiplanar bone anchor system 10 in a fixation procedure, the surgical insertion and use of the multiplanar bone anchor system 1500a, 1500b will not be discussed in great detail herein. Briefly, however, once the multiplanar bone anchor system 1500a, 1500b is secured to the anatomy, the multiplanar coupling system 1504 and the saddle 1506 can be moved, pivoted or rotated relative to the bone fastener 802 into the desired alignment for the fixation procedure. Once the aligned, the connecting rod 20 can be inserted into a desired number of multiplanar bone anchor systems 1500.

With the connecting rod 20 positioned in the saddles 1506 of the multiplanar bone anchor systems 1500a, 1500b, the set screw 22 can be coupled to each mating portion 84 of each saddle 1506. The coupling of the set screw 22 to the saddle 1506 can apply a force to the head 810 of the bone fastener 802 to fixedly couple or lock the position of the bone fastener 802 relative to the saddle 1506.

With reference now to FIGS. 72-75, in one example, a multiplanar bone anchor system 1554 can be employed with the connecting rod 20 to repair a damaged portion of an anatomy. As the multiplanar bone anchor system 1554 can be similar to the multiplanar bone anchor system 800 described with reference to FIGS. 31-36, only the differences between the multiplanar bone anchor system 800 and the multiplanar bone anchor system 1554 will be discussed in great detail herein, and the same reference numerals will be used to denote the same or similar components. The multiplanar bone anchor system 1554 can include a bone fastener 1555, a multiplanar coupling arrangement or system 1556 and a saddle 1557. The multiplanar bone anchor system 1554 can define a longitudinal axis L12, and the multiplanar bone anchor system 1554 can be configured such that the bone fastener 1555 and the saddle 1557 can move relative to the longitudinal axis L12 in multiple planes.

Figure 73:
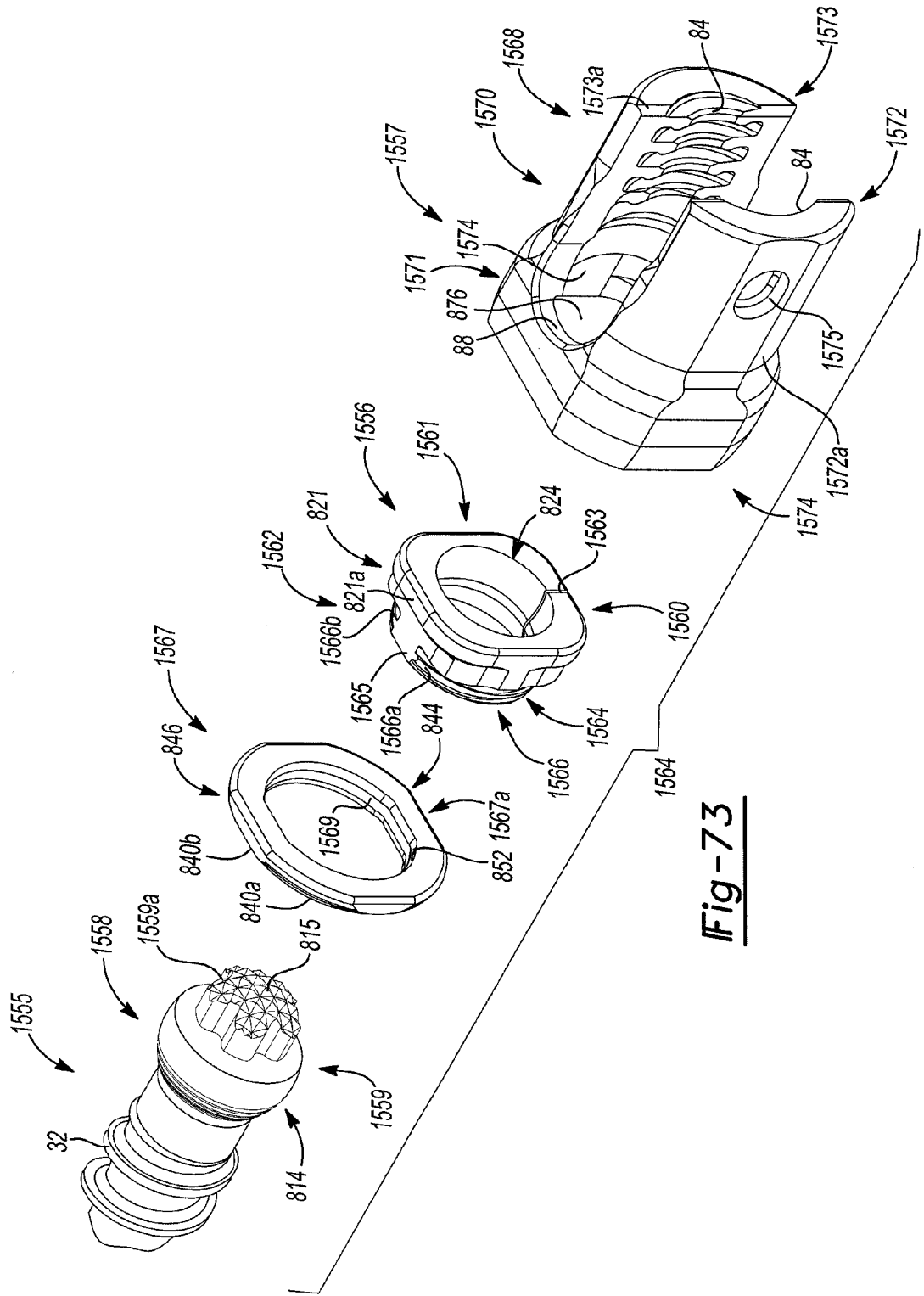
FIG. 73 is an exploded view of the multiplanar bone anchor system of FIG. 72.
Figure 76:
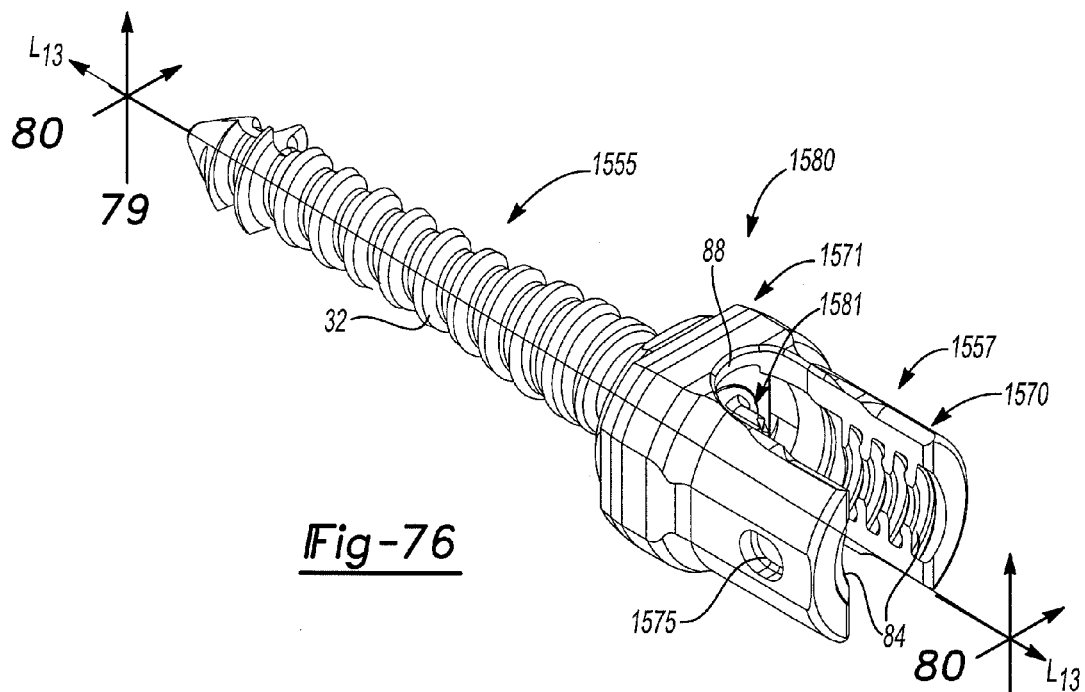
FIG. 76 is a perspective view of an exemplary multiplanar bone anchor system for use with a connecting device in a fixation procedure according to the present teachings.

With reference to FIGS. 72 and 73, the bone fastener 1555 can be configured to engage the anatomy to couple the multiplanar bone anchor system 1554 to the anatomy. The bone fastener 1555 can be composed of any suitable biocompatible material, such as titanium, stainless steel, biocompatible metals, metal alloys, polymers, etc. The bone fastener 1555 can include a proximal end or head 1558 (FIG. 73) and the distal end or shank 32. In one example, the head 1558 can be larger than the head 810 of the multiplanar bone anchor system 800, and the larger head 1558 can be coupled to and received within the saddle 1557. It should also be noted that the shank 32 illustrated herein is merely exemplary, as the shank 32 could have any desired length or thread. With reference to FIG. 73, the head 1558 can include a first or upper portion 1559 and the second or lower portion 814.

The upper portion 1559 can include the contact surface 815 and a driver connection feature 1559a. The driver connection feature 1559a can comprise any mating connection interface for a driver, such as a pentalobe, hexalobe, hexagon, torx, Philips, cruciate, straight, etc. In one example, the driver connection feature 1559a can comprise a pentalobe, and the contact surface 815 can be formed on the driver connection feature 1559a.

With continued reference to FIG. 73, in one example, the multiplanar coupling system 1556 can include a connecting arm 1560. The connecting arm 1560 can be composed of any suitable biocompatible material, such as a biocompatible metal, metal alloy or polymer. The connecting arm 1560 can be disposed about the head 1558 of the bone fastener 1555 to allow relative movement between the bone fastener 1555 and the saddle 1557. The connecting arm 1560 can be sized to fit within the saddle 1557, and can also allow a portion of the saddle 1557 to move or translate relative to another portion of the saddle 1557, as will be discussed in greater detail herein. The connecting arm 1560 can include a first or upper portion 1561, a second or lower portion 1562, the bore 824 and at least one slot 1563.

The upper portion 1561 can be shaped to be received within a portion of the saddle 1557, and can be generally rectangular with rounded corners. In one example, the upper portion 1561 can have the opposite curved features 821. The opposite curved features 821 can include generally straight portions 821*a*. The straight portion 821*a* can cooperate with the saddle 1557 to enable the saddle 1557 to move or translate relative to the upper portion 1561 of the connecting arm 1560. The upper portion 1561 can include the rail 829 as illustrated in FIG. 75.

With reference to FIG. 73, the lower portion 1562 can include a connection surface 1564. The connection surface 1564 can comprise at least one flat surface 1565 and at least one rib 1566. The at least one flat surface 1565 and at least one rib 1566 can cooperate with a portion of the saddle 1557 to couple that portion of the saddle 1557 immovably to the connecting arm 1560. In one example, the connection surface 1564 can comprise two flat surfaces 1565*a*, 1565*b* and two ribs 1566*a*, 1566*b*. The flat surfaces 1565*a*, 1565*b* can be substantially opposite each other about a perimeter of the connecting arm 1560. The flat surfaces 1565*a*, 1565*b* can prevent the connecting arm 1560 from rotating relative to the portion of the saddle 1557. The ribs 1566*a*, 1566*b* can be formed along arcuate surfaces of the lower portion 1562 and can generally be positioned a distance from a bottommost surface 1562*a* of the lower portion 1562 (FIG. 74). The ribs 1566*a*, 1566*b* can create an overlap, interference or snap fit between the portion of the saddle 1557 and the lower portion 1562, as will be discussed in greater detail herein.

With reference to FIG. 73, the at least one slot 1563 can be defined through the upper portion 1561 and the lower portion 1562. The at least one slot 1563 can enable the connecting arm 1560 to expand to accept the bone fastener 1555. In this regard, the at least one slot 1563 can enable the connecting arm 1560 to expand to except a larger sized head of a bone fastener, such as the head 1558 of the bone fastener 1555, without requiring the use of a larger sized connecting arm 1560 and saddle 1557. In addition, the at least one slot 1563 can enable the connecting arm 1560 to expand to accept the bone fastener 1555 after the connecting arm 1560 is retained within the saddle 1557 from a bottom loading position, as will be discussed in greater detail herein. It should be noted that any suitable technique can be used to couple the bone fastener 1555 to the saddle 1557 from a bottom loading position, such as freezing the head 1558 of the bone fastener 1555 so that it contracts and heating the connecting arm 1560 so that it expands to accept the head 1558.

With reference to FIGS. 73 and 74, the saddle 1557 can be coupled to the connecting arm 1560 and can move or translate relative to the connecting arm 1560. In this regard, the saddle 1557 can include a first portion or bottom portion 1567 and a second portion or top portion 1568. The bottom portion 1567 can be immovably coupled to the connecting arm 1560, and the top portion 1568 can move or translate relative to the bottom portion 1567 and the connecting arm 1560.

In one example, with reference to FIG. 73, the bottom portion 1567 can include the opposed generally arcuate surfaces 840*a*, which can be interconnected by the generally straight or flat surfaces 840*b*. The shape of the bottom portion 1567 can cooperate with the shape of the connecting arm 1560 so that the bottom portion 1567 can be coupled to the connecting arm 1560. The bottom portion 1567 can include the first or proximal end 844, the second or distal end 846 and a bore 1567*a*.

With reference to FIG. 74, the bore 1567*a* can be formed along the longitudinal axis L12 from the proximal end 844 to the distal end 846. The bore 1567*a* can be sized and configured to be immovably coupled about the connecting arm 1560. With reference to FIG. 73, the bore 1567*a* can include the chamfered edge 852 and at least one groove 1569.

The at least one groove 1569 can cooperate with the at least one rib 1565 of the connecting arm 1560 to couple the bottom portion 1567 to the connecting arm 1560 (FIG. 74). In one example, the bore 1567*a* can include two grooves 1569*a*, 1569*b*. A respective one of each of the grooves 1569*a*, 1569*b* can engage a respective one of each of the ribs 1566*a*, 1566*b*. Generally, the grooves 1569*a*, 1569*b* can be configured to enable the ribs 1566*a*, 1566*b* to snap-fit into the grooves 1569*a*, 1569*b* to couple the bottom portion 1567 with the connecting arm 1560.

With reference to FIG. 75, the top portion 1568 of the saddle 1557 can be disposed about the curved features 821 of the connecting arm 1560. The top portion 1568 can move or translate relative the connecting arm 1560, and thus, move or translate relative to the bottom portion 1567. With reference to FIG. 72, the top portion 1568 can be substantially U-shaped and symmetrical with respect to a longitudinal axis L12 defined by the multiplanar bone anchor system 1554. The top portion 1568 can include a first or proximal end 1570 and a second or distal end 1571. In one example, with reference to FIG. 73, the proximal end 1570 can include a first arm 1572 and a second arm 1573. The first arm 1572 and second arm 1573 can extend upwardly from the distal end 1571 to define the U-shape. Each of the first arm 1572 and the second arm 1573 can include the mating portion 84, a cavity 1574 and a connector feature 1575.

With reference to FIGS. 73 and 74, the cavity 1574 can be defined in each interior surface 1572*a*, 1573*a* of the first arm 1572 and the second arm 1573. The cavity 1574 can provide clearance for the movement or articulation of the top portion 1568 relative to the bottom portion 1567 of the saddle 1557. In this regard, the cavity 1574 can be defined so as to allow the top portion 1568 to move over the head 1558 of the bone fastener 1555, which can provide a range of motion for the top portion 1568 relative to the bottom portion 1567. Thus, contact between the head 1558 of the bone fastener 1555 and/or the connecting arm 1560 and the cavity 1574 can act as a stop to limit the movement or translation of the top portion 1568 relative to the bottom portion 1567, however, other techniques could be used to stop or limit the movement or translation of the top portion 1568 relative to the bottom portion 1567, such as features formed on the connecting arm 1560. In addition, the cavity 1574 can be sized to enable the connecting arm 1560 to expand to accept a larger diameter head 1558 of the bone fastener 1555.

With reference to FIG. 73, the connector feature 1575 can be defined in an exterior surface 1572*b*, 1573*b* of the first arm 1572 and the second arm 1573. The connector feature 1575 can enable the multiplanar bone anchor system 1554 to be coupled to instrumentation, such as a rod reduction instrument, or a suitable cross-connector device in a spinal fixation procedure. The connector feature 1575 is illustrated herein as comprising an oblong recess with rounded corners formed in each of the first arm 1572 and the second arm 1573, however, it should be noted that the connector feature 1575 can have any selected shape and dimension to cooperate with a selected cross-connector device or instrument.

With continuing reference to FIG. 73, the distal end 1571 of the top portion 1568 can be generally rectangular, and can include rounded corners to correspond with the shape of the bottom portion 1567. The distal end 1571 can include the first or receiver surface 88, a second or bottom surface 1574 and the central bore 876.

With reference to FIG. 75, the bottom surface 1574 can include at least one guide 1577. In one example, the bottom surface 1574 can include two guides 1577a, 1577b, which can be positioned opposite each other. The guides 1577a, 1577b can allow the top portion 1568 to move or translate relative to the connecting arm 1560. The guides 1577a, 1577b can retain the top portion 1568 on the connecting arm 1560 and can be configured to mate with the curved features 821 of the connecting arm 1560. An end of each of the guides 1577a, 1577b can contact the rail 829 to guide the movement of the top portion 1568 relative to the connecting arm 1560.

With reference to FIG. 73, in order to assemble the multiplanar bone anchor system 1554 according to one exemplary method, the connecting arm 1560 can be inserted into the central bore 876 of the saddle 1557. Generally, the connecting arm 1560 can be rotated about 90° around a main axis of the connecting arm 1560 in order to insert the connecting arm 1560 through the top portion 1568. The connecting arm 1560 can be rotated back about 90° around the main axis until the curved features 821 are engaged with the guides 1577a, 1577b of the top portion 1568. Then, the bone fastener 1555 can be inserted through the bore 824 of the connecting arm 1560. The at least one slot 1563 in the connecting arm 1560 and the size of the cavity 1574 can enable the connecting arm 1560 to expand to accept the head 1558 of the bone fastener 1555. Then, the bottom portion 1567 can be coupled to the connecting arm 1560.

Once assembled, with reference to FIGS. 72-74, the connecting arm 1560 can enable the bone fastener 1555 to move or rotate within the bore 824 of the connecting arm 1560. The connecting arm 1560 can also allow the bone fastener 1555 to move or angulate relative to the longitudinal axis L12 of the multiplanar bone anchor system 1554. The top portion 1568 of the saddle 1557 can move or translate relative to the bottom portion 1567 and connecting arm 1569 to a selected position. Thus, when assembled, the multiplanar bone anchor system 1554 can have at least three degrees of movement or can be movable in at least three planes. For example, the bone fastener 1555 can rotate about the longitudinal axis L12. The bone fastener 1555 can also pivot relative to the longitudinal axis L12 in at least a first direction and a second direction. The saddle 1557 can translate relative to the longitudinal axis L12. By allowing the multiplanar bone anchor system 1554 to move in at least three planes, the surgeon can manipulate the multiplanar bone anchor system 1554 as necessary to conform to the anatomy of the patient.

As the surgical insertion and use of the multiplanar bone anchor system 1554 in a fixation procedure can be similar to the surgical insertion and insertion of the multiplanar bone anchor system 10 in a fixation procedure, the surgical insertion and use of the multiplanar bone anchor system 1554 will not be discussed in great detail herein. Briefly, however, once the multiplanar bone anchor system 1554 is secured to the anatomy, the multiplanar coupling system 1556 and the saddle 1557 can be moved, pivoted or rotated relative to the bone fastener 1555 into the desired alignment for the fixation procedure. Once the aligned, the connecting rod 20 can be inserted into a desired number of multiplanar bone anchor systems 1554.

With the connecting rod 20 positioned in the saddles 1557 of the multiplanar bone anchor systems 1554, the set screw 22 can be coupled to each mating portion 84 of each saddle 1557. The coupling of the set screw 22 can apply a force to the head 1558 of the bone fastener 1555 to fixedly couple or lock the position of the bone fastener 1555 relative to the saddle 1557.

With reference now to FIGS. 76-80, in one example, a multiplanar bone anchor system 1580 can be employed with the connecting rod 20 to repair a damaged portion of an anatomy. As the multiplanar bone anchor system 1580 can be similar to the multiplanar bone anchor system 1554 described with reference to FIGS. 72-75, only the differences between the multiplanar bone anchor system 1554 and the multiplanar bone anchor system 1580 will be discussed in great detail herein, and the same reference numerals will be used to denote the same or similar components. The multiplanar bone anchor system 1580 can include the bone fastener 1555, a multiplanar coupling arrangement or system 1581 and the saddle 1557. The multiplanar bone anchor system 1580 can define a longitudinal axis L13, and the multiplanar bone anchor system 1580 can be configured such that the bone fastener 1555 and the saddle 1557 can move relative to the longitudinal axis L13 in multiple planes.

Figure 77:
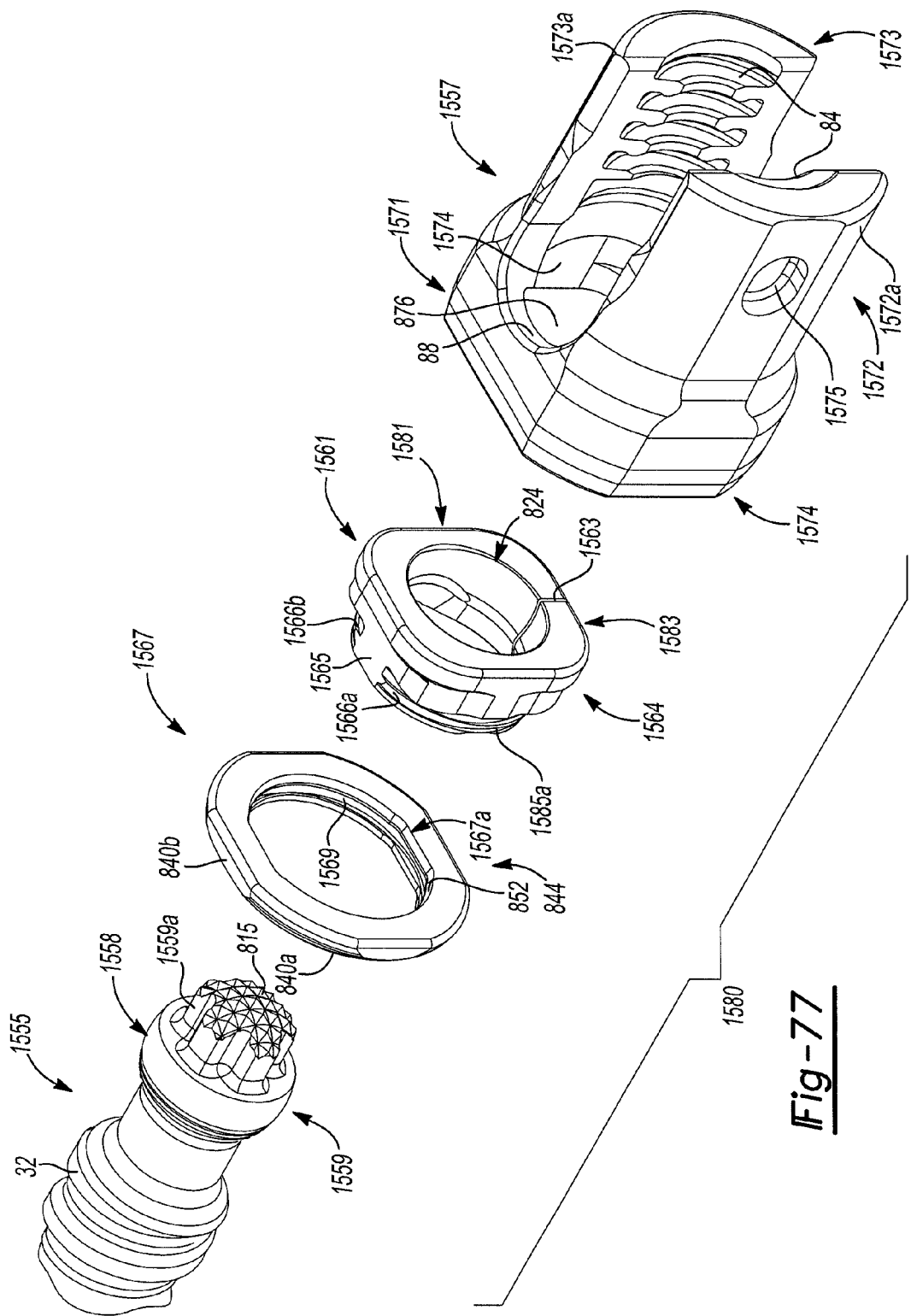
FIG. 77 is an exploded view of the multiplanar bone anchor system of FIG. 76.

With reference to FIG. 77, in one example, the multiplanar coupling system 1581 can include a connecting arm 1583. The connecting arm 1583 can be composed of any suitable biocompatible material, such as a biocompatible metal, metal alloy or polymer. The connecting arm 1583 can be disposed about the head 1558 of the bone fastener 1555 to allow relative movement between the bone fastener 1555 and the saddle 1557. The connecting arm 1583 can be sized to fit within the saddle 1557, and can also allow a portion of the saddle 1557 to move or translate relative to another portion of the saddle 1557, as will be discussed in greater detail herein. The connecting arm 1583 can include the first or upper portion 1561, a second or lower portion 1584, the bore 824 and the at least one slot 1563.

Figures 79, 80:
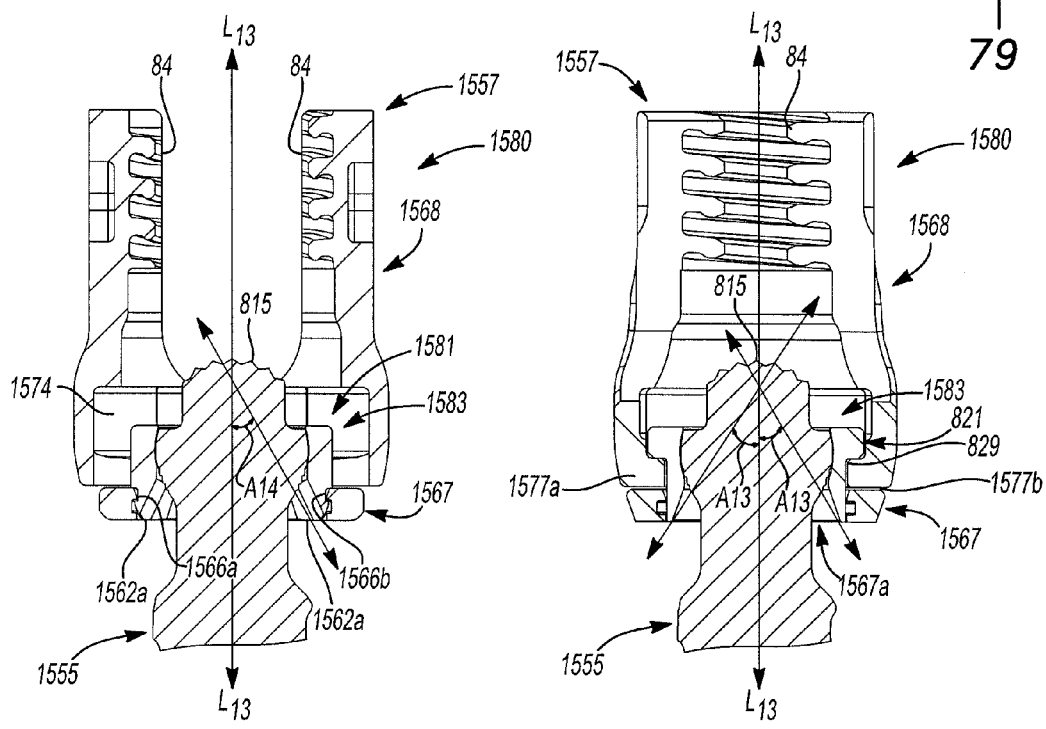
FIG. 79 is a cross-sectional illustration of the multiplanar bone anchor system of FIG. 76, taken along line 79-79 of FIG. 76.
FIG. 80 is a cross-sectional illustration of the multiplanar bone anchor system of FIG. 76, taken along line 80-80 of FIG. 76.
Figure 78:
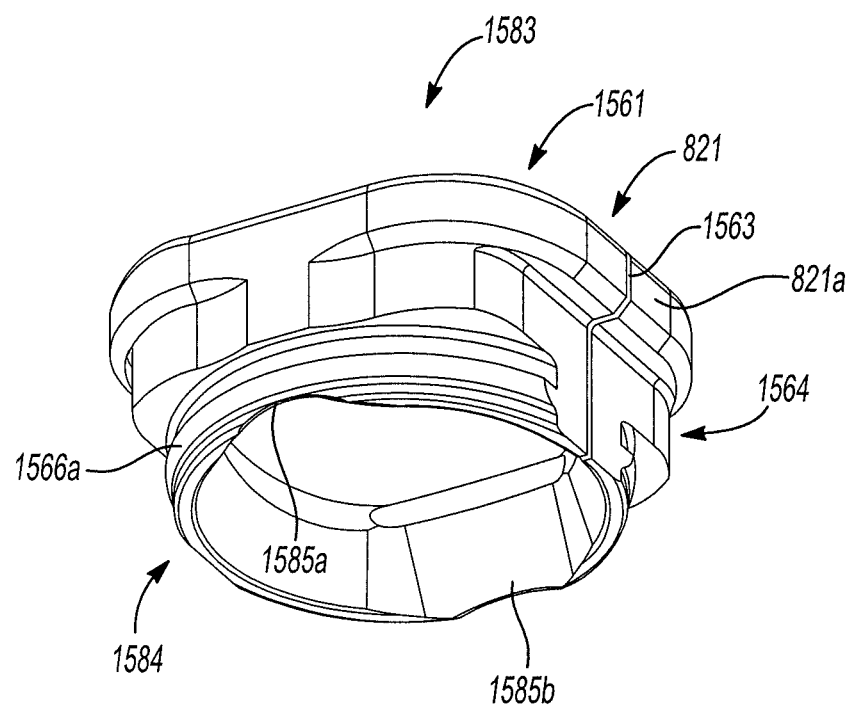
FIG. 78 is a perspective view of a connecting arm for use with the multiplanar bone anchor system of FIG. 76.

With reference to FIGS. 77 and 78, the lower portion 1584 can include the connection surface 1564 and at least one preferred angle slot 1585. In one example, the preferred angle slot 1585 can comprise a two preferred angle slots 1585a, 1585b. The preferred angle slots 1585a, 1585b can enable the bone fastener 1555 to articulate to a greater angle A13 relative to a longitudinal axis L13 of the multiplanar bone anchor system 1580. In this regard, with reference to FIG. 79, the bone fastener 1555 can generally articulate to an angle A14 relative to the longitudinal axis L13 along the portion of the connecting arm 1583 that does not include the preferred angle slots 1585a, 1585b. With reference to FIG. 80, at the location of the preferred angle slots 1585a, 1585b, the bone fastener 1555 can generally articulate to the greater angle A13 relative to the longitudinal axis L13. In one example, the angle A14 can be less than the greater angle A13, and the greater angle A13 can be between about 15 degrees and 90 degrees. The preferred angle slots 1585a, 1585b can comprise an arcuate cut-out defined through the lower portion 1584 of the connecting arm 1583, which can be in communication with the bore 824. The arcuate cut-out of the preferred angle slots 1585a, 1585b can enable the bone fastener 1555 to move or articulate to the greater angle A13 relative to the longitudinal axis L13.

It should be noted that although two preferred angle slots 1585a, 1585b is illustrated in the drawings, the connecting arm 1583 can include any number of preferred angle slots

1585 at any location along the connecting arm 1583 to enable the bone fastener 1555 to articulate in any selected direction. It should also be noted that the shape of the cut-out that forms the preferred angle slots 1585a, 1585b can be modified to reduce or increase the greater angle A13 of the articulation of the bone fastener 1555 relative to the longitudinal axis L13.

With reference to FIG. 77, in order to assemble the multiplanar bone anchor system 1580 according to one exemplary method, the connecting arm 1583 can be inserted into the central bore 876 of the saddle 1557. Generally, the connecting arm 1583 can be rotated about 90° around a main axis of the connecting arm 1583 in order to insert the connecting arm 1583 through the top portion 1568. The connecting arm 1583 can be rotated back about 90° around the main axis until the curved features 821 are engaged with the guides 1577a, 1577b of the top portion 1568. Then, the bone fastener 1555 can be inserted through the bore 824 of the connecting arm 1583. The at least one slot 1563 in the connecting arm 1583 and the size of the cavity 1574 can enable the connecting arm 1583 to expand to accept the head 1558 of the bone fastener 1555. Then, the bottom portion 1567 can be coupled to the connecting arm 1560.

Once assembled, with reference to FIGS. 77, 79 and 80, the connecting arm 1583 can enable the bone fastener 1555 to move or rotate within the bore 824 of the connecting arm 1583. The connecting arm 1583 can also allow the bone fastener 1555 to move or angulate relative to the longitudinal axis L13 of the multiplanar bone anchor system 1580. The preferred angle slot 1585 of the connecting arm 1583 can enable the bone fastener 1555 to move or articulate to the greater angle A13. The top portion 1568 of the saddle 1557 can move or translate relative to the bottom portion 1567 and connecting arm 1583 to a selected position. Thus, when assembled, the multiplanar bone anchor system 1580 can have at least three degrees of movement or can be movable in at least three planes. For example, the bone fastener 1555 can rotate about the longitudinal axis L13. The bone fastener 1555 can also pivot relative to the longitudinal axis L13 in at least a first direction and a second direction. The saddle 1557 can translate relative to the longitudinal axis L13. By allowing the multiplanar bone anchor system 1580 to move in at least three planes, the surgeon can manipulate the multiplanar bone anchor system 1580 as necessary to conform to the anatomy of the patient.

As the surgical insertion and use of the multiplanar bone anchor system 1580 in a fixation procedure can be similar to the surgical insertion and insertion of the multiplanar bone anchor system 10 in a fixation procedure, the surgical insertion and use of the multiplanar bone anchor system 1580 will not be discussed in great detail herein. Briefly, however, once the multiplanar bone anchor system 1580 is secured to the anatomy, the multiplanar coupling system 1581 and the saddle 1557 can be moved, pivoted or rotated relative to the bone fastener 1555 into the desired alignment for the fixation procedure. Once the aligned, the connecting rod 20 can be inserted into a desired number of multiplanar bone anchor systems 1580.

With the connecting rod 20 positioned in the saddles 1557 of the multiplanar bone anchor systems 1580, the set screw 22 can be coupled to each mating portion 84 of each saddle 1557. The coupling of the set screw 22 can apply a force to the head 1558 of the bone fastener 1555 to fixedly couple or lock the position of the bone fastener 1555 relative to the saddle 1557.

With reference now to FIGS. 81-84, in one example, a lateral connector 1600 can be employed with any one of the multiplanar bone anchor systems 10, 100, 200, 300, 400, 500, 600, 700, 800, 900, 1000, 1100, 1200, 1300, 1400, 1500a, 1500b, 1554, 1580 and can be coupled to the connecting rod 20 to repair a damaged portion of an anatomy. In an exemplary procedure, the lateral connector 1600 can be used to connect one of the multiplanar bone anchor systems 10, 100, 200, 300, 400, 500, 600, 700, 800, 900, 1000, 1100, 1200, 1300, 1400, 1500a, 1500b, 1554, 1580 to a laterally spaced connecting rod 20. Generally, the lateral connector 1600 can be coupled to each of the connecting rods 20 in a direction transverse to a longitudinal axis of the connecting rods 20. The lateral connector 1600 can include a body 1602 and an arm 1604. The lateral connector 1600 can be composed of a suitable biocompatible material, such as a biocompatible metal or polymer.

Figure 82:
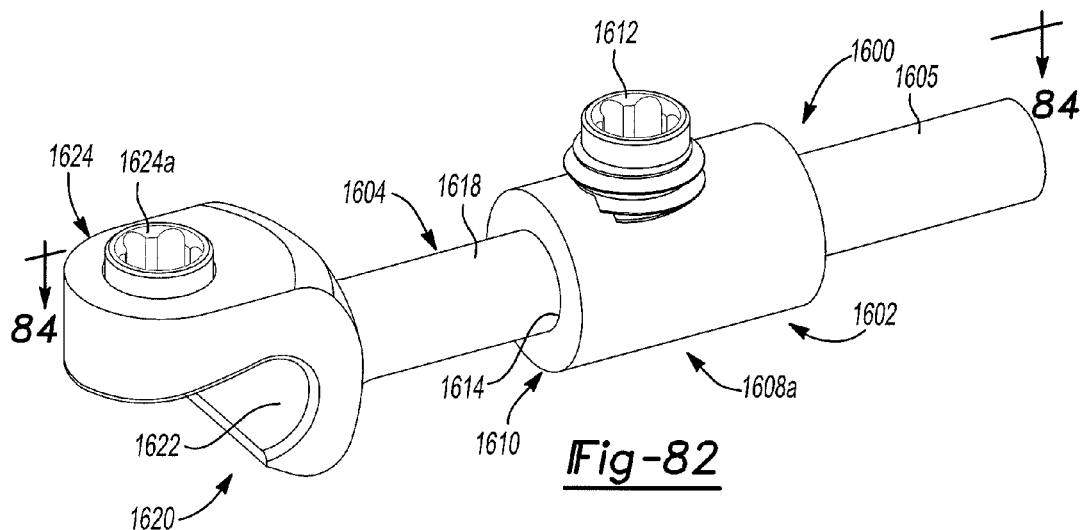
FIG. 82 is a perspective view of the lateral connector of FIG. 81.
Figure 83:
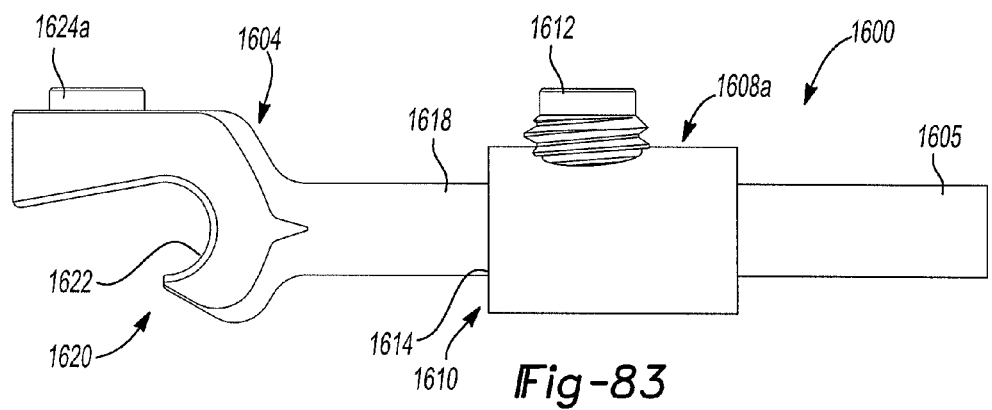
FIG. 83 is a side view of the lateral connector of FIG. 81.
Figure 84:
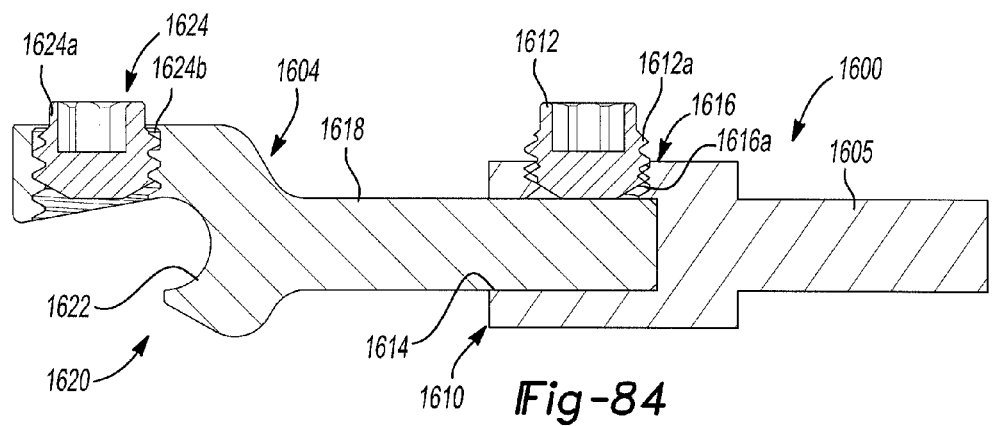
FIG. 84 is a cross-sectional illustration of the lateral connector of FIG. 82, taken along line 84-84 of FIG. 82.

With reference to FIGS. 82-84, the body 1602 can include a main portion 1605 and at least one translation assembly 1608. The main portion 1605 can be substantially linear and cylindrical. The at least one translation assembly 1608 can be coupled to the main portion 1605.

The translation assembly 1608 can include a cylindrical housing 1610 and a locking device 1612. The cylindrical housing 1610 can be integrally formed with the main portion 1605 if desired, or could be coupled to the main portion 1605 in a suitable post processing step, such as welding. With reference to FIG. 84, the cylindrical housing 1610 can define a cross bore 1614 and a locking bore 1616. The cross bore 1614 can be sized to receive a portion of the arm 1604. The locking bore 1616 can be configured to receive the locking device 1612, and can extend along an axis transverse to an axis of the cross bore 1614. In one example, the locking bore 1616 can include a plurality of threads 1616a, which can engage a plurality of threads 1612a associated with the locking device 1612.

The locking device 1612 can include the plurality of threads 1612a, which can mate with the plurality of threads 1616a of the locking bore 1616. In one example, the locking device 1612 can comprise a set screw, which can lock the arm 1604 to the body 1602.

The arm 1604 can include a rod 1618 and a hook 1620. It should be noted that although the arm 1604 is described and illustrated herein as including a rod 1618 having an annular cross-section, the rod 1618 could have any shape, such as square. In this example, the rod 1618 can be configured to be slidably received in the cross bore 1614, and can be cylindrical. As will be discussed, the rod 1618 can be movable relative to the body 1602 to enable the lateral connector 1600 to adapt to a variety of patient anatomies. The rods 1618 can be coupled to the body 1602 via pressure applied by the locking device 1612.

The hook 1620 can be coupled to the rod 1618, and in one example, the hook 1620 can be integrally formed with the rod 1618. Alternatively, the hook 1620 could be coupled to the rod 1618 in a suitable post processing step. The hook 1620 can include a C-shaped cavity 1622 and a coupling device 1624. The C-shaped cavity 1622 can be configured to receive a connecting rod 20. The coupling device 1624 can couple the connecting rod 20 to the C-shaped cavity 1622. In one example, with reference to FIG. 84, the coupling device 1624 can comprise a set screw 1624a, which can be threadably engaged with a threaded bore 1624b. The advancement of the set screw 1624a within the threaded bore 1624b can couple the lateral connector 1600 to the connecting rod 20.

Figure 81:
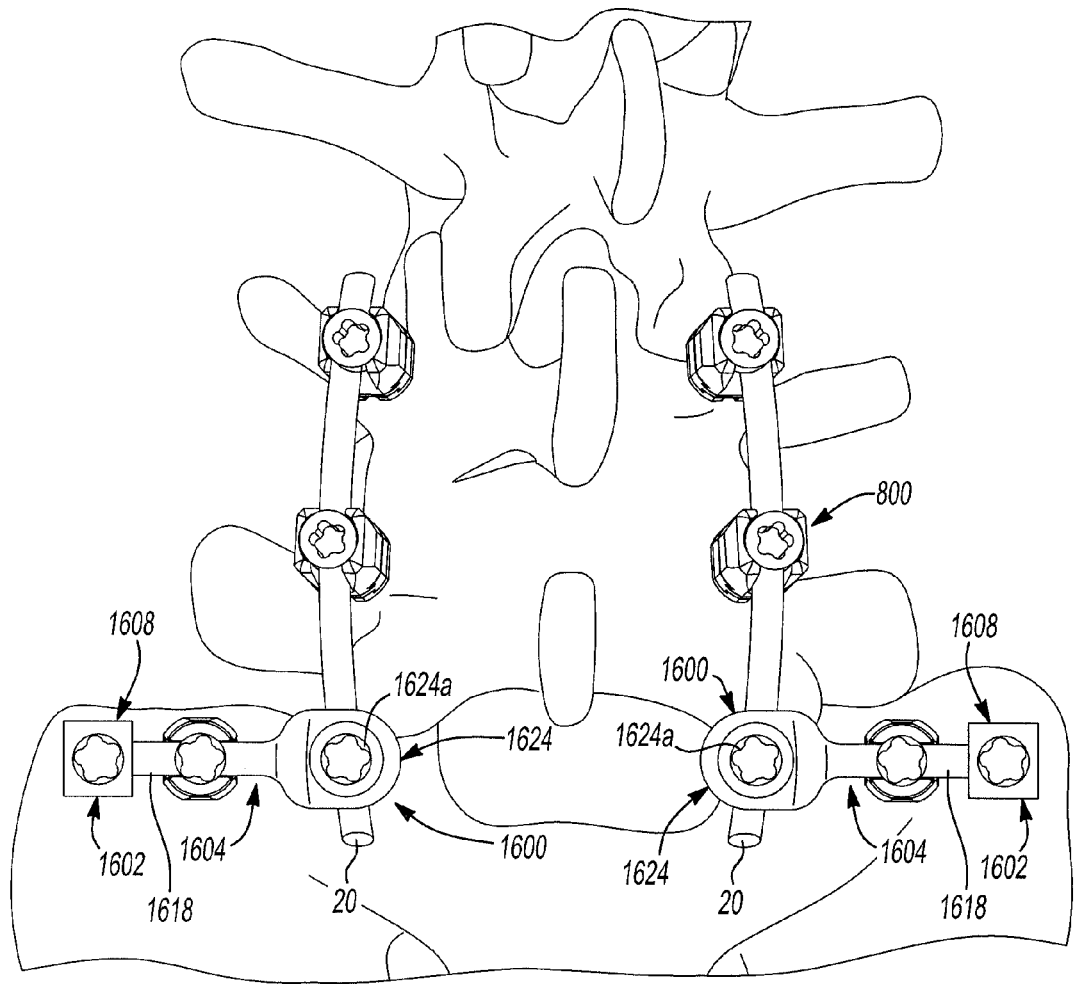
FIG. 81 is a schematic environmental illustration of a lateral connector for use with a connecting device in a fixation procedure according to the present teachings.

With reference to FIGS. 81 and 84, the lateral connector 1600 can be assembled by inserting the arm 1604 into the cross bore 1614. Then, the locking device 1612 can be tightened to secure the arm 1604 to the body 1602. The lateral connector 1600 can then be positioned so as to span between an exemplary multiplanar bone anchor system 800 and a connecting rod 20. The hook 1620 of the arm 1604 can be coupled to the connecting rod 20 by tightening the set screw 1624a and the arm 1604 can be coupled to the exemplary multiplanar bone anchor system 800 by tightening a set screw 22.

If, due to the patient's anatomy, the lateral connector 1600 is too short or too long, the arm 1604 can be moved or translated within the cross bore 1614 to enable the lateral connector 1600 to be coupled to the connecting rod 20. For example, the locking device 1612 of the translation assembly 1608 can be loosened to enable the arm 1604 to move to a desired position within the cross bore 1614 to extend a length of the lateral connector 1600 or to reduce the length of the lateral connector 1600. This can allow the lateral connector 1600 to be used with a variety of differently sized patients.

Figure 85:
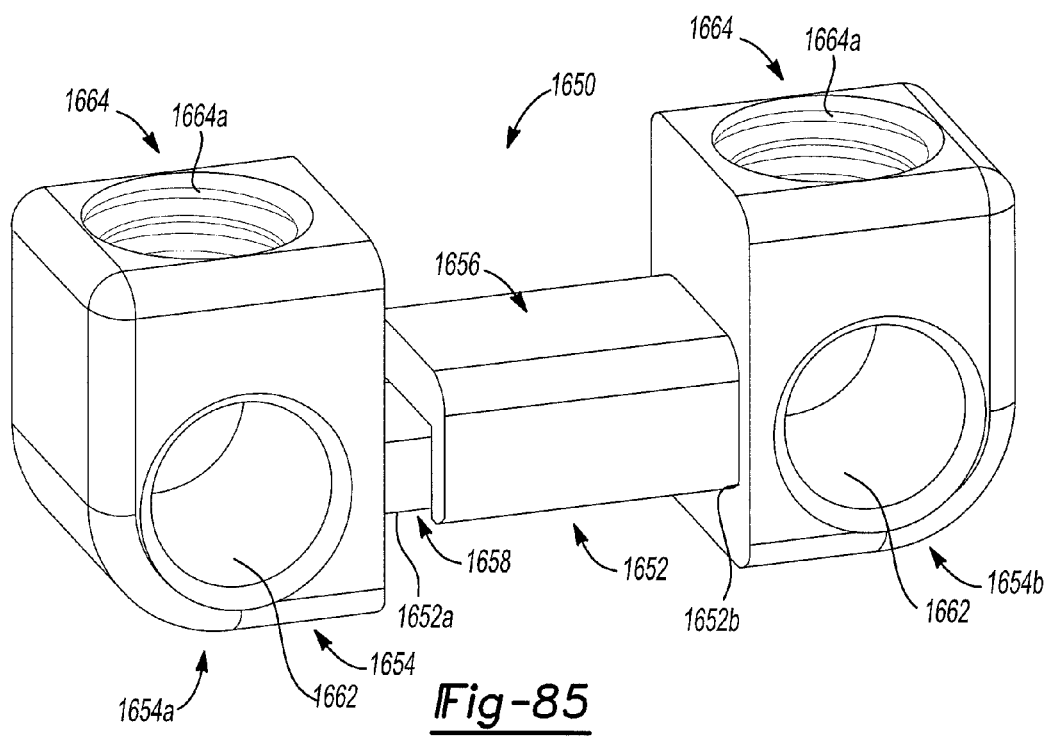
FIG. 85 is a perspective view of a rod to rod or domino connector for use with multiple connecting devices in a fixation procedure according to the present teachings.
Figure 86:
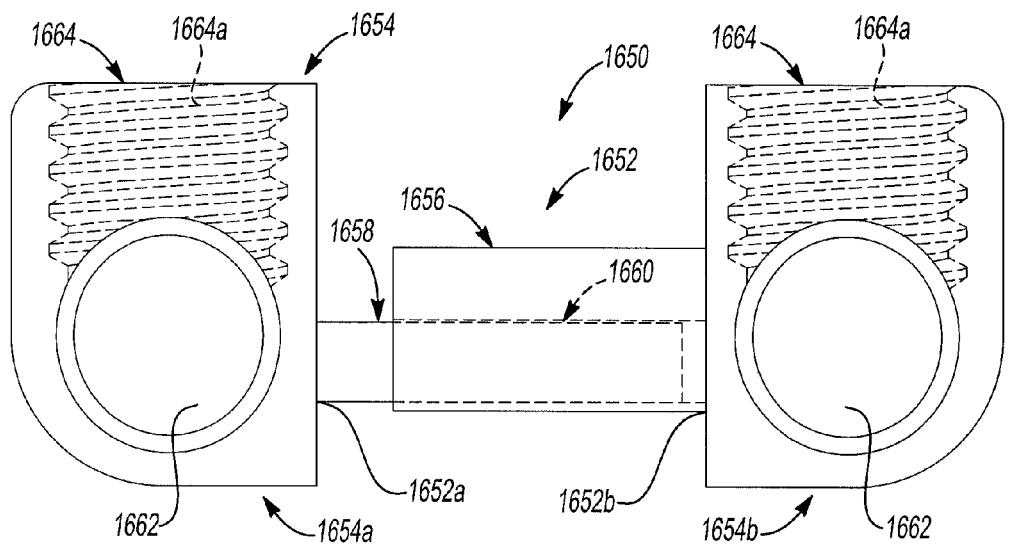
FIG. 86 is a side view of the domino connector of FIG. 85.

With reference now to FIGS. 85 and 86, in one example, a domino connector 1650 can be employed with any one of the multiplanar bone anchor systems 10, 100, 200, 300, 400, 500, 600, 700, 800, 900, 1000, 1100, 1200, 1300, 1400, 1500a, 1500b, 1554, 1580 and can be coupled to one or more connecting rods 20 to repair a damaged portion of an anatomy. In an exemplary procedure, the domino connector 1650 can be used to impart rigidity to two vertically extending multiplanar bone anchor systems 10, 100, 200, 300, 400, 500, 600, 700, 800, 900, 1000, 1100, 1200, 1300, 1400, 1500a, 1500b, 1554, 1580 having connecting rods 20. Generally, the domino connector 1650 can be coupled to each of the connecting rods 20 in a direction transverse to a longitudinal axis of the connecting rods 20.

The domino connector 1650 can include a movable body 1652 and at least one connector 1654. The domino connector 1650 can be composed of a suitable biocompatible material, such as a biocompatible metal or polymer. In one example, the domino connector 1650 can include two connectors 1654a, 1654b positioned on either end 1652a, 1652b of the movable body 1652.

The movable body 1652 can include a first portion 1656 and a second portion 1658. The first portion 1656 can define a cross bore 1660 (FIG. 86). The cross bore 1660 can receive the second portion 1658 so that the second portion 1658 can move or translate relative to the first portion 1656. It should be noted that the second portion 1658 can include a stop, which can enable the second portion 1658 to move or translate relative to the first portion 1656 without disconnecting, if desired. Alternatively, a mechanical fastener or other technique could be used to movably secure the first portion 1656 to the second portion 1658. The movement of the second portion 1658 relative to the first portion 1656 can enable a length of the domino to increase or decrease in a medial-lateral direction depending upon the particular anatomy of the patient. It should be noted that the domino connector 1650 could also be configured to enable translation in a cephalad-caudal direction, if desired.

With continued reference to FIGS. 85 and 86, the connectors 1654a, 1654b can be coupled to a respective one of the connecting rods 20. The connectors 1654a, 1654b can each include a throughbore 1662 and a locking bore 1664. The throughbore 1662 can be sized to receive the connecting rod 20, and can extend in a direction transverse to the locking bore 1664. The locking bore 1664 can include threads 1664a, which can be configured to receive a suitable locking device, such as a set screw, to couple the domino connector 1650 to the connecting rod 20.

The domino connector 1650 can be assembled by inserting a connecting rod 20 through the throughbore 1662 of the connector 1654a, and then inserting a connecting rod 20 through the throughbore 1662 of the connector 1654b. Then, the second portion 1658 can be slid into the first portion 1656. As the second portion 1658 is movable or slidable relative to the first portion 1656, the length of the domino connector 1650 can be sized during the procedure to correspond to the particular patient's anatomy.

Figure 87:
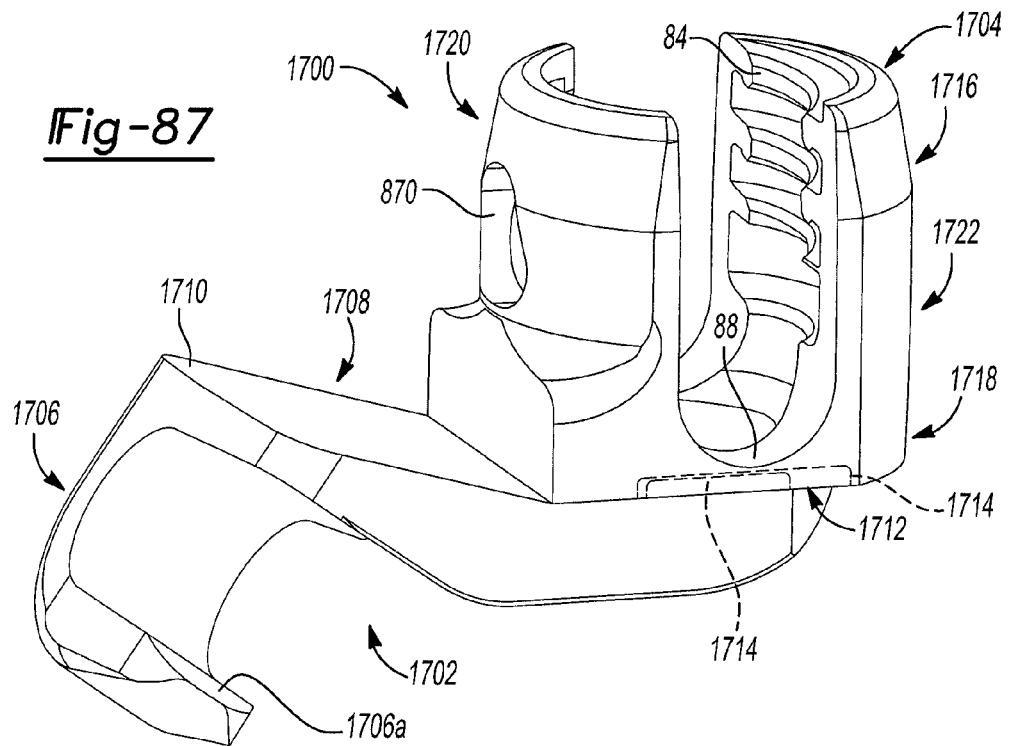
FIG. 87 is a perspective view of a multiplanar bone anchor system for use with a connecting device in a fixation procedure according to the present teachings.
Figure 88:
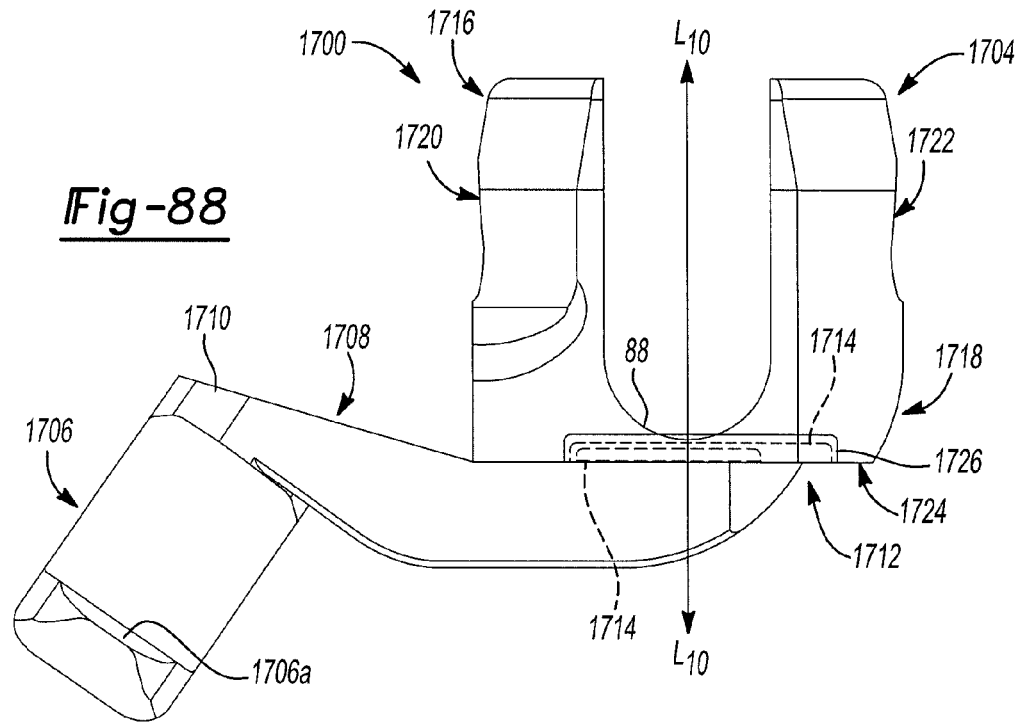
FIG. 88 is a side view of the multiplanar bone anchor system of FIG. 87.

With reference now to FIGS. 87 and 88, in one example, a multiplanar bone anchor system 1700 can be employed with the connecting rod 20 to repair a damaged portion of an anatomy. As the multiplanar bone anchor system 1700 can be similar to the multiplanar bone anchor system 800 described with reference to FIGS. 31-36, only the differences between the multiplanar bone anchor system 800 and the multiplanar bone anchor system 1700 will be discussed in great detail herein, and the same reference numerals will be used to denote the same or similar components. The multiplanar bone anchor system 1700 can include a bone fastener 1702 and a saddle 1704.

In one example, the bone fastener 1702 can comprise a bone hook having a C-shaped hook portion 1706 and a base 1708. The C-shaped hook portion 1706 can be impacted into the anatomy to secure the C-shaped hook portion 1706 to the anatomy. In order to facilitate engagement of the C-shaped hook portion 1706 with the anatomy, the C-shaped hook portion 1706 can include a tapered tip 1706a. The C-shaped hook portion 1706 can be positioned below the base 1708.

The base 1708 can couple the C-shaped hook portion 1706 to the saddle 1704. The base 1708 can have a first end 1710 and a second end 1712. The first end 1710 can be coupled to the C-shaped hook portion 1706. The second end 1712 can be coupled to the base 1708. The first end 1710 can be angled relative to the second end 1712, however, the first end 1710 need not be angled relative to the second end 1712. The second end 1712 can include at least one rail 1714. The at least one rail 1714 can cooperate with the saddle 1704 to enable the saddle 1704 to move or translate relative to the bone fastener 1702.

The saddle 1704 can be substantially U-shaped and symmetrical with respect to a longitudinal axis L10 defined by the saddle 1704 (FIG. 88). The saddle 1704 can include a first or proximal end 1716 and a second or distal end 1718. In one example, the proximal end 1716 can include a first arm 1720 and a second arm 1722. The first arm 1720 and second arm 1722 can extend upwardly from the distal end 1718 to define the U-shape. Each of the first arm 1720 and the second arm 1722 can include the mating portion 84 and the connector feature 870.

With reference to FIGS. 87 and 88, the distal end 1718 of the saddle 1704 can be generally rectangular. It should be noted that the distal end 1718 can have any desired shape, such as generally square, cylindrical, oval, etc. The distal end 1718 can include the first or receiver surface 88 and a second or bottom surface 1724. The bottom surface 1724 can include at least one guide 1726. The at least one guide 1726 can be coupled to the at least one rail 1714 to enable the saddle 1704 to move or translate relative to the bone fastener 1702. It should be noted that the movement or translation of the saddle 1704 relative to the bone fastener 1702 need not be limited to a single direction, but rather, multiple rails and guides could be employed to enable movement or translation along multiple planes.

In order to assemble the multiplanar bone anchor system 1700, the saddle 1704 can be slid onto the base 1708 so that the at least one guide 1726 engages the at least one rail 1714. Then, in order to couple the multiplanar bone anchor system 1700 to the anatomy, with access provided to the anatomy, the C-shaped hook portion 1706 can be impacted into the anatomy to secure the multiplanar bone anchor system 1700 to the anatomy. Then, the saddle 1704 can be moved or translated relative to the C-shaped hook portion 1706 into a selected position for receipt of the connecting rod 20. Once the connecting rod 20 is received within the saddle 1704, the set screw 22 can be inserted into the mating portion 84 of the first arm 1720 and second arm 1722 to couple the connecting rod 20 to the multiplanar bone anchor system 1700.

With reference now to FIGS. 89-92, in one example, a multiplanar occipital plate seat 1750 can be employed with the connecting rod 20 to repair a damaged portion of an anatomy. As the multiplanar occipital plate seat 1750 can be similar to the multiplanar bone anchor system 800 described with reference to FIGS. 31-36, only the differences between the multiplanar bone anchor system 800 and the multiplanar occipital plate seat 1750 will be discussed in great detail herein, and the same reference numerals will be used to denote the same or similar components. The multiplanar occipital plate seat 1750 can include a saddle 1754.

The saddle 1754 can include a first portion or bottom portion 1756 and a second portion or top portion 1758. The top portion 1758 can move or translate relative to the bottom portion 1756, as will be discussed in greater detail herein. In one example, the bottom portion 1756 can include a first or proximal end 1760, a second or distal end 1762 and a pin 1764. The proximal end 1760 can be coupled to the top portion 1758. The proximal end 1760 can include at least one rail 1766. In one example, the proximal end 1760 can include two rails 1766a, 1766b. The rails 1766a, 1766b can be positioned on opposed sides of bottom portion 1756 such that the rails 1766a, 1766b are about 180° apart. The rails 1766a, 1766b can be T-shaped, however, any shape could be employed. The distal end 1762 can be generally rectangular with rounded corners, and can be substantially planar.

The pin 1764 can extend from the bottom portion 1756 to couple the saddle 1754 to an exemplary bone plate P. The pin 1764 can be generally square, but the pin 1764 could have any selected shape to couple the saddle 1754 to the bone plate P.

Figure 89:
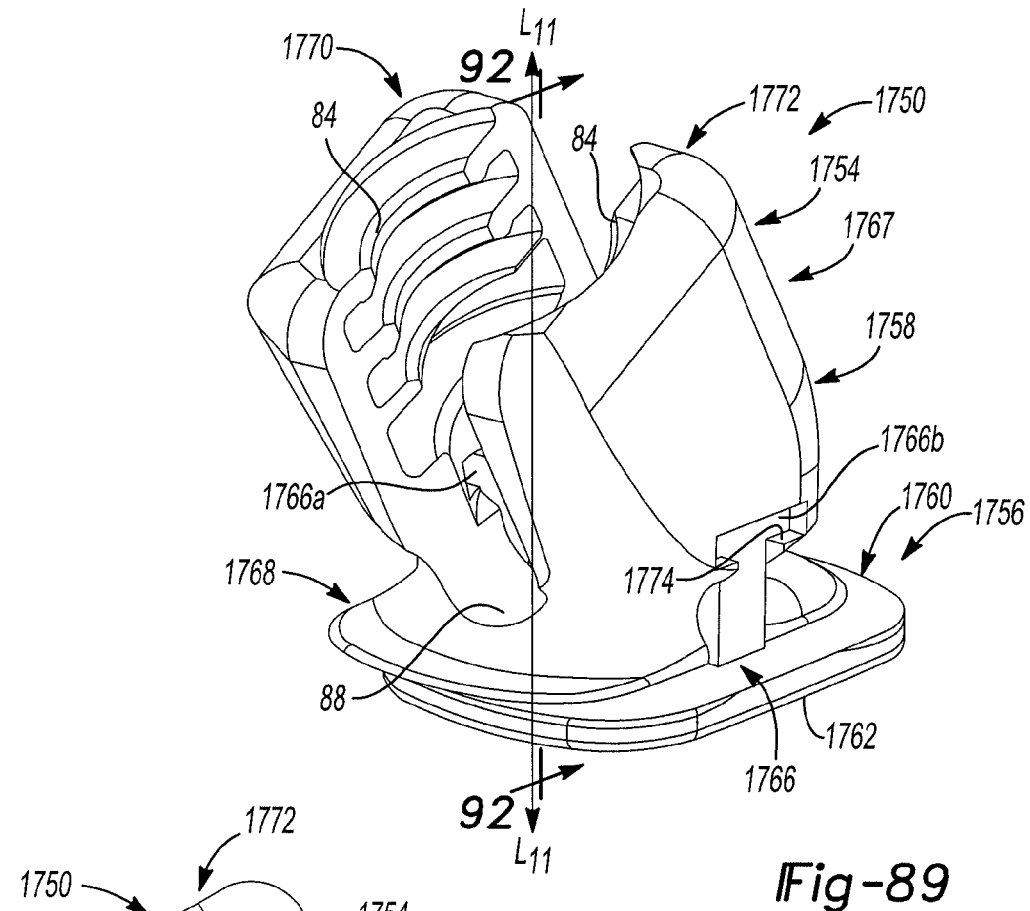
FIG. 89 is a perspective view of another multiplanar bone anchor system for use with a connecting device in a fixation procedure according to the present teachings.
Figure 90:
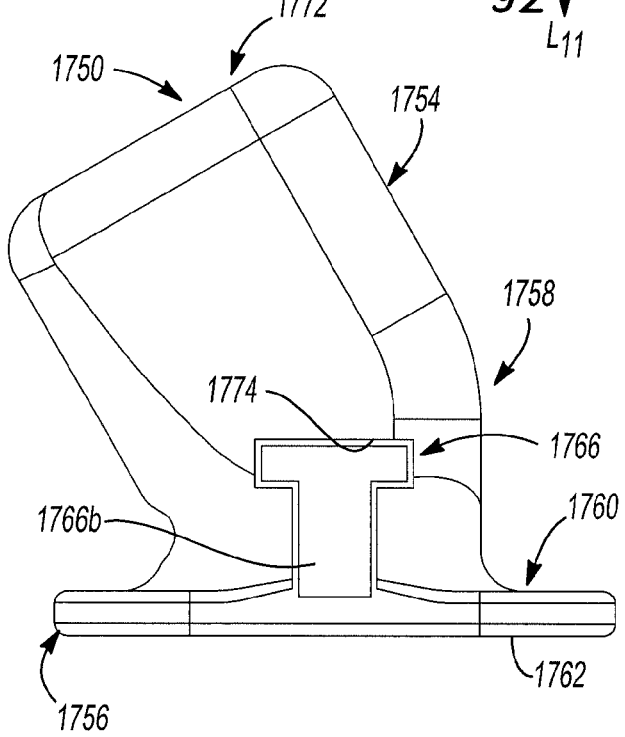
FIG. 90 is a side view of the multiplanar bone anchor system of FIG. 89.
Figure 91:
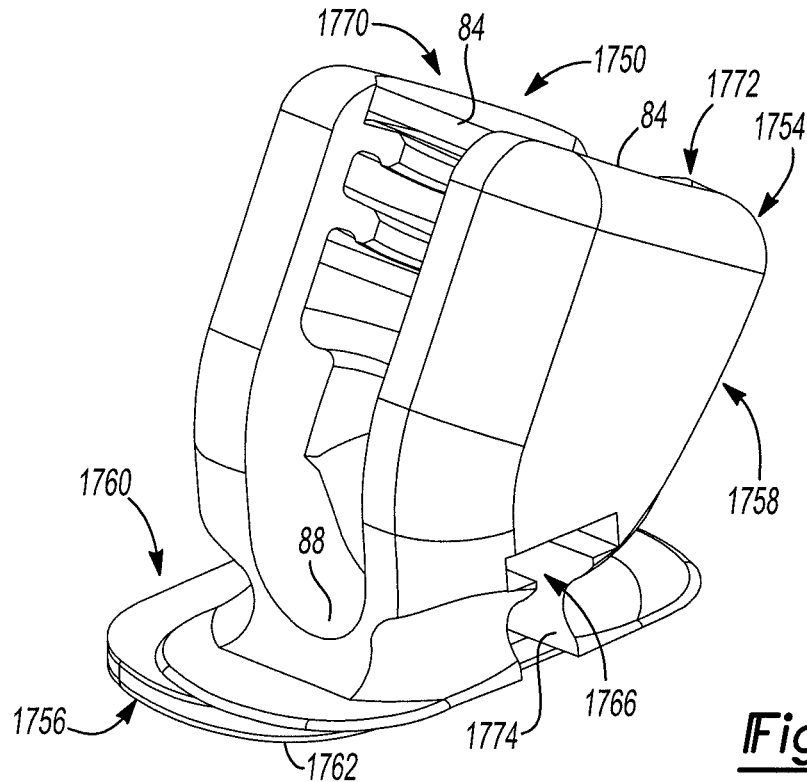
FIG. 91 is a schematic illustration of the multiplanar bone anchor system of FIG. 89 in a second, translated position.
Figure 92:
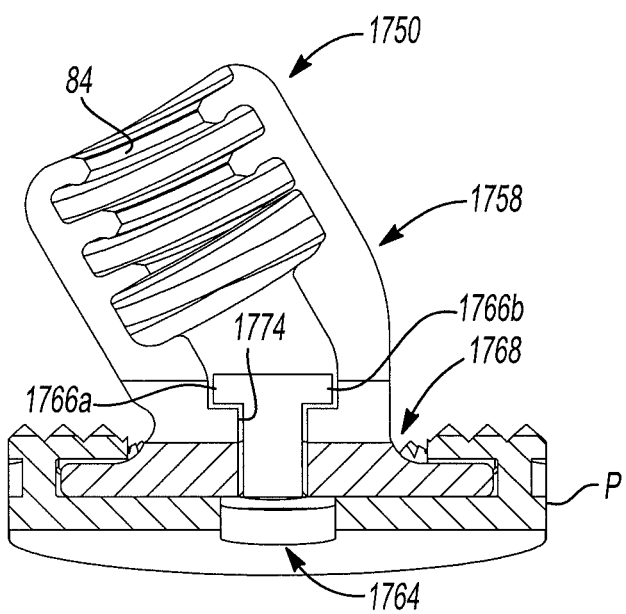
FIG. 92 is a schematic cross-sectional illustration of the multiplanar bone anchor system of FIG. 89, taken along line 92-92 of FIG. 89, illustrating the multiplanar bone anchor system of FIG. 89 coupled to an exemplary portion of a bone plate.

The top portion 1758 of the saddle 1754 can be substantially U-shaped and symmetrical with respect to a longitudinal axis L11 defined by the multiplanar occipital plate seat 1750 (FIG. 89). The top portion 1758 can include a first or proximal end 1767 and a second or distal end 1768. In one example, the proximal end 1767 can include a first arm 1770 and a second arm 1772. The first arm 1770 and second arm 1772 can extend upwardly from the distal end 1768 to define the U-shape. Each of the first arm 1770 and the second arm 1772 can include the mating portion 84.

The distal end 1768 of the top portion 1758 can be generally rectangular, and can include rounded corners to correspond with the shape of the bottom portion 1756. The distal end 1768 can include the first or receiver surface 88 and a guide 1774.

The guide 1774 can be configured to mate with the rails 1766a, 1766b of the bottom portion 1756. In one example, the guide 1774 can comprise a T-shape, however, any suitable shape could be employed to meet with the rails 1766a, 1766b. The engagement of the guide 1774 with the rails 1766a, 1766b can enable the top portion 1758 to move or translate relative to the bottom portion 1756.

In order to assemble the multiplanar occipital plate seat 1750, the top portion 1758 can be slid onto the bottom portion 1756 so that the guide 1774 engages the rails 1766a, 1766b. Then, the pin 1764 of the bottom portion 1756 can be coupled to the bone plate P to couple the saddle 1704 to the bone plate P. Once the bone plate P is positioned within the anatomy, the top portion 1758 can be moved relative to the bottom portion 1756 into a selected position for receipt of the connecting rod 20. With the connecting rod 20 inserted between the first arm 1770 and the second arm 1772, the set screw 22 can be inserted to couple the connecting rod 20 to the multiplanar occipital plate seat 1750.

Accordingly, the multiplanar bone anchor system 10, 100, 200, 300, 400, 500, 600, 700, 800, 900, 1000, 1100, 1200, 1300, 1400, 1500a, 1500b, 1554, 1580 can be used to repair damaged tissue in the anatomy, such as in the case of a spinal fixation or fusion procedure. By allowing the bone fastener 12, 102, 302, 802, 952, 1002, 1102, 1555 and/or the saddle 18, 106, 206, 308, 406, 506, 606, 806, 906, 956, 1006, 1106, 1108, 1308, 1408, 1506, 1557 to move in multiple planes, but in a controlled fashion. In addition, the ability to manipulate the position of the bone fastener 12, 102, 302, 802, 952, 1002, 1102, 1555 and/or the saddle 18, 106, 206, 308, 406, 506, 606, 806, 906, 956, 1006, 1106, 1108, 1308, 1408, 1506, 1557 can enable the multiplanar bone anchor system 10, 100, 200, 300, 400, 500, 600, 700, 800, 900, 1000, 1100, 1200, 1300, 1400, 1500a, 1500b, 1554, 1580 to be used with a variety of different anatomical structures.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

Figure 94:
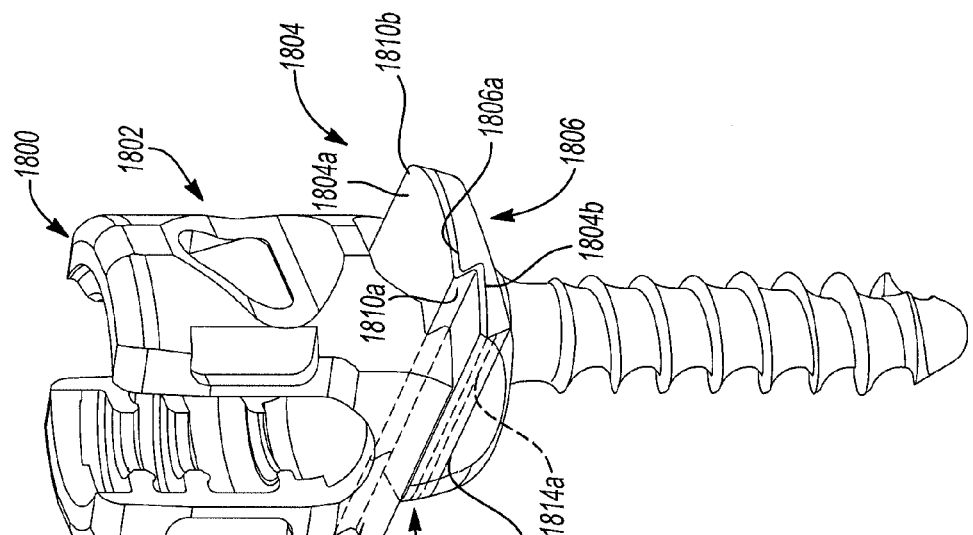
FIG. 94 is a schematic illustration of the multiplanar bone anchor system of FIG. 93 in a second position.
Figure 93:
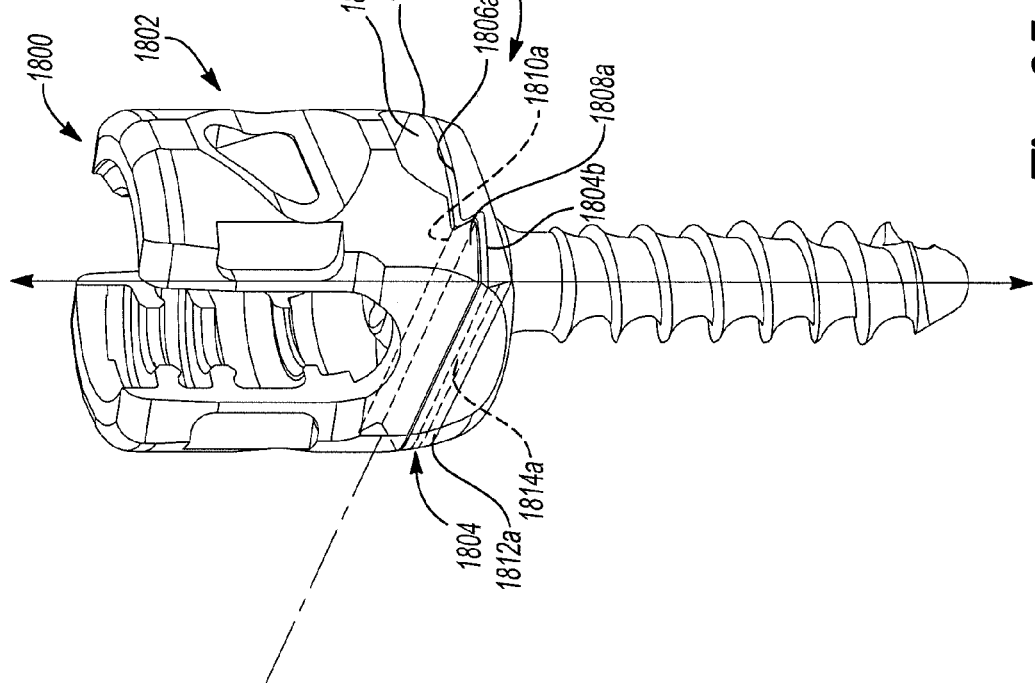
FIG. 93 is a schematic illustration of another multiplanar bone anchor system for use with a connecting device in a fixation procedure according to the present teachings in a first position.

For example, while the multiplanar bone anchor system 1000 has been described herein with reference to FIGS. 42-45 as including the saddle 1006 having a bottom portion 1022 with rails 1032a, 1032b and a top portion 1024 with guides 1050a, 1050b, those of skill in the art will appreciate that the present disclosure, in its broadest aspects, may be constructed somewhat differently. In this regard, with reference to FIGS. 93 and 94, a saddle 1800 can include a first or top portion 1802, a second or middle portion 1804 and a third or bottom portion 1806. The top portion 1802 can include rails 1808a, 1808b. The rails 1808a, 1808b can slidably engage guides 1810a, 1810b defined on a top surface 1804a of the middle portion 1804. A bottom surface 1804b of the middle portion 1804 can include rails 1812a, 1812b, which can engage guides 1814a, 1814b formed on a top surface 1806a of the bottom portion 1806. Thus, the saddle 1800 can have two dovetail connections, which can allow for translation along a line or in a two-dimensional plane. It should be noted that the rails 1808a, 1808b, 1812a, 1812b can be orientated at any angle relative to a longitudinal axis defined by the saddle 1800 to allow translation in any plane.

In this regard, translation along a single dovetail (ex. movement along rails 1808a, 1808b and guides 1810a, 1810b or rails 1812a, 1812b and guides 1814a, 1814b) allows for movement along a line of translation. Translation along both dovetails (e.g. movement along rails 1808a, 1808b and guides 1810a, 1810b, and rails 1812a, 1812b and guides 1814a, 1814b) allows for movement along a two-dimensional plane of translation. It should be noted that the use of dovetail connections is merely exemplary, as any suitable connection mechanism could be used to enable translation along a plane.

In another example, while the multiplanar bone anchor system 1000 has been described herein with reference to FIGS. 42-45 as including the saddle 1006 having a bottom portion 1022 with rails 1032a, 1032b and a top portion 1024 with guides 1050a, 1050b, those of skill in the art will appreciate that the present disclosure, in its broadest aspects, may be constructed somewhat differently. In this regard, with reference to FIGS. 95-97, a saddle 1850 can include a first or top portion 1852, a second or middle portion 1854 and a third or bottom portion 1856. The top portion 1852 can include rails 1858a, 1858b, which can be formed along a first arc. The rails 1858a, 1858b can slidably engage guides 1860a, 1860b defined on a top surface 1854a of the middle portion 1854. The guides 1860a, 1860b can also be formed along the first arc.

Figure 99:
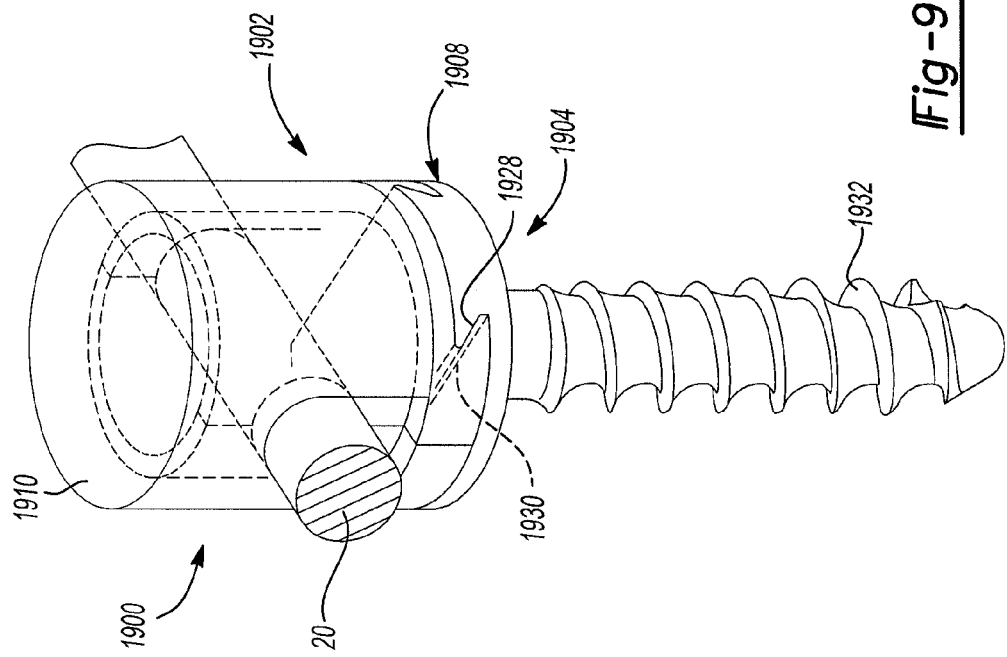
FIG. 99 is a schematic illustration of the multiplanar bone anchor system of FIG. 98 assembled.

A bottom surface 1854b of the middle portion 1854 can also include rails 1862a, 1862b, which can be formed along a second arc. The rails 1862a, 1862b can engage guides 1864a, 1864b formed on a top surface 1856a of the bottom portion 1856. The guides 1864a, 1864b can also be formed along the second arc (FIG. 99).

The first arc and the second arc can be orientated relative to each other at any selected non-zero angle to enable three-dimensional movement of the saddle 1850. In addition, it should be noted that if the first arc and the second arc are sufficiently large, the movement could approximate planar motion. Further, it should be noted, that the use of dovetail connections is merely exemplary, as any suitable connection mechanism could be used to enable translation along a plane. In addition, it should be noted that the use of two arcs is merely exemplary, as only one arc could be used, or an arc and a linear dovetail connection could be used.

Figure 98:
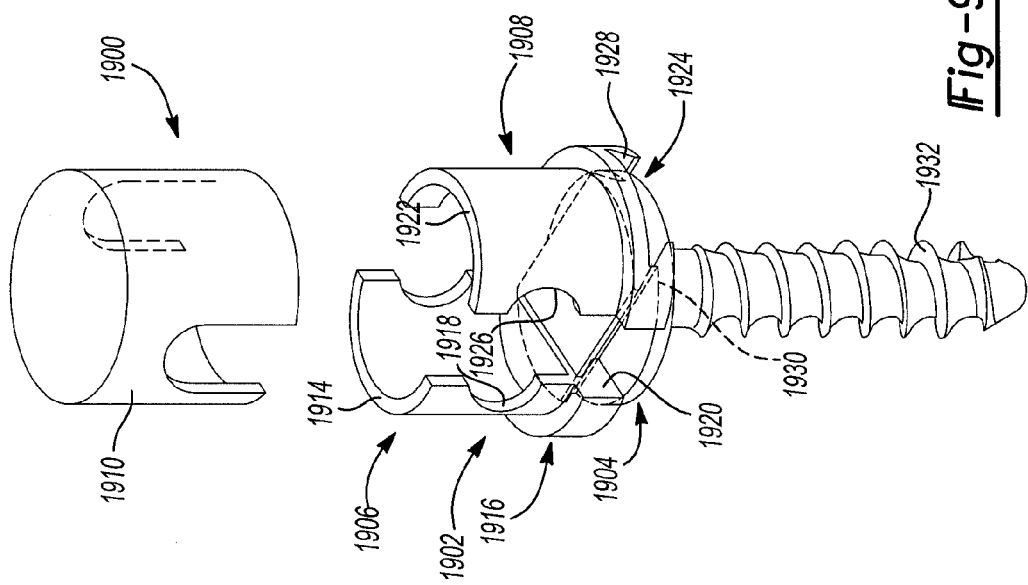
FIG. 98 is a partially exploded schematic illustration of another multiplanar bone anchor system for use with a connecting device in a fixation procedure according to the present teachings.

In another of various examples, while the multiplanar bone anchor system 1000 has been described herein with reference to FIGS. 42-45 as including a U-shaped top portion 1024 for receipt of a connecting rod 20 that is translatable relative to a bone fastener 1002, those of skill in the art will appreciate that the present disclosure, in its broadest aspects, may be constructed somewhat differently. In this regard, with reference to FIGS. 98 and 99, a saddle 1900 can include a first or top portion 1902 movable relative to a bottom portion 1904. The top portion 1902 can include a first half 1906, a second half 1908 and a locking device 1910. The first half 1906 can include a first end 1914, a second end 1916 and an opening 1918. The first end 1914 can be coupled to the locking device 1910. The second end 1916 can include at least one guide 1920, which can enable the top portion 1902 to move relative to the bottom portion 1904. The opening 1918 can be semi-circular and configured to receive a portion of the connecting rod 20 (FIG. 99). The opening 1918 can be positioned between the first end 1914 and the second end 1916.

The second half 1908 can include a first end 1922, a second end 1924 and an opening 1926. The first end 1922 can be coupled to the locking device 1910. The second end 1924 can include at least one guide 1928, which can enable the top portion 1902 to move relative to the bottom portion 1904. The opening 1926 can be semi-circular and configured to receive a portion of the connecting rod 20 (FIG. 99). The opening 1926 can be positioned between the first end 1922 and the second end 1924.

The locking device 1910 can be U-shaped, and can be positionable over the first end 1914 of the first half 1906 and the first end 1922 of the second half 1908. The locking device 1910 can be positioned over the first half 1906 and the second half 1908 to retain the connecting rod 20 within the openings 1918, 1926 (FIG. 99).

The bottom portion 1904 can include at least one rail 1930, which can enable both the first half 1906 and the second half 1908 to move or translate relative to the bottom portion 1904. The bottom portion 1904 can also receive a bone fastener 1932 therethrough, which can move, rotate and/or articulate relative to the saddle 1900, if desired.

In use, the bottom portion 1904 can be coupled to the anatomy via the bone fastener 1932. Then, the first half 1906 and the second half 1908 can be slidably engaged with the bottom portion 1904. The first half 1906 and the second half 1908 can be slid about the connecting rod 20. Once the connecting rod 20 is received within the openings 1918, 1926, the locking device 1910 can be positioned over the first half 1906 and the second half 1908 to secure the connecting rod 20 to the saddle 1900.

In another example, with reference to FIGS. 100 and 101, a saddle 1950 can be employed with the connecting rod 20 to repair a damaged portion of an anatomy. As the saddle 1950 can be similar to the saddle 1900 described with reference to FIGS. 98 and 99, only the differences between the saddle 1900 and the saddle 1950 will be discussed in great detail herein, and the same reference numerals will be used to denote the same or similar components. The saddle 1950 can include a first or top portion 1952 movable relative to a bottom portion 1954. The top portion 1952 can include the second half 1908 and the locking device 1910.

The bottom portion 1954 can include an arm 1956 and at least one rail 1957 (FIG. 100). The arm 1956 can include an opening 1958 and a ledge 1960. The opening 1958 can be semi-circular and configured to receive a portion of the connecting rod 20. The ledge 1960 can support a portion of the locking device 1910 to couple the connecting rod 20 to the saddle 1950. The bottom portion 1904 can also receive a bone fastener 1962 therethrough, which can move, rotate and/or articulate relative to the saddle 1950, if desired.

In use, the bottom portion 1954 can be secured to the anatomy via the bone fastener 1962. Then, the second half 1908 can be slidably engaged with the bottom portion 1954. The second half 1908 can be slid about the connecting rod 20. Once the connecting rod 20 is received within the openings 1926, 1958 the locking device 1910 can be positioned over the arm 1956 and the second half 1908 to secure the connecting rod 20 to the saddle 1950 (FIG. 101).

Figure 103:
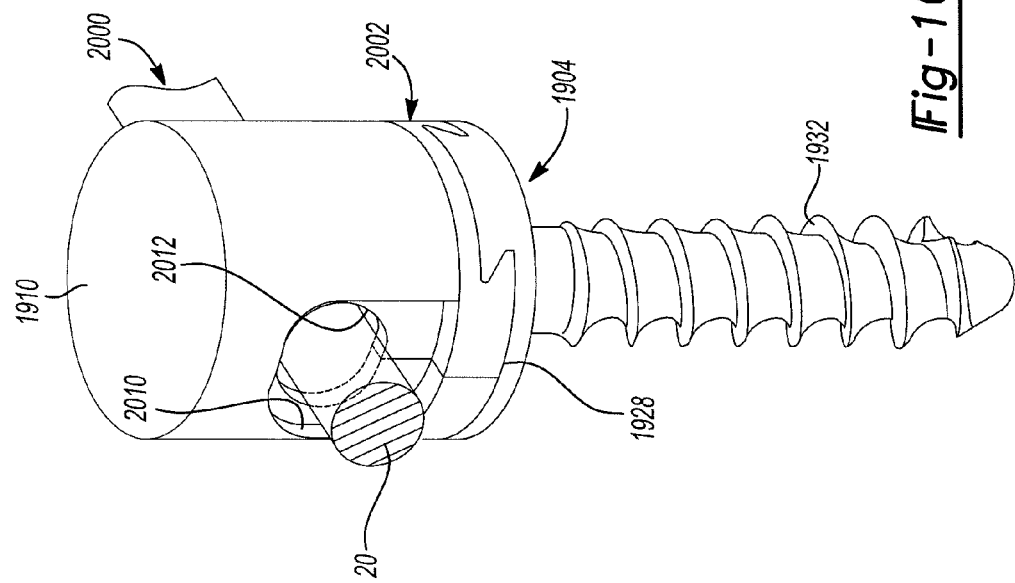
FIG. 103 is a schematic illustration of the multiplanar bone anchor system of FIG. 102 assembled.
Figure 102:
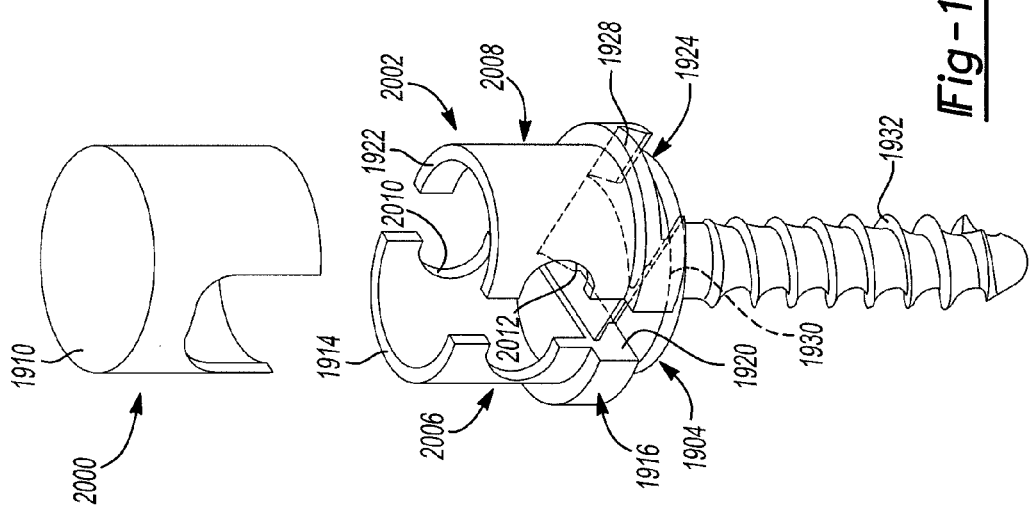
FIG. 102 is a partially exploded schematic illustration of another multiplanar bone anchor system for use with a connecting device in a fixation procedure according to the present teachings.

In another of various examples, with reference to FIGS. 102 and 103, a saddle 2000 can be employed with the connecting rod 20 to repair a damaged portion of an anatomy. As the saddle 2000 can be similar to the saddle 1900 described with reference to FIGS. 98 and 99, only the differences between the saddle 1900 and the saddle 2000 will be discussed in great detail herein, and the same reference numerals will be used to denote the same or similar components. The saddle 2000 can include a first or top portion 2002 movable relative to the bottom portion 1904.

The top portion 2002 can include a first half 2006, a second half 2008 and the locking device 1910. The first half 2006 can include the first end 1914, the second end 1916 and an opening 2010. The opening 2010 can be semi-circular and elongated to receive a portion of the connecting rod 20 (FIG. 103). The elongated opening 2010 can enable the connecting rod 20 to move in the approximate medial-lateral direction. The opening 2010 can be positioned between the first end 1914 and the second end 1916.

The second half 2008 can include the first end 1922, the second end 1924 and an opening 2012. The opening 2012 can be semi-circular and elongated to receive a portion of the connecting rod 20 (FIG. 103). The elongated opening 2012 can enable the connecting rod 20 to move in the medial-lateral direction. The opening 2012 can be positioned between the first end 1922 and the second end 1924.

In use, the bottom portion 1904 can be secured to the anatomy via the bone fastener 1932. Then, the first half 1906 and the second half 1908 can be slidably engaged with the bottom portion 1904. The first half 1906 and the second half 1908 can be slid about the connecting rod 20. Once the connecting rod 20 is received within the openings 2010, 2012, the locking device 1910 can be positioned over the first half 1906 and the second half 1908 to secure the connecting rod 20 to the saddle 2000, while permitting the connecting rod 20 to move in a medial-lateral direction (FIG. 103).

Figure 105:
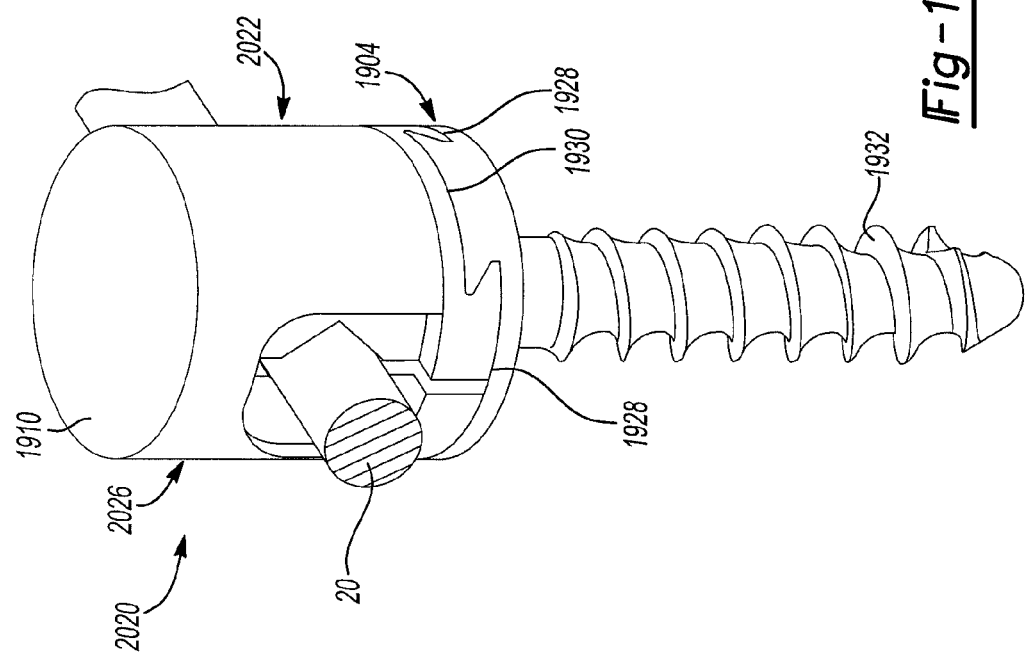
FIG. 105 is a perspective schematic illustration of the multiplanar bone anchor system of FIG. 104.
Figure 104:
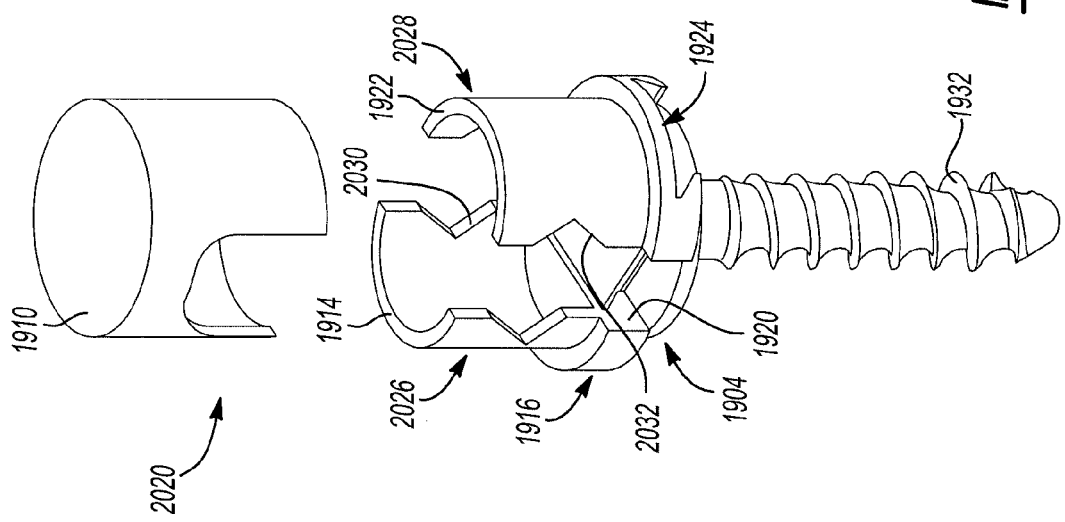
FIG. 104 is a partially exploded schematic illustration of another multiplanar bone anchor system for use with a connecting device in a fixation procedure according to the present teachings.

In another example, with reference to FIGS. 104 and 105, a saddle 2020 can be employed with the connecting rod 20 to repair a damaged portion of an anatomy. As the saddle 2020 can be similar to the saddle 1900 described with reference to FIGS. 98 and 99, only the differences between the saddle 1900 and the saddle 2020 will be discussed in great detail herein, and the same reference numerals will be used to denote the same or similar components. The saddle 2020 can include a first or top portion 2022 movable relative to the bottom portion 1904.

With reference to FIG. 104, the top portion 2022 can include a first half 2026, a second half 2028 and the locking device 1910. The first half 2026 can include the first end 1914, the second end 1916 and an opening 2030. The opening 2030 can be wedge-shaped to receive a portion of the connecting rod 20. The wedge-shaped opening 2030 can enable the opening 2030 to accept connecting rods 20 of varying diameters (FIG. 105). The opening 2030 can be positioned between the first end 1914 and the second end 1916.

With reference to FIG. 104, the second half 2028 can include the first end 1922, the second end 1924 and an opening 2032. The opening 2032 can be wedge-shaped to receive a portion of the connecting rod 20. The wedge-shaped opening 2032 can enable the opening 2032 to accept connecting rods 20 of varying diameters (FIG. 105). The opening 2032 can be positioned between the first end 1914 and the second end 1916.

In use, the bottom portion 1904 can be secured to the anatomy via the bone fastener 1932. Then, the first half 1906 and the second half 1908 can be slidably engaged with the bottom portion 1904. The first half 1906 and the second half 1908 can be slid about the connecting rod 20. Once the connecting rod 20 is received within the openings 2030, 2032, the locking device 1910 can be positioned over the first half 1906 and the second half 1908 to secure the connecting rod 20 to the saddle 2020 (FIG. 105).

Figure 106:
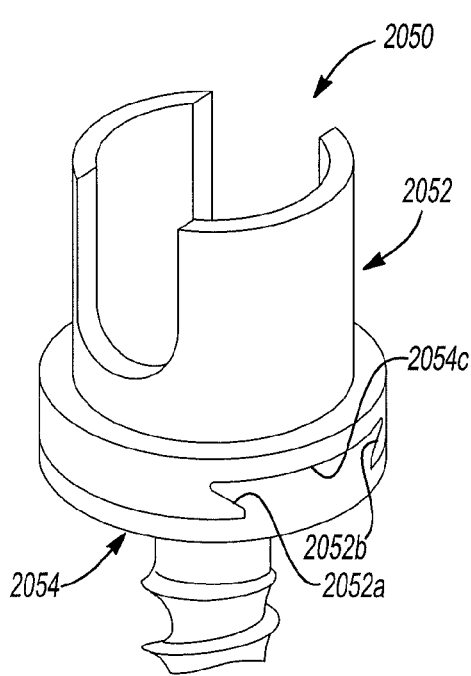
FIG. 106 is a schematic illustration of another multiplanar bone anchor system for use with a connecting device in a fixation procedure according to the present teachings.

In addition, while the multiplanar bone anchor system 1000 has been described herein with reference to FIGS. 42-45 as including the saddle 1006 having a bottom portion 1022 with rails 1032a, 1032b and a top portion 1024 with guides 1050a, 1050b, those of skill in the art will appreciate that the present disclosure, in its broadest aspects, may be constructed somewhat differently. In this regard, with reference to FIGS. 106 and 107, a saddle 2050 can include a first or top portion 2052 and a second or bottom portion 2054. The top portion 2052 can include guides 2052a, 2052b. The guides 2052a, 2052b can slidably engage rails 2054a, 2054b defined on a top surface 2054c of the bottom portion 2054.

Figure 107:
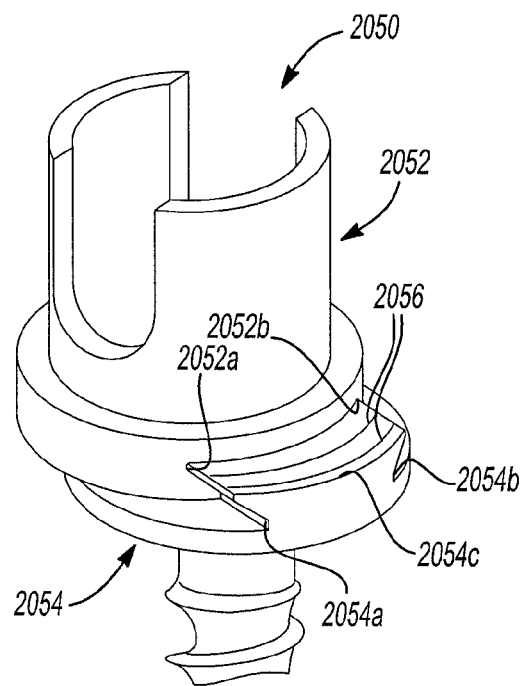
FIG. 107 is a schematic, side illustration of the multiplanar bone anchor system of FIG. 106 in a second position.

The bottom portion 2054 can include the rails 2054a, 2054b and at least one marking 2056 (FIG. 107). As discussed, the rails 2054a, 2054b can cooperate with the guides 2052a, 2052b to enable the top portion 2052 to move or translate relative to the bottom portion 2054. With reference to FIG. 107, the at least one marking 2056 can provide the operator with a visual indicator of the presence or amount of translation of the top portion 2052 relative to the bottom portion 2054.

Thus, in use, with the bottom portion 2054 coupled to the anatomy via a suitable bone fastener, the operator can move or translate the top portion 2052 a selected amount based on a reading of the at least one marking 2056 (FIG. 107).

Figure 108:
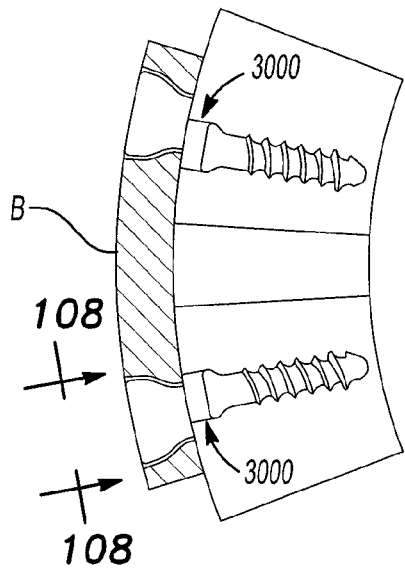
FIG. 108 is a schematic environmental illustration of an exemplary bone fastener for use in a fixation procedure according to the present teachings.
Figure 109:
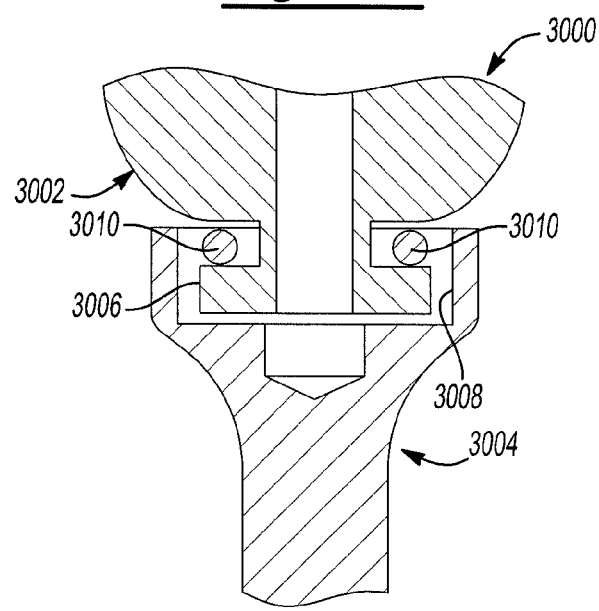
FIG. 109 is a cross-sectional view of the bone fastener of FIG. 108, taken along line 109-109 of FIG. 108.

In another of various examples, a translating fastener 3000 can be used with a plate, such as a bone plate B, to repair a damaged portion of an anatomy. In one example, with reference to FIGS. 108 and 109, a translating fastener 3000 can include a head 3002 and a shank 3004. With reference to FIG. 109, the head 3002 can include at least one T-shaped rail 3006. The T-shaped rail 3006 can be received within a pocket 3008 defined in the shank 3004. One or more pins 3010 can be inserted between the T-shaped rail 3006 and the pocket 3008. The one or more pins 3010 can prevent the head 3002 from disassembling from the shank 3004, while enabling the head 3002 to move relative to the shank 3004. The use of the T-shaped rail 3006 and the pocket 3008 is merely exemplary as any geometry could be employed to enable the head 3002 to move relative to the shank 3004. Further, the geometry employed could enable the head 3002 to move relative to the shank 3004 in a line, plane, arc, two-dimensional path, three-dimensional path, etc. The movement between the head 3002 and the shank 3004 can enable the translating fastener 3000 to provide compression when used in a fixation procedure, such as when used with a cervical plate (FIG. 108).

It should be noted that the translation techniques described herein are merely exemplary, as translation could be achieved through any suitable technique, such as the use of flexible materials, shape memory materials, springs, etc. Further, the various systems incorporating the translation techniques described and illustrated herein are merely exemplary, as the translation techniques described herein could be applied to top-loading bone screws, posted bone screws, closed bone screws, polyaxial bone screws, uniplanar bone screws, fixed screws, etc.

What is claimed is:

1. A bone anchor comprising:
   a bone fastener having a head including a first bearing surface;
   a connecting arm defining a first bore extending along a longitudinal axis and having a second bearing surface that cooperates with the first bearing surface of the bone fastener to enable the bone fastener to move relative to the connecting arm, the connecting arm including a first preferred angle slot that defines a preferred angle for the bone fastener to articulate relative to the longitudinal axis; and
   a saddle having a first member and a second member that cooperate to define a second bore that extends along the longitudinal axis, the connecting arm received within the second bore such that the entire first member is movable relative to the second member and the connecting arm in a common direction transverse to the longitudinal axis.

2. The anchor of claim 1, wherein the second member is immovably coupled to the connecting arm.

3. The anchor of claim 1, wherein the second bore includes a second preferred angle slot that cooperates with the first preferred angle slot of the connecting arm to enable the bone fastener to articulate to the preferred angle.

4. The anchor of claim 1, wherein the first member of the saddle is configured to receive a connecting rod.

5. The anchor of claim 4, wherein the head of the bone fastener includes a contact portion for directly frictionally engaging the connecting rod when the connecting rod is positioned within the first member.

6. The anchor of claim 1, wherein the connecting arm includes at least one friction surface to control the movement of the first member relative to the second member.

7. The anchor of claim 6, wherein the at least one friction surface further comprises a first leaf spring and a second leaf spring defined on a proximal most surface of the connecting arm.

8. The anchor of claim 7, wherein the saddle further comprises a first pin bore and a second pin bore each extending in a direction transverse to the longitudinal axis that receive a first pin and a second pin, respectively.

9. A bone anchor comprising:
a bone fastener having a head including a first bearing surface;
a connecting arm defining a first bore extending along a longitudinal axis and having a second bearing surface that cooperates with the first bearing surface of the bone fastener to enable the bone fastener to move relative to the connecting arm, the connecting arm including a first preferred angle slot that defines a preferred angle for the bone fastener to articulate relative to the longitudinal axis; and
a saddle having a first member and a second member that cooperate to define a second bore that extends along the longitudinal axis, the connecting arm received within the second bore such that the first member is movable relative to the second member and the connecting arm in a direction transverse to the longitudinal axis, wherein the connecting arm includes opposed curved features each having a straight portion, and the first member moves relative to the second member and the connecting arm along the straight portions.

10. A bone anchor comprising:
a bone fastener having a head including a first bearing surface and extending along a longitudinal axis;
a connecting arm defining a first bore having a second bearing surface that cooperates with the first bearing surface of the bone fastener to enable the bone fastener to move relative to the connecting arm, the connecting arm including a first preferred angle slot that defines a preferred angle for the bone fastener to articulate relative to the longitudinal axis; and
a saddle having a first member and a second member that cooperate to define a second bore that extends along the longitudinal axis, the connecting arm received within the second bore such that the first member is movable relative to the second member and the connecting arm in a direction transverse to the longitudinal axis, wherein the connecting arm includes at least one friction surface to control the movement of the first member relative to the second member, wherein the at least one friction surface further comprises a first leaf spring and a second leaf spring defined on a proximal most surface of the connecting arm, wherein the saddle further comprises a first pin bore and a second pin bore each extending in a direction transverse to the longitudinal axis that receive a first pin and a second pin, respectively, wherein the first pin and the second pin bias against the first leaf spring and the second leaf spring to control the motion of the first member.

11. A bone anchor comprising:
a bone fastener having a head disposed at a proximal end of the bone fastener and including a first bearing surface;
a connecting arm having a first portion, a second portion and a first bore having a second bearing surface, the first portion including at least one friction surface facing proximally and disposed at a proximal most end of the connecting arm and the second portion defining a first preferred angle slot in communication with the first bore, the head of the bone fastener being received within the first bore such that the first bearing surface of the head of the bone fastener cooperates with the second bearing surface of the first bore to enable the bone fastener to move relative to the connecting arm; and
a saddle having a first member and a second member that cooperate to define a second bore that extends along a longitudinal axis, the connecting arm received within the second bore such that the first member is movable relative to the second member along the at least one friction surface.

12. The anchor of claim 11, wherein the at least one friction surface further comprises a first leaf spring and a second leaf spring, and the first leaf spring is formed opposite the second leaf spring about the first bore.

13. The anchor of claim 12, wherein the first leaf spring and the second leaf spring extend in a vertical direction parallel to the longitudinal axis.

14. The anchor of claim 12, wherein the first leaf spring and the second leaf spring extend in a horizontal direction transverse to the longitudinal axis.

15. The anchor of claim 11, wherein the second member is immovably coupled to the connecting arm.

16. The anchor of claim 11, wherein the second member includes a second preferred angle slot that cooperates with the first preferred angle slot of the connecting arm to enable the bone fastener to articulate to a preferred angle.

17. The anchor of claim 11, wherein the first member is movable relative to the second member in a direction transverse to the longitudinal axis.

18. A bone anchor comprising:
a bone fastener having a head including a first bearing surface;
a connecting arm having a first portion, a second portion and a first bore having a second bearing surface, the first portion including at least one friction surface and the second portion defining a first preferred angle slot in communication with the first bore, the head of the bone fastener being received within the first bore such that the first bearing surface of the head of the bone fastener cooperates with the second bearing surface of the first bore to enable the bone fastener to move relative to the connecting arm; and
a saddle having a first member and a second member that cooperate to define a second bore that extends along a longitudinal axis, the connecting arm received within the second bore such that the first member is movable relative to the second member over the at least one friction surface, wherein the first member defines at least one throughbore that extends along an axis transverse to the longitudinal axis, with at least one pin received within the at least one throughbore that biases against the at least one friction surface to enable the first member to move relative to the second member in a direction transverse to the longitudinal axis.

19. A bone anchor comprising:
a bone fastener having a head including a hemispherical bearing surface;
a connecting arm including a first portion, a second portion and defining a first bore having a bearing surface that cooperates with the hemispherical bearing surface of the bone fastener to enable the bone fastener to move relative to the connecting arm, the first portion having opposed curved features each including a straight portion, the second portion including a first preferred angle slot; and a saddle having a first member and a second member that cooperate to define a second bore that extends along a longitudinal axis, the first member coupled to the first portion of the connecting arm such that the first member moves relative to the connecting arm along the straight portions, the second member coupled to the second portion of the connecting arm and defining a second preferred angle slot that cooperates with the first preferred angle slot to define a preferred angle for the bone fastener to articulate relative to the longitudinal axis.

20. A bone anchor comprising:

a bone fastener having a head including a hemispherical bearing surface;

a connecting arm including a first portion, a second portion and defining a first bore having a bearing surface that cooperates with the hemispherical bearing surface of the bone fastener to enable the bone fastener to move relative to the connecting arm, the first portion having opposed curved features each including a straight portion, the second portion including a first preferred angle slot; and a saddle having a first member and a second member that cooperate to define a second bore that extends along a longitudinal axis, the first member coupled to the first portion of the connecting arm such that the first member moves relative to the connecting arm along the straight portions, the second member coupled to the second portion of the connecting arm and defining a second preferred angle slot that cooperates with the first preferred angle slot to define a preferred angle for the bone fastener to articulate relative to the longitudinal axis, wherein the second member includes a plurality of grooves and the second portion of the connecting arm includes a plurality of ribs that snap into the plurality of grooves to couple the second member to the connecting arm.

* * * * *